United States Patent [19]
Carpino et al.

[11] Patent Number: 5,936,089
[45] Date of Patent: Aug. 10, 1999

[54] DIPEPTIDES WHICH PROMOTE RELEASE OF GROWTH HORMONE

[75] Inventors: Philip A. Carpino, Groton, Conn.; Paul A. Dasilva-Jardine, Providence, R.I.; Bruce A. Lefker; John A. Ragan, both of Gales Ferry, Conn.

[73] Assignee: Pfizer Inc, New York, N.Y.

[21] Appl. No.: 08/973,268

[22] PCT Filed: May 29, 1995

[86] PCT No.: PCT/IB95/00410

§ 371 Date: Nov. 26, 1997

§ 102(e) Date: Nov. 26, 1997

[87] PCT Pub. No.: WO96/38471

PCT Pub. Date: Dec. 5, 1996

[51] Int. Cl.$^6$ .................. A61K 31/475; C07D 217/06
[52] U.S. Cl. .................. 546/143; 546/146; 514/307; 514/310
[58] Field of Search .................. 546/143, 146; 514/310

[56] References Cited

U.S. PATENT DOCUMENTS

| | | |
|---|---|---|
| 3,239,345 | 3/1966 | Hodge et al. . |
| 4,306,979 | 7/1977 | Asato . |
| 4,411,890 | 10/1983 | Momany . |
| 5,206,235 | 4/1993 | Fisher et al. . |
| 5,284,841 | 2/1994 | Chu et al. . |
| 5,310,737 | 5/1994 | Fisher et al. . |
| 5,317,017 | 5/1994 | Ok et al. . |

FOREIGN PATENT DOCUMENTS

| | | |
|---|---|---|
| 9411012 | 5/1994 | WIPO . |
| 9413696 | 6/1994 | WIPO . |
| 9509633 | 4/1995 | WIPO . |
| 9511029 | 4/1995 | WIPO . |

OTHER PUBLICATIONS

Strobel and Thomas, Pharm. Rev., 46(1), 1–34 (1994).

*Primary Examiner*—Robert W. Ramsuer
*Attorney, Agent, or Firm*—Peter C. Richardson; Paul H. Ginsburg; Raymond M. Speer

[57] ABSTRACT

Compounds of formula (I) are growth hormone releasing peptide mimetics which are useful for the treatment and prevention of osteoporosis.

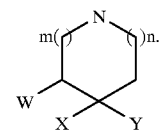

14 Claims, No Drawings

DIPEPTIDES WHICH PROMOTE RELEASE OF GROWTH HORMONE

This is a 371 of PCT/IB95/00410 May 29, 1995.

This invention relates to dipeptide compounds which are growth hormone releasing peptide (GHRP) mimetics and are useful for the treatment and prevention of osteoporosis.

BACKGROUND OF THE INVENTION

Growth hormone, which is secreted from the pituitary, stimulates growth of all tissues of the body that are capable of growing. In addition, growth hormone is known to have the following basic effects on the metabolic process of the body:

1. Increased rate of protein synthesis in all cells of the body;
2. Decreased rate of carbohydrate utilization in cells of the body;
3. Increased mobilization of free fatty acids and use of fatty acids for energy.

A deficiency in growth hormone secretion can result in various medical disorders, such as dwarfism.

It is now widely recognized that most human growth deficiencies are due to hypothalamic defects that impair the release of pituitary growth hormone and are not the result of a primary deficit in the production of growth hormone by the pituitary. As a result, the development of synthetic growth hormone-releasing agents and the use of drugs acting through established neurotransmitter systems in the brain to stimulate growth hormone release are being considered as alternatives to highly expensive growth hormone replacement therapy for the restoration of normal serum growth hormone levels. Strobel and Thomas, Pharm. Rev. 46, No. 1, pg. 1–34 (1994).

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recently, recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low.

WO 94/13696 refers to certain spiropiperidines and homologs which promote release of growth hormone. Preferred compounds are of the general structure shown below.

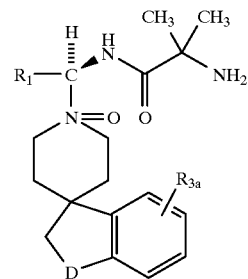

WO 94/11012 refers to certain dipeptides that promote release of growth hormone. These dipeptides have the general structure

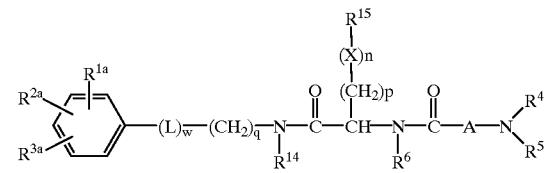

where L is

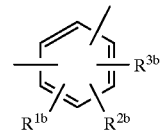

The compounds of WO 94/11012 and WO 94/13696 are reported to be useful in the treatment of osteoporosis in combination with parathyroid hormone or a bisphosphonate.

SUMMARY OF THE INVENTION

This invention provides a compound of the formula:

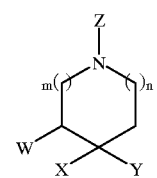

wherein

Z is —COC*$R^1R^{2c}$LCOANR$^4R^5$;

L is NR$^6$, O or CH$_2$;

W is hydrogen or in combination with X is a benzo fusion in which W and X are linked to form a phenyl ring optionally substituted with one to three substituents independently selected from R$^{3a}$, T-R$^{3b}$ and R$^{12}$;

Y is hydrogen, $C_1$–$C_6$ alkyl, $C_4$–$C_{10}$ cycloalkyl or aryl-K-, phenyl-($C_1$–$C_6$ alkyl)-K- or thienyl-($C_1$–$C_6$ alkyl)-K-, each ring optionally substituted with one to three substituents selected from R$^{3a}$, R$^{3b}$ and R$^{12}$, wherein K is a bond, O, S(O)$_m$, or NR$^{2a}$, X is $OR^2$, $R^2$,

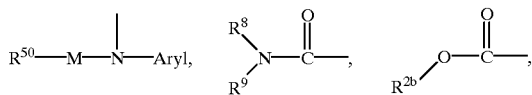

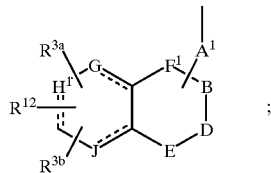

or in combination with W is a benzofusion in which W and X are linked to form a phenyl ring optionally substituted with one to three substituents independently selected from $R^{3a}$, $-T-R^{3b}$ and $R^{12}$;

$R^1$ is $C_1-C_{10}$ alkyl, aryl, aryl ($C_1-C_6$ alkyl) and $C_3-C_7$ cycloalkyl ($C_1-C_6$ alkyl) or $C_1-C_5$ alkyl-$K^1$-$C_1-C_5$ alkyl, aryl ($C_0-C_5$ alkyl)-$K^1$-($C_1-C_5$ alkyl), ($C_3-C_7$) cycloalkyl ($C-C_5$alkyl)-$K^1$-($C_1-C_5$ alkyl) where $K^1$ is O, $S(O)_m$, $N(R^2)$ $C(O)$, $C(O)N(R^2)$, $OC(O)$, $C(O)O$, $-CR^2=CR^2-$ or $-C\equiv C-$ where the aryl groups are defined below and $R^2$ and the alkyl groups may be further substituted by 1–5 halogens, $S(O)_m R^{2a}$, 1 to 3 of $OR^{2a}$ or $C(O)OR^{2a}$ and the aryl groups may be further substituted by phenyl, phenoxy, arylalkyloxy, halophenyl, 1 to 3 of $C_1-C_6$ alkyl, 1 to 3 of halogen, 1 to 2 of $OR^2$, methylenedioxy, $S(O)_m R^2$, 1 to 2 of $CF_3$, $OCF_3$, nitro, $N(R^2)(R^2)$, $N(R^2)C(O)(R^2)$, $C(O)OR^2$, $C(O)N(R^2)(R^2)$, $SO_2N(R^2)(R^2)$, $N(R^2)SO_2$ aryl or $N(R^2)SO_2R^2$;

$R^{2c}$ is hydrogen, $C_1-C_6$ alkyl, $C_3-C_7$ cycloalkyl, and may be joined with $R^1$ to form a $C_3-C_8$ ring optionally including oxygen, sulfur or $NR^{2a}$;

$R^2$ is hydrogen, $C_1-C_6$ alkyl, $C_3-C_7$ cycloalkyl, $C_1-C_6$ halogenated alkyl;

$R^{2a}$ is hydrogen or $C_1-C_6$ alkyl;

$R^{2b}$ is hydrogen $C_1-C_8$ alkyl, $C_1-C_8$ halogenated alkyl, $C_3-C_8$ cycloalkyl, alkylaryl or aryl;

$R^{3a}$ is H, F, Cl, Br, I, $CH_3$, $OCF_3$, $OCF_2H$, $OCH_3$ or $CF_3$;

$R^{12}$ is H, F, Cl, Br, I, $CH_3$, $OCF_3$, $OCF_2H$, $OCH_3$ or $CF_3$;

T is a bond or is phenyl or a 5 or 6-membered heterocycle containing 1 to 3 hetero atoms selected from nitrogen, sulfur or oxygen, each optionally substituted with one to three substituents selected from F, Cl, Br, I, $CH_3$, $OCH_3$, $OCF_3$ and $CF_3$;

$R^{3b}$ is hydrogen, $CONR^8R^9$, $SO_2NR^8R^9$, COOH, COO ($C_1-C_6$)alkyl, $NR^2SO_2R^9$, $NR^2CONR^8R^9$, $NR^2SO_2NR^8R^9$, $NR^2C(O)R^9$, imidazolyl, thiazolyl or tetrazolyl;

$R^4$ and $R^5$ are independently hydrogen, $C_1-C_6$ alkyl, substituted $C_1-C_6$ alkyl where the substituents may be 1 to 5 halo, 1 to 3 hydroxy, 1 to 3 $C_1-C_{10}$ alkanoyloxy, 1 to 3 $C_1-C_6$ alkoxy, phenyl, phenoxy, 2-furyl, $C_1-C_6$ alkoxycarbonyl, $S(O)_m(C_1-C_6$ alkyl); or $R^4$ and $R^5$ can be taken together to form $-(CH_2)_r L_a(CH_2)_s-$ where $L_a$ is $C(R^2)_2$O, $S(O)_m$ or $N(R^2)$, r and s are independently 1 to 3 and $R^2$ is as defined above;

$R^6$ is hydrogen or $C_1-C_6$ alkyl, and may be joined with $R^{2c}$ to form a $C_3-C_8$ ring;

$R^{50}$ is 4-morpholino, 4-(1-methylpiperazinyl), $C_3-C_7$ cycloalkyl or $C_1-C_6$ alkyl each optionally substituted with one to three substituents individually selected from F, OH, $OCH_3$, $OCF_3$, $CF_3$ and $C_3-C_7$ cycloalkyl;

M is $-C(O)-$ or $-SO_2-$;

$A^1$ is a bond, $C_1-C_6$ alkylene, $C_1-C_6$ haloalkylenyl or $C_1-C_6$ hydroxyalkylenyl;

A is a bond or is

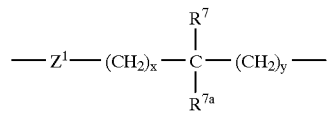

where x and y are independently 0–3;

$Z^1$ is $N-R^2$ or O; or $Z^1$ is a bond;

$R^7$ and $R^{7a}$ are independently hydrogen, $C_1-C_6$ alkyl, trifluoromethyl, phenyl, substituted $C_1-C_6$ alkyl where the substituents are imidazolyl, phenyl, indolyl, p-hydroxyphenyl, $OR^2$, $S(O)_m R^2$, $C(O)OR^2$, $C_3-C_7$ cycloalkyl, $N(R^2)(R^2)$, $C(O)N(R^2)(R^2)$; or $R^7$ and $R^{7a}$ can independently be joined to one or both of $R^4$ and $R^5$ groups to form alkylene bridges between the terminal nitrogen and the alkyl portion of the $R^7$ and $R^7a$ groups, wherein the bridge contains 1 to 5 carbon atoms; or $R^7$ and $R^{7a}$ may be joined to form a 3- to 7-membered ring.

$R^9$ is hydrogen, $C_1-C_6$ alkyl, phenyl, thiazolyl, imidazolyl, furyl or thienyl each optionally substituted with one to three substituents selected from Cl, F, $CH_3$, $OCH_3$, $OCF_3$ and $CF_3$;

$R^8$ is hydrogen, $C_1-C_6$ alkyl, substituted $C_1-C_6$ alkyl where the substituents may be 1 to 5 halo, 1 to 3 hydroxy, 1 to 3 $C_1-C_{10}$ alkanoyloxy, 1 to 3 $C_1-C_6$ alkoxy, phenyl, phenoxy, $C_1-C_6$ alkoxycarbonyl, $S(O)_m(C_1-C_6$ alkyl); or $R^8$ and $R^9$ can be taken together to form $-(CH_2)_r L_a(CH_2)_s-$ where $L_a$ is $C(R^2)_2$, O, $S(O)_m$ or $N(R^2)$, r and s are independently 1 to 3.

$F^1$, B, D and E are carbon, nitrogen, one of which is joined to $A^1$ and each of the remaining of $F^1$, B, D and E may be optionally substituted with $R^{aa}$, $R^{bb}$; or $F^1$, B, D and E, if not joined to $A^1$ may also be sulfur, oxygen or carbonyl; $F^1$, B, D and E may form a saturated or unsaturated ring; and one of $F^1$, B, D or E may be optionally missing to afford a saturated or unsaturated five-membered ring;

$R^{aa}$ is H, $C_1-C_8$ alkyl optionally substituted with one to three halogens; or phenyl optionally substituted with one to three substituents independently selected from halogen, $CH_3$, $OCH_3$, $OCF_3$, $CF_3$ and $C_1-C_8$ alkyl aryl;

$R^{bb}$ is $C_1-C_8$ alkyl, $C_1-C_8$ alkoxy, $C_1-C_8$ thioalkyl, each optionally substituted with one to three substituents independently selected from halogen, $CH_3$, $OCH_3$, $OCF_3$, $CF_3$; $C_3-C_8$ cycloalkyl; phenyl optionally substituted with one to three substituents independently selected from halo, $CH_3$, $OCH_3$, $OCF_3$ or $CF_3$; $-O-C_1-C_8$ alkyl; or $-S-C_1-C_8$ alkyl.

G, $H^1$, I and J are carbon, nitrogen, sulfur or oxygen atoms which form an aromatic ring, a partially saturated ring or a saturated ring; one of G, $H^1$, I or J may be optionally missing to afford a five-membered ring;

aryl is phenyl, naphthyl or a 5- or 6-membered ring with 1 to 3 heteroatoms selected from oxygen, sulfur and nitrogen; or a bicyclic ring system consisting of a 5 or 6 membered heterocyclic ring with 1 to 3 heteroatoms of nitrogen, sulfur or oxygen, fused to a phenyl ring, each aryl ring being optionally and independently substituted with up to three substituents selected from $R^{3a}$, $R^{3b}$ and $R^{12}$;

m is 0 to 2;

n is 0 to 2;

q is 0 to 3;

and pharmaceutically acceptable salts and individual diastereomers thereof.

In one aspect, this invention provides a compound of Formula I wherein

Z is —COCR$^1$R$^{2c}$NHCOANR$^4$R$^5$

A is —CR$^7$R$^{7a}$(CH$_2$)$_y$—; y is 0 to 3;

and R$^{2c}$ is H or CH$^3$;

R$^7$ is C$_1$–C$_3$ alkyl;

R$^{7a}$ is H or C$_1$–C$_3$ alkyl;

R$^4$ is hydrogen or C$_1$–C$_3$ alkyl; or R$^4$ and R$^{7a}$ are combined to form an alkylene bridge;

R$^5$ is hydrogen or C$_1$–C$_3$ alkyl optionally substituted with one or two hydroxyl groups.

Within the above group of compounds, a preferred class are those wherein

R$^1$ is selected from the group consisting of 1-indolyl-CH$_2$-, 2-indolyl-CH$_2$, 3-indolyl-CH$_2$-, 1-naphthyl-CH$_2$-, 2-naphthyl-CH$_2$-, 1-benzimidazolyl-CH$_2$-, 2-benzimidazolyl-CH$_2$-, phenyl-(C$_1$–C$_4$) alkyl-, 2-, 3- or 4-pyridyl-(C$_1$–C$_4$) alkyl, thienyl-(C$_1$–C$_4$) alkyl, and phenyl-(CO—C$_3$ alkyl)—O—CH$_2$—, phenyl-CH$_2$O-phenyl-CH$_2$-, and 3-benzothienyl-CH$_2$-, or any of the above groups substituted in the aryl portion with one to three F, Cl, CH$_3$, OCH$_3$, OCF$_3$ or CF$_3$ substituents.

Still further preferred within this class are compounds wherein R$^1$ is C$_6$H$_5$CH$_2$OCH$_2$-, phenyl-CH$_2$-S-CH$_2$-, 1-naphthyl-CH$_2$-, 2-naphthyl-CH$_2$-, phenylpropyl or

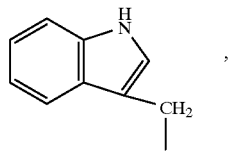

, and the aryl portion of R$^1$ is optionally substituted with fluorine, CH$_3$ or CF$_3$.

In another aspect, this invention provides a compound of Formula I which is:

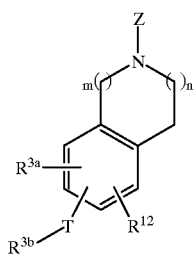

II wherein n is zero or one; m is one or two;

R$^{3a}$ is H, F, Cl, Br, I, CH$_3$, OCH$_3$ or CF$_3$;

R$^{12}$ is H, F, Cl, Br, I, CH$_3$, OCH$_3$ or CF$_3$;

T is a bond or is an aryl group selected from phenyl, pyridyl, pyrimidyl, thienyl, pyrrolyl, pyrazolyl, oxazolyl, isoxazolyl, imidazolyl, thiazolyl and tetrazolyl; each optionally substituted with one to three F, CH$_3$, Cl, OR$^8$, OCH$_3$, OCF$_3$ or CF$_3$;

R$^{3b}$ is hydrogen, CONR$^8$R$^9$, SO$_2$NR$^8$R$^9$, COOH, COO(C$_1$–C$_6$)alkyl, NHSO$_2$R$^9$, NHC(O)NR$^8$R$^9$, NHSO$_2$NR$^8$R$^9$, NHC(O)R$^9$, NR$^8$R$^9$, imidazolyl, thiazolyl or tetrazolyl;

R$^9$ is hydrogen, C$_1$–C$_6$ alkyl, phenyl, thiazolyl, imidazolyl, furyl or thienyl each optionally substituted with one to three substituents selected from Cl, F, CH$_3$, OCH$_3$, OCF$_3$ and CF$_3$;

R$^8$ is hydrogen, C$_1$–C$_6$ alkyl, C$_3$–C$_7$ cycloalkyl, substituted C$_1$–C$_6$ alkyl where the substituents may be 1 to 5 halo, 1 to 3 hydroxy, 1 to 3 C$_1$–C$_{10}$ alkanoyloxy, 1 to 3 C$_1$–C$_6$ alkoxy, phenyl, phenoxy, C$_1$–C$_6$ alkoxycarbonyl, S(O)$_2$(C$_1$–C$_6$ alkyl); or R$^8$ and R$^9$ can be taken together to form —(CH$_2$)$_r$L$_a$(CH$_2$)$_s$— where L$_a$ is C(R$^2$)$_2$O, S(O)$_2$ or N(R$^2$), r and s are independently 1 to 3.

In another aspect, this invention provides a compound of Formula II wherein:

m is one;

R$^{12}$ is hydrogen;

R$^{3a}$ is hydrogen, F or Cl;

T is phenyl, thienyl, thiazolyl, oxazolyl, isoxazolyl or pyrazolyl, each optionally substituted with one to three substituents, selected from F, OH, OCH$_3$, OCF$_3$, CF$_3$ and CH$_3$;

R$^{3b}$ is hydrogen, C(O)NR$^8$R$^9$, NHC(O)NR$^8$R$^9$, NHS(O)$_2$R$^9$, NHC(O)R$^9$;

In another aspect, this invention provides a compound of Formula II wherein:

m is one;

T is a bond; preferred within this class are those compounds wherein;

n is one;

R$^{3a}$ and R$^{12}$ are hydrogen.

R$^{3b}$ is CONR$^8$R$^9$, SO$_2$NR$^8$R$^9$, COOH, COO(C$_1$–C$_6$) alkyl, NHSO$_2$R$^9$, NHSO$_2$NR$^8$R$^9$, NHC(O)NR$^8$R$^9$, NHC(O)R$^9$, NR$^8$R$^9$ or OR$^8$;

R$^9$ is hydrogen, phenyl, or thienyl optionally substituted with one to three substituents selected from F, CH$_3$, OCH$_3$, OCF$_3$ and CF$_3$; or R$^9$ is C$_1$–C$_6$ alkyl optionally substituted with one to three substituents selected from F, OH, OCH$_3$, OCF$_3$ and CF$_3$; or R$^8$;

R$^8$ is hydrogen, C$_1$–C$_6$ alkyl, optionally substituted C$_1$–C$_6$ alkyl or C$_3$–C$_7$ cycloalkyl where the substituents may be 1 to 5 halo or 1 to 3 hydroxy; or R$^8$ and R$^9$ can be taken together to form —(CH$_2$)$_r$L$_a$(CH$_2$)$_s$— wherein L$_a$ is C(R$^2$)$_2$, O, S(O)$_m$ or N(R$^2$) where r and s are independently 1 to 3.

Within the above class still further preferred compounds are those wherein;

n is zero;

m is one;

R$^{3a}$ is hydrogen;

R$^{12}$ is hydrogen;

R$^{3b}$ is CONR$^8$R$^9$, NHC(O)NR$^8$R$^9$, NHS(O)$_2$R$^9$, SO$_2$NR$^8$R$^9$, NHSO$_2$NR$^8$R$^9$, NHCOR$^9$ or OR$^8$;

R$^9$ is phenyl, or thienyl optionally substituted with one to three substituents selected from F, CH$_3$, OCH$_3$, OCF$_3$ and CF$_3$; or R$^9$ is C$_1$–C$_6$ alkyl optionally substituted with one to three substituents selected from F, OH, OCH$_3$, OCF$_3$ and CF$_3$; and R$^8$ is hydrogen, C$_1$–C$_6$ alkyl, or C$_3$–C$_7$ cycloalkyl each optionally substituted with 1 to 5 halo or 1 to 3 hydroxy; or R$^8$ and R$^9$ can be taken together to form —(CH$_2$)$_n$La(CH$_2$)$_s$— wherein La is C(R$^2$)$_2$, O, s(O)m or N(R$^2$) where r and s are independently 1 to 3.

In another aspect, this invention provides a compound of Formula I n is one;

m is one;

W is hydrogen;

Y is hydrogen or methyl;

M is —C(O)—;

R$^{50}$ is 4-morpholino, 4-(1-methylpiperazinyl), C$_3$–C$_7$ cycloalkyl or C$_1$–C$_6$ alkyl each optionally substituted with one to three substituents individually selected from F, OH, OCH$_3$, OCF$_3$ and CF$_3$;

Ar is phenyl, pyridyl, thienyl, pyrimidyl or thiazolyl, each optionally substituted with one to three substituents individually selected from F, Cl, CH$_3$, OCH$_3$, OCF$_3$ and CF$_3$.

In another aspect, this invention provides a compound of Formula I wherein

W is hydrogen;

n and m are one;

Y is phenyl-K, pyridyl, pyrimidyl, thienyl-K, or thiazolyl, C$_4$–C$_{10}$ cycloalkyl, oxazolyl, phenyl-(C$_1$–C$_4$ alkyl)-K-, thienyl-(C$_1$–C$_4$ alkyl)-K- where K is O or is a bond and each of the above aryl groups is optionally substituted with one to three substituents independently selected from F, Cl, CH$_3$, OCH$_3$, OCF$_2$H, OCF$_3$ and CF$_3$;

X is R$^2$ or —C(O)—NR$^8$R$^9$;

R$^9$ is hydrogen, C$_1$–C$_6$ alkyl, phenyl, thiazolyl, imidazolyl, furyl or thienyl each optionally substituted with one to three substituents selected from Cl, F, CH$_3$, OCH$_3$, OCF$_3$ and CF$_3$;

R$^8$ is hydrogen, C$_1$–C$_6$ alkyl, substituted C$_1$–C$_6$ alkyl where the substituents may be 1 to 5 halo, 1 to 3 hydroxy, 1 to 3 C$_1$–C$_{10}$ alkanoyloxy, 1 to 3 C$_1$–C$_6$ alkoxy, phenyl, phenoxy, C$_1$–C$_6$ alkoxycarbonyl, S(O)$_m$(C$_1$–C$_6$ alkyl); or R$^8$ and R$^9$ can be taken together to form —(CH$_2$)$_r$L$_a$(CH$_2$)$_s$— where L$_a$ is C(R$^2$)$_2$, O, S(O)$_m$ or N(R$^2$), r and s are independently 1 to 3.

In another aspect this invention provides a compound of Formula I wherein;

Z is —COCR$^1$R$^{2c}$NHCOANR$^4$R$^5$

A is —CR$^7$R$^{7a}$(CH$_2$)$_y$—; y is 0 to 3;

and R$^{2c}$ is H or CH$_3$;

R$^7$ is C$_1$–C$_3$ alkyl;

R$^{7a}$ is H or C$_1$–C$_3$ alkyl;

R$^4$ is hydrogen or C$_1$–C$_3$ alkyl; or R$^4$ and R$^7$ are combined to form an alkylene bridge;

R$^5$ is hydrogen or C$_1$–C$_3$ alkyl optionally substituted with one or two hydroxyl groups;

R$^1$ is selected from the group consisting of 1-indolyl-CH$_2$-, 2-indolyl-CH$_2$-; 3-indolyl-CH$_2$-, 1-naphthyl-CH$_2$-, 2-naphthyl-CH$_2$-, 1-benzimidazolyl-CH$_2$-, 2-benzimidazolyl-CH$_2$-, phenyl-C$_1$–C$_4$ alkyl-, 2-, 3- or 4-pyridyl-C$_1$–C$_4$ alkyl, phenyl-CH$_2$-S-CH$_2$-, thienyl-C$_1$–C$_4$ alkyl, and phenyl-(CO-C$_3$ alkyl)-O-CH$_2$-, phenyl-CH$_2$O-phenyl-CH$_2$-, and 3-benzothienyl-CH$_2$-, or any of the above groups substituted in the aryl portion with one to three F, Cl, CH$_3$, OCH$_3$, OCF$_3$ or CF$_3$ substituents;

R$^{2c}$ is hydrogen; y=0; R$^7$ and R$^{7a}$ are methyl and R$^4$ and R$^5$ are hydrogen and R$^1$ is C$_6$H$_5$CH$_2$-O-CH$_2$-, phenyl-CH$_2$-S-CH$_2$-, 1-napthyl-CH$_2$-, 2-napthyl-CH$_2$-, phenylpropyl or,

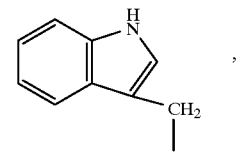

and the aryl portion of R$^1$ is optionally substituted with fluorine, CH$_3$ or CF$_3$; and n is zero one; m is zero or one; Y is C$_4$–C$_{10}$ cycloalkyl, phenyl, phenyl-CH$_2$-, phenyl-O-, pyridyl, pyrimidyl, thienyl, thienyl-CH$_2$-, thiazolyl or oxazolyl, each optionally substituted with one to three substituents independently selected from F, Cl, CH$_3$, OCH$_3$, OCF$_3$, OCF$_2$H and CF$_3$; X is H, C$_1$ to C$_4$ alkyl or C$_1$ to C$_4$ alkyl substituted with one to five fluorine atoms; W is hydrogen.

In another aspect, this invention provides a compound of Formula I wherein: Y is phenyl-CH$_2$-, thienyl-CH$_2$- or phenyl-O- each optionally substituted with F, Cl, CH$_3$, OCH$_3$, OCF$_3$, OCF$_2$H and CF$_3$; X is H, CH$_3$ or CF$_3$.

In another aspect, this invention provides a compound of Formula I wherein

Z is —COCR$^1$R$^{2c}$NHCOANR$^4$R$^5$

A is —CR$^7$R$^{7a}$(CH$_2$)$_y$; y is 0 to 3;

and R$^{2c}$ is H or CH$_3$;

R$^7$ is C$_1$–C$_3$ alkyl;

R$^{7a}$ is H or C$_1$–C$_3$ alkyl;

R$^4$ is hydrogen or C$_1$–C$_3$ alkyl; or R$^4$ and R$^{7a}$ are combined to form an alkylene bridge;

R$^5$ is hydrogen or C$_1$–C$_3$ alkyl optionally substituted with one or two hydroxyl groups;

R$^1$ is selected from the group consisting of 1-indolyl-CH$_2$-; 2-indolyl-CH$_2$-; 3-indolyl-CH$_2$-; 1-naphthyl-CH$_2$-; 2-naphthyl-CH$_2$-; 1-benzimidazolyl-CH$_2$-; 2-benzimidazolyl-CH$_2$-; phenyl-C$_1$–C$_4$ alkyl-; 2-, 3- or 4-pyridyl-C$_1$–C$_4$ alkyl; thienyl-C$_1$–C$_4$ alkyl; phenyl-(CH$_2$)$_n$-O-CH$_2$- where n is zero to three; phenyl-CH$_2$O-phenyl-CH$_2$-; and 3-benzothienyl-CH$_2$-; or any of the above groups substituted in the aryl portion with one to three F, Cl, CH$_3$, OCH$_3$, OCF$_3$ or CF$_3$ substituents;

Y is hydrogen and X is:

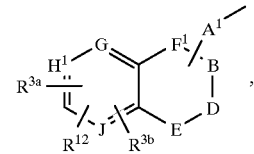

wherein n and m are one and A$^1$ is a bond and W is hydrogen; or X is:

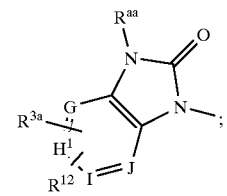

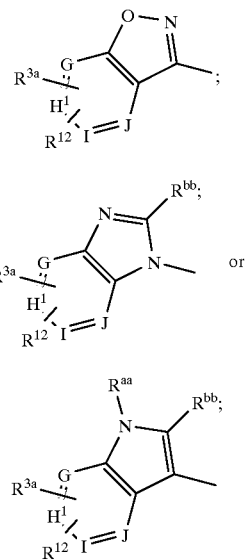

wherein $R^{3a}$ is hydrogen, F, Cl, $CH_3$, $OCH_3$, $OCF_3$ or $CF_3$;

$R^{12}$ is hydrogen, F, Cl, $CH_3$, $OCH_3$, $OCF_3$ or $CF_3$;

$R^{aa}$ is hydrogen, $C_1-C_8$ alkyl optionally substituted with one to three halogens; or phenyl optionally substituted with one to three substituents independently selected from halogen, $CH_3$, $OCH_3$, $OCF_3$, $CF_3$ and $C_1-C_8$ alkyl aryl;

$R^{bb}$ is hydrogen, $C_1-C_8$ alkyl, optionally substituted with one to three substituents independently selected from halogen, $CH_3$, $OCH_3$, $OCF_3$, $CF_3$; $C_3-C_8$ cycloalkyl; phenyl optionally substituted with one to three substituents independently selected from halo, $CH_3$, $OCH_3$, $OCF_3$ or $CF_3$; $-O-C_1-C_8$ alkyl; or $-S-C_1-C_8$ alkyl.

In a preferred aspect this invention provides a compound of Formula I wherein Z is

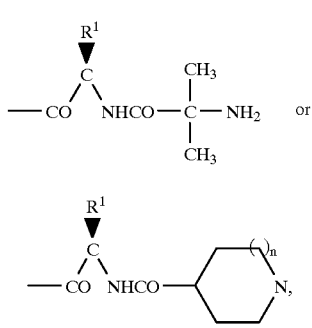

wherein each n is independently zero or one;

$R_1$ is 1-naphthyl $CH_2-$, 2-naphthyl $CH_2$, phenyl $CH_2CH_2CH_2-$ optionally substituted with F, Cl, $CH_3$ or $CF_3$;
or $-CH_2OCH_2C_6H_5$.

Preferred compounds of Formula I are:
(R)-2-Amino-N-{2-(1H-indol-3-yl)-1-[6-(toluene-4-sulfonylamino)-3,4-dihydro-1H-isoquinoline-2-carbonyl]-ethyl}-isobutyramide hydrochloride;

(R)-2-[2-(2-Amino-2-methyl-propionylamino)-3-(1H-indol-3-yl)-propionyl]-1,2,3,4-tetrahydro-isoquinoline-6-carboxylic acid ethylamide hydrochloride;

(R)-2-[2-(2-Amino-2-methyl-propionylamino)-3-(1H-indol-3-yl)-propionyl]-1,2,3,4-tetrahydro-isoquinoline-6-carboxylic acid phenylamide hydrochloride;

(R)-2-Amino-N-(2-(1H-indol-3-yl)-1-{6-[2-(3-methyl-ureido)-phenyl]-3,4-dihydro-1H-isoquinoline-2-carbonyl}-ethyl)-isobutyramide hydrochloride;

(R)-2-Amino-N-{2-(1H-indol-3-yl)-1-[7-(toluene-4-sulfonylamino)-3,4-dihydro-1H-isoquinoline-2-carbonyl]-ethyl}-isobutyramide;

(R)-N-{2-[2-(2-Amino-2-methyl-propionylamino)-3-(1H-indol-3-yl)-propionyl]-1,2,3,4-tetrahydro-isoquinolin-7-yl}-benzamide;

(R)-2-Amino-N-{1-benzyloxymethyl-2-oxo-2-[7-(toluene-4-sulfonylamino)-3,4-dihydro-1H-isoquinolin-2-yl]-ethyl}-isobutyramide;

2-Amino-N-{1-(R)-benzyloxymethyl-2-oxo-2-[4-(phenyl-propionyl-amino)-piperidin-1-yl]-ethyl}-isobutyramide hydrochloride;

(R)-N-[1-[4-(Acetyl-phenyl-amino)-piperidine-1-carbonyl]-2-(1H-indol-3-yl)-ethyl]-2-amino-isobutyramide;

(R)-2-Amino-N-{1-(1H-indol-3-ylmethyl)-2-[4-(morpholine-4-carbonyl)-4-phenyl-piperidin-1-yl]-2-oxo-ethyl}-isobutyramide hydrochloride;

2-Amino-N-{1-(R)-benzyloxymethyl-2-oxo-2-[4-(2-oxo-2,3-dihydro-benzoimidazol-1-yl)-piperidin-1-yl]-ethyl)-;

2-Amino-N-{1-(R)-(1H-indol-3-ylmethyl)-2-oxo-2-[4-(2-oxo-2,3-dihydro-benzoimidazol-1-yl)-piperidin-1-yl]-ethyl}-isobutyramide;

(R)-2-Amino-N-{2-(1H-indol-3-yl)-1-[7-(toluene-4-sulfonylamino)-3,4-dihydro-1H-isoquinoline-2-carbonyl]-ethyl}-isobutyramide;

2-Amino-N-{1-(1H-indol-3-ylmethyl)-2-[4-(1H-indol-3-yl)-piperidin-1-yl]-2-oxo-ethyl}-isobutyramide hydrochloride;

(R)-2-Amino-N-{1-(1H-indol-3-ylmethyl)-2-[4-(2-methyl-benzoimidazol-1-yl)-piperidin-1-yl]-2-oxo-ethyl}-isobutyramide hydrochloride;

(R)-2-Amino-N-{1-(1H-indol-3-ylmethyl)-2-oxo-2-[4-(2-phenyl-benzoimidazol-1-yl)-piperidin-1-yl]-ethyl}-isobutyramide hydrochloride;

(R)-2-Amino-N-[2-[4-(6-fluoro-benzo[d]isoxazol-3-yl)-piperidin-1-yl]-1-(1H-indol-3-ylmethyl)-2-oxo-ethyl]-isobutyramide hydrochloride;

(R)-2-Amino-N-{1-(1H-indol-3-ylmethyl)-2-oxo-2-[4-(2-oxo-1,2-dihydro-imidazo[4,5-b]pyridin-3-yl)-piperidin-1-yl]-ethyl}-isobutyramide hydrochloride;

(R)-2-Amino-N-[2-[4-(5-chloro-2-oxo-2,3-dihydro-benzoimidazol-1-yl)-piperidin-1-yl]-1-(1H-indol-3-ylmethyl)-2-oxo-ethyl]-isobutyramide;

(R)-2-Amino-N-{1-benzo[b]thiophen-3-ylmethyl-2-oxo-2-[4-(2-oxo-2,3-dihydro-benzoimidazol-1-yl)-piperidin-1-yl]-ethyl}-isobutyramide hydrochloride;

2-Amino-N-{1-(R)-benzyloxymethyl-2-[4-(morpholine-4-carbonyl)-4-phenyl-piperidin-1-yl]-2-oxo-ethyl}-isobutyramide;

(R)-Piperidine-4-carboxylic acid {1-naphthalen-2-ylmethyl-2-oxo-2-[5-(toluene-4-sulfonylamino)-1,3-dihydro-isoindol-2-yl]-ethyl}-amide hydrochloride;

2-Amino-N-{1-(R)-benzyloxymethyl-2-[4-(morpholine-4-carbonyl)-4-phenyl-piperidin-1-yl]-2-oxo-ethyl)-isobutyramide;

(R)-2-Amino-N-{1-(1H-indol-3-ylmethyl)-2-oxo-2-[4-phenyl-4-(pyrrolidine-1-carbonyl)-piperidin-1-yl]-ethyl}-isobutyramide hydrochloride;

(R)-1-[2-(2-Amino-2-methyl-propionylamino)-3-(1H-indol-3-yl)-propionyl]-4-phenyl-piperidine-4-carboxylic acid (4-hydroxy-butyl)-amide hydrochloride;

2-Amino-N-{1-(5-fluoro-1H-indol-3-ylmethyl)-2-oxo-2-[4-(2-oxo-2,3-dihydro-benzoimidazol-1-yl)-piperidin-1-yl]-ethyl}-isobutyramide hydrochloride;

2-Amino-N-{1-(1-methyl-1H-indol-3-ylmethyl)-2-oxo-2-[4-(2-oxo-2,3-dihydro-benzoimidazol-1-yl)-piperidin-1-yl]-ethyl}-isobutyramide hydrochloride;

(R)-Piperidine-4-carboxylic acid {1-naphthalen-2-ylmethyl-2-oxo-2-[4-(2-phenyl-benzoimidazol-1-yl)-piperidin-1-yl]-ethyl}-amide hydrochloride;

(R)-3-Amino-N-{1-(1H-indol-3-ylmethyl)-2-oxo-2-[4-(2-phenyl-benzoimidazol-1-yl)-piperidin-1-yl]-ethyl}-3-methyl-butyramide hydrochloride; and (R)-Piperidine-4-carboxylic acid {2-[4-(3-methyl-2-oxo-2,3-dihydro-benzoimidazol-1-yl)-piperidin-1-yl]-1-naphthalen-2-ylmethyl-2-oxo-ethyl}-amide hydrochloride Further preferred compounds are:

(R)-2-Amino-N-[2-benzyloxy-1-(4-phenyl-piperidine-1-carbonyl)-ethyl]-isobutyramide hydrochloride, (R)-2-Amino-N-[2-(1H-indol-3-yl)-1-(4-phenyl-piperidine-1-carbonyl)-ethyl]-isobutyramide hydrochloride, (R)-2-Amino-N-{2-(1H-indol-3-yl )-1-[4-(4-trifluoromethyl-phenyl)-piperidine-1-carbonyl]-ethyl}-isobutyramide hydrochloride, (R)-2-Amino-N-[1-[4-(4-fluoro-phenyl)-piperidine-1-carbonyl]-2-(1H-indol-3-yl)-ethyl]-isobutyramide hydrochloride, (R)-2-Amino-N-(2-(5-fluoro-1H-indol-3-yl)-1-[4-(4-fluoro-phenyl)-piperidine-1-carbonyl]-ethyl}-isobutyramide hydrochloride, (R)-2-Amino-N-[2-(6-fluoro-1H-indol-3-yl)-1-(4-phenyl-piperidine-1-carbonyl)-ethyl]-isobutyramide hydrochloride, (R)-2-Amino-N-[2-(5-fluoro-1H-indol-3-yl)-1-(4-phenyl-piperidine-1-carbonyl)-ethyl]-isobutyramide hydrochloride, (R)-2-Amino-N-[2-benzylsulfanyl-1-(4-phenyl-piperidine-1-carbonyl)-ethyl]-isobutyramide hydrochloride, (R)-2-Amino-N-[2-naphthalen-1-yl-1-(4-phenyl-piperidine-1-carbonyl)-ethyl]-isobutyramide hydrochloride, (R)-2-Amino-N-[2-(1H-indol-3-yl)-1-(4-thiophen-2-yl-piperidine-1-carbonyl)-ethyl]-isobutyramide hydrochloride, (R)-2-Amino-N-[3-phenyl-1-(4-phenyl-piperidine-1-carbonyl)-propyl]-isobutyramide, (R)-2-Piperidine-4-carboxylic acid {2-naphthalen-1-yl-1-[4-(phenyl-propionyl-amino)-piperidine-1-carbonyl]-ethyl}-amide hydrochloride, (R)-2-Amino-N-[1-naphthalen-1-ylmethyl-2-oxo-2-(4-phenoxy-piperidin-1-yl)-ethyl]-isobutyramide hydrochloride, (R)-2-Amino-N-[2-(2-methyl-1H-indol-3-yl)-1-(4-phenyl-piperidine-1-carbonyl)-ethyl]-isobutyramide hydrochloride, and (R)-2-Amino-N-[4-phenyl-1-(4-phenyl-piperidine-1-carbonyl)-butyl]-isobutyramide hydrochloride.

Still further preferred compounds are:

(R)-2-Amino-N-[2-(1H-indol-3-yl)-1-(4-phenoxy-piperidine-1-carbonyl)-ethyl]-isobutyramide hydrochloride or (R)-2-Amino-N-[1-(4-benzyl-piperidine-1-carbonyl)-2-(1H-indol-3-yl)-ethyl]-isobutyramide hydrochloride.

This invention also provides:

a method for increasing levels of endogenous growth hormone in a human or an animal which comprises administering to such human or animal an effective amount of a compound of Formula I;

a composition useful for increasing the endogenous production or release of growth hormone in a human or an animal which comprises an inert carrier and an effective amount of a compound of Formula l;

a composition useful for increasing the endogenous production or release of growth hormone in a human or an animal which comprises an inert carrier and an effective amount of a compound of Formula I used in combination with other growth hormone secretagogues such as, GHRP-6, Hexorelan, GHRP-1, growth hormone releasing factor (GRF) or one of its analogs or IGF-1 or IGF-2, or B-HT920; and a method for the treatment of osteoporosis which comprises administering to a patient with osteoporosis a combination of a bisphosphonate compound such as alendronate, and a compound of Formula I.

This invention further provides a method for treating or preventing diseases or conditions which may be treated or prevented by growth hormone which comprises administering to a mammal in need of such treatment or prevention an amount of a compound of Formula I which is effective in promoting release of said growth hormone.

In another aspect this invention provides compositions and methods which are useful for treating obesity, fraility associated with old age, and cachexia associated with AIDS and cancer.

The instant compounds are highly substituted dipeptide analogs for promoting the release of growth hormone which are stable under various physiological conditions which may be administered parenterally, nasally or by the oral route.

DETAILED DESCRIPTION OF THE INVENTION

One of ordinary skill will recognize that certain substituents listed in this invention may have reduced chemical stability when combined with one another or with heteroatoms in the compounds. Such compounds with reduced chemical stability are not preferred.

In general the compounds of Formula I can be made by processes which include processes known in the chemical arts for the production of structurally analogous compounds. Certain processes for the manufacture of Formula I compounds are provided as further features of the invention and are illustrated by the following reaction schemes.

In the above structural formulae and throughout the instant specification, the following terms have the indicated meanings:

The alkyl groups specified above are intended to include those alkyl groups of the designated length in either a straight or branched configuration which may optionally contain double or triple bonds. Exemplary of such alkyl groups are methyl, ethyl, propyl, isopropyl, butyl, sec-butyl, tertiary butyl, pentyl, isopentyl, hexyl, isohexyl, allyl, ethinyl, propenyl, butadienyl, hexenyl and the like.

The alkoxy groups specified above are intended to include those alkoxy groups of the designated length in either a straight or branched configuration which may optionally contain double or triple bonds. Exemplary of such alkoxy groups are methoxy, ethoxy, propoxy, isopropoxy, butoxy, isobutoxy, tertiary butoxy, pentoxy, isopentoxy, hexoxy, isohexoxy, allyloxy, 2-propinyloxy, isobutenyloxy, hexenyloxy and the like.

The term "halogen" or "halo" is intended to include the halogen atoms fluorine, chlorine, bromine and iodine.

The term "aryl" is intended to include phenyl and naphthyl and aromatic 5- and 6-membered rings with 1 to 3 heteroatoms or fused 5- or 6-membered bicyclic rings with 1 to 3 heteroatoms of nitrogen, sulfur or oxygen. Examples of such heterocyclic aromatic rings are pyridine, thiophene, furan, benzothiophene, tetrazole, indole, N-methylindole, dihydroindole, indazole, N-formylindole, benzimidazole, thiazole, pyrimidine, and thiadiazole.

Certain of the above defined terms may occur more than once in the above formula and upon such occurrence each term shall be defined independently of the other.

Throughout the instant application the following abbreviations are used with the following meanings:

| | |
|---|---|
| BOC | t-butyloxycarbonyl |
| BOP | Benzotriazol-1-yloxy tris(dimethylamino) phosphonium hexafluorophosphate |
| CBZ | Benzyloxycarbonyl |
| CDI | N,N'-Carbonyldiimidazole |
| CH$_2$Cl$_2$ | Methylene chloride |
| CHCl$_3$ | Chloroform |
| DCC | Dicyclohexylcarbodiimide |
| DMF | Dimethylformamide |
| EDC | 1-(3-dimethylaminopropyl)-3-ethylcarbodiimide hydrochloride |
| EtOAc | Ethyl acetate |
| FMOC | 9-Fluorenylmethoxycarbonyl |
| Hex | Hexane |
| HOBT | Hydroxybenzotriazole hydrate |
| HPLC | High pressure liquid chromatography |
| MHz | Megahertz |
| MS | Mass Spectrum |
| NMR | Nuclear Magnetic Resonance |
| PTH | Parathyroid hormone |
| TFA | Trifluoroacetic acid |
| THF | Tetrahydrofuran |
| TLC | Thin layer chromatography |
| TRH | Thyrotropin releasing hormone |

The compounds of the instant invention all have at least one asymmetric center as noted by the asterisk in the structural Formula I, group Z above. Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the ambit of the instant invention. In the case of the asymmetric center represented by the asterisk, it has been found that the absolute stereochemistry of the more active and thus more preferred isomer is shown in Formula IA. This preferred absolute configuration also applies to Formula I. With the R$_2$ substituent as hydrogen, the spatial configuration of the asymmetric center corresponds to that in a D-amino acid. In most cases this is also designated an R-configuration although this will vary according to the values of R$_1$ and R$_2$ used in making R- or S-stereochemical assignments.

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic, methane sulfonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, to improve feed efficiency and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical by acceptable carrier. Optionally, the active ingredient of the pharmaceutical compositions can comprise an anabolic agent in addition to at least one of the compounds of Formula I or another composition which exhibits a different activity, e.g., an antibiotic growth permittant or an agent to treat osteoporosis or in combination with a corticosteroid to minimize the catabolic side effects or with other pharmaceutically active materials wherein the combination enhances efficacy and minimizes side effects.

Growth promoting and anabolic agents include, but are not limited to, TRH, PTH, diethylstilbestercl, estrogens, β-agonists, theophylline, anabolic steroids, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the growth hormone secretagogues of this invention is in combination with other growth hormone secretagogues such as the growth hormone releasing peptides GHRP-6, GHRP-1 as described in U.S. Pat. Nos. 4,411,890 and publications WO 89/07110, WO 89/07111 and B-HT920 as well as hexarelin and the newly discovered GHRP-2 as described in WO 93/04081 or growth hormone releasing hormone (GHRH, also designated GRF) and its analogs or growth hormone and its analogs or somatomedins including IGF-1 and IGF-2 or $\mu$-adrenergic agonists such as clonidine or serotonin 5HTID agonists such as sumitriptan or agents which inhibit somatostatin or its release such as physostigmine and pyridostigmine.

As is well known to those skilled in the art, the known and potential uses of growth hormone are varied and multitudinous. See "Human Growth Hormone", Strobel and Thomas, Pharmacological Reviews 46, pg. 1–34 (1994) which describes possible use of growth hormone. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; treating growth hormone deficient adults; prevention of catabolic side effects of glucocorticoids, treatment of osteoporosis, stimulation of the immune system, acceleration of wound healing, accelerating bone fracture repair, treatment of growth retardation, treating acute or chronic renal failure or insufficiency, treatment of physiological short stature, including growth hormone deficient children, treating short stature associated with chronic illness, treatment of obesity, treating growth retardation associated with Prader-Willi syndrome and Turner's syndrome; accelerating the recovery and reducing hospitalization of burn patients or following major surgery such as gastrointestinal surgery; treatment of intrauterine growth retardation, skeletal dysplasia, hypercortisonism and Cushings syndrome; replacement of growth hormone in stressed patients; treatment of osteochondrodysplasias, Noonans syndrome, sleep disorders, Alzheimer's disease, delayed wound healing, and psychosocial deprivation; treatment of pulmonary dysfunction and ventilator dependency; attenuation of protein catabolic response after a major operation; treating malabsorption syndromes, reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; to stimulate thymic development and prevent for age-related decline of thymic function; adjunctive therapy for patients on chronic hemodialysis; treatment of immunosuppressed patients and to enhance antibody response following vaccination; improvement in muscle strength, mobility, maintenance of skin thickness, metabolic homeostasis, renal hemeostasis in the frail elderly; stimulation of osteoblasts, bone remodeling, and cartilage growth; treatment of neurological diseases such as peripheral and drug induced neuropathy, Guillian-Barre Syndrome, amyotrophic lateral sclerosis, multiple sclerosis, cerebrovascular accidents and demyelinating diseases; stimulation of the immune system in companion animals and treatment of disorders of aging in companion animals; growth promotant in livestock; and stimulation of wool growth in sheep.

It will be known to those skilled in the art that there are numerous compounds now being used in an effort to treat the diseases or therapeutic indications enumerated above. Combinations of these therapeutic agents some of which have also been mentioned above with the growth promotant, anabolic and desirable properties of these various therapeutic agents. In these combinations, the therapeutic agents and the growth hormone secretagogues of this invention may be independently present in dose ranges from one one-hundredth to one times the dose levels which are effective when these compounds and secretagogues are used singly.

Combined therapy to inhibit bone resorption, prevent osteoporosis and enhance the healing of bone fractures can be illustrated by combinations of bisphosphonates and the growth hormone secretagogues of this invention. The use of bisphosphonates for these utilities has been reviewed, for example, by Hamdy, N. A. T., Role of Bisphosphonates in Metabolic Bone Diseases. *Trends in Endocrinol. Metab.*, 1993, 4, 19–25. Bisphosphonates with these utilities include alendronate, tiludronate, dimethyl—APD, risedronate, etidronate, YM-175, clodronate, pamidronate, and BM-210995. According to their potency, oral daily dosage levels of the bisphosphonate of between 0.1 mg and 5 g and daily dosage levels of the growth hormone secretagogues of this invention of between 0.01 mg/kg to 20 mg/kg of body weight are administered to patients to obtain effective treatment of osteoporosis.

Compounds that have the ability to stimulate GH secretion from cultured rat pituitary cells are identified using the following protocol. This test is also useful for comparison to standards to determine dosage levels. Cells are isolated from anterior pituitaries of 6-week old male Wistar rats following decapitation. Tissues are finely minced, then subjected to mechanical and enzymatic dispersion using 10 U/mL bacterial protease (EC 3.4.24.4, Sigma P-6141) in Hank's balanced salt solution without calcium or magnesium. The cell suspension is plated at $5 \times 10^4$ cells per square cm in 24-well Costar dishes and cultured for 3 days in Dulbecco's Modified Eagles Medium (D-MEM) supplemented with 4.5 g/L glucose, 10% horse serum, 2.5% fetal bovine serum, non-essential amino acids, 100 U/mL nystatin and 50 mg/mL gentamycin sulfate.

Just prior to beginning the assay, culture wells are rinsed twice, then equilibrated for 30 minutes in release medium (D-MEM buffered with 25 mM Hepes, pH 7.4 and containing 0.5% bovine serum albumin at 37° C. Test compounds are dissolved in DMSO, then diluted into pre-warmed release medium. The assay is initiated by adding 1 mL of release medium (with test compounds) to each culture well. Incubation is carried out at 37° C. for 15 minutes, then terminated by removal of the culture medium, which is centrifuged at 2000×g for 15 minutes to remove cellular material before being assayed for rat growth hormone by a radioimmunoassay procedure using reagents provided by A. F. Parlow (Harbor-UCLA Medical Center, Torrance, Calif.). Active compounds typically stimulate growth hormone release by 3-4 fold.

Nonpeptidyl GH secretogogues are shown to mimic growth hormone releasing peptides based on one or more of the following criteria: synergistic stimulation of GH release when added together with GHRH, inability to further increase GH secretion by GHRP-6, sensitivity to protein kinase C inhibitors, and selective stimulation of biphasic calcium flux in GH-containing cells.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions.

Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg of body weight daily are administered to patients and animals, e.g., mammals, to obtain effective release of growth hormone.

A preferred dosage range is 0.01 to 5.0 mg/kg of body weight daily.

The following structures prepared in the Examples indicated exemplify the nomenclature used in this document:

(R)-2-[2-(2-Amino-2-methyl-propionylamino)-3-(1H-indol-3-yl)-propionyl]-1,2,3,4-tetrahydro-isoquinoline-6-carboxylic Acid Ethylamide Hydrochloride

EXAMPLE 26

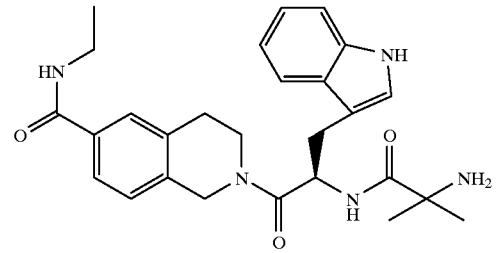

(R)-Piperidine-4-carboxylic Acid {1-naphthalen-2-ylmethyl-2-oxo-2-[5-(toluene-4-sulfonylamino)-1,3-dihydro-isoindol-2-yl]-ethyl}-amide

EXAMPLE 83

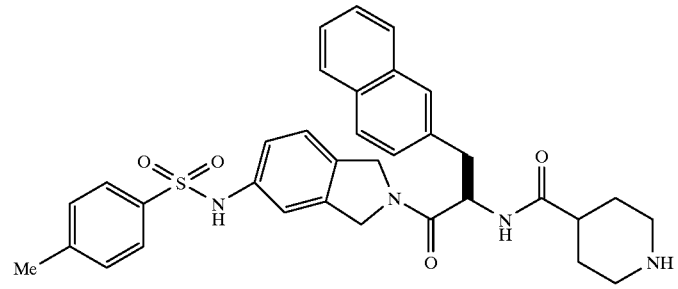

(R)-N-[1-[4-(Acetyl-phenyl-amino)-piperidine-1-carbonyl]-2-(1H-indol-3-yl)-ethyl]-2-amino-isobutyramide

EXAMPLE 34

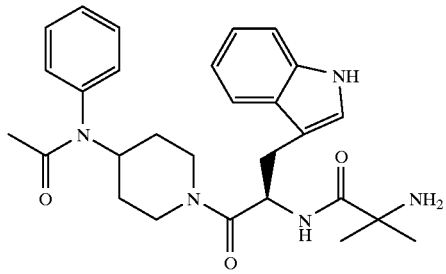

(R)-2-Amino-N-{1(1H-indol-3-ylmethyl)-2-oxo-2-[4-phenyl-4-(pyrrolidine-1-carbonyl)-piperidin-1-yl]-ethyl}-isobutyramide

EXAMPLE 46

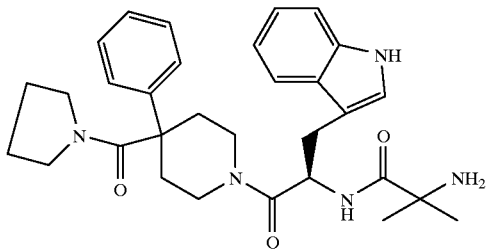

2-Amino-N-{1-(R)-benzyloxymethyl-2-oxo-2-[4-(2-oxo-2,3-dihydro-benzoimidazol-1-yl)-piperidin-1-yl]-ethyl}-isobutyramide

EXAMPLE 1

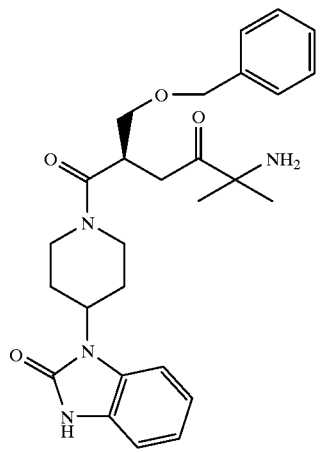

(R)-2-Amino-N-(2-(1H-indol-3-yl)-1-{6-[2-(3-methyl-ureido)-phenyl]-3,4-dihydro-1H-isoquinoline-2-carbonyl}-ethyl)-isobutyramide

EXAMPLE 29

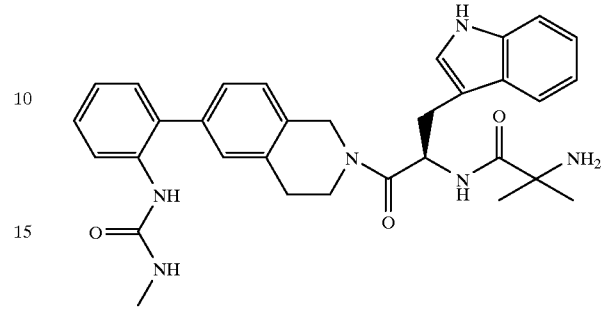

(R)-3-Amino-N-{1-(1H-indol-3-ylmethyl)-2-oxo-2-[4-(2-phenyl-benzoimidazol-1-yl)-piperidin-1-yl]-ethyl}-3-methyl-butyramide

EXAMPLE 91

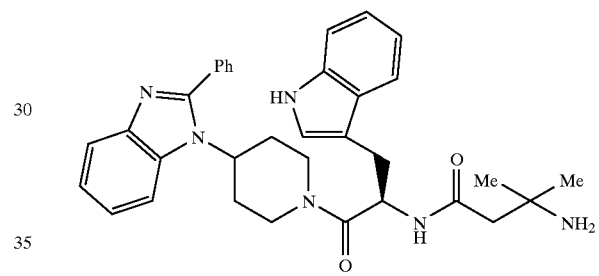

The preparation of the compounds of Formula I of the present invention can be carried out in sequential or convergent synthetic routes. Syntheses detailing the preparation of the compounds of Formula I in a sequential manner are presented in the following reaction schemes.

Many protected amino acid derivatives are commercially available, where the protecting groups P are, for example, BOC, CBZ, FMOC, benzyl or ethoxycarbonyl groups. Other protected amino acid derivatives can be prepared by literature methods. Some substituted pyrrolidines, piperidines and tetrahydroisoquinolines are commercially available, and many other pyrrolidines, 4-substituted piperidines, and 1,2,3,4-tetrahydroisoquinolines are known in the literature. Various phenyl or heteroaryl substituted piperidines and 1,2,3,4-tetrahydroisoquinolines can be prepared following literature methods using derivatized phenyl and heteroaryl intermediates. Alternatively the phenyl or heteroaryl rings of such compounds can be derivatized by standard means, such as halogenation, nitration, sulfonylation etc.

Many of the schemes illustrated below describe compounds which contain protecting groups P. Benzyloxycarbonyl groups can be removed by a number of methods including, catalytic hydrogenation with hydrogen in the presence of a palladium or platinum catalyst in a protic solvent such as methanol. Preferred catalysts are palladium hydroxide on carbon or palladium on carbon. Hydrogen pressures from 1–1000 psi may be employed; pressures from 10 to 70 psi are preferred. Alternatively, the benzyloxycarbonyl group can be removed by transfer hydrogenation.

Removal of BOC protecting groups can be carried out using a strong acid such as trifluoroacetic acid or hydrochloric acid with or without the presence of a cosolvent such as dichloromethane or methanol at a temperature of about −30 to 70° C., preferably about −5 to about 35° C.

Benzyl esters of amines can be removed by a number of methods including, catalytic hydrogenation with hydrogen in the presence of a palladium catalyst in a protic solvent such as methanol. Hydrogen pressures from 1-1000 psi may be employed; pressures from 10 to 70 psi are preferred. The addition and removal of these and other protecting groups is discussed by T. Greene in Protective Groups in Organic Synthesis, John Wiley & Sons, New York, 1981.

SCHEME 1

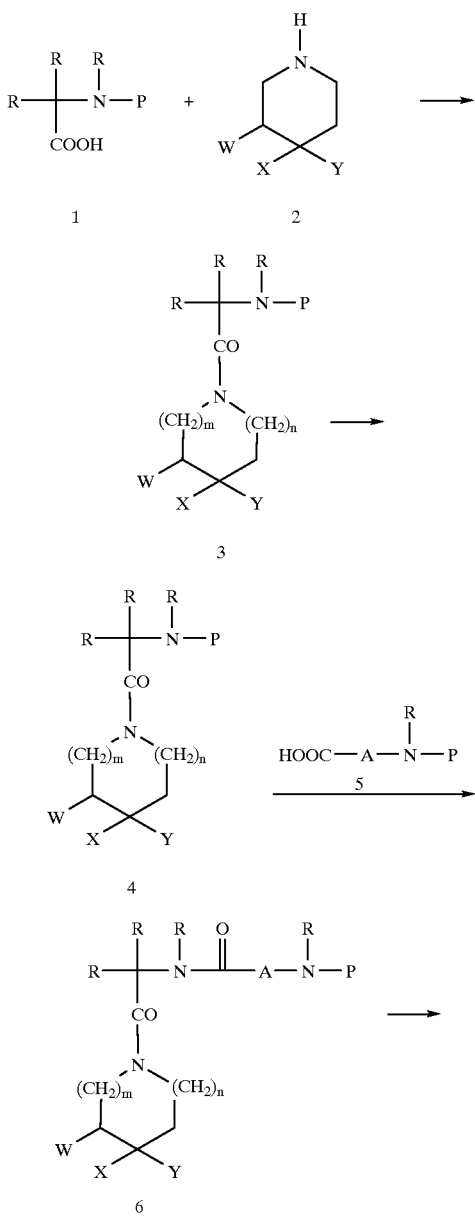

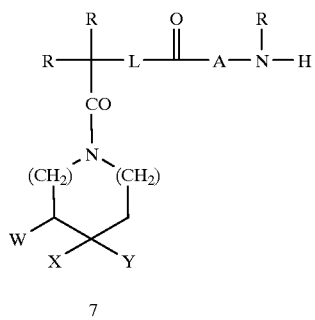

The protected amino acid derivatives 1 are in many cases commercially available, where the protecting group P is, for example, BOC or CBZ groups. Other amino acids can be prepared by literature methods.

As illustrated in Scheme 1, coupling of amines of formula 2 with protected amino acids of formula 1, where P is a suitable protecting group, is conveniently carried out in an inert solvent such as dichloromethane or DMF by a coupling reagent such as EDC or DCC in the presence of HOBT. In the case where the amine is present as the hydrochloride salt, it is preferable to add one equivalent of a suitable base such as triethylamine to the reaction mixture. Alternatively, the coupling can be effected with a coupling reagent such as BOP in an inert solvent such as methanol. Such coupling reactions are generally conducted at temperatures of about −30 to about 80° C., preferably 0 to about 25° C. For a discussion of other conditions used for coupling peptides see Houben-Weyl, Vol. XV, part 11, E. Wunsch, Ed., George Theime Verlag, 1974, Stuttgart. Separation of unwanted side products and purification of intermediates is achieved by chromatography on silica gel, employing flash chromatography (W. C. Still, M. Kahn and A. Mitra, J. Org. Chem. 43 2923 1978), by crystallization, or by trituration.

Transformation of 3 into intermediates of formula 4 can be carried out by removal of the protecting group P as described above. Coupling of intermediates of formula 4 to amino acids of formula 5 can be effected as described above to give intermediates of formula 6. Deprotection of the amine 6 gives compounds of formula 7.

SCHEME 2

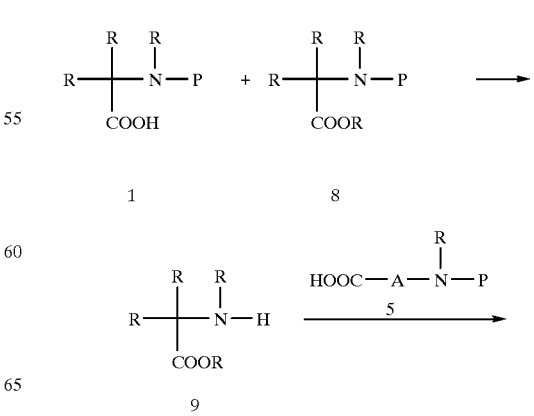

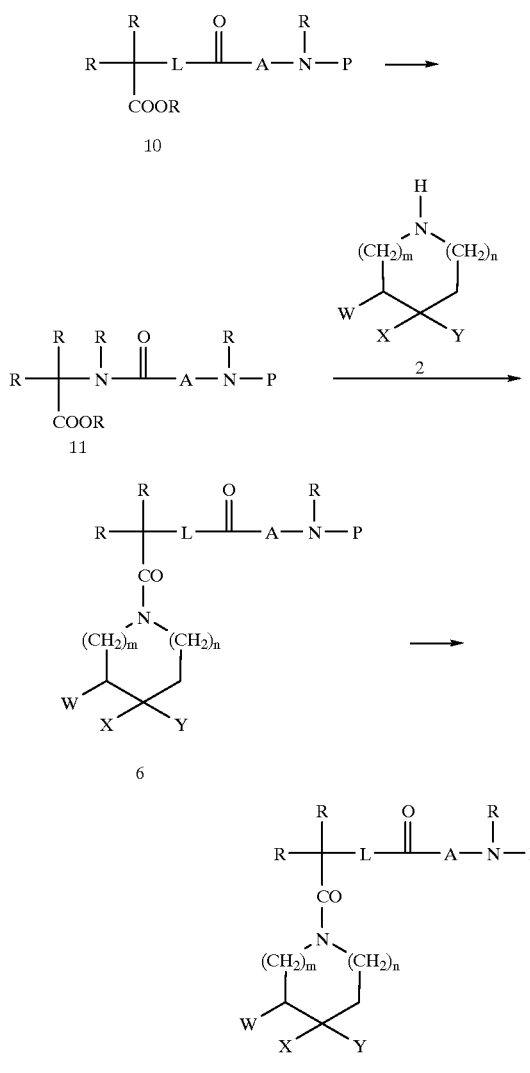

SCHEME 3

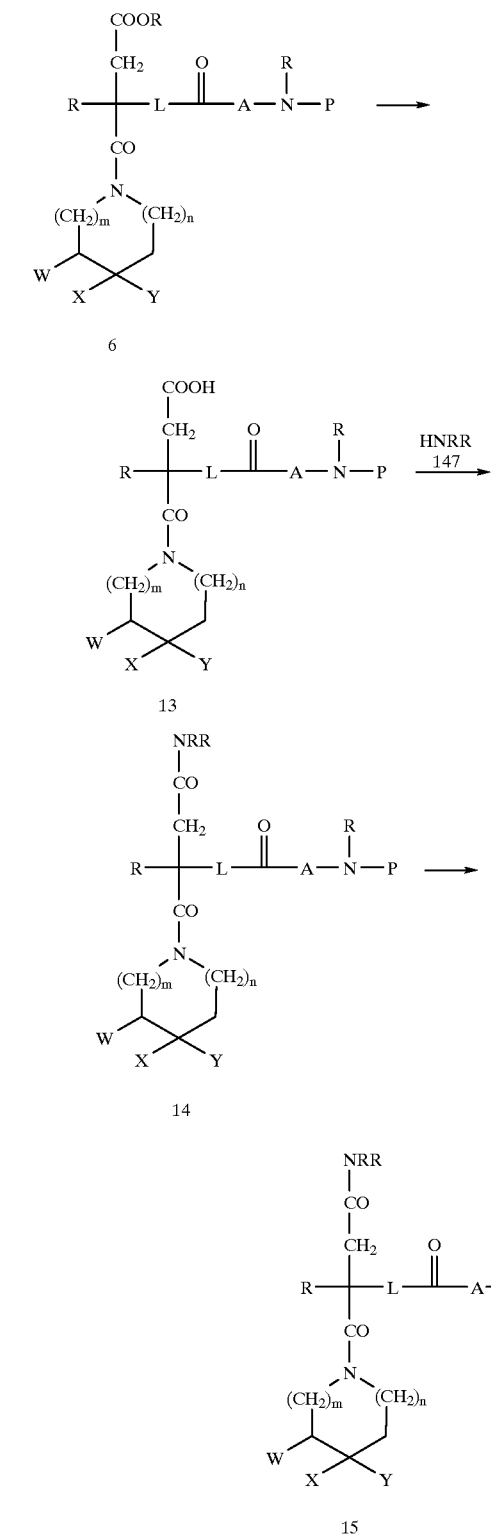

Alternatively, compounds of formula 7 can be prepared by a convergent route as shown in Scheme 2. Intermediate esters of formula 8 can be prepared by treating amino acids 1, where P is a suitable protecting group, with a base such as potassium carbonate followed by an alkyl halide such as iodomethane in a suitable solvent such as DMF. Deprotection of the amine transforms 8 into 9. Alternatively, many amino acids of formula 9 are commercially available.

Intermediate 10 is generated by coupling 9 to amino acid 5. The ester of intermediate 10 can be converted to intermediate acid 11 by a number of methods known in the art; for example, methyl and ethyl esters can be hydrolyzed with lithium hydroxide in a protic solvent such as aqueous methanol or aqueous THF at a temperature of about −20 to 120° C., preferably about 20 to 70° C. In addition, removal of a benzyl group can be accomplished by a number of reductive methods including hydrogenation in the presence of platinum or palladium catalyst in a protic solvent such as methanol. Acid 11 can then be coupled to amine 2 to give intermediates of formula 6. Transformation of 6 to 7 can be achieved by removal of the protecting group P.

Compounds of formula 6 where R=CH$_2$COOR, can be converted to intermediate acids of formula 13 by any of the methods outlined in Scheme 2. Coupling the acid 13 to amine 147 generates the intermediates of formula 14 as illustrated in Scheme 3. Transformation of 14 to 15 can be achieved by removal of the protecting group P.

SCHEME 4

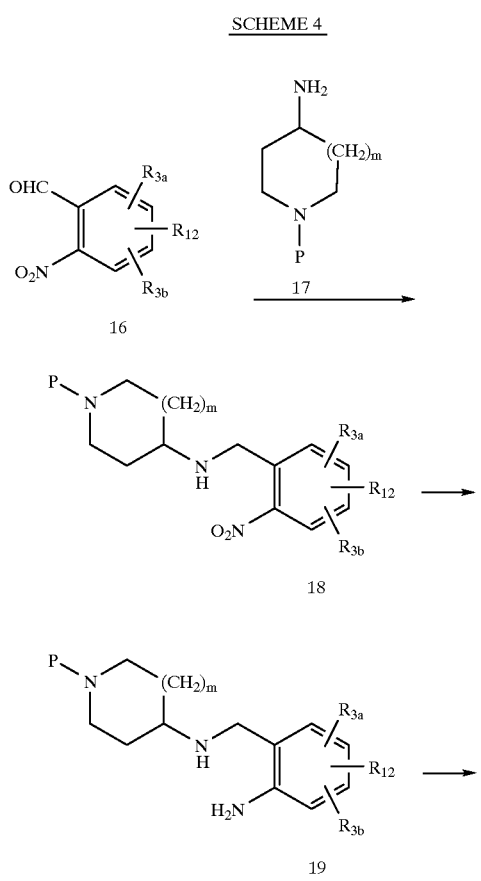

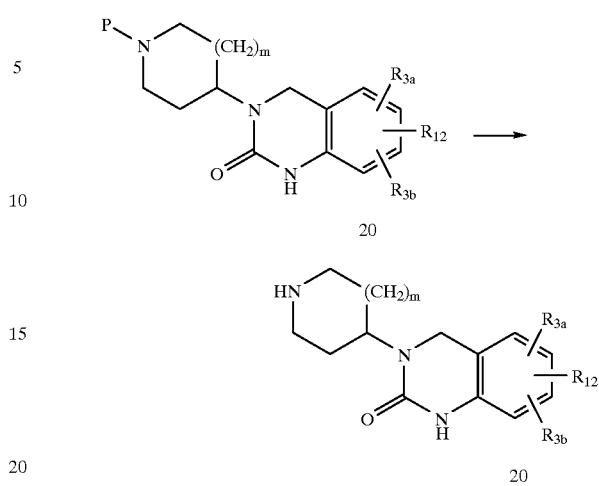

As shown in Scheme 4, compounds of formula 18 can be prepared by treating 2-nitrobenzaldehydes of formula 16 with amines of formula 17 in the presence of a suitable reducing agent which include alkali metal borohydrides and cyanoborohydrides. The preferred reducing agent is sodium cyanoborohydride. Sodium borohydride and sodium triacetoxyborohydride may also be used. For a general review of reductive aminations see R. F. Borch, Aldrichimica Acta, 8, 3–10 (1975). The nitro group of compound 18 can be reduced by a number of methods including hydrogenation with a catalyst such as palladium in a protic solvent such as methanol to give compounds of formula 19. Cyclization of the diamine with N,N'-carbonyldiimidazole (CDI) or other phosgene equivalents generates compounds of formula 20. Removal of the protecting group transforms 20 into 12.

SCHEME 5

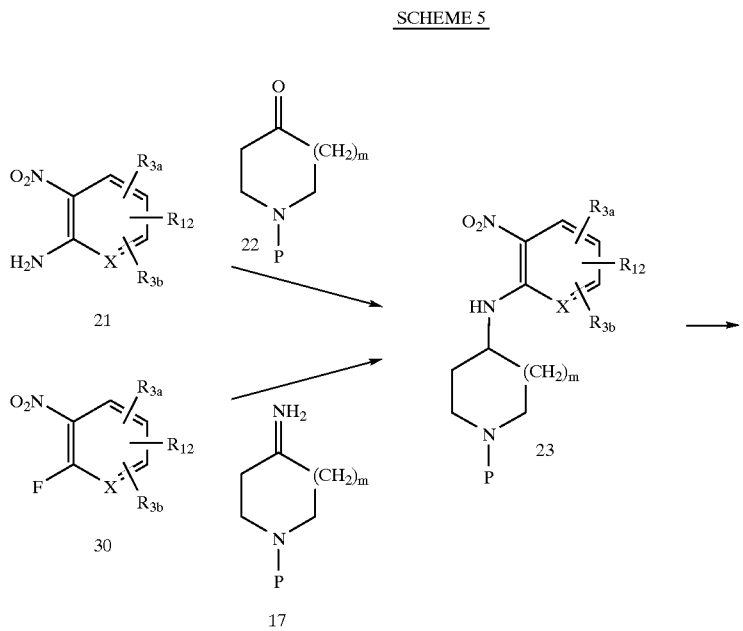

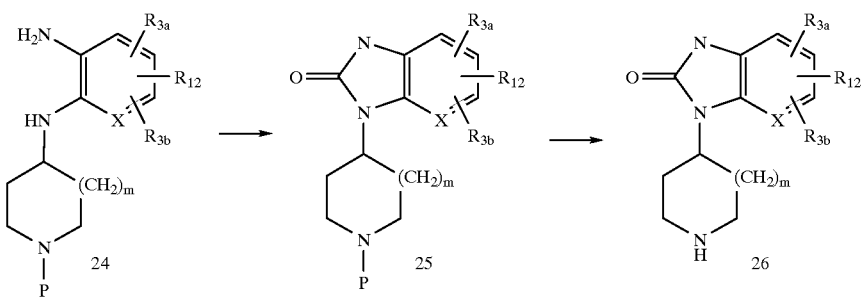

As shown in Scheme 5, compounds of formula 23 can be prepared by treating 2-nitroanilines of formula 21, where X=N or C, with N-protected piperidones of formula 22 in the presence of a hydride reducing agent such as sodium borohydride. Alternatively intermediates of formula 23 can be prepared by heating a protected 4-aminopiperidine 17 and a compound of formula 30, where X=N or C, in a solvent such as ethanol or DMF in the presence of an acid acceptor such as triethylamine or potassium carbonate. The nitro group of formula 23 can be reduced by a number of methods including hydrogenation with a catalyst such as palladium in a solvent such as methanolic HCl to give compounds of formula 24. Cyclization with CDI or other phosgene equivalents produces the benzimidazolinones of formula 25. Transformation of 25 into 26 can be achieved by removal of the protecting group P.

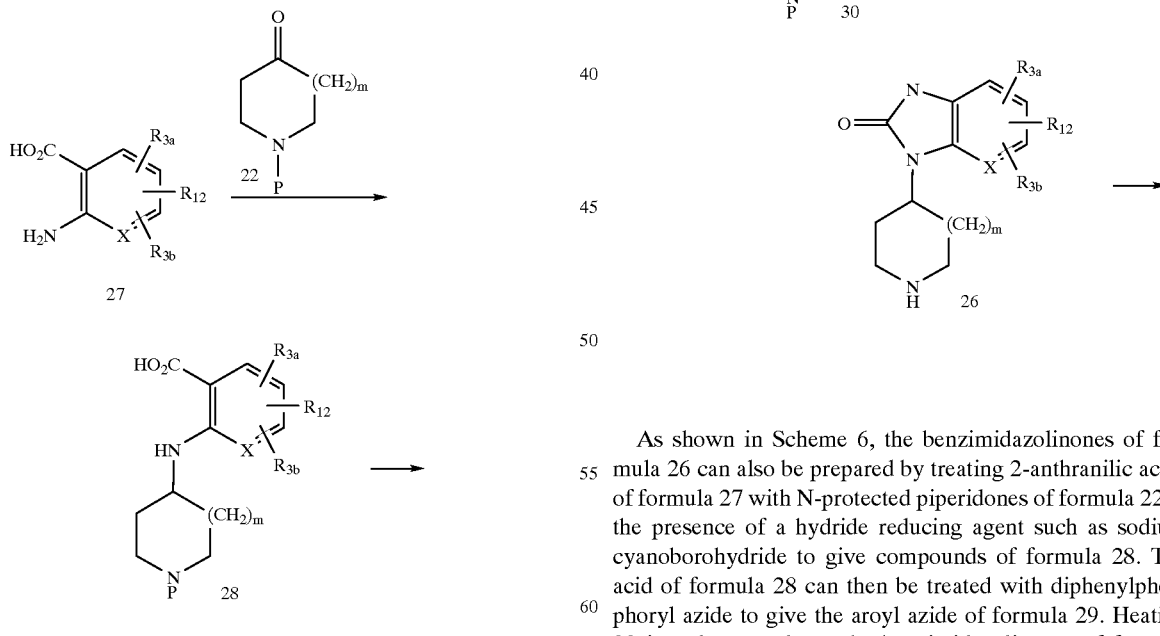

SCHEME 6

As shown in Scheme 6, the benzimidazolinones of formula 26 can also be prepared by treating 2-anthranilic acids of formula 27 with N-protected piperidones of formula 22 in the presence of a hydride reducing agent such as sodium cyanoborohydride to give compounds of formula 28. The acid of formula 28 can then be treated with diphenylphosphoryl azide to give the aroyl azide of formula 29. Heating 29 in xylene produces the benzimidazolinones of formula 30. Transformation of 30 into 26 can be achieved by removal of the protecting group P.

SCHEME 7

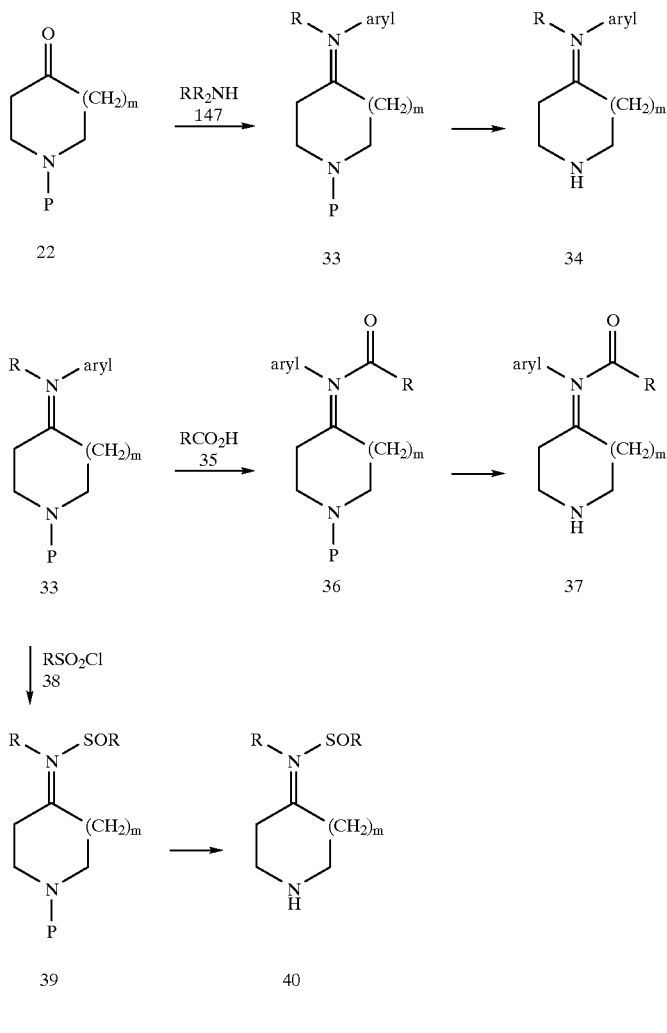

Compounds of formula 33 can be prepared by treating a 4-piperidone of formula 22, where P is a protecting group such as benzyl, with a primary ($R_2$=H) or secondary amine of formula 147 in the presence of a hydride reducing agent such as sodium cyanoborohydride as shown in Scheme 7. Compounds of formula 33 can either be deprotected by conventional means to give compounds of formula 34, or in the case where $R_{2a}$=H, the amine can be coupled to a carboxylic acid of formula 35 using a coupling agent such as EDC in the presence of HOBT in an inert solvent such as dichloromethane to give compounds of formula 36. Subsequent removal of the protecting group generates compounds of formula 37. Alternatively, 33 can be treated with an aryl or alkyl sulfonyl chloride 38 in the presence of an acid scavenger to generate the sulfonamide 39. Transformation of 39 into 40 proceeds by removal of the protecting group.

SCHEME 8

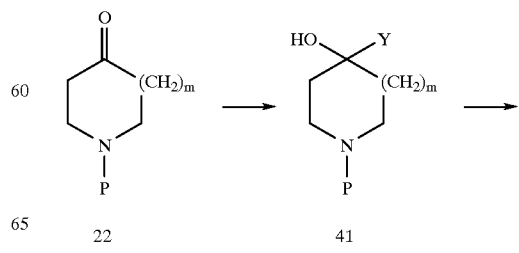

-continued

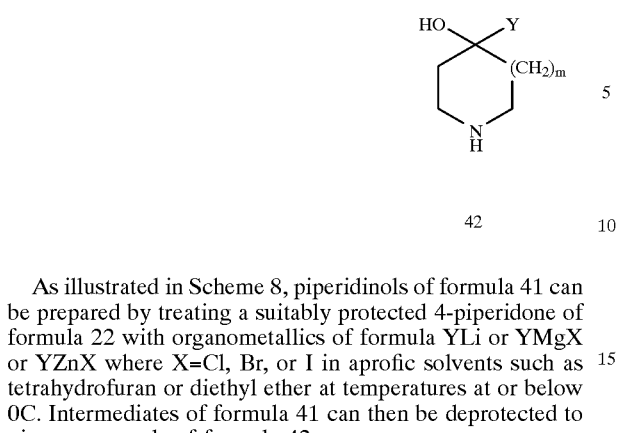

As illustrated in Scheme 8, piperidinols of formula 41 can be prepared by treating a suitably protected 4-piperidone of formula 22 with organometallics of formula YLi or YMgX or YZnX where X=Cl, Br, or I in aprofic solvents such as tetrahydrofuran or diethyl ether at temperatures at or below 0C. Intermediates of formula 41 can then be deprotected to give compounds of formula 42.

SCHEME 9

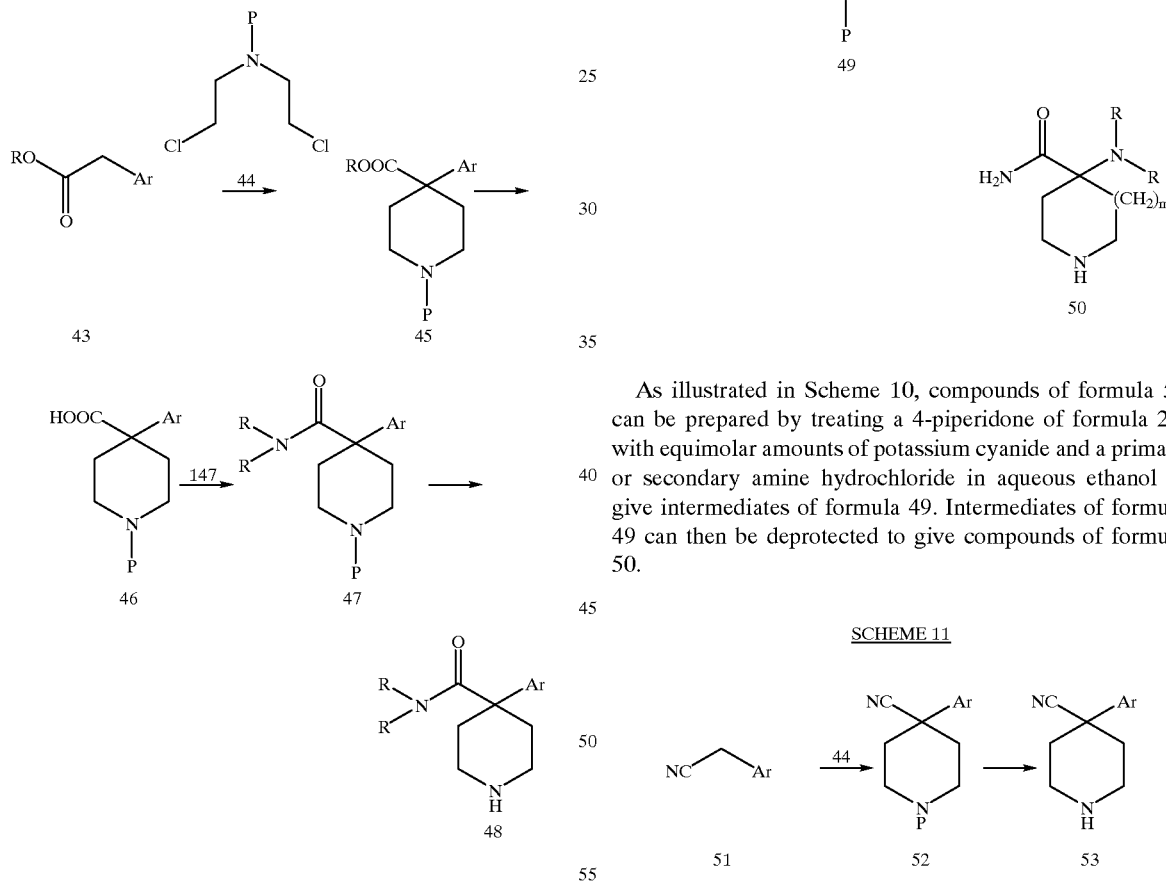

Treating a methyl arylacetate 43 and a protected bis (chloroethyl)amine 44 (Bercz and Ice; J. Pharm. Sci. 1972 61 pp 1316–1317) with two equivalents of a base such as lithium diisopropylamide in a solvent such as THF generates the piperidine ester 45 as shown in Scheme 9. The ester can then be hydrolyzed under mild basic conditions to give intermediates of formula 46. The resulting acid can then be coupled to amines of formula 147 to give 4,4'disubstituted piperidines of formula 47. Deprotection of the amine generates compounds of formula 48.

As illustrated in Scheme 10, compounds of formula 50 can be prepared by treating a 4-piperidone of formula 22, with equimolar amounts of potassium cyanide and a primary or secondary amine hydrochloride in aqueous ethanol to give intermediates of formula 49. Intermediates of formula 49 can then be deprotected to give compounds of formula 50.

Treating an aryl nitrile of formula 51 with intermediate 44 with two equivalents of a base such as sodium amide in a suitable solvent such as DMSO generates the 4,4'disubstituted piperidines of formula 52. Subsequent deprotection of the piperidine amine gives rise to compounds of formula 53 as shown in Scheme 11.

SCHEME 12

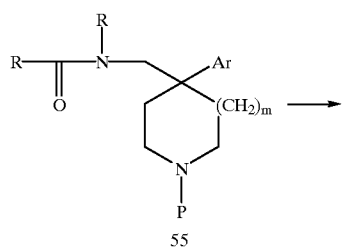
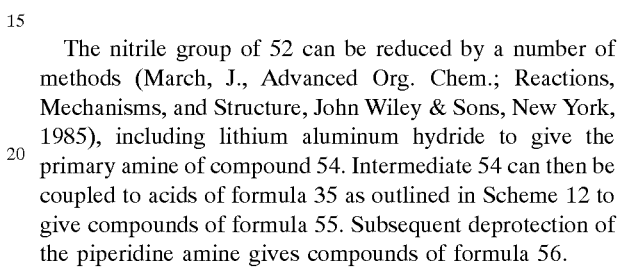
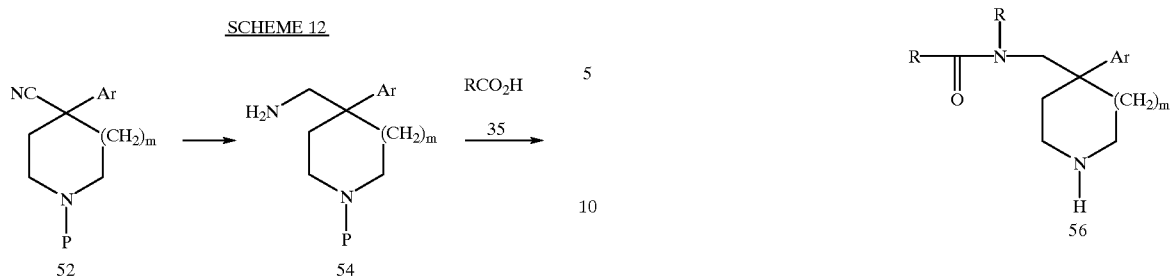

The nitrile group of 52 can be reduced by a number of methods (March, J., Advanced Org. Chem.; Reactions, Mechanisms, and Structure, John Wiley & Sons, New York, 1985), including lithium aluminum hydride to give the primary amine of compound 54. Intermediate 54 can then be coupled to acids of formula 35 as outlined in Scheme 12 to give compounds of formula 55. Subsequent deprotection of the piperidine amine gives compounds of formula 56.

SCHEME 13

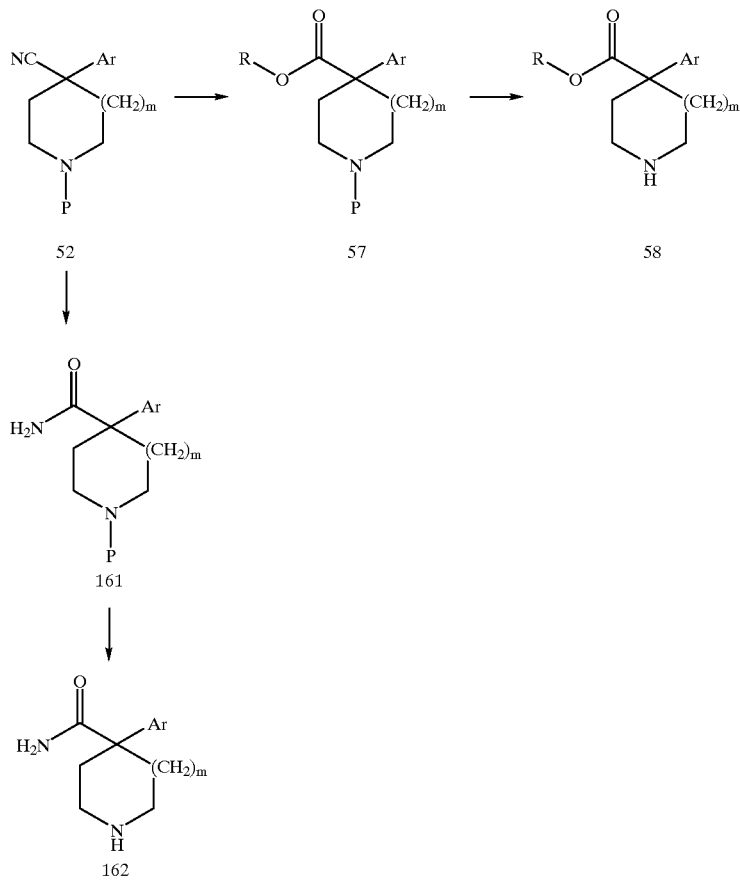

The nitrile 52 can also be converted to an ester as described in Scheme 13 by heating intermediate 52 with concentrated sulfuric acid and a small amount of water to temperatures around 150° C., followed by heating the mixture in an alcohol solvent to temperatures around 125° C. Deprotection of the piperidine amine 57 generates compounds of formula 58. Alternatively, the nitrile can be hydrolyzed to the amide 161 using a number of methods known in the literature (March, J., Advanced Org. Chem.; Reactions, Mechanisms, and Structure, p. 788, John Wiley & Sons, New York, 1985); for example, heating the amide in concentrated sulfuric acid to temperatures around 100–150° C. will convert the nitrile to the amide as will treating the nitrile with hydrogen peroxide and sodium hydroxide in aqueous acetone. Transformation of 161 to 162 proceeds by removal of the protecting group.

SCHEME 14

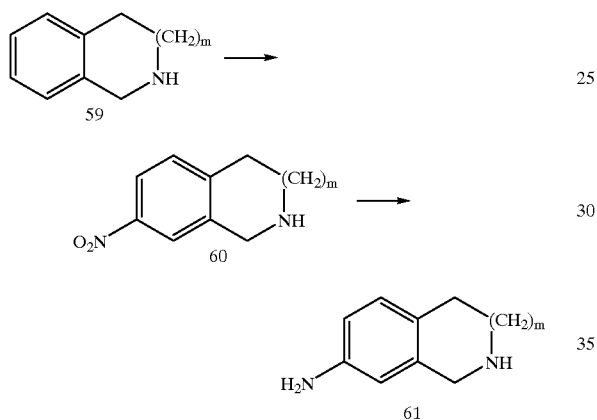

Many 1,2,3,4-tetrahydroisoquinolines and substituted 1,2, 3,4-tetrahydroisoquinolines can be prepared by methods described in the literature (R. Adams, Org. Reactions vol. VI; pp 74–206, John Wiley & Sons, New York, N.Y. 1964). As illustrated in Scheme 14, treating an amine of formula 59, such as 1,2,3,4-tetrahydroisoquinoline, with potassium nitrate in concentrated sulfuric acid at temperatures below 5° C. generates the nitro amine of formula 60. Reduction of the nitro functionality to the corresponding amine using iron powder and ammonium chloride in refluxing aqueous ethanol is one of many suitable literature procedures (see March, J., p. 1103–4, Advanced Org. Chem.; Reactions, Mechanisms, and Structure, John Wiley & Sons, New York, 1985) for carrying out this transformation to generate compounds of formula 61.

SCHEME 15

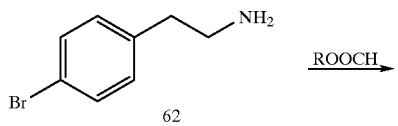

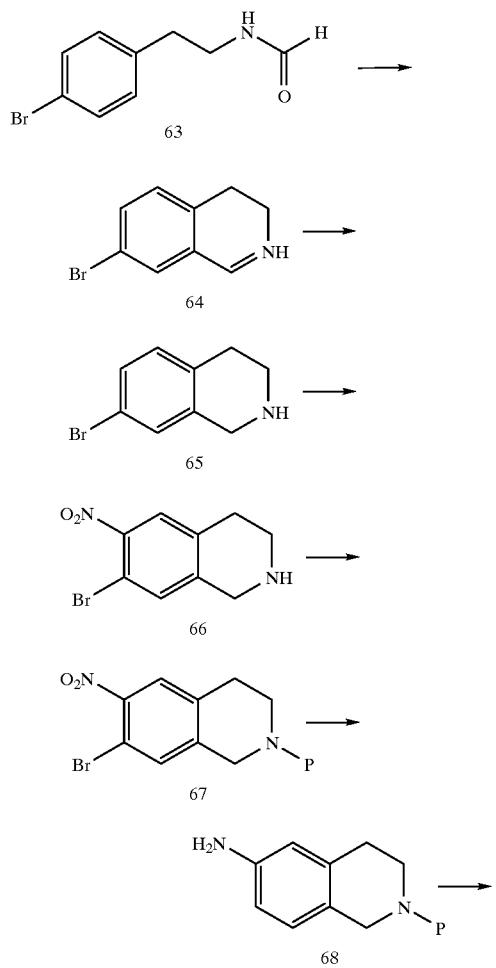

As described in Scheme 15, the β-phenethylamide of compound 63 can be prepared by treating 4-bromophenethylamine, 62, with ethyl formate. Treating intermediate 63 with polyphosphoric acid and phosphorous pentoxide in a Bischler-Napieralski cyclodehydration produces the 7-bromo-3,4-dihydroisoquinoline 64. Sodium borohydride reduction of the hydrochloride salt of compound 64 in water produces the 7-bromo-1,2,3,4-tetrahydroisoquinoline 65. Following the method outlined in Scheme 14, nitration of 7-bromo-1,2,3,4-tetrahydroisoquinoline generates intermediate 66. Protection of the tetrahydroisoquinoline amine 66 with a suitable protecting group P, such as tert-butoxycarbonyl, can be achieved by methods known to those skilled in the art and produces intermediates of formula 67. Reduction of the nitro group and dehalogenation can be accomplished by hydrogenation using a catalyst such as palladium in a solvent such as acetic acid with ammonium acetate as a buffer and gives compounds of formula 68.

SCHEME 16

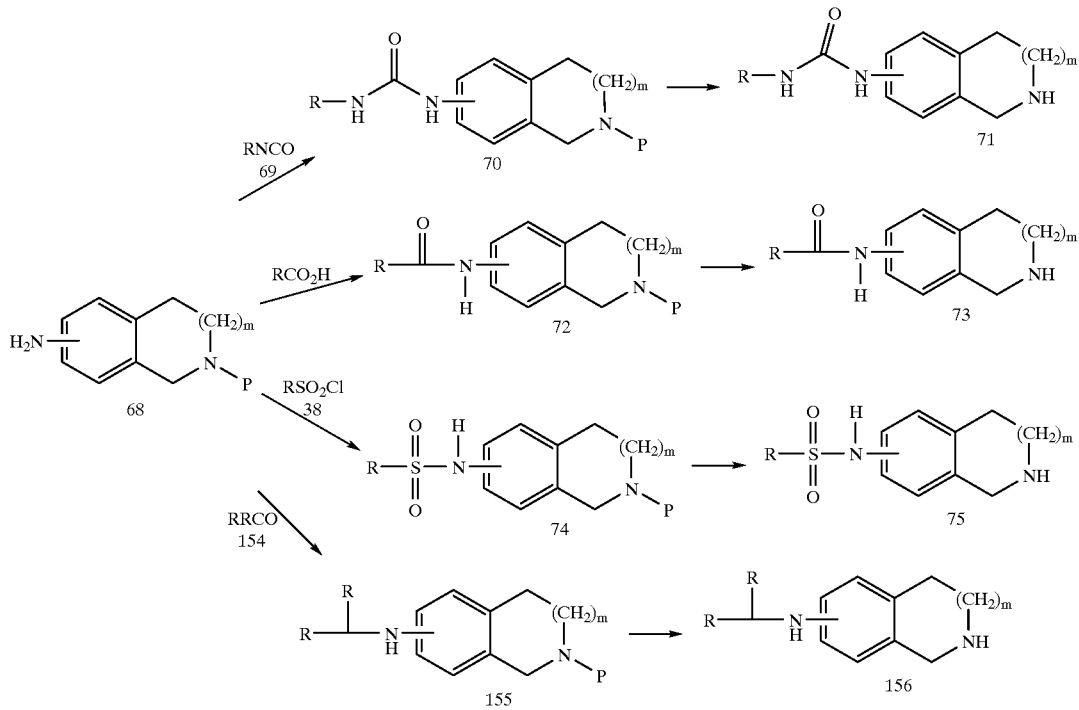

Treating the amines of formula 68 with an isocyanate of formula 69 gives the urea of formula 70 as illustrated in Scheme 16. Alternatively the amine 68 can be functionalized with an acid chloride or acid to give the amide of formula 72, a sulfonyl chloride of formula 38 to give the sulfonamide 74, or a ketone of formula 154 and a reducing agent to give the amine of formula 155. The resulting amines can be deprotected to give intermediates 71, 73, 75 and 156 respectively.

SCHEME 17

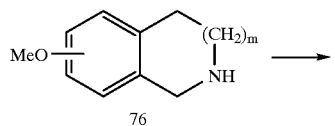

-continued

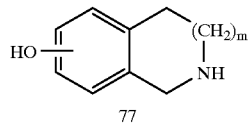

The synthesis of 6-, 7-, and 8-methoxy substituted 1,2,3,4-tetrahydroisoquinolines is described by Sall and Grunewald in J. Med. Chem. 30, 1987 pp 2208–2216. The methoxy group can be removed by a number of methods; for example, refluxing compounds of formula 76 with 48% HBr generates compounds of formula 77 as shown in Scheme 17.

SCHEME 18

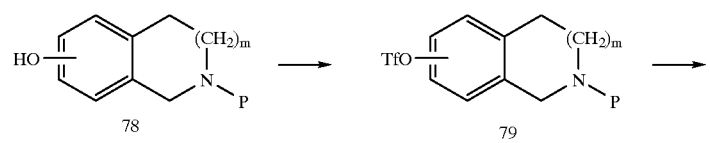

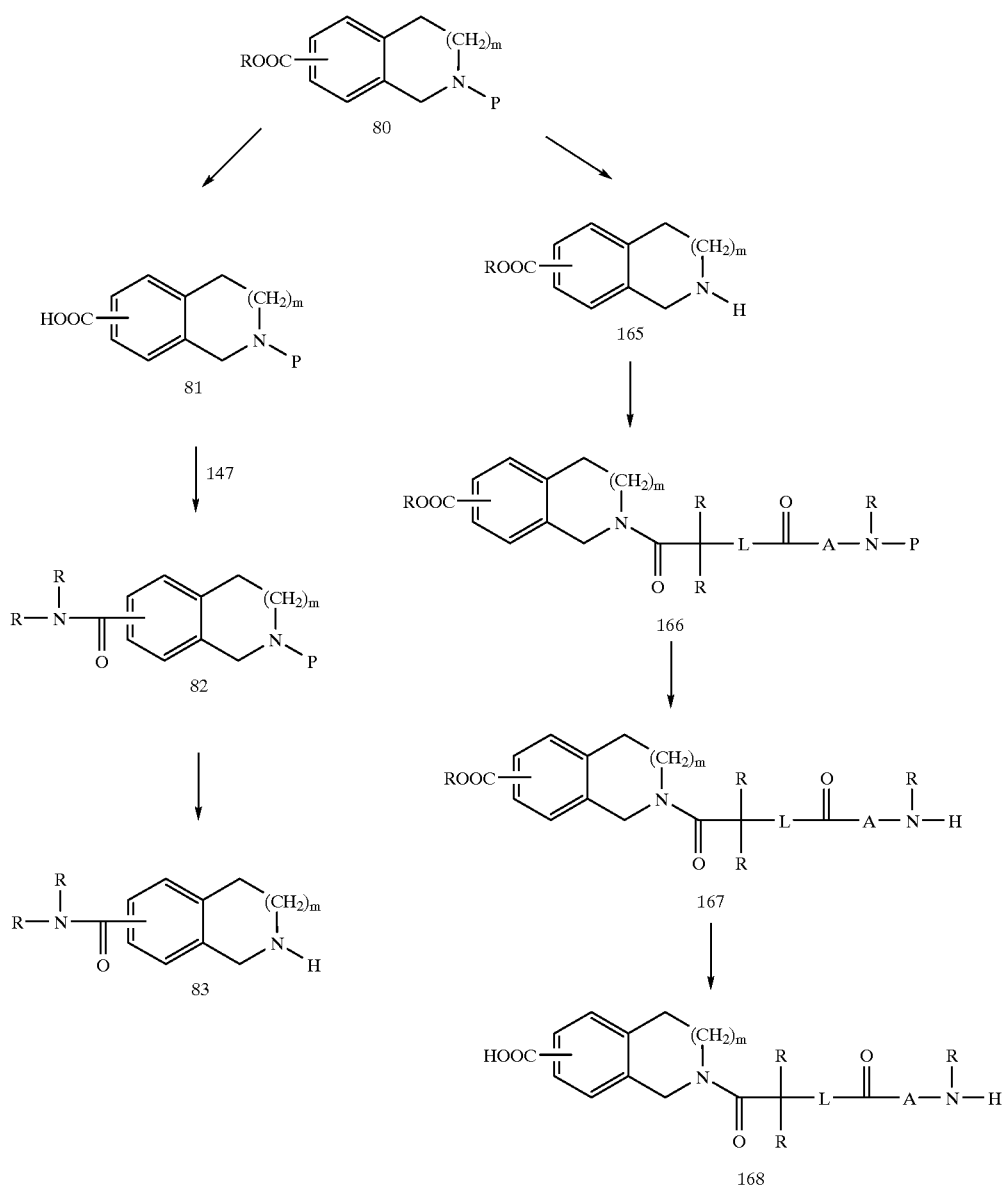

Treating compound of formula 78, where P is a suitable protecting group, with pyridine and triflic anhydride in a suitable solvent such as dichloromethane generates the triflate of formula 79 as shown in Scheme 18. The triflate can then be carbonylated with carbon monoxide and a catalyst such as palladium acetate in the presence of a base such as triethylamine and a ligand such as 1,3-bis (diphenylphosphine)propane in an alcohol solvent such as methanol to generate the ester of formula 80. The ester can then be hydrolyzed by a number of different methods to give the acid of formula 81. The acid can then be coupled to amines of formula 147 to give compounds of formula 82. Subsequent deprotection of the amine generates compounds of formula 83. Alternatively, compound of formula 80 can be deprotected to give intermediate 165. The amine can then be coupled to acids of formula 11 to give compounds of formula 166. Subsequent deprotection of the amine generates intermediate 167. Hydrolysis of the ester transforms 167 into 168.

SCHEME 19

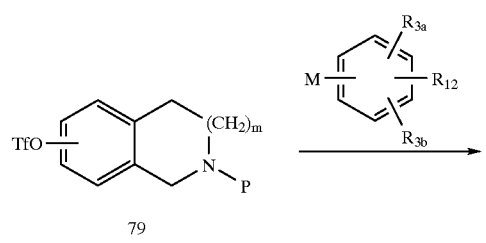

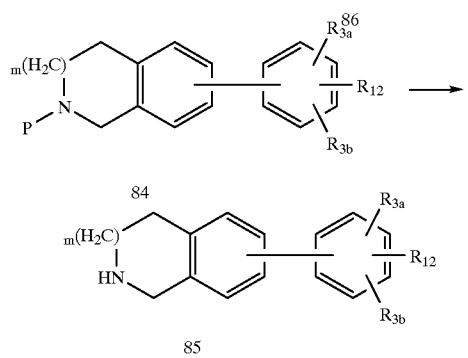

Alternatively, as shown in Scheme 19, the triflate of formula 79 can undergo a biaryl cross-coupling reaction with a suitable nucleophile such as an arylboronic acid or aryl zincate 86 (where M=metal) in the presence of a catalyst such as tetrakis (triphenylphosphine) palladium(0) and potassium carbonate in toluene and aqueous ethanol to give the intermediate of formula 84. Deprotection of the isoquinoline amine transforms 84 to 85.

SCHEME 20

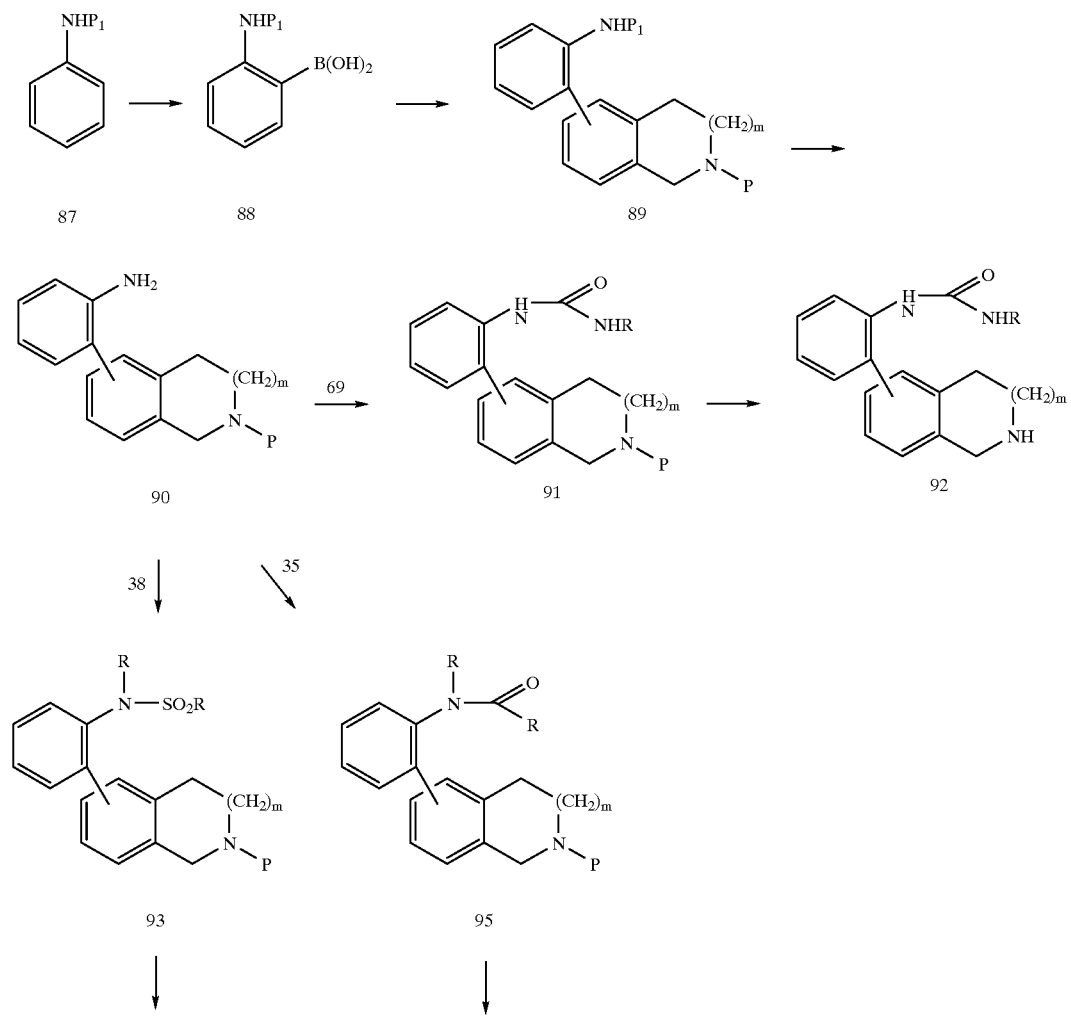

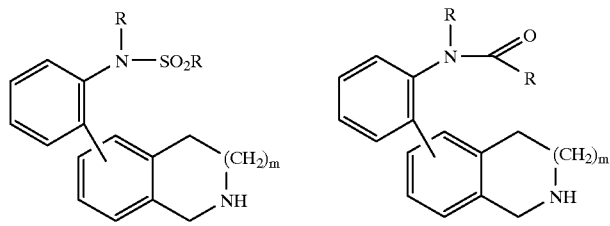

As shown in Scheme 20, the boronic acid of formula 88 can be prepared by treating a suitably protected aniline 87 with t-butyllithium and trimethylborate at temperatures near −78° C. Intermediate 88 can then be coupled to triflate 79 using conditions defined in Scheme 19 to give 89. The aniline protecting group can then be selectively removed, and the resulting amine 90 treated with an isocyanate 69 and a suitable base to give the urea of formula 91. Deprotection of the amine transforms 91 to 92. Alternatively, the amine of formula 90 can also be sulfonylated with a sulfonyl chloride in the presence of an acid scavenger to give compounds of formula 93. Deprotection of the amine transforms 93 to 94. Acylation of 90 with a carboxylic acid 35 using a coupling agent such as EDC in the presence of HOBT in an inert solvent such as DMF gives the compound of formula 95. Deprotection of the amine transforms 95 to 96.

SCHEME 21

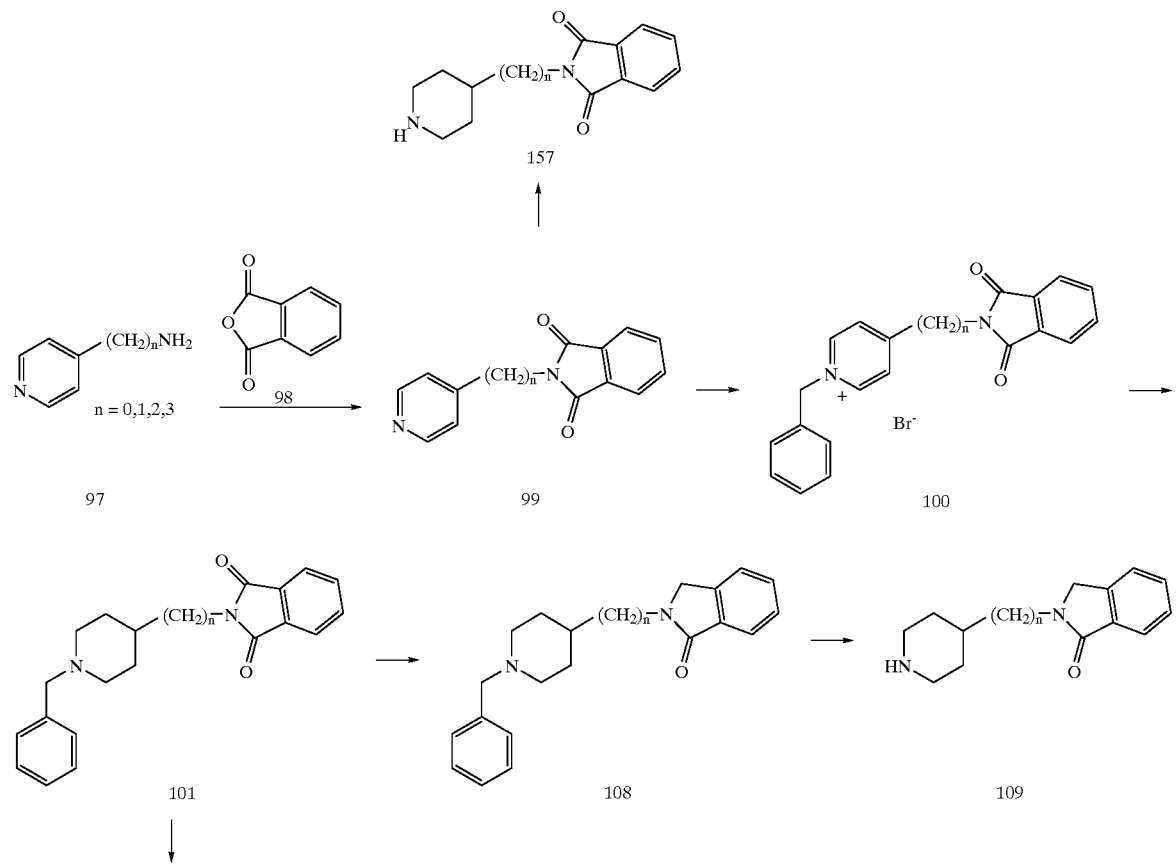

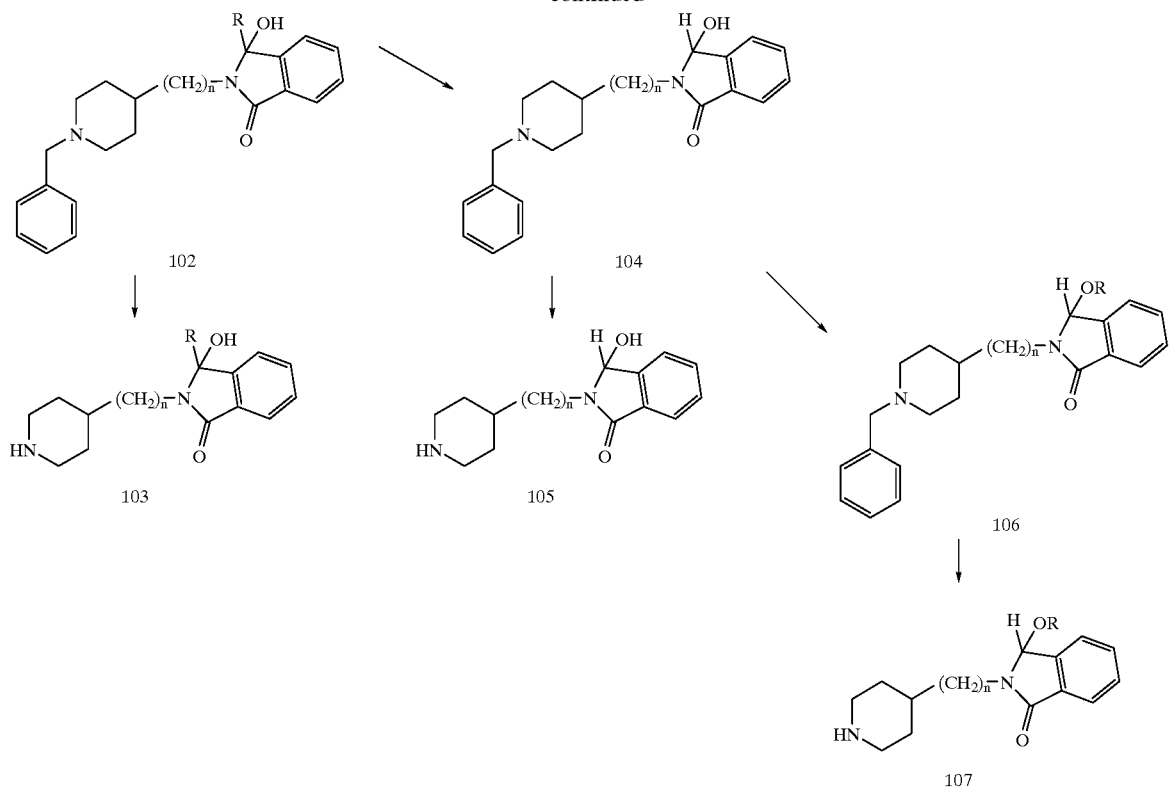

As illustrated in Scheme 21, phthalimides of formula 99 can be prepared from 4-aminopyridines 97 and phthalic anhydride 98 as described by Ciganek et al. U.S. Pat. application Ser. No. 92/876,542. The pyridine ring of 99 can be reduced by a number of methods including hydrogenation in the presence of a platinum catalyst in a solvent such as methanolic HCl to give the piperidine ring of formula 157. Alternatively, quaternization of the pyridine ring with benzyl bromide in ethanol leads to the quaternary salt 100. The pyridine ring can then be reduced by a number of methods including hydrogenation in the presence of a platinum catalyst in glacial acetic acid or methanol to give 101. Many other anhydrides are commercially available and one skilled in the art can apply such chemistry to these compounds.

Addition of organometallics such as RLi or RMgX where X=Cl, Br, or I to compounds of formula 101 followed by hydrolysis produces compounds of formula 102. Deprotection of the piperidine amine transforms 102 to 103.

Compounds of formula 101 can be converted to compounds of formula 104 with hydride reducing agents such as sodium borohydride in methanol, or lithium borohydride in an aprotic solvent such as THF. Phthalimides may also be reduced to compounds of type 104 with zinc in acetic acid. Deprotection of the piperidine ring transforms 104 to 105.

Compounds of formula 104 can be treated with a base such as sodium hydride in appropriate solvents such as tetrahydrofuran, or metal alkoxides such as sodium methoxide in alcohol solvents such as methanol, followed by addition of an alkylating agent to give compounds of formula 106. Alternatively, such compounds can be prepared by treating compounds of formula 104 with an alcohol in the presence of an acid such as hydrochloric or methanesulfonic at temperatures of about 0–100° C. Deprotection of the piperidine ring transforms 106 into 107.

Treating compounds of formula 101 or 104 with zinc in acetic acid or tin in acetic acid in the presence of hydrochloric acid generates intermediates of formula 108. Deprotection of the amine transforms 108 to 109.

SCHEME 22

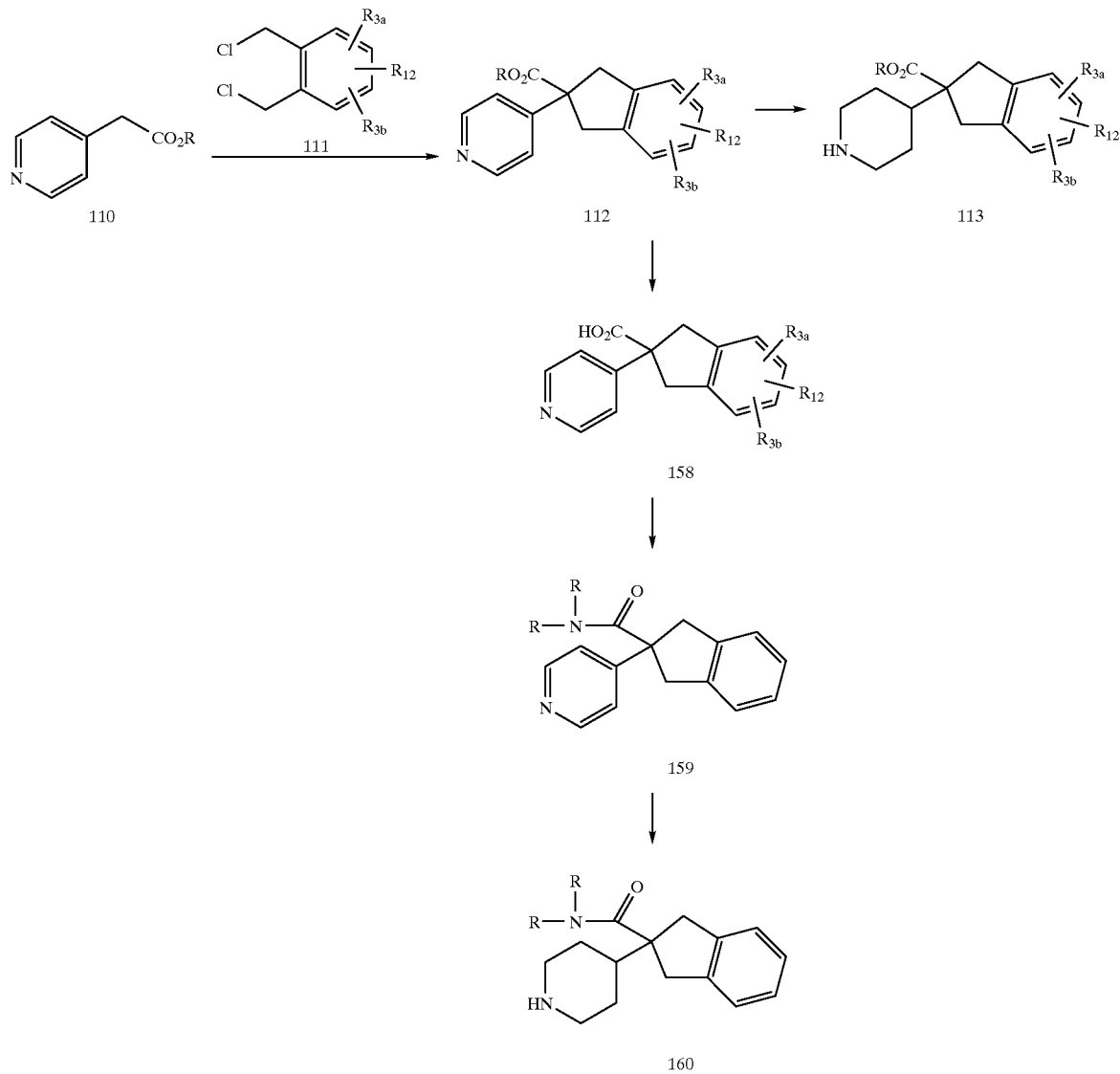

Treating 110 with one equivalent of a base such as potassium tert-butoxide in a solvent such as THF, followed by addition of 111 and then by a second equivalent of base generates intermediate of formula 112 as illustrated in Scheme 22. Conversion of 112 to 113 can be accomplished by a number of methods, including hydrogenation with a catalyst such as palladium in a mixture of ethanol and aqueous HCl. Alternatively, the ester of 112 can be deprotected to give the intermediate acid 158. The acid 158 can be coupled to amine 147 to give the amide of formula 159. Conversion of 159 to 160 can be accomplished by a number of methods including hydrogenation with a catalyst such as platinum in methanolic HCl.

Scheme 23

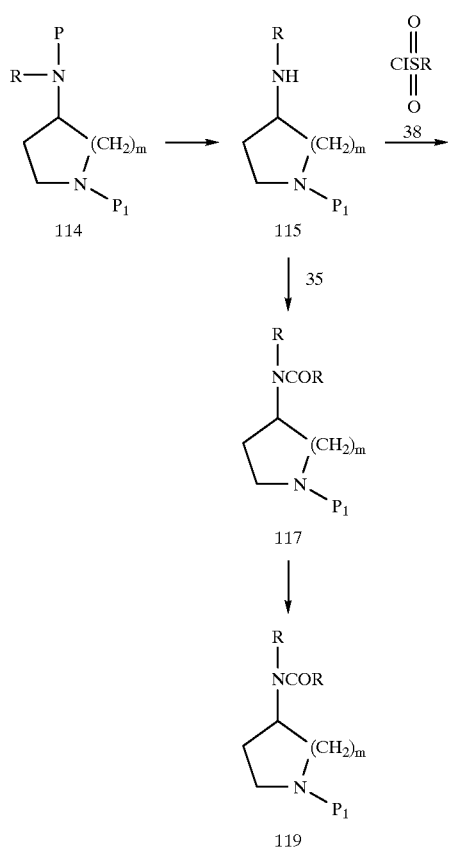

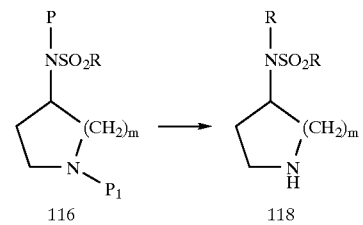

As illustrated in Scheme 23, a differentially protected 3-aminopyrrolidine of formula 114 is selectively deprotected at the 3-amino position to give intermediate 115. The amine can then be sulfonylated with a sulfonyl chloride 38 in the presence of an acid scavenger in a solvent such as dichloromethane to give 116. Alternatively, the amine can be coupled to acid 35 as above to give 117. Deprotection of the pyrrolidine nitrogen of 116 and 117 generates compounds of formula 118 and 119 respectively.

Scheme 25

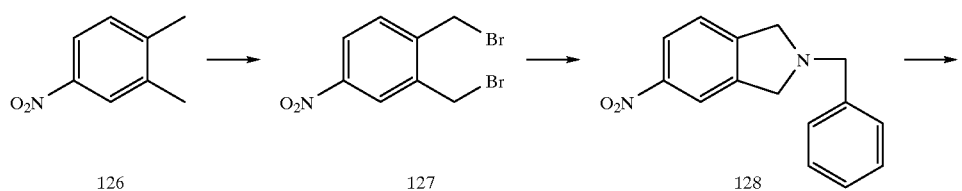

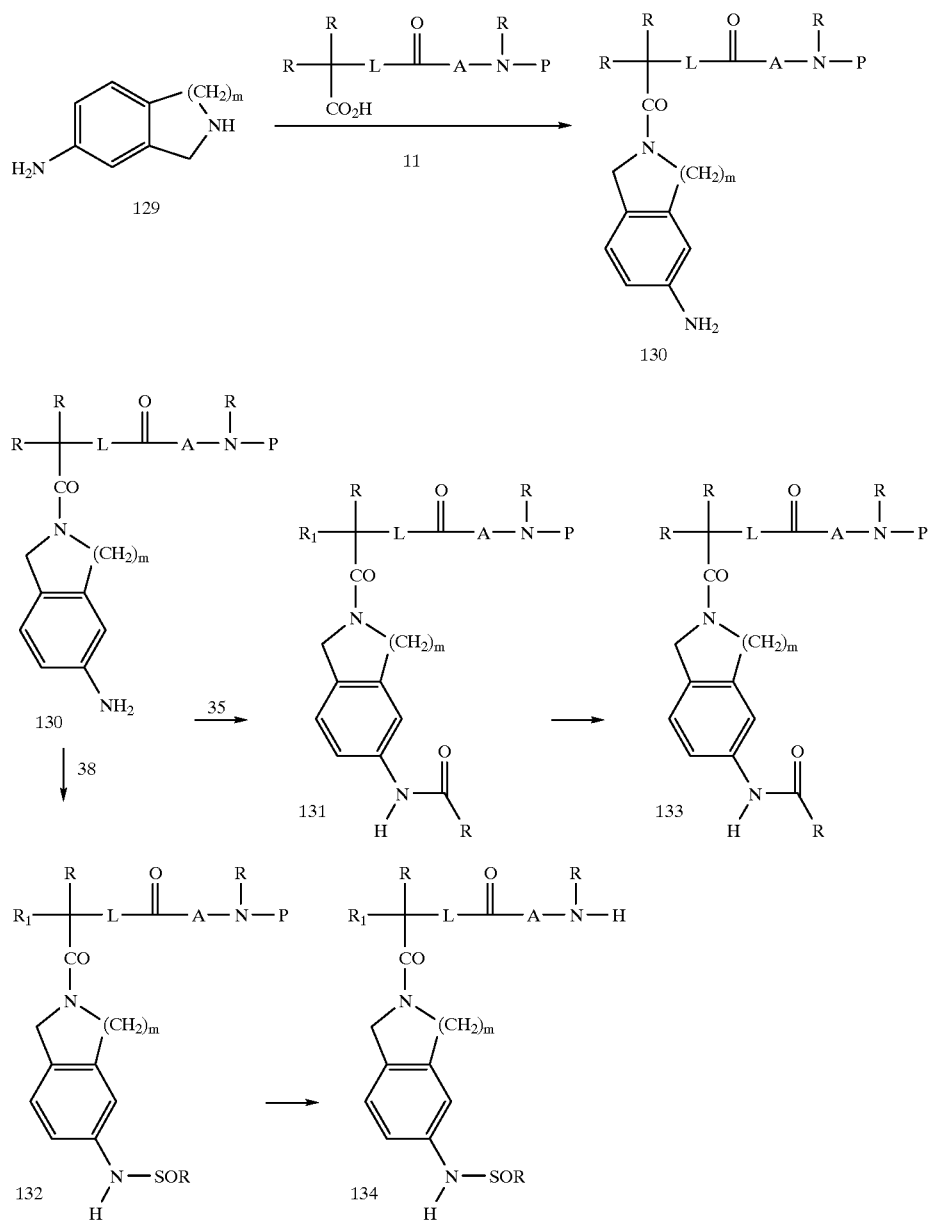

As shown in Scheme 25, isoindolines of formula 129 can be prepared from 126 by radical bromination using a suitable source of bromine radical such as N-bromosuccinimide and a suitable radical initiator such as AIBN (2,2'-azobis (isobutyronitrile) in an inert solvent such as carbon tetrachloride to produce intermediates 127. The dibromide can then be treated with a suitably protected primary amine such as benzylamine in aqueous acetone using a base such as sodium carbonate to give compounds of formula 128.

Deprotection of the amine and nitro reduction to give 129 can be accomplished by hydrogenation with hydrogen in a protic solvent such as ethanol using a catalyst such as palladium. The coupling of intermediate 129 to acid 11 gives 130. The free amine can then be acylated or sulfonylated by methods mentioned above to give 131 and 132. Transformation of 131 into 133 and 132 into 134 can be accomplished by removal of the protecting group P.

Scheme 26

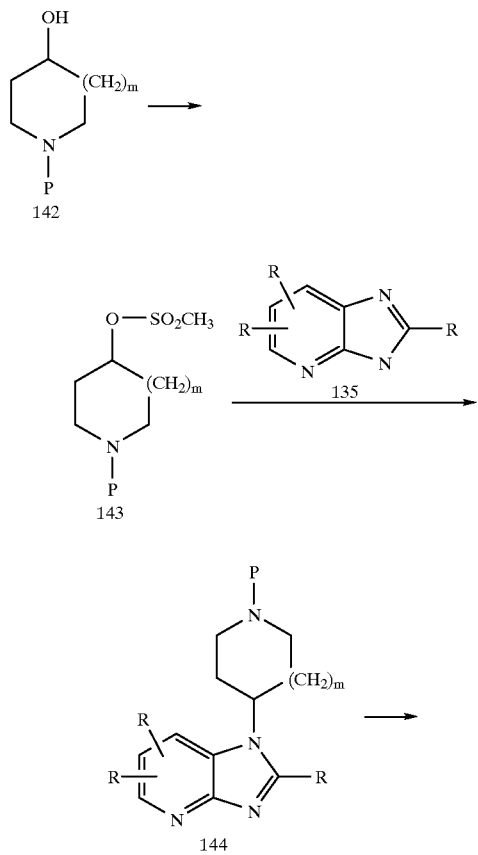

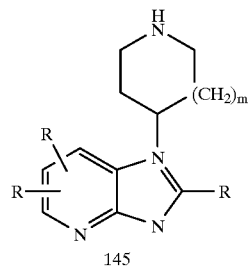

As shown in Scheme 26, an N-protected 4-hydroxypiperidine 142 can be treated with methanesulfonyl chloride in the presence of a base such as triethylamine in an inert solvent such as methylene chloride to give the intermediate mesylate of formula 143. The mesylate can then be displaced with an imidazo[4,5-b]pyridine of formula 135 (for example, see Carpino et al., Biorg. & Med. Chem. Lett. 1994 4, pp 93–98 and references cited within) using base such as sodium hydride in a solvent such as DMF or dioxane to give 44. Deprotection of the amine transforms 144 into 145.

Scheme 27

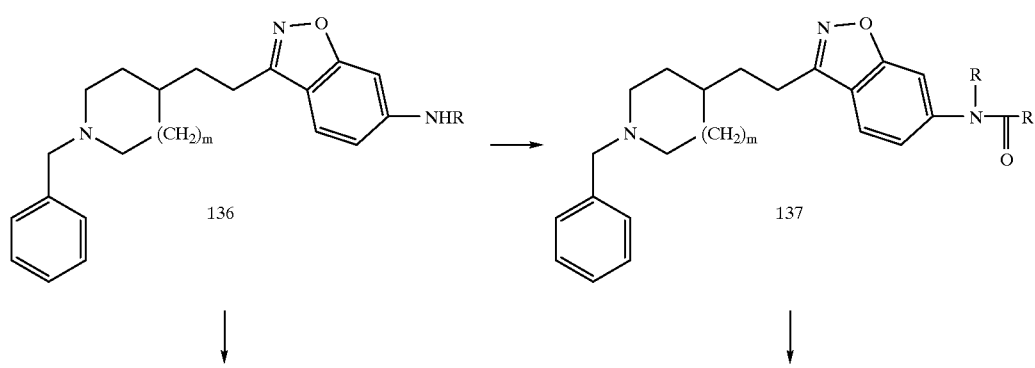

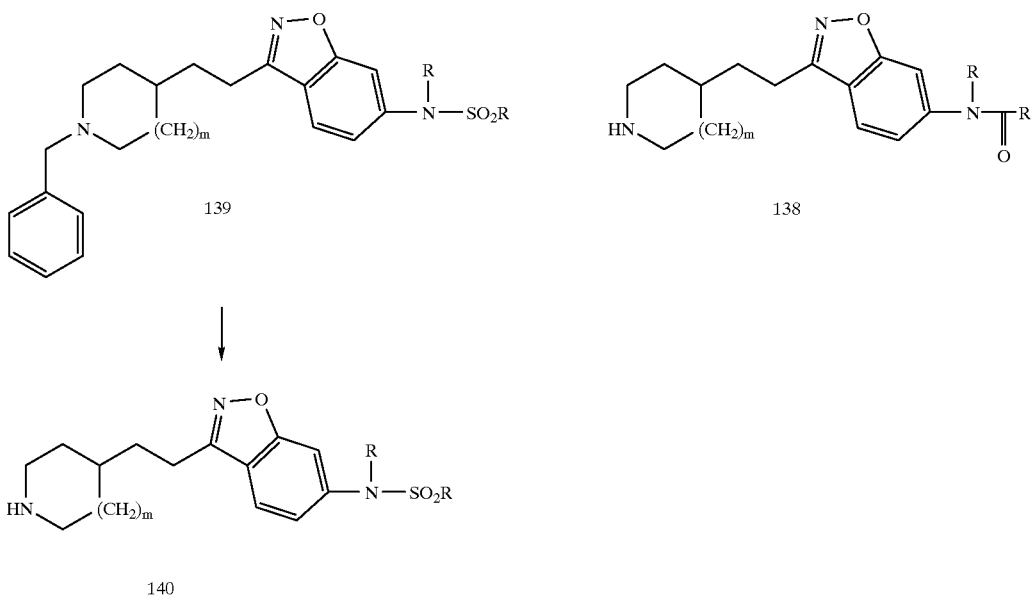

Benzisoxazoles of formula 136 can be prepared as described by Villabolos et al., J. Med. Chem. 1994 37 pp 2721–2724. The amine 136 can be coupled to acids of formula 35 as illustrated in Scheme 27 to give intermediates 137. Deprotection of the piperidine amine gives 138. Alternatively the amine 136 can be sulfonylated to give 139. Deprotection of the amine generates compounds of formula 140.

Esters of formula 146 can be prepared by treating an acid of formula 5 with hydroxysuccinimide in the presence of a coupling agent such as EDC in an inert solvent such as methylene chloride as illustrated in Scheme 28. Treating the ester with an amino acid of formula 1 in a solvent such as DMF in the presence of a base such as diisopropylethylamine produces 11.

Scheme 28

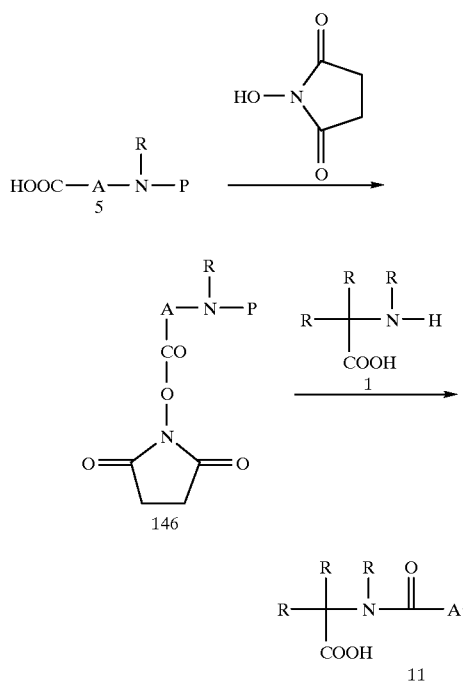

Scheme 29

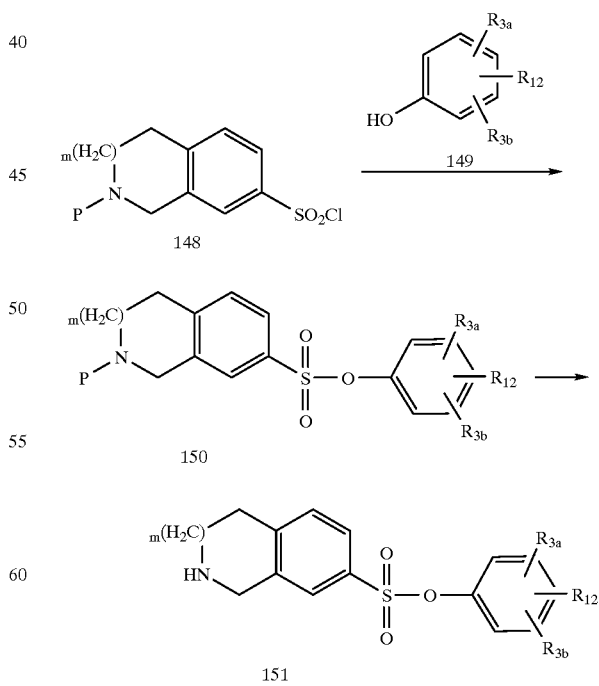

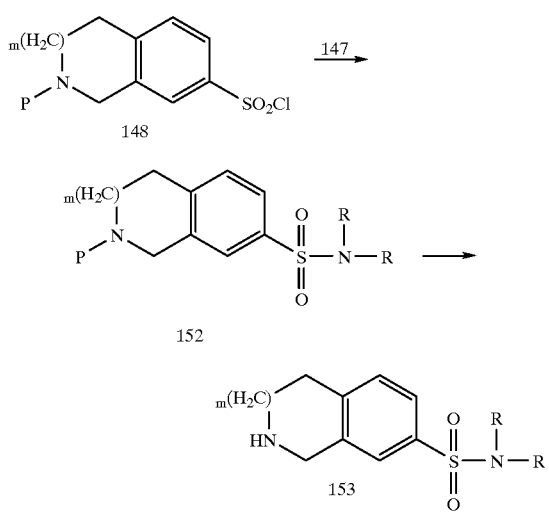

The preparation of compounds of formula 148 has been described by Blank et al., J. Med. Chem. 1980 23 pp 837–840. Treating the sulfonyl chloride 148 with a phenol of formula 149 and a base such as potassium carbonate in a polar solvent such as acetonitrile or acetone generates intermediates of formula 150. Deprotection of the amine transforms 150 into 151. Alternatively the sulfonyl chloride can be treated with an amine 147 in the presence of an acid scavenger such as triethylamine in an inert solvent such as dichloromethane to give the sulfonamide of formula 152. Deprotection of the tetrahydroisoquinoline amine transforms 152 into 153.

Scheme 30

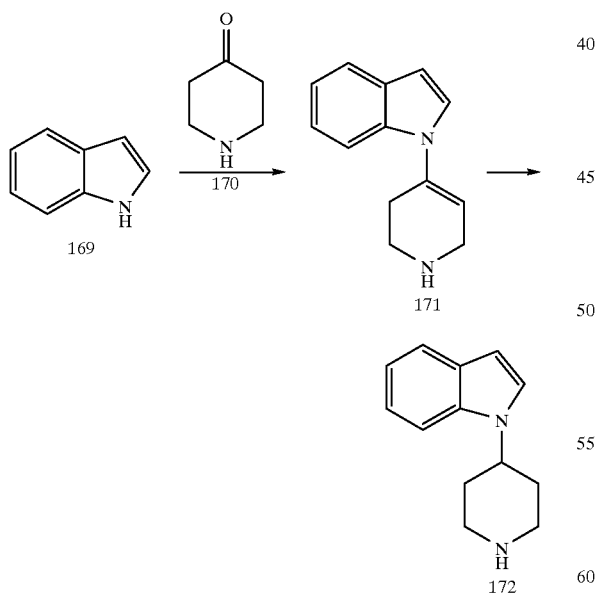

As illustrated in Scheme 30, treating an indole of formula 169 with a base such as methoxide ion in a solvent such as methanol, followed by addition of a ketone of formula 170 produces intermediates of formula 171. Conversion of 171 to 172 can be accomplished by a number of reductive methods including hydrogenation in the presence of a protic solvent such as ethanol using a catalyst such as palladium.

Scheme 31

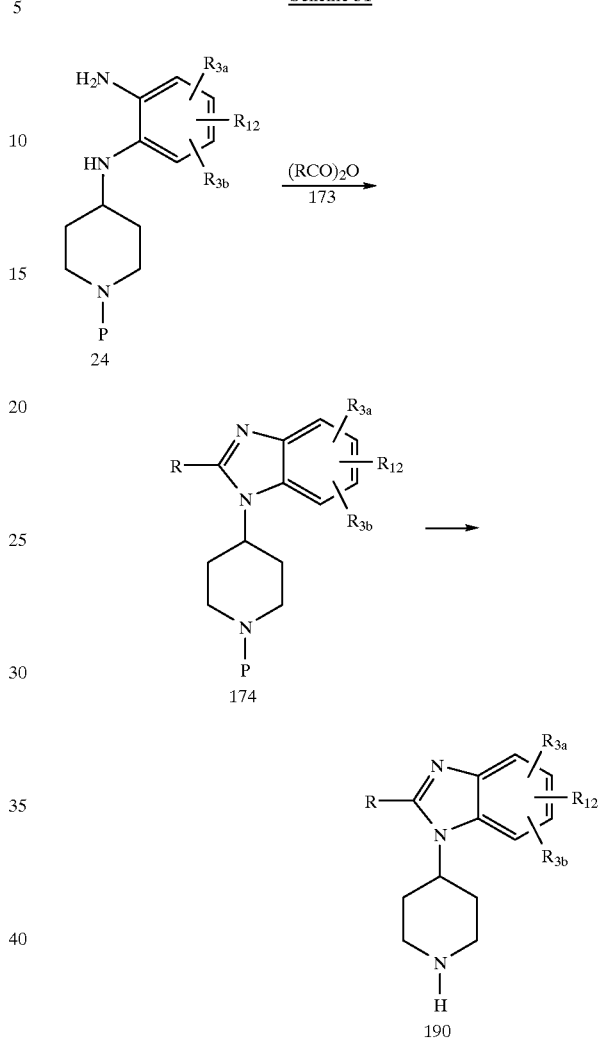

As shown in Scheme 31, treating an amine of formula 24 with three equivalents of anhydride 173, neat, at temperatures near or around 160° C. overnight, followed by decomposition of excess anhydride with a base such as sodium hydroxide generates compounds of formula 174. Deprotection of the amine transforms 174 into 190.

SCHEME 32

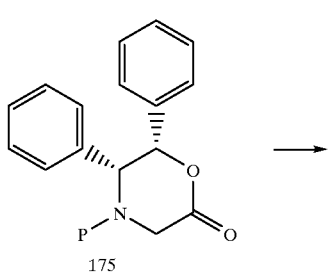

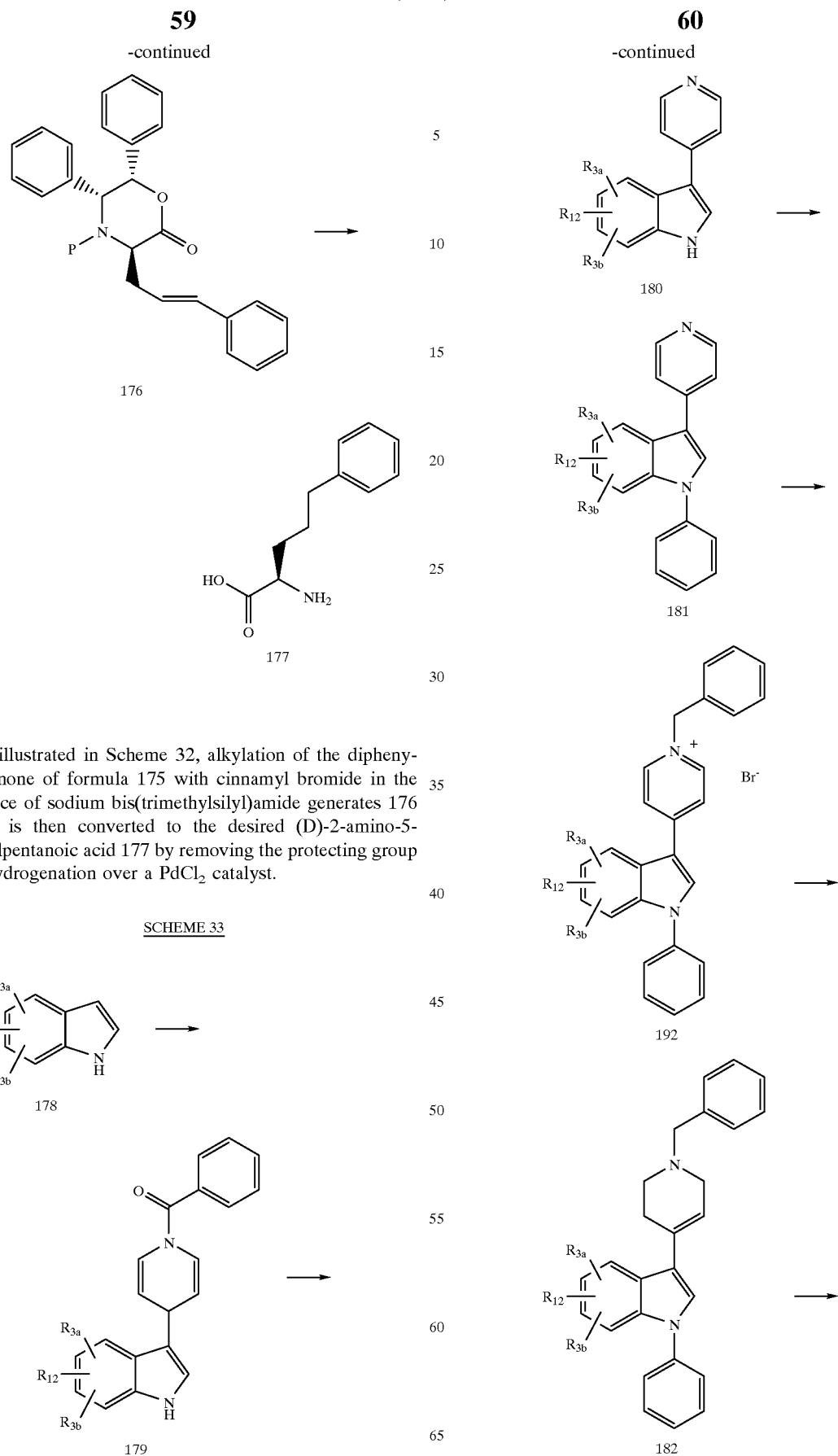
As illustrated in Scheme 32, alkylation of the diphenyloxazinone of formula 175 with cinnamyl bromide in the presence of sodium bis(trimethylsilyl)amide generates 176 which is then converted to the desired (D)-2-amino-5-phenylpentanoic acid 177 by removing the protecting group and hydrogenation over a PdCl$_2$ catalyst.
SCHEME 33

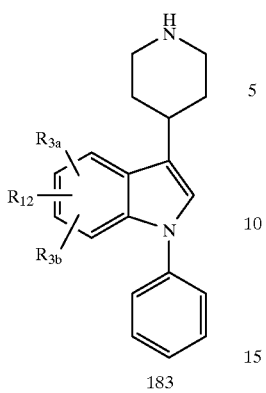

Compounds of formula 179 can be prepared by treating an indole of formula 178 with benzoyl chloride in pyridine as illustrated in Scheme 33. Subsequent heating of 179 with dibenzylamine and a catalyst such as palladium on carbon at temperatures at or near 210° C. in a solvent such as diphenyl ether generates the intermediate of formula 180. The indole nitrogen can be alkylated by treating 180 with cuprous bromide and bromobenzene in the presence of a base such as potassium carbonate in a suitable solvent such as N-methylpyrrolidine at reflux overnight to give intermediates of formula 181. Quaternization of the pyridine nitrogen can be accomplished by treating 181 with benzyl bromide in a solvent such as benzene at refluxing temperatures to give intermediates of formula 192. Treating 192 with excess sodium borohydride in methanol generates the tetrahydropyridine 182. Hydrogenation of 182 with hydrogen in a solvent such as ethanol using a catalyst such as palladium produces the piperidine of formula 183.

SCHEME 34

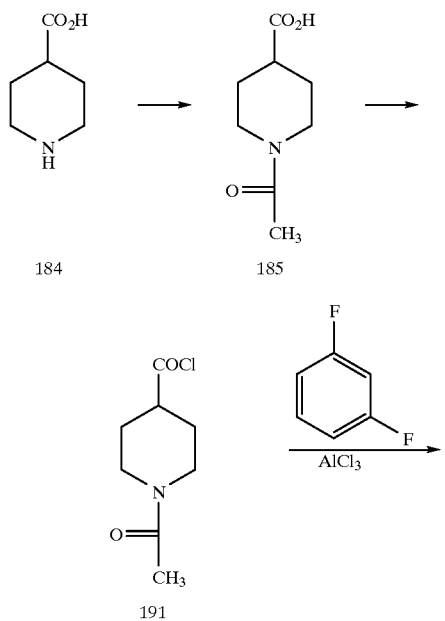

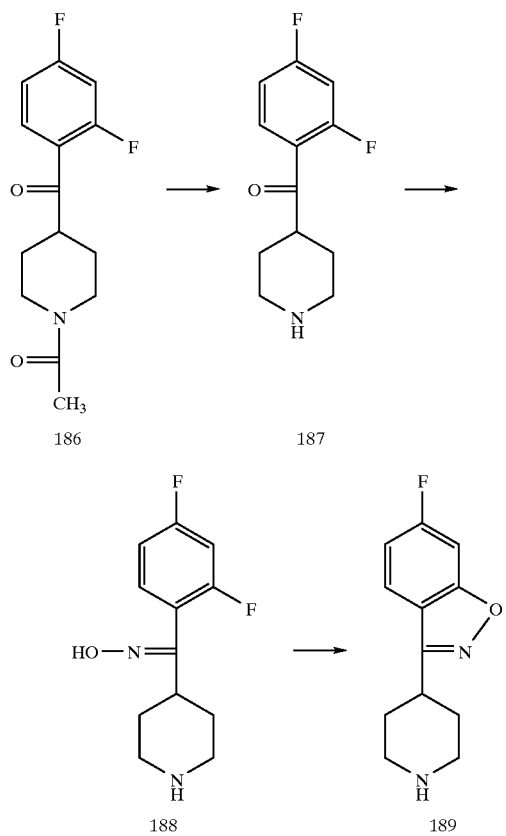

Compound of formula 185 is prepared by refluxing a mixture of 184 in acetic anhydride for several hours. The acid chloride can be prepared by treating 185 with either thionyl chloride or oxalyl chloride to give intermediates of formula 191. Friedel-Crafts acylation of m-difluorobenzene with 191 in the presence of aluminum chloride as a catalyst produces 186. Removal of the acetyl protecting group can be accomplished by heating 186 in a mixture of concentrated HCl and glacial acetic acid to give intermediate of formula 187. The oxime 188 can then be prepared by refluxing 187 with triethylamine and hydroxylamine hydrochloride in ethanol for several hours. Refluxing the oxime in 50% NaOH produces the benzoisoxazole 189.

SCHEME 35

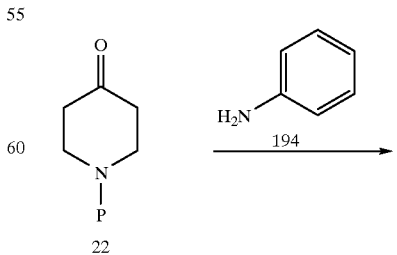

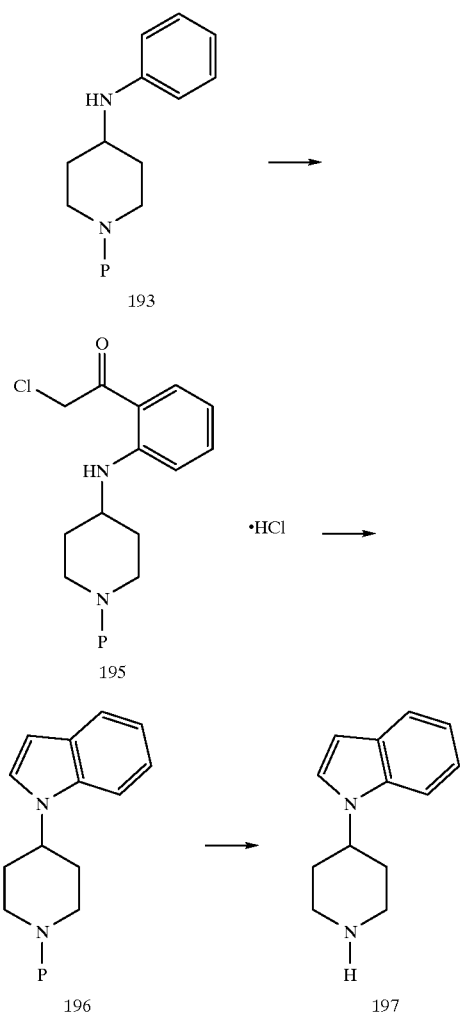

As shown in Scheme 35, compounds of formula 193 can be prepared by treating anilines of formula 194 with N-protected piperidones of formula 22 in the presence of a hydride reducing agent such as sodium triacetoxyborohydride in a solvent such as acetic acid which contains an excess of sodium sulfate. Treating compounds of formula 193 with chloroacetonitrile at temperatures at or near 0° C. in the presence of a Lewis acid such as boron trichloride followed by refluxing the mixture overnight and then treating the solution with 10% HCl and refluxing again for 0.5 h produces intermediate of formula 195. Treating 195 with sodium borohydride in a solvent such as ethanol generates the indole of formula 196. Deprotection of the amine transforms 196 into 197.

The following examples are provided for the purpose of further illustration only and are not intended to be limitations on the disclosed invention.

General Experimental Procedures

Amicon silica 30 uM, 60 Å pore size, was used for column chromatography. Melting points were taken on a Buchi 510 apparatus and are uncorrected. Proton and carbon NMR spectra were recorded on a Varian XL-300, Bruker AC-300, or Bruker AC-250 at 25° C. Chemical shifts are expressed in parts per million downfield from trimethylsilane. Particle beam mass spectra (MS) were obtained on a Hewlett-Packard 5989A spectrometer using ammonia as the source of chemical ionization. For initial sample dissolution chloroform or methanol were employed. Liquid secondary ion mass spectra (LSIMS) were obtained on a Kratos Concept-1S high resolution spectrometer using cesium ion bombardment on sample dissolved in a 1:5 mixture of dithioerythritol and dithiothreitol or in a thioglycerol matrix. For initial sample dissolution chloroform or methanol were employed. Reported data are sums of 3–20 scans calibrated against cesium iodide. TLC analyses were performed using E. Merck Kieselgel 60 F254 silica plates visualized (after elution with the indicated solvent(s)) by UV, iodine or by staining with 15% ethanolic phosphomolybdic acid or ceric sulfate/ammonium molybdate and heating on a hot plate. The terms "concentrated" and "coevaporated" refer to removal of solvent at water aspirator pressure on a rotary evaporator with a bath temperature of less than 40° C.

General Procedure A (Peptide coupling using EDC). A 0.2–0.5 M solution of the primary amine (1.0 equivalent) in dichloromethane (or a primary amine hydrochloride and 1.0–1.3 equivalents of triethylamine) was treated sequentially with 1.0–1.2 equivalents of the carboxylic acid coupling partner, 1.5–1.8 equivalents hydroxybenzotriazole hydrate (HOBT), and 1.0–1.2 equivalents (stoichiometrically equivalent to the quantity of carboxylic acid) 1-(3-dimethylaminopropyl)-3-ethylcarbodiimide hydrochloride (EDC) and the mixture was stirred overnight in an ice bath (the ice bath was allowed to warm, thus the reaction mixture was typically held at 0–20° C. for 4–6 h and 20–25° C. for the remaining period). The mixture was diluted with ethyl acetate or other solvent as specified, and the resulting mixture washed twice with 1 N NaOH, twice with 1 N HCl (if the product is not basic), once with brine, dried over $Na_2SO_4$, and concentrated giving the crude product which was purified as specified. The carboxylic acid component could be used as the dicyclohexylamine salt in coupling to the primary amine or hydrochloride of the latter; in this case no triethylamine was employed.

General Procedure B. (Cleavage of a t-Boc-protected Amine using TFA). Cold trifluoroacetic acid (usually 0–10° C.) was added to the t-Boc amine (typically 10 mL per mmol amine) neat or dissolved in a minimum volume of $CH_2Cl_2$ and the resulting solution was stirred at 0° C. for 0.25–2 h (the time required for complete disappearance of the starting material to a more polar product as judged by TLC). The resulting solution or suspension was concentrated, and the residue coevaporated several times with added methylene chloride. The residue was then dissolved in ethyl acetate and washed twice with 1 N NaOH and once with brine. The organic phase was then dried over $Na_2SO_4$ and evaporated to give the free amine which was used without further purification or purified as specified.

General Procedure C. (Cleavage of a t-Boc-protected Amine and HCl salt exchange). Cold trifluoroacetic acid (usually 0–10° C.) was added to the t-Boc amine (typically 10 mL per mmol amine) and the resulting solution was stirred at 0° C. for 0.25–2 h (the time required for complete disappearance of the starting material to a more polar product as judged by TLC). The resulting solution or suspension was concentrated, the residue coevaporated several times with added methylene chloride and then dried in vacuo. The trifluoroacetate salt was dissolved in ethanol (typically 5 mL per mmol of salt) and cooled to 0° C. Two equivalents of either aqueous 1 N HCl or 1 M HCl in ether was added to the cold solution, and the mixture stirred for 10 min. at 0° C. The mixture was then concentrated and the residue coevaporated several times with ethanol and then dried in vacuo. The resulting oil in most cases could be triturated to a solid with diethyl ether.

General Procedure D. (Lithium Hydroxide Hydrolysis of Esters). To a 0.20–0.50 M solution of ester dissolved in THF, 3.5 equivalents of lithium hydroxide hydrate dissolved in a volume of water equal to 25% the volume of THF was added. The mixture was stirred overnight at room temperature. Excess THF was removed by evaporation, and the basic aqueous mixture was extracted three times with ethyl acetate, and then acidified to pH4 with dilute acetic or hydrochloric acid. The product was extracted with ethyl acetate and the combined organic extracts were washed with brine, dried over $MgSO_4$ and evaporated to give the desired acid which was used without further purification, or triturated to a solid as specified.

EXAMPLE 1

2-Amino-N-{1-(R)-benzyloxymethyl-2-oxo-2-[4-(2-oxo-2,3-dihydro-benzoimidazol-1-yl)-piperidin-1-yl]-ethyl}-isobutyramide Hydrochloride A. {1-(R)-Benzyloxymethyl-2-oxo-2-[4-(2-oxo-2,3-di hydro-benzoimidazol-1-yl)-piperidin-1-yl]-ethyl}-carbamic acid tert-butyl ester According to General Procedure A, 420 mg (1.94 mmol) of N-t-BOC-O-benzyl-D-serine and 571 mg (1.94 mmol) of 4-(2-keto-1-benzimidazolinyl) piperidine were coupled and the product purified by silica gel chromatography (1:1 v/v EtO Ac/hexanes) to afford 630 mg of 1A.

$^1$H NMR ($CD_3OD$ 250 MHz) δ 7.18–7.44 (m, 5H), 6.85–7.10 (m, 4H), 4.16–4.84 (m, 6H), 3.60–3.74 (m, 2H), 2.73–2.90 (m, 1H), 2.25–2.67 (m, 2H), 1.71–1.90 (m, 3H), 1.45–1.55 (m, 9H).

B. (R)-1-[1-[(2-Amino-3-benzyloxy-propionyl)]-piperidin-4-yl]-1,3-dihydro-benzoimidazol-2-one According to General Procedure B, 630 mg (1.27 mmol) of the product from 1A was deprotected to afford 550 mg of 1B.

C. (1-{1-(R)-Benzyloxymethyl-2-oxo-2-[4-(2-oxo-2,3-dihydro-benzoimidazol-1-yl)-piperidin-1-yl]-ethylcarbamoyl}-1-methyl-ethyl)-carbamic acid tert-butyl ester According to General Procedure A, 44 mg (0.22 mmol) of N-t-BOC-α-methylalanine and 78 mg (0.20 mmol) of 1B were coupled, and the product was purified by silica gel chromatography (10:1.5 v/v EtO Ac:hexanes) to give 24 mg of 1C.

$^1$H NMR ($CDCl_3$ 250 MHz) δ 9.25–9.40 (d, 1H), 6.78–7.41 (m, 9H), 4.79–5.30 (m, 3H), 4.45–4.65 (m, 3H), 4.17–4.42(m, 1H), 3.58–3.79 (m, 2H), 2.62–3.45 (m, 2H), 2.19–2.47 (m, 2H), 1.75–1.98 (m, 3H), 1.38–1.55 (m, 15H).

D. 2-Amino-N-{1-(R)-benzyloxymethyl-2-oxo-2-[4-(2-oxo-2,3-dihydro-benzoimidazol-1-yl)-piperidin-1-yl]-ethyl}-isobutyramide hydrochloride The product from 1C was deprotected according to General Procedure C to give 15 mg of the title compound as a white solid.

$^1$H NMR ($CD_3OD$ 250 MHz) δ 7.39–7.41 (m, 7H), 6.93–7.15 (m, 4H), 5.12–5.22 (m, 1H), 4.42–4.76 (m, 5H), 4.20–4.30 (m, 1H), 3.70–3.86 (m, 2H), 3.28–3.25 (m, 1H), 2.22–2.49 (m, 1H), 1.75–1.92 (m, 2H), 1.53–1.61 (s, 6H).
MS (Cl, $NH_3$) 480 ($MH^+$)

EXAMPLE 2

3-Amino-N-{1-(R)-benzyloxymethyl-2-oxo-2-[4-(2-oxo-2,3-dihydro-benzoimidazol-1-yl)-piperidin-1-yl]-ethyl}-3-methyl-butyramide Hydrochloride A. (2-{1-(R)-Benzyloxymethyl-2-oxo-2-[4-(2-oxo-2,3-dihydro-benzoimidazol-1-yl)-piperidin-1-yl]-ethylcarbamoyl}-1,1-dimethyl-ethyl)-carbamic acid tert-butyl ester According to General Procedure A, 78 mg (0.20 mmol) of 1B and 48 mg (0.22 mmol) of 3-tert-Butoxycarbonylamino-3-methyl-butyric acid were coupled and the product purified by silica gel chromatography (10:1.5 v/v EtO Ac/hexanes) to give 108 mg of 2A as a clear oil.

$^1$H NMR ($CDCl_3$ 250 MHz) δ 7.19–7.38 (m, 5H), 6.79–7.17 (m, 5H), 5.22–5.52 (m, 2H), 4.82–4.97 (m,1H), 4.49–4.63 (m, 3H), 4.20–4.38 (m,1H), 3.60–3.72 (m, 2H), 3.03–3.32 (m, 1H), 2.50–2.82 (m, 3H), 2.11–2.49 (m, 3H), 1.77–1.98 (m, 2H), 1.35–1.53 (m, 15H).

B. 3-Amino-N-{1-(R)-benzyloxymethyl-2-oxo-2-[4-(2-oxo-2,3-dihydro-benzoimidazol-1-yl)-piperidin-1-yl]-ethyl}-3-methyl-butyramide hydrochloride According to General Procedure C, 94 mg (0.16 mmol) of 2A was deprotected to give 58 mg of the title compound as a white solid.

$^1$H NMR ($CD_3OD$ 250 MHz) δ 7.20–7.44 (m, 6H), 6.88–7.24 (m, 4H), 5.13–5.23 (m, 1H), 4.20–4.83 (m, 6H), 3.65–3.82 (m, 2H), 2.21–2.90 (m, 6H), 1.78–1.91 (m, 2H), 1.32–1.40 (bs, 6H).
MS (Cl, $NH_3$) 494 ($MH^+$).

EXAMPLE 3

(R)-3-Benzyloxy-2-(2-tert-butoxycarbonylamino-2-methyl-propionylamino)-propionic Acid To 1.83 g (6.2 mmol) of N-t-BOC-O-benzyl-D-serine in 35 mL of DMF was added 1.02 g (7.4 mmol) of potassium carbonate followed by 0.92 g (6.5 mmol) of iodomethane. The mixture was stirred overnight at 24° C. under an atmosphere of nitrogen. The reaction mixture was diluted with 200 mL of water, and extracted three times with ethyl acetate. The combined organics were washed five times with water and once with brine, dried over $MgSO_4$ and concentrated. The crude (R)-3-Benzyloxy-2-tert-butoxycarbonylamino-propionic acid methyl ester was then deprotected according to General Procedure B and 0.84 g (4.02 mmol) of the resulting (R)-2-Amino-3-benzyloxy-propionic acid methyl ester was coupled to 0.81 g (4.02 mmol) of N-t-BOC-α-methylalanine to give 1.80 g of (R)-3-Benzyloxy-2-(2-tert-butoxycarbonylamino-2-methyl-propionylamino)-propionic acid methyl ester. The crude product was hydrolyzed according to the method outlined in General Procedure D, and 1.60 g of the title compound was recovered as an oil which solidified on standing.

$^1$H NMR ($CDCl_3$ 300 MHz) δ 7.30 (m, 5H), 7.10 (d, 1H), 5.07 (bs, 1H), 4.68 (m, 1H), 4.53 (q, 2H) 4.09 (m,1H), 3.68 (m,1H), 1.3–1.5 (m, 15H)

EXAMPLE 4

2-Amino-N-{ 1-(R)-(1H-indol-3-ylmethyl)-2-oxo-2-[4-(2-oxo-2,3-dihydro-benzoimidazol-1-yl)-piperidin-1-yl]-ethyl}-isobutyramide A. (R)-2-Amino-3-[(1H-indol-3-yl)-propionic acid methyl ester To 4.92 g (16.2 mmol) of N-α-t-BOC-D-tryptophan in 100 mL of DMF was added 2.46 g (17.8 mmol) of potassium carbonate followed by 2.41 g (17.0 mmol) of iodomethane, and the mixture was stirred overnight at 24° C. under an atmosphere of nitrogen. The reaction mixture was diluted with water, and extracted three times with ethyl acetate. The combined organics were washed five times with 500 mL of water and once with brine, dried over $MgSO_4$ and concentrated to give 4.67 g of a white solid. The crude (R)-2-tert- Butoxycarbonylamino-3-(1H-indol-3-yl)-propionic acid methyl ester was deprotected according to General Procedure B to give 4A as an orange oil in quantitative yield.

B. (R)-2-(2-tert-Butoxycarbonylamino-2-methyl-propionylamino)-3-(1H-indol-3-yl)-propionic acid methyl ester.

According to General Procedure A 1.55 g (7.1 mmol) of 4A was coupled to 1.44 g (7.1 mmol) of N-t-BOC-α-methylalanine to give an oil which was purified by silica gel chromatography using a gradient of 10%, 20%, 30%, 40% and 50% ethyl acetate in hexane to afford 1.32 g of (R)-2-(2-tert-Butoxycarbonylamino-2-methyl-propionylamino)-3-(1H-indol-3-yl)-propionic acid methyl ester.

C. (R)-2-(2-tert-Butoxycarbonylamino-2-methyl-propionylamino)-3-(1H-indol-3-yl)-propionic acid The product from 4B was hydrolyzed according to the method described in General Procedure D to give 1.03 g of 4C as an orange foam.

$^1$H NMR (CDCl$_3$ 300 MHz) δ 7.61 (d, 1H), 7.48 (d,1H), 7.27 (t,1H), 7.10 (t, 1H), 4.81 (bs, 1H), 3.35 (m, 1H), 1.49 (s, 6H), 1.32 (s, 9H).

MS (Cl, NH$_3$) 390 (MH$^+$)

D. (1-{1-(R)-(1H-Indol-3-ylmethyl)-2-oxo-2-[4-(2-oxo-2,3-dihydro-benzoimidazol-1-yl)-piperidin-1-yl]-ethylcarbamoyl}-1-methyl-ethyl)-carbamic acid tert-butyl ester According to General Procedure A, 75 mg (0.19 mmol) of 4C was coupled to 39 mg (0.18 mmol) of 4-(2-keto-1-benzimidazolinyl)piperidine and the product was purified by silica gel chromatography (99:0.5 v/v CHCl$_3$:MeOH) to give 90 mg of 4D as a white foam.

E. 2-Amino-N-(1-(R)-(1H-indol-3-ylmethyl)-2-oxo-2-[4-(2-oxo-2 3-dihydro-benzoimidazol-1-yl)-piperidin-1-yl]-ethyl}-isobutyramide According to General Procedure B, 90 mg (0.15 mmol) of 4D was deprotected to give 70 mg of the title compound as a yellow solid.

$^1$H NMR (CDCl$_3$ 250 MHz) (1:1 mixture of rotamers) δ 8.80 (bs, 0.5H), 8.58 (bs, 0.5H), 8.48–8.52 (dd,1H), 7.83 (d,1H), 7.52 (d,1H), 7.34–7.40 (m, 1.5H), 6.93–7.12 (m, 7H), 6.65–6.71 (m, 1H), 4.70–4.88 (m, 1H), 4.39–4.45(m, 0.5H), 4.08–4.39 (m, 0.5H), 3.72–3.92 (m,1H), 2.80–2.99 (0.5H), 2.50–2.66 (m, 0.5H), 1.92–2.41 (m, 3H), 1.30–1.82 (m, 11H).

MS (Cl, NH$_3$) 489 (MH$^+$)

EXAMPLE 5

(R)-2-[2-(2-Amino-2-methyl-propionylamino)-3-(1H-indol-3-yl)-propionyl-1,2,3,4-tetrahydro-isoquinoline-6-carboxylic Acid Methyl Ester Hydrochloride A. 6-Hydroxy-3,4-dihydro-1H-isoquinoline-2-carboxylic acid tert-butyl ester To 4.75 g (20.7 mmol) of 1,2,3,4-Tetrahydro-isoquinolin-6-ol hydrobromide (see 7D) in 150 mL of 1:1 water:dioxane at 0° C. was added 4.95 g (22.7 mmol) of di-tert-butyldicarbonate and sufficient 1 N NaOH to maintain the pH of the solution between 10 and 10.5. The ice bath was removed after 30 min and the reaction was stirred at room temperature for an additional 2 h. The solution was concentrated, diluted with water and acidified with 1 N HCl. The mixture was extracted three times with ethyl acetate and the organic phase was washed with water and brine, dried over MgSO$_4$ and concentrated to give 5.24 g of crude product. The product was crystallized from hexane/ether to give 3.99 g of 5A as a solid.

B. 6-(4-Trifluoro-methanesulfonyloxy)-3,4-dihydro-1H-isoquinoline-2-carboxylic acid tert-butyl ester To 3.97 g (15.94 mmol) of 5A in 13 mL of methylene chloride was added 8.2 mL (101.4 mmol) of pyridine and the mixture was cooled to 0° C. A solution of 3.16 mL (18.81 mmol) of triflic anhydride in 26 mL of methylene chloride was then added dropwise to the stirring mixture over 20 min. The mixture was stirred for 30 min. at 0° C. and then poured into saturated brine and extracted with ether. The ether phase was washed three times with 1 N HCl, and once each with water and brine. The solution was dried over MgSO$_4$ and concentrated to give 6.08 g of 5B as an oil which crystallized on standing.

C. 3,4-Dihydro-1H-isoquinoline-2.6-dicarboxylic acid 2-tert-butyl ester-6-methyl ester A Parr bottle containing 381 mg (1.0 mmol) of 5B, 6 mg (0.03 mmol) of palladium acetate, 25 mg (0.06 mmol) of 1,3-bis(diphenylphosphino)propane, 0.28 mL (2.0 mmol) of triethylamine in 4 mL of dimethylformamide and 1.8 mL of methanol was charged to 5 psi with carbon monoxide, and the mixture agitated for 0.5 h. The mixture was then heated to 60° C. and the pressure increased to 30 psi of carbon monoxide, and the mixture agitated overnight. After cooling to room temperature, the mixture was dissolved in ether and washed three times with water and once with brine. The solution was dried over MgSO$_4$ and concentrated to give 365 mg of 5C as an oil.

D. 1,2,3,4-Tetrahydro-isoquinoline-6-carboxylic acid methyl ester

According to General Procedure B, 563 mg (1.93 mmol) of 5C was deprotected to give 370 mg of 5D as an oil.

E. (R)-2-[2-(2-tert-Butoxycarbonylamino-2-methyl-propionylamino)-3-(1H-indol-3-yl)-propionyl]-1,2,3,4-tetrahydro-isoquinoline-6-carboxylic acid methyl ester According to General Procedure A, 303 mg (1.59 mmol) of 5D was coupled to 617 mg (1.59 mmol) of 4C and the product was purified by silica gel chromatography (1:1 v/v ethyl acetate:hexanes) to give 866 mg of 5E.

F. (R)-2-{2-(2-Amino-2-methyl-propionylamino)-3-(1H-indol-3-yl)-propionyl]-1,2,3,4-tetrahydro-isoquinoline-6-carboxylic acid methyl ester hydrochloride According to General Procedure C, 60 mg (0.107 mmol) of 5E was deprotected to give 41 mg of the title compound as a solid.

$^1$H NMR (CD$_3$OD, 300 MHz) δ (1:1 mixture of rotamers) 7.79 (d, 0.5H), 7.54–7.65 (m, 2.5H), 7.29 (d, 0.5H), 7.17 (d, 0.5H), 6.95–7.10 (m, 3.5H), 6.61 (d, 0.5H), 5.28–5.30 (m, 1H), 4.61–4.70 (d, 0.5H), 4.42–4.51 (m, 1H), 4.10–4.19 (d, 0.5H), 3.87 (d, 3H), 3.54–3.12 (m, 1H), 3.17–3.34 (m, 3H), 2.53–2.74 (m, 1H), 2.36–2.51 (m, 0.5H), 2.08–2.21 (m, 0.5H), 1.56 (s, 6H).

MS (Cl, NH$_3$) 463 (MH$^+$)

EXAMPLE 6

2-Amino-N-{1-(R)-benzyloxymethyl-2-[7-(3-methyl-ureido)-3,4-dihydro-1H-isoquinolin-2-yl]-2-oxo-ethyl}-isobutyramide A. 7-Nitro-1,2,3,4-tetrahydro-isoquinoline To 43.1 g (324 mmol) of 1,2,3,4-tetrahydro-isoquinoline was added 160 mL of concentrated sulfuric acid with ice bath cooling. Potassium nitrate 35.2 g (348 mmol) was added in portions to the stirring mixture, while maintaining an internal temperature below 5° C. The mixture was allowed to stand at ambient temperature for 72 h, and then basified with aqueous ammonia and extracted four times with chloroform. The combined organics were dried over MgSO$_4$ and concentrated to give a dark brown oil. The oil was dissolved in 240 mL of ethanol and 40 mL of concentrated hydrochloric acid was added to the mixture with cooling. The precipitated material was collected by filtration and washed with cold ethanol to give 25.0 g of a tan solid. The crude material was partitioned between 1 N NaOH and ethyl acetate. The ethyl acetate layer was washed once with brine, dried over Na$_2$SO$_4$ and concentrated. The dinitrated tetrahydroisoquinoline was removed by crystallization from ether/hexanes. The mother liquor was concentrated to give 2.19 g of 7-Nitro-1,2,3,4-tetrahydro-isoquinoline.

B. {1-[1-(R)-Benzyloxymethyl-2-(7-nitro-3,4-dihydro-1H-isoquinolin-2-yl)-2-oxo-ethylcarbamoyl]-1-methyl-ethyl]-carbamic acid tert-butyl ester According to General Procedure A, 100 mg (0.57 mmol) of 6A and 228 mg (0.60 mmol) of 3 were coupled, and the product was purified by silica gel chromatography (99:1 v/v CH$_2$Cl$_2$:MeOH) to give 220 mg of 6B as a white foam.

C. {1-[2-(7-Amino-3,4-dihydro-1H-isoquinolin-2-yl)-1-(R)-benzyloxymethyl-2-oxo-ethylcarbamoyl]1-methyl-ethyl}-carbamic acid tert-butyl ester To a solution of 222 mg (0.41 mmol) of 6B in 2.5 mL of ethanol and 1.5 mL of water was added 110 mg (1.96 mmol) of iron powder, and 12 mg (0.22 mmol) of ammonium chloride. The mixture was refluxed for 45 min, and another 110 mg of iron powder, and 24 mg of ammonium chloride was added to the reaction mixture and refluxing continued for another 1 h. The hot solution was filtered through celite and concentrated. The residue was dissolved in ethyl acetate and washed once each with water and brine, dried over Na$_2$SO$_4$ and concentrated. The product was purified by silica gel chromatography (98:2 v/v CHCl$_3$:MeOH) to give 147 mg of 6C as a white foam.
MS (Cl, NH$_3$) 511 (MH$^+$)

D. (1-{1-(R)-Benzyloxymethyl-2-[7-(3-methyl-ureido)-3,4-dihydro 1H-isoquinolin-2-yl]-2-oxo-ethylcarbamoyl}-1-methyl-ethyl)-carbamic acid tert-butyl ester To a solution of 68 mg (0.13 mmol) of 6C in 3 mL of methylene chloride was added 0.40 mL (6.67 mmol) of methyl isocyanate, and the mixture was stirred for 17 h under nitrogen at 24° C. The mixture was concentrated and the product was purified by silica gel chromatography (98:2 v/v CHCl$_3$:MeOH) to give 55 mg of the title compound as a white foam.

E. 2-Amino-N-{1-(R)-benzyloxymethyl-2-[7-(3-methyl-ureido)-3,4-dihydro-1H-isoquinolin-2-yl]-2-oxo-ethyl}-isobutyramide According to General Procedure B, 55 mg (0.097 mmol) of 6D was deprotected to give 41 mg of the title compound as a white foam.
$^1$H NMR (CDCl$_3$ 250 MHz) (2:1 mixture of rotamers) δ 8.37–8.52 (m, 1H), 7.54 (bs, 0.67H), 7.41 (bs, 0.33H), 7.11–7.31 (m, 7H), 6.89–7.03 (m, 2H), 5.52–5.60 (m, 0.67H), 5.42–5.50 (m, 0.33H), 4.64 (bs, 1H), 4.59 (bs, 1H), 4.50 (d, 2H), 4.42 (bs, 1H), 3.61–3.90 (m, 4H), 2.62–2.77 (m, 4H), 1.55–1.72 (bs, 2H), 1.32 (s, 6H).
MS (Cl, NH$_3$) 468 (MH$^+$)

EXAMPLE 7

2-Amino-N-(1-(R)-benzyloxymethyl-2-{6-[2-(3-methyl-ureido)-phenyl]-3,4-dihydro-1H-isoquinolin-2-yl}-2-oxo-ethyl)-isobutyramide A. Phenyl-carbamic acid tert-butyl ester To a solution of 21.8 g (100 mmol) of di-tert-butyl-dicarbonate in 1 L of methylene chloride was added 10.0 g (100 mmol) of aniline. The mixture was stirred at 24° C. overnight and then concentrated. The residue was dissolved in ether and washed ten times with dilute aqueous acetic acid, once each with 1 N NaOH and brine, dried over MgSO$_4$ and concentrated to give 8.6 g of 7A as a white solid.

B. 2-tert-Butoxycarbonylamino-phenylboronic acid

To 8.00 g (41.4 mmol) of Phenyl-carbamic acid tert-butyl ester in 103 mL of tetrahydrofuran at -78° C., 58.5 mL (99.5 mmol) of 1.7 M tert-butyllithium in pentane was added dropwise. The mixture was warmed to -20° C and stirred at that temperature for 1 h after which time the reaction was cooled to -78° C., and 12.2 mL (107.7 mmol) of trimethylborate was added dropwise. The mixture was concentrated and 500 mL of ether and 125 mL of 1 N HCl was added. The mixture was stirred at 24° C. for 10 min. The layers were separated and the ethereal portion was washed once each with water and brine, dried over MgSO$_4$ and concentrated. The product was purified by silica gel chromatography (50:50 v/v EtO Ac:hexanes) to give 4.49 g of 7B as a foam.
$^1$H NMR (CDCl$_3$ 300 MHz) δ 9.16 (s, 1H), 8.85 (d, 1H), 7.37 (t, 1H), 7.06 (t, 1H), 1.48 (s, 9H).

C. 6-Methoxy-1,2,3,4-tetrahydro-isoquinoline

To 20.0 g (132 mmol) of β-(m-methoxy) phenylethylamine was added 20.4 g (140 mmol) of 20% formaldehyde solution, and the mixture heated at 85° C. for 1 h. After cooling to room temperature, the mixture was extracted with benzene. The organic phase was washed three times with water, once with brine, dried over Na$_2$SO$_4$ and concentrated to give 26.8 g of an oil. To the resulting oil was added 26.0 g of a 20% aqueous hydrochloric acid solution, and the mixture was heated at 85° C. for 45 min. The mixture was basified with 1 N NaOH to pH 11 and extracted with ether. The ether layer was washed with water and brine, dried over MgSO$_4$, and evaporated. The crude product was purified by silica gel chromatography using a gradient of 5%, 10%, and 20% methanol in chloroform to give 8.00 g of 7C as an oil.

D. 6-Hydroxy-3,4-dihydro-1H-isoquinoline-2-carboxylic acid benzyl ester

A solution of 8.00 g (49 mmol) of 6-Methoxy-1,2,3,4-tetrahydro-isoquinoline in 196 mL of 48% hydrobromic acid was refluxed for 3 h. The mixture was then concentrated and coevaporated several times with ethanol. The resulting slurry was filtered and dried under vacuum to give 7.43 g of 1,2,3,4-Tetrahydro-isoquinolin-6-ol hydrobromide as a solid. To 7.38 g of the crude hydrobromide dissolved in 117 mL each of dioxane and water was added 6.34 g (35.3 mmol) of benzyl chloroformate with ice bath cooling. A 1 M solution of potassium carbonate was slowly added until a pH of 10 was maintained. The mixture was stirred overnight at room temperature. Excess dioxane was removed by evaporation, and the resulting aqueous mixture was acidified with 1 N HCl and the product extracted with ethyl acetate. The organic portion was washed with water and brine, dried over Na$_2$SO$_4$ and concentrated to give 10.4 g of an oil which was crystallized from ether/hexane to give 7.05 g of 7D as a solid.

E. 6-(2-tert-Butoxycarbonylamino-phenyl)-3,4-dihydro-1H-isoquinoline-2-carboxylic acid benzyl ester To a solution of 4.00 g (14.1 mmol) of 7D in 11 mL of methylene chloride was added 7.09 g (89.7 mmol) of pyridine. The mixture was cooled in an ice bath, and a of 4.70 g (16.7 mmol) of triflic anhydride was added to the stirring solution over 20 min. Once the addition was complete, the mixture was stirred at 0° C. for 30 min. The reaction mixture was then poured into brine and the product extracted with ether. The ether phase was then washed three times with 1 N HCl, once each with water and brine, dried over MgSO$_4$ and evaporated to give the 6-(Trifluoromethanesulfonyloxy)-3,4-dihydro-1H-isoquinoline-2-carboxylic acid benzyl ester as an oil which crystallized on standing.

A mixture of 4.10 g (10.3 mmol) of crude 6-(Trifluoromethanesulfonyloxy)-3,4-dihydro-1H-isoquinoline-2-carboxylic acid benzyl ester, 3.25 g (13.7 mmol) of 7B, 1.0 g of tetrakis(triphenylphosphine)palladium(0), 3.77 g (27.3 mmol) potassium carbonate, 45 mL toluene, 28 mL ethanol, and 18 mL of water were heated at 90° C. overnight. The mixture was diluted with ethyl acetate and washed twice with saturated aqueous sodium bicarbonate, once with brine, dried over MgSO$_4$ and concentrated to give an oil which was purified by silica gel chromatography (85:15 v/v hexanes:EtO Ac) to give 3.80 g of 7E.

F. 6-(2-Amino-phenyl)-3,4-dihydro-1H-isoquinoline-2-carboxylic acid benzyl ester The product from 7E 3.80 g (8.3 mmol) was deprotected according to General Procedure B to give 2.63 g of 7F as a glass.

G. 6-[2-(3-Methyl-ureido)-phenyl-]3,4-dihydro-1H-isoquinoline-2-carboxylic acid benzyl ester To a solution of 1.36 g (3.8 mmol) of 7F in 45 mL of methylene chloride and 0.403 g (3.99 mmol) triethylamine was added a solution of 0.376 g (1.27 mmol) triphosgene in 8 mL of methylene chloride dropwise. The mixture was stirred at room temperature for 5 h. The mixture was purged with nitrogen for 25 min and then concentrated. The residue was dissolved in 21 mL of methanol and 15.8 mL of 40% aqueous methylamine was added to the stirring solution. The mixture was stirred at room temperature for 72 h and then concentrated. The mixture was diluted with water and extracted with ethyl acetate. The organic phase was washed with brine, dried over MgSO$_4$ and concentrated to give a foam which was crystallized from ethyl acetate/hexanes to give 0.711 g of 7G as a white solid.

H. 1-Methyl-3-[2-(1,2,3,4-tetrahydro-isoquinolin-6-yl)-phenyl]-urea

To 0.70 g (1.69 mmol) of 7G in 10 mL ethanol was added 0.350 g of 10% palladium on carbon and the mixture hydrogenated at 55 psi for 1.5 h.

The catalyst was removed by filtration through celite, and the mixture concentrated. 7H was obtained in quantitative yield and used in the following step without purification.

I. (1-(R)-Benzyloxymethyl-2-{6-[2-(3-methyl-ureido)-phenyl]-3,4-dihydro-1H-isoquinolin-2-yl}-2-oxo-ethyl)-carbamic acid tert-butyl ester According to General Procedure A, 150 mg (0.53 mmol) of 7H and 157 mg (0.53 mmol) of N-t-BOC-O-benzyl-D-serine were coupled. The product was purified by silica gel chromatography (60:40 v/v EtOAc:hexanes) to give 211 mg of 7I as a foam.

J. 1-{2-[2-(2-Amino-3-benzyloxy-propionyl)-1,2,3,4-tetrahydro-isoquinolin-6-yl]-phenyl}-3-methyl-urea Following the method outlined in General Procedure B, 205 mg (0.367 mmol) of 7I was deprotected to give 132 mg of 7J.

K. [1-(1-(R)-Benzyloxymethyl-2-{6-[2-(3-methyl-ureido)-phenyl]-3,4-dihydro-1H-isoquinolin-2-yl}-2-oxo-ethylcarbamoyl)-1-methyl-ethyl]-carbamic acid tert-butyl ester According to General Procedure A, 130 mg (0.28 mmol) of 7J and 58 mg (0.28 mmol) of N-t-BOC-α-methylalanine were coupled and the resulting product was purified by silica gel chromatography (75:25 v/v EtOAc:hexanes) to give 142 mg of 7K as a foam.

L. 2-Amino-N-(1-(R)-benzyloxymethyl-2-{6-[2-(3-methyl-ureido)-phenyl]-3,4-dihydro-1H-isoquinolin-2-yl}-2-oxo-ethyl)-isobutyramide According to General Procedure B, 142 mg (0.22 mmol) of 7K was deprotected to give 96 mg of the title compound as a white foam.

$^1$H NMR (CDCl$_3$ 300 MHz) δ 8.32 (m,1H), 7.86 (m,1H), 7.01–7.45 (m, 12H), 6.10–6.33 (m,1H), 5.09–5.27 (m,1H), 4.43–4.84 (m, 5H), 3.60–3.85 (m, 3H), 2.62–2.96 (m, 5H), 1.32 (bs, 6H). MS (Cl, NH$_3$) 544 (MH$^+$)

EXAMPLE 8

(R)-N-[3-(2-{1-[2-(2-Amino-2-methyl-propionylamino)-3-benzyloxy-propionyl]-piperidin-4-yl}-ethyl)-benzo[d]isoxazol-6-yl]-benzamide A. N-[3-(2-Piperidin-4-yl-ethyl)-benzo[d]isoxazol-6-yl]-benzamide 4-[2-(6-Benzoylamino-benzo[d]isoxazol-3-yl)-ethyl]-piperidine-1-carboxylic acid tert-butyl ester was prepared as described by Villabolos et al., in J. Med. Chem. 1994 37 p2721–24 (example 2h). According to General Procedure B, 200 mg (0.44 mmol) of this material was then deprotected to give 8A in quantitative yield.

B. [1-(2-{4-[2-(6-Benzoylamino-benzo[d]isoxazol-3-yl)-ethyl]-piperidin-1-yl}-1-(R)-benzyloxymethyl-2-oxo-ethylcarbamoyl)-1-methyl-ethyl]-carbamic acid tert-butyl ester Following the method outlined in General Procedure A, 55 mg (0.16 mmol) of 8A and 60 mg (0.16 mmol) of 3 were coupled and the product was purified by silica gel chromatography (60:40 v/v ethyl acetate:hexanes) to give 8B as a foam.

C. (R)-N-[3-(2-{1-[2-(2-Amino-2-methyl-propionylamino)-3-benzyloxy-propionyl]-piperidin-4-yl}-ethyl)-benzo[d]isoxazol-6-yl]-benzamide According to General Procedure B, 29 mg (0.04 mmol) of 8B was deprotected to give 20 mg of the title compound as a foam.

$^1$H NMR (CDCl$_3$ 250 MHz) (1:1 mixture of rotamers) δ 8.19–8.31 (m, 2H), 8.09 (m, 1H), 7.93 (d, 2H) 7.38–7.52 (m, 5H), 7.20–7.38 (m, 4H), 5.01–5.16 (m, 1H), 4.54–4.67 (m,1H), 4.42–4.53 (q, 2H), 3.90–4.03 (m,1H), 3.54–3.68 (m, 2H), 2.84–3.01 (m, 3H), 2.37–2.70 (m, 6H), 1.49–1.88 (m, 5H), 1.40 (s, 6H).

EXAMPLE 9

N-[2-(7-Acetylamino-3,4-dihydro-1H-isoquinolin-2-yl)-1-(R)-benzyloxymethyl-2-oxo-ethyl]-2-amino-isobutyramide A. (1-[2-(7-Acetylamino-3,4-dihydro-1H-isoquinolin-2-yl)-1-(R)-benzyloxymethyl-2-oxo-ethylcarbamoyl]-1-methyl-ethyl}-carbamic acid tert-butyl ester To a mixture of 75 mg (0.15 mmol) of 6C, and 36 mg (0.44 mmol) of sodium acetate in 2 mL of methylene chloride was added 12 mL (0.16 mmol) of methanesulfonyl chloride and the resulting mixture was stirred overnight at 24° C. The mixture was diluted with 20 mL of ethyl acetate, and washed three times with 1 N NaOH, and once each with 1 N HCl and brine. The solution was dried over MgSO$_4$ and concentrated to give 52 mg of 9A as a clear oil.

B. N-[2-(7-Acetylamino-3,4-dihydro-1H-isoquinolin-2-yl)-1-(R)-benzyloxymethyl-2-oxo-ethyl]-2-amino-isobutyramide According to General Procedure B, 52 mg (0.091 mmol) of 9A was deprotected and 26 mg of the title compound was obtained as a clear oil.

$^1$H NMR (CDCl$_3$ 250 MHz) (2:1 mixture of rotamers) δ 8.33 (d, 1H), 7.65 (s, 0.67H), 7.56 (s, 0.33H), 7.15–7.38 (m, 7H), 6.99–7.19 (m, 1H), 5.10–5.23 (m, 1H), 4.65–4.72 (m, 2H), 4.42–4.50 (m, 2H), 3.55–3.87 (m, 5H), 2.65–2.82 (m, 2H), 2.16 (s, 3H), 1.34 (s, 6H).
MS (Cl, NH$_3$) 453 (MH$^+$)

EXAMPLE 10

2-Amino-N-1-(R)-benzyloxymethyl-2-oxo-2-[4-(2-oxo-1,4-dihydro-2H-quinazolin-3-yl)-piperidin-1-yl]-ethyl}-isobutyramide Hydrochloride A. (1-{1-(R)-Benzyloxymethyl-2-oxo-2-[4-(2-oxo-1,4-dihydro-2H-quinazolin-3-yl)-piperidin-1-yl]-ethylcarbamoyl}-1-methyl-ethyl)-carbamic acid tert-butyl ester Following the method outlined in General Procedure A, 14 mg (0.052 mmol) of 3,4-Dihydro-1H-quinazolin-2-one and 21 mg (0.055 mmol) of 3 were coupled and the product was purified by silica gel chromatography (99:0.75 v/v CHCl$_3$:MeOH) to give 27 mg of 10A as a clear oil.

B. 2-Amino-N-{1-(R)-benzyloxymethyl-2-oxo-2-[4-(2-oxo-1,4-dihydro-2H-quinazolin-3-yl)-piperidin-1-yl]-ethyl}-isobutyramide hydrochloride According to General Procedure C, 27 mg (0.045 mmol) of 10A was deprotected to give 21 mg of the title compound as a yellow solid.

$^1$H NMR (CD$_3$OD 250 MHz) δ 7.20–7.41 (m, 6H), 7.03–7.20 (m, 2H), 6.73–7.01 (m, 1H), 5.11–5.22 (m, 1H), 3.98–4.79 (m, 8H), 3.70–3.84 (m, 2H), 3.10–3.26 (m, 1H), 2.61–2.90 (m, 1H), 1.85–2.32 (m, 2H), 1.55–1.78 (m, 9H).
MS (Cl, NH$_3$) 494 (MH$^+$)

EXAMPLE 11

2-Amino-N-{1-(R)-benzyloxymethyl-2-[6-(2-methanesulfonylamino-phenyl)-3,4-dihydro-1H-isoquinolin-2-yl]-2-oxo-ethyl]-isobutyramide Hydrochloride A. 6-(2-Methanesulfonylamino-phenyl)-3,4-dihydro-1H-isoquinoline-2-carboxylic acid benzyl ester To 249 mg (0.695 mmol) of 7F and 84 mg (0.083 mmol) of triethylamine in 3.5 mL of methylene chloride was added 87 mg (0.765 mmol) of methanesulfonyl chloride and the mixture stirred overnight at 24° C. An additional 16 mg of triethylamine and 18 mg of methanesulfonyl chloride were added, and the mixture stirred for an additional 6 h. The reaction mixture was poured into an aqueous sodium bicarbonate solution, and the product extracted twice with methylene chloride. The combined organics were dried over Na$_2$SO$_4$ and concentrated. The product was purified by silica gel chromatography (2:1 v/v hexanes:EtOAc) to give 291 mg of 11A as an oil.

B. N-[2-(1,2,3,4-Tetrahydro-isoquinolin-6-yl)-phenyl]-methanesulfonamide

A mixture of 280 mg (0.642 mmol) of 11A and 160 mg of 10% palladium on carbon in 20 mL of ethanol was hydrogenated at 50 psi for 2 h. An additional 100 mg of catalyst was added and the hydrogenation continued for an additional 1.5 h. The catalyst was removed by filtration through celite, and the solution concentrated to give 120 mg of a white solid which was recrystallized from methanol/hexane to give 61 mg of 11B as a white solid.

C. (1-{1-(R)-Benzyloxymethyl-2-[6-(2-methanesulfonylamino-phenyl)-3,4-dihydro-1H-isoquinolin-2-yl]-2-oxo-ethylcarbamoyl}-1-methyl-ethyl)-carbamic acid tert-butyl ester According to the method outlined in General Procedure A, 55 mg (0.18 mmol) of 11B, and 68 mg (0.18 mmol) of 3 were coupled and the product was purified by silica gel chromatography (1:1 v/v hexanes:ethyl acetate) to give 15 mg of 11C as a foam.

D. 2-Amino-N-{1-(R)-benzyloxymethyl-2-[6-(2-methanesulfonylamino-phenyl)-3,4-dihydro-1H-isoquinolin-2-yl]-2-oxo-ethyl}-isobutyramide hydrochloride According to General Procedure C, 15 mg (0.02 mmol) of 11C was deprotected to give 10 mg of the title compound as a white solid.

$^1$H NMR (CD$_3$OD 250 MHz) (1:1 mixture of rotamers) δ 8.28 (d, 1H), 7.14–7.52 (m, 12H), 5.14–5.37 (m, 1H), 4.69–4.82 (m, 3H), 4.46–4.56 (m, 2H), 3.70–3.93 (m, 4H), 2.75–3.06 (m, 2H), 2.72 (s, 3H), 1.52 (bs, 6H).
MS (Cl, NH$_3$) 565 (MH$^+$)

EXAMPLE 12

2-Amino-N-1-(R)-benzyloxymethyl-2-oxo-2-[4-(phenyl-propionyl-amino)-piperidin-1-yl]-ethyl}-isobutyramide Hydrochloride A. (1-{1-(R)-Benzyloxymethyl-2-oxo-2-[4-(phenyl-propionyl-amino)-piperidin-1-yl]-ethylcarbamoyl}-1-methyl-ethyl)-carbamic acid tert-butyl ester According to the method outlined in General Procedure A, 30 mg (0.13 mmol) of 4-(N-propionylanilino)-piperidine and 48 mg (0.13 mmol) of 3 were coupled and the product was purified by silica gel chromatography (1:1 v/v hexanes:ethyl acetate) to give 67 mg of 12A as an oil.

B. 2-Amino-N-{1-(R)-benzyloxymethyl-2-oxo-2-[4-(phenyl-propionyl-amino)-piperidin-1-yl]-ethyl}-isobutyramide hydrochloride According to General Procedure C, 67 mg (0.11 mmol) of 12A was deprotected to give 50 mg of the title compound as a white solid.

$^1$H NMR (CD$_3$OD 250 MHz) δ 7.11–7.47 (m, 12H), 5.00–5.10 (m, 1H), 4.63–4.81 (m, 2H), 4.49–4.62 (m, 2H), 4.27–4.38 (m, 1H), 3.94–4.21 (m,1H), 3.45–3.68 (m, 2H), 2.99–3.23 (m, 1H), 2.62–2.80 (m, 1H), 1.81–2.00 (m, 4H), 1.52 (s, 6H), 1.07–1.38 (m, 3H), 0.97 (t, 3H).
MS (Cl, NH$_3$) 495 (MH$^+$)

EXAMPLE 13

(R)-N-{2-[2-(2-Amino-2-methyl-propionylamino)-3-(1H-indol-3-yl)-propionyl]-2,3-dihydro-1H-isoindol-5-yl}-benzamide Hydrochloride A. (R)-{1-[1-(5-Amino-1,3-dihydro-isoindole-2-carbonyl)-2-(1H-indol-3-yl)-ethylcarbamoyl]-1-methyl-ethyl}-carbamic acid tert-butyl ester According to General Procedure A, 330 mg (2.46 mmol) of 43C and 960 mg (2.46 mmol) of 4C were coupled and 1.10 g of 13A was recovered as a yellow solid.

B. (R)-{1-[1-(5-Benzoylamino-1,3-dihydro-isoindole-2-carbonyl)-2-(1H-indol-3-yl)-ethylcarbamoyl]-1-methyl-ethyl}-carbamic acid tert-butyl ester A mixture of 300 mg (0.59 mmol) of 13A, 98 mg (0.69 mmol) of benzoyl chloride and 85 mg (0.69 mmol) of 4-dimethylaminopyridine in 5 mL of methylene chloride was stirred overnight at room temperature. The mixture was diluted with chloroform and washed twice each with 10% hydrochloric acid, saturated aqueous sodium bicarbonate and brine. The solution was dried over MgSO$_4$ and concentrated and the product was purified by silica gel chromatography using a gradient of 75% ethyl acetate in hexane to 100% ethyl acetate to give 60 mg of 13B as a white solid.

C. (R)-N-{2-[2-(2-Amino-2-methyl-propionylamino)-3-(1H-indol-3-yl)-propionyl]-2,3-dihydro-1H-isoindol-5-yl}-benzamide hydrochloride To 60 mg (0.10 mmol) of 13B in 2 mL of ethanol was added 2 mL of concentrated hydrochloric acid, and the mixture was stirred at room temperature for 1 h. The mixture was concentrated and dissolved in a trace amount of methanol. Methylene chloride was added until the product precipitated from solution giving 50 mg of 13C as a white solid.

$^1$H NMR (CD$_3$OD, 250 MHz) δ 10.12 (d, 1H), 8.45 (d, 1H), 7.93 (d, 2H), 7.49–7.72 (m, 7H), 7.04–7.35 (m, 5H), 4.98–5.08 (m, 1H), 4.65–4.81 (m, 1H), 4.46–4.60 (m, 1H), 3.34–3.52 (m, 2H), 1.62 (s, 6H).
LSIMS-MS 533 (M$^+$Na)

EXAMPLE 14

N-{2-[4-(Acetylamino-methyl)-4-phenyl-piperidin-1-yl]-1-(R)-benzyloxymethyl-2-oxo-ethyl}-2-amino-isobutyramide A. (1-{2-[4-(Acetylamino-methyl)-4-phenyl-piperidin-1-yl]-1-(R)-benzyloxymethyl-2-oxo-ethylcarbamoyl}-1-methyl-ethyl)-carbamic acid tert-butyl ester According to the method outlined in General Procedure A, 46 mg (0.21 mmol) of N-(4-Phenyl-piperidin-4-ylmethyl)-acetamide and 85 mg (0.22 mmol) of 3 were coupled, and the product was purified by silica gel chromatography (95:5 v/v chloroform:methanol) to give 111 mg of 14A as a clear oil.

B. N-{2-[4-(Acetylamino-methyl)-4-phenyl-piperidin-1-yl]-1(R)-benzyloxymethyl-2-oxo-ethyl}-2-amino-isobutyramide According to General Procedure B, 110 mg (0.18 mmol) of 14A was deprotected to give 72 mg of the title compound as a white foam.

$^1$H NMR (CDCl$_3$ 250 MHz) (1:1 mixture of rotamers) δ 7.16–7.40 (m, 10H), 5.92–6.03 (t, 0.5H), 5.61–5.68 (t, 0.5H), 4.93–5.04 (m,1H), 4.43–4.58 (q, 1H), 4.30–4.43 (q, 1H), 3.84–4.03 (m, 1H), 3.46–3.78 (m, 3H), 3.00–3.42 (m, 6H), 1.87–2.17 (m, 2H), 1.83 (d, 3H), 1.61–1.82 (m, 1H), 1.28 (d, 3H), 1.24 (d, 3H).
MS (Cl, NH$_3$) 495 (MH$^+$)

EXAMPLE 15

(R)-N -{2-[2-(2-Amino-2-methyl -propionylamino)-3-benzyloxy-propionyl]-1,2,3,4-tetrahydro-isoquinolin-7-yl}-benzamide Hydrochloride A. {1-[2-(7-Benzoylamino-3,4-dihydro-1H-isoquinolin-2-yl)-1-(R)-benzyloxymethyl-2-oxo-ethylcarbamoyl]-1-methyl-ethyl}-carbamic acid tert-butyl ester To a mixture of 50 mg (0.10 mmol) of 6C in 1 mL of methylene chloride was added 14 mg (0.14 mmol) of triethylamine. The mixture was cooled to 0° C., and 17 mg (0.12 mmol) of benzoyl chloride was added. The stirring mixture was allowed to warm to room temperature over 1.5 h, and the mixture was then poured into a saturated solution of sodium bicarbonate and extracted with ethyl acetate. The organic phase was washed once with brine, dried over Na$_2$SO$_4$ and concentrated. The product was purified by silica gel chromatography using 100% chloroform followed by 5% methanol in chloroform to elute. Recovered 48 mg of 15A as a foam.

B. (R)-N-{2-[2-(2-Amino-2-methyl-propionylamino)-3-benzyloxy-propionyl]-1,2,3,4-tetrahydro-isoquinolin-7-yl}-benzamide hydrochloride According to General Procedure C, 48 mg (0.08 mmol) of 15A was deprotected, to give 44 mg of the title compound as a white solid.

$^1$H NMR (CD$_3$OD 250 MHz) δ 7.78–7.92 (m, 2H), 7.41–7.22 (m, 5H), 7.04–7.38 (m, 8H), 5.22–5.40 (m, 1H), 4.41–4.72 (m, 4H), 3.62–3.90 (m, 5H), 2.71–2.90 (m, 2H), 1.60 (bs, 6H).
MS (Cl, NH$_3$) 515 (MH$^+$)

EXAMPLE 16

2-Amino-N-{1-(R)-benzyloxymethyl-2-[4-(1,3-dioxo-1,3-dihydro-isoindol-2-ylmethyl)-piperidin-1-yl]-2-oxo-ethyl}-isobutyramide A. 2-Piperidin-4-ylmethyl-isoindole-1,3-dione hydrochloride To a mixture of 148.0 g (1.0 mol) of phthalic anhydride and 15 mL of triethylamine in 1.5 L of xylene was slowly added 108.0 g (1.0 mol) of 4-(Aminomethyl)pyridine with mechanical stirring. The resulting solid was collected by filtration. The N-Pyridin-4-ylmethyl-phthalamic acid was then cyclized, by heating 235 g (0.88 mol) to the melt stage for 15 min. The mixture was allowed to cool slightly and 2.5 L of ethanol was added to the warm reaction mixture, and the solution filtered. Upon cooling, the mixture crystallized to give 188.0 g of 2-Pyridin-4-ylmethyl-isoindole-1,3-dione (m.p. 166–167.5° C.). A mixture of 23.8 g (0.1 mol) of 2-Pyridin-4-ylmethyl-isoindole-1,3-dione and 1.3 g of platinum oxide in 400 mL of methanolic HCl was reduced at 50 psi until no starting material could be detected by TLC. The mixture was filtered through celite and concentrated to give 22.0 g of 2-Piperidin-4-ylmethyl-isoindole-1,3-dione hydrochloride as a white solid. A small sample was recrystallized from ethanol to give an analytically pure sample of 16A (m.p. 241–242.5° C.).

B. (1-{1-(R)-Benzyloxymethyl-2-[4-(1,3-dioxo-1,3-dihydro-isoindol-2-ylmethyl)-piperidin-1-yl]-2-oxo-ethylcarbamoyl}-1-methyl-ethyl)-carbamic acid tert-butyl ester According to the method outlined in General Procedure A, 83 mg (0.21 mmol) of 3 and 53 mg (0.21 mmol) of 2-Piperidin-4-ylmethyl-isoindole-1,3-dione hydrochloride were coupled, and the product was purified by silica gel chromatography (95:5 v/v chloroform:methanol) to give 14 mg of 16B as a clear oil.

C. 2-Amino-N-{1-(R)-benzyloxymethyl-2-[4-(1,3-dioxo-1,3-dihydro-isoindol-2-ylmethyl)-piperidin-1-yl]-2-oxo-ethyl}-isobutyramide According to General Procedure B, 10 mg (0.016 mmol) of 16B was deprotected to give 7 mg of the title compound as a clear oil.

$^1$H NMR (CD$_3$OD 250 MHz) (1:1 mixture of rotamers) δ 7.75–7.89 (m, 4H), 7.20–7.39 (m, 6H), 4.98–5.09 (m,1H), 4.41–4.59 (m, 4H), 3.94–4.07 (m,1H), 3.60–3.78 (m, 2H), 3.57–3.60 (d, 1H), 2.96–3.12 (m, 1H), 2.57–2.74 (m, 1H), 2.00–2.12 (bm, 1H), 1.60–1.78 (m, 2H), 1.26–1.37 (m, 8H). MS (Cl, NH$_3$) 507 (MH$^+$)

EXAMPLE 17

2-Amino-N-{1-(R)-benzyloxymethyl-2-[4-(morpholine-4-carbonyl)-4-phenyl-piperidin-1-yl]-2-oxo-ethyl}-isobutyramide A. (1-{1-(R)-Benzyloxymethyl-2-[4-(morpholine-4-carbonyl)-4-phenyl-piperidin-1-yl]-2-oxo-ethylcarbamoyl}-1-methyl-ethyl)-carbamic acid tert-butyl ester According to General Procedure A, 26 mg (0.068 mmol) of Morpholin-4-yl-(4-phenyl-piperidin-4-yl)-methanone hydrochloride and 20 mg (0.065 mmol) of 3 were coupled and the product was purified by silica gel chromatography (99:1 v/v chloroform:methanol) to give 42 mg of 17A as a clear oil.

B. 2-Amino-N-{1-(R)-benzyloxymethyl-2-[4-(morpholine-4-carbonyl)-4-phenyl-piperidin-1-yl]-2-oxo-ethyl}-isobutyramide According to General Procedure B, 42 mg (0.66 mmol) of 17A was deprotected to give 27 mg of the title compound as a clear oil.

$^1$H NMR (CDCl$_3$ 250 MHz) δ 7.13–7.39 (m, 10H), 6.97–7.02 (d, 1H), 5.00–5.12 (m, 1H), 4.38–4.52 (m, 3H), 3.82–4.00 (m, 1H), 3.51–3.67 (m, 3H), 2.96–3.50 (m, 9H), 2.20–2.34 (m,1H), 1.57–2.11 (bm, 3H), 1.29 (s, 6H). MS (Cl, NH$_3$) 537 (MH$^+$)

EXAMPLE 18

(R)-1'-[2-(2-Amino-2-methyl-propionylamino)-3-benzyloxy-propionyl]-[1,4']bipiperidinyl-4'-carboxylic Acid Amide Hydrochloride A. {1-[1-(R)-Benzyloxymethyl-2-(4'-carbamoyl-[1,4']bipiperidinyl-1'-yl)-2-oxo-ethylcarbamoyl]-1-methyl-ethyl}-carbamic acid tert-butyl ester According to the method outlined in General Procedure A, 21 mg (0.055 mmol) of 3 and 11 mg (0.052 mmol) of 4-carbamyl-4-piperidinopiperidine were coupled and the product was purified by silica gel chromatography (99:0.75 v/v chloroform:methanol) to give 25 mg of 18A as a glass.

B. (R)-1'-[2-(2-Amino-2-methyl-propionylamino)-3-benzyloxy-propionyl]-[1,4']bipiperidinyl-4'-carboxylic acid amide hydrochloride According to General Procedure C, 25 mg (0.044 mmol) of 18A was deprotected to give 19 mg of the title compound as a white solid.

$^1$H NMR (CD$_3$OD 250 MHz) (1:1 mixture of rotamers) δ 8.32 (d, 0.5H), 8.27 (d, 0.5H), 7.26–7.42 (m, 5H), 5.06–5.19 (m, 1H), 4.48–4.70 (m, 3H), 4.21–4.34 (m, 1H), 3.64–3.79 (m, 3H), 3.38–3.50 (m, 1H), 2.91 3.18 (m, 2H), 2.48–2.91 (m, 4H), 1.76–2.12 (m, 8H), 1.57 (s, 6H). MS (Cl, NH$_3$) 474 (MH$^+$)

EXAMPLE 19

(R)-2-Amino-N-[2-(5-diphenylacetylamino-1,3-dihydro-isoindol-2-yl)-1-(1H-indol-3-ylmethyl)-2-oxo-ethyl]-isobutyramide Hydrochloride A. (R)-{1-[2-(5-Diphenylacetylamino-1,3-dihydro-isoindol-2-yl)-1-(1H-indol-3-ylmethyl)-2-oxo-ethylcarbamoyl]-1-methyl-ethyl}-carbamic acid A mixture of 300 mg (0.59 mmol) of 13A, 160 mg (0.68 mmol) of diphenylacetylchloride and 83 mg (0.68 mmol) of 4-dimethylaminopyridine in 5 mL of methylene chloride was stirred overnight at room temperature. The mixture was diluted with chloroform and washed twice each with 10% hydrochloric acid, saturated aqueous sodium bicarbonate and brine. The solution was dried over MgSO$_4$ and concentrated. The product was purified by silica gel chromatography using a gradient of 75% ethyl acetate in hexane to 100% ethyl acetate to give 150 mg of 19A as a white solid.

B. (R)-2-Amino-N-[2-(5-diphenylacetylamino-1,3-dihydro-isoindol-2-yl)-1-(1H-indol-3-ylmethyl)-2-oxo-ethyl]-isobutyramide hydrochloride To 150 mg (0.20 mmol) of 19B in 2 mL of ethanol was added 2 mL of concentrated hydrochloric acid, and the mixture was stirred at room temperature for 1 h. The mixture was concentrated to give 140 mg of the title compound as a white solid.

$^1$H NMR (CD$_3$OD, 300 MHz) (mixture rotamers) δ 7.60 (d, 1H), 7.52 (s, 0.5H), 7.41 (s, 0.5H), 7.21–7.34 (m, 12H), 6.93–7.13 (m, 4H), 5.13 (s, 1H), 4.92–5.00 (m, 1H), 4.06–4.18 (m, 1H), 4.40–4.51 (m, 1H), 4.01–4.19 (m, 2H), 3.20–3.42 (m, 2H), 1.59 (s, 3H), 1.51 (s, 3H). MS (Cl, NH$_3$) 600 (MH$^+$)

EXAMPLE 20

(R)-2-Amino-N-{2-(1H-indol-3-yl)-1-[6-(toluene-4-sulfonylamino)-3,4-dihydro-1H-isoquinoline-2-carbonyl]-ethyl}-isobutyramide Hydrochloride A. 6-(Toluene-4-sulfonylamino)-3,4-dihydro-1H-isoquinoline-2-carboxylic acid tert butyl ester To a mixture of 275 mg (1.10 mmol) of 6-amino-3,4-dihydro-1H-isoquinoline-2-carboxylic acid tert-butyl ester, 134 mg (1.33 mmol) of triethylamine in 6 mL of methylene chloride at 00C was added 233 mg (1.2 mmol) of toluenesulfonyl chloride in one portion. The mixture was allowed to warm to room temperature and was stirred overnight. An additional 62 mg (0.61 mmol) of triethylamine and 105 mg (0.55 mmol) of toluenesulfonylchloride was added and stirring was continued for an additional 4 h. The mixture was concentrated and the residue dissolved in ethyl acetate. The organic portion was washed twice each with 1 N NaOH and brine, dried over Na$_2$SO$_4$ and the product was purified by silica gel chromatography (1:3 v/v ethyl acetate:hexane) to give 274 mg of 20A as a foam.

B. 4-Methyl-N-(1,2,3,4-tetrahydro-isoquinolin-6-yl)-benzenesulfonamide

According to General Procedure B, 253 mg (0.63 mmol) of 20A was deprotected to give 175 mg of 20B as a foam.

C. (R)-(1-{2-(1H-Indol-3-yl)-1-[6-(toluene-4-sulfonylamino)-3,4-dihydro-1H-isoquinoline-2-carbonyl]-ethylcarbamoyl}-1-methyl-ethyl)-carbamic acid tert-butyl ester According to General Procedure A, 84 mg (0.278 mmol) of 20B was coupled to 108 mg (0.278 mmol) of 4C and the product was purified by silica gel chromatography (70:30 v/v ethyl acetate:hexane) to give 114 mg of 20C.

D. (R)-2-Amino-N-{2-(1H-indol-3-yl)-1-[6-(toluene-4-sulfonylamino)-3,4-dihydro-1H-isoquinoline-2-carbonyl]-ethyl}-isobutyramide hydrochloride According to General Procedure C, 114 mg (0.17 mmol) of 20C was deprotected to give 68 mg of the title compound as a solid.

$^1$H NMR (CDCl$_3$ 250 MHz) (mixture of rotamers) δ 8.41 (d, 0.5H), 8.33 (d, 0.5H), 8.15 (bs 0.5H), 7.75 (d, 2H), 7.67 (d, 2H), 7.53 (bs, 0.5H), 6.51–7.31 (m, 8.5H), 6.07 (d, 0.5H), 5.13–5.32 (m, 1H), 4.38–4.61 (q, 1H), 4.04–4.19 (m, 1H), 3.77–4.04 (m, 1H), 2.98–3.44 (m, 3H), 2.46–2.62 (m, 5H), 1.30 (bs, 6H).

EXAMPLE 21

(R)-Piperidine-4-carboxylic acid {1-benzyl-2-oxo-2-[4-(2-phenyl-benzoimidazol-1-yl)-piperidin-1-yl]-ethyl}-amide Hydrochloride A. (R)-4-(1-Carboxy-2-phenyl-ethylcarbamoyl)-piperidine-1-carboxylic acid tert-butyl ester A mixture of 1.00 g (6.05 mmol) of D-phenylalanine, 1.98 g (6.05 mmol) of 77A and 1.84 g (18.2 mmol) of triethylamine in 10 mL of water and 40 mL of dioxane was stirred at room temperature for 15 h. The mixture was diluted with chloroform and acidified to pH 4 with acetic acid. The layers were separated and the organic portion was washed three times with brine, dried over $MgSO_4$ and concentrated to give 2.16 g of 21A as a white solid.

B. (R)-4-{1-Benzyl-2-oxo-2-[4-(2-phenyl-benzoimidazol-1-yl)-piperidin-1-yl]-ethylcarbamoyl}-piperidine-1-carboxylic acid tert-butyl ester According to General Procedure A, 80 mg (0.29 mmol) of 50D and 109 mg of 96A were coupled and the product was purified by silica gel chromatography (75:25 v/v ethyl acetate:hexanes) to give 140 mg of 21 B.

C. (R)-Piperidine-4-carboxylic acid {1-benzyl-2-oxo-2-[4-(2-phenyl-benzoimidazol-1-yl)-piperidin-1-yl]-ethyl}-amide hydrochloride To a solution of 140 mg (0.22 mmol) of 21 B in 5 mL of ethanol was added 5 mL of concentrated HCl and the mixture was stirred at room temperature for 1 h. The mixture was concentrated and the residue crystallized from methanol/ethyl acetate to give 107 mg of the title compound as a white solid.

$^1$H NMR (CD$_3$OD, 300 MHz) (mixture of rotamers) (partial) δ 8.32 (m, 0.5H), 7.66–7.89 (m, 8.5H), 7.19–7.40 (m, 5H), 5.13–5.21 (m, 0.33H), 5.02–5.10 (m, 0.67H), 4.15–4.27 (m, 0.33H), 4.03–4.14 (m, 0.67H).
MS (Cl, NH$_3$) 536 (MH$^+$)

EXAMPLE 22

N-[2-(4-Acetyl-4-phenyl-piperidin-1-yl)-1-(R)-benzyloxymethyl-2-oxo-ethyl]-2-amino-isobutyramide Hydrochloride According to General Procedure A, 3.15 mg (13.1 mmol) of 4-acetyl-4-phenylpiperidine hydrochloride and 5.0 mg (13.1 mmol) of 3 were coupled to give {1-[2-(4-Acetyl-4-phenyl-piperidin-1-yl)-1-(R)-benzyloxymethyl-2-oxo-ethylcarbamoyl]-1-methyl-ethyl}-carbamic acid tert-butyl ester. The crude product was deprotected according to General Procedure C to give 5.09 mg of the title compound.
MS (Cl, NH$_3$) 508 (MH$^+$)

EXAMPLE 23

(R)-1-[2-(2-Amino-2-methyl-propionylamino)-3-benzyloxy-propionyl]-4-phenyl-piperidine-4-carboxylic Acid Ethyl Ester Hydrochloride A. 4-Phenyl-piperidine-4-carboxylic acid ethyl ester hydrochloride A mixture of 10.0 g (45 mmol) 4-cyano-4-phenylpiperidine hydrochloride, 10 g of sulfuric acid and 2.5 mL of water was heated at 150° C. for 1 h. The mixture was allowed to cool to 110° C. and 10 mL of ethanol was added. The ethanol was then distilled off. This ethanol addition/distillation was repeated four more times. Following the last addition, the mixture was heated to 125° C. cooled to room temperature and poured onto ice. The mixture was basified with 10% NaOH and extracted twice with ether. The organic extracts were dried over $MgSO_4$ and concentrated to give 2.3 g of a yellow oil. A solution of 2.0 g of the free base in 100 mL of ether was treated with an ether solution saturated with HCl. The white precipitate was filtered and recrystallized from EtOAc/hexanes to give 1.73 g of 23A.

B. (R)-1-[2-(2-Amino-2-methyl-propionylamino)-3-benzyloxy-propionyl]-4-phenyl-piperidine-4-carboxylic acid ethyl ester hydrochloride According to the method outlined in General Procedure A, 3.55 mg (13.1 mmol) of 23A and 5.0 mg (13.1 mmol) of 3 were coupled to give 1-[3-benzyloxy-2-(2-tert-butoxycarbonylamino-2-methyl-propionylamino)-propionyl]-4-phenyl-piperidine-4-carboxylic acid ethyl ester. The crude product was then deprotected according to General Procedure C to give 6.97 mg of the title compound as a solid.
MS (Cl, NH$_3$) 496 (MH$^+$)

EXAMPLE 24

2-Amino-N-{1-(R)-benzyloxymethyl-2-[4-hydroxy-4-(4-trifluoromethyl-phenyl)-piperidin-1-yl]-2-oxo-ethyl}-isobutyramide Hydrochloride A. 4-Oxo-piperidine-1-carboxylic acid benzyl ester To a mixture of 50.0 g (0.325mol) of 4-piperidone hydrate hydrochloride and 181.9 g (1.82mol) of potassium bicarbonate in 750 mL of EtOAc and 75 mL of water, was added 49 mL (0.343mol) of benzyl chloroformate over 10 min. with stirring. The mixture was stirred at 24° C. for 2.5 h and then diluted with water. The layers were separated, and the aqueous portion extracted with 500 mL of ethyl acetate. The combined organic extracts were washed once each with water and brine, dried over $MgSO_4$ and concentrated to give 81.41 g of 24A as a yellow oil. The crude product was used without further purification.

B. 4-Hydroxy-4-trifluoromethyl-phenyl-piperidine-1-carboxylic acid benzyl ester

To 1.25 g (51.4 mmol) of magnesium in 10 mL of ether was added a solution of 4-bromobenzotrifluoride in 10 mL of ether. The reaction initiated soon after the addition was complete. The mixture was stirred for 1.5 h at 24° C. and then cooled to 0° C. A solution of 10.0 g (42.87 mmol) of 24A in 50 mL of ether was added and the mixture allowed to warm to room temperature and was stirred for 17 h. The reaction mixture was quenched by adding 150 mL of saturated aqueous ammonium chloride. The organic layer was separated and the aqueous phase was extracted with ether. The combined organic extracts were washed once each with water and brine, dried over $MgSO_4$ and concentrated. The crude material was purified by silica gel chromatography (3:7 v/v EtO Ac:hexanes) to give 12.48 g of 24B as an orange oil which solidified on standing.

C. 4-(4-Trifluoromethyl-phenyl)-piperidin-4-ol

To 12.3 g (32.4 mmol) of 24B in 150 mL of ethanol was added 1.4 g of 10% palladium on carbon. The mixture was hydrogenated on a Parr shaker at 48 psi for 2.5 h. The solution was filtered through celite and concentrated. The resulting solid was triturated with ether/hexane to give 4.98 g of 24C as a white solid.

D. 2-Amino-N-{1-(R)-benzyloxymethyl-2-[4-hydroxy-4-(4-trifluoromethyl-phenyl)-piperidin-1-yl]-2-oxo-ethyl}-isobutyramide hydrochloride According to General Procedure A, 3.22 mg (13.1 mmol) of 24C, and 5 mg (13.1 mmol) of 3 were coupled to give (1-{1-(R)-Benzyloxymethyl-2-[4-hydroxy-4-(4-trifluoromethyl-phenyl)-piperidin-1-yl]-2-oxo-ethylcarbamoyl}-1-methyl-ethyl)-carbamic acid tert-butyl ester. The crude product was deprotected according to General Procedure C to give 7.35 mg of the title compound. MS (Cl, NH$_3$) 466 (MH$^+$)

EXAMPLE 25

(R)-1-[2-(2-Amino-2-methyl-propionylamino)-3-benzyloxy-propionyl]-piperidine-4-carboxylic Acid Cyclohexylamide Hydrochloride A. Piperidine-1,4-dicarboxylic acid monobenzyl ester To a slurry of 66.4 g (0.50 mol) of isonipecotic acid, and 145 mL (0.50 mol) of triethylamine in 600 mL of methylene chloride was added a solution of 72 mL (0.50 mol) of benzyl chloroformate in 200 mL of toluene at 10° C. The slurry was allowed to warm to room temperature and after stirring for 17 h was treated with 1 L of a 10% aqueous sodium carbonate solution. The layers were separated, and the aqueous portion was extracted once with ether and then acidified to pH 3. The aqueous portion was then extracted with methylene chloride. The organic extract was washed with brine, dried over MgSO$_4$ and concentrated to give 35.2 g of the title compound as an oil which was used without further purification.

B. 4-Cyclohexylcarbamoyl-piperidine-1-carboxylic acid benzyl ester

To 3.82 g (14.3 mmol) of 25A was added 1.2 mL (15.7 mmol) of thionyl chloride in 50 mL of methylene chloride which contained 1 drop of DMF. The slurry was refluxed on a steam bath for 10 min. to give a clear solution. The mixture was concentrated, and the resulting oil was dissolved in 30 mL of THF and was added to a solution of 3.54 g (35.8 mmol) of cyclohexylamine in 20 mL of THF at 0° C. The mixture was stirred at 24° C. for 0.5 h and then filtered. The filtrate was concentrated and then dissolved in methylene chloride. The organic solution was washed once each with water, 1 N HCl, saturated aqueous sodium bicarbonate, and brine, dried over MgSO$_4$ and concentrated to give 3.46 g of 25B as a solid.

C. Piperidine-4-carboxylic acid cyclohexylamide

To 3.46 g (10 mmol) of 25B was added 30 mL of methanol, and the mixture refluxed in 20% NaOH for 8 h. The methanol was removed, and the aqueous phase extracted with methylene chloride. The aqueous solution was acidified to pH 5 with acetic acid and extracted with methylene chloride. The combined organic extracts were dried over MgSO$_4$ and concentrated to give 1.81 g of the title compound as an off-white solid.

D. (R)-1-[2-(2-Amino-2-methyl-propionylamino)-3-benzyloxy-propionyl]-piperidine-4-carboxylic acid cyclohexylamide hydrochloride According to General Procedure A, 2.76 mg (13.1 mmol) of 25C, and 5 mg (13.1 mmol) of 3 were coupled to give {1-[1-(R)-Benzyloxymethyl-2-(4-cyclohexylcarbamoyl-piperidin-1-yl)-2-oxo-ethylcarbamoyl]-1-methyl-ethyl}-carbamic acid tert-butyl ester. The crude product was deprotected according to General Procedure C to give 6.60 mg of the title compound.
MS (Cl, NH$_3$) 473 (MH$^+$)

EXAMPLE 26

(R)-2-[2-(2-Amino-2-methyl-propionylamino)-3-(1H-indol-3-yl)-propionyl]-1,2,3,4-tetrahydro-isoquinoline-6-carboxylic Acid Ethylamide Hydrochloride A. (R)-2-[2-(2-tert-Butoxycarbonylamino-2-methyl-propionylamino)-3-(1H-indol-3-yl )-propionyl]-1,2,3,4-tetrahydro-isoquinoline-6-carboxylic acid To 756 mg (1.35 mmol) of 5E in 10.8 mL of THF was added a solution of 97 mg (4.04 mmol) of lithium hydroxide in 2.7 mL of water. The mixture was stirred for 17 h at room temperature. The mixture was concentrated and dissolved in 100 mL of water. The aqueous solution was extracted twice with methylene chloride, acidified with acetic acid, and extracted twice with ethyl acetate. The ethyl acetate extracts were washed twice with brine, dried over Na$_2$SO$_4$ and concentrated to give 632 mg of 26A as a white solid.

B. (R)-{1-[1-(6-Ethylcarbamoyl-3,4-dihydro-1H-isoquinoline-2-carbonyl)-2-(1H-indol-3-yl)-ethylcarbamoyl]-1-methyl-ethyl}-carbamic acid According to General Procedure A, 60 mg (0.11 mmol) of 26A and 13.4 mg (0.16 mmol) of ethylamine hydrochloride were coupled and the product was purified by silica gel chromatography (100% ethyl acetate) to give 47 mg of 26B as a foam.

C. (R)-2-[2-(2-Amino-2-methyl-propionylamino)-3-(1H-indol-3-yl)-propionyl]-1,2,3,4-tetrahydro-isoquinoline-6-carboxylic acid ethylamide hydrochloride According to General Procedure C, 47 mg (0.081 mmol) of 26B was deprotected to give 39 mg of the title compound as a solid.

$^1$H NMR (CD$_3$OD 250 MHz) (mixture of rotamers) (partial) δ 8.32 (d, 1H), 7.53–7.64 (m, 1.5H), 7.40–7.50 (m, 1.5H), 7.30 (d, 0.5H), 6.91–7.18 (m, 4H), 6.61 (d, 0.5H), 5.14–5.32 (m, 1H), 4.63–4.74 (d, 0.5H), 4.39–4.54 (m, 1H), 4.07–4.18 (d, 0.5H), 3.80–3.91 (m, 0.5H), 3.54–3.16 (m, 0.5H), 1.57 (s, 6H), 1.06–1.27 (m, 3H).
MS (Cl, NH$_3$) 476 (MH$^+$)

EXAMPLE 27

(R)-2-[2-(2-Amino-2-methyl-propionylamino)-3-(1H-indol-3-yl)-propionyl]-1,2,3,4-tetrahydro-isoquinoline-6-carboxylic Acid Phenylamide Hydrochloride A. (R)-{1-[2-(1H-Indol-3-yl)-1-(6-phenylcarbamoyl-3,4-dihydro-1H-isoquinoline-2-carbonyl)-ethylcarbamoyl]-1-methyl-ethyl}-carbamic acid tert-butyl ester To 60 mg (0.11 mmol) of 26A in 0.6 mL of methylene chloride was added 11.4 mg (0.112 mmol) of triethylamine. The mixture was cooled to 0° C. and 13.5 mg (0.112 mmol) of pivaloyl chloride was added in one portion. The mixture was stirred for 1.5 h at 0° C. and then 10 mg (0.107 mmol) of aniline was added and the mixture was allowed to warm to room temperature and stirred for 17 h. The mixture was diluted with ethyl acetate and washed twice with 1 N NaOH and brine. The solution was dried over Na$_2$SO$_4$ and concentrated. The product was purified by silica gel chromatography (2:1 v/v ethyl acetate:hexanes) to give 39 mg of 27A as a foam.

B. (R)-2-[2-(2-Amino-2-methyl-propionylamino)-3-(1H-indol-3-yl)-propionyl]-1,2,3,4-tetrahydro-isoquinoline-6-carboxylic acid phenylamide hydrochloride According to the method outlined in General Procedure C, 37 mg (0.06 mmol) of 27A was deprotected to give 32 mg of the title compound as a solid.

$^1$H NMR (CD$_3$OD 250 MHz) (mixture of rotamers) (partial) δ 7.53–7.79 (m, 6H), 7.37–7.42 (m, 3H), 6.95–7.22 (m, 5.5H), 6.67 (d, 0.5H), 5.29–5.32 (m, 1H), 4.63–4.79 (m, 0.5H), 4.43–4.59 (m,1H), 4.09–4.19 (m, 0.5H), 3.78–3.92 (m, 0.5H), 3.39–3.63 (m, 2.5H), 1.59 (s, 6H).
MS (Cl, NH$_3$) 524 (MH$^+$)

EXAMPLE 28

(R)-2-[2-(2-Amino-2-methyl-propionylamino)-3-(1H-tetrahydro-isoquinoline-6-carboxylic Acid Hydrochloride A. (R)-2-[2-(2-Amino-2-methyl-propionylamino)-3-(1H-indol-3-yl)-propionyl]-1,2,3,4-tetrahydro-isoquinoline-6-carboxylic acid hydrochloride According to General Procedure C, 40 mg (0.073 mmol) of 26A was deprotected to give 25 mg of the title compound as a solid.

$^1$H NMR (CD$_3$OD 250 MHz) (mixture of rotamers) (partial) δ 7.78 (d, 0.5H), 7.52–7.68 (m, 2.5H), 7.39 (d, 0.5H), 7.23 (d, 0.5H), 6.95–7.19 (m, 3.5H), 6.58 (d, 0.5H), 5.17–5.31 (m, 1H), 4.63–4.74 (d, 0.5H), 4.42–4.53 (q, 1H), 4.09–4.20 (d,1H), 1.58 (s, 6H).

MS (Cl, NH$_3$) 449 (MH$^+$)

EXAMPLE 29

(R)-2-Amino-N-(2-(1H-indol-3-yl)-1-{6-[2-(3-methyl-ureido)-phenyl]-3,4-dihydro-1H-isoquinoline-2-carbonyl}-ethyl)-isobutyramide Hydrochloride A. (R)-[1-(2-(1H-Indol-3-yl)-1-{6-[2-(3-methyl-ureido)-phenyl]-3,4-dihydro-H-isoquinoline-2-carbonyl}-ethylcarbamoyl)-1-methyl-ethyl]-carbamic acid tert-butyl ester According to General Procedure A, 72 mg (0.26 mmol) of 7H and 100 mg (0.26 mmol) of 4C were coupled and the product was purified by silica gel chromatography using 100% chloroform, followed by 2% methanol in chloroform to give 130 mg of 29A as a foam.

B. (R)-2-Amino-N-(2-(1H-indol-3-yl)-1-{6-[2-(3-methyl-ureido)-phenyl]-3,4-dihydro-1H-isoquinoline-2-carbonyl}-ethyl)-isobutyramide hydrochloride According to General Procedure C, 130 mg (0.20 mmol) of 29A was deprotected to give 120 mg of the title compound as a tan solid.

$^1$H NMR (CD$_3$OD 250 MHz) (1:1 mixture of rotamers) δ 7.57–7.72 (m, 2H), 6.99–7.37 (m, 10.5H), 6.68 (d, 0.5H), 5.18–5.32 (m, 1H), 4.37–4.75 (m, 2H), 3.58–3.81 (m, 0.5H), 3.53–3.68 (m, 0.5H), 3.17–3.32 (m, 2H), 2.62–2.80 (m, 4H), 2.41–2.60 (m, 0.5H), 2.14–2.39 (m, 0.5H), 1.58 (s, 6H).

MS (Cl, NH$_3$) 552 (MH$^+$)

EXAMPLE 30

2-Amino-N-{1-(R)-benzyloxymethyl-2-oxo-2-[3-(toluene-4-sulfonylamino)-pyrrolidin-1-yl]-ethyl}-isobutyramide Trifluoroacetate A. 3-tert-Butoxycarbonylamino-pyrrolidine-1-carboxylic acid benzyl ester To a mixture of 19.0 g (102 mmol) of 3-(t-butoxycarbonylamino) pyrrolidine and 14.28 g (117 mmol) of 4-dimethylaminopyridine in 115 mL of methylene chloride at 0° C. was added 20.0 g (117 mmol) of benzyl chloroformate dropwise. The mixture was allowed to warm to 24° C. and was stirred overnight. The mixture was diluted with chloroform and washed twice with 10% HCl, twice with saturated aqueous sodium bicarbonate and once with brine. The mixture was dried over MgSO$_4$ and concentrated to give 30A in quantitative yield. The crude material was used without further purification.

B. 3-Amino-pyrrolidine-1-carboxylic acid benzyl ester trifluoroacetate

To 9.4 g (29.3 mmol) of 30A at 0° C. was added 100 mL of trifluoroacetic acid and the mixture stirred at 24° C. for 1 h. The mixture was concentrated, and coevaporated three times from ethyl acetate/heptane to give 11.0 g of 30B as an orange oil.

C. 3-(Toluene-4-sulfonylamino)-pyrrolidine-1-carboxylic acid benzyl ester

To a mixture of 2.0 g (6.0 mmol) of 30B, 0.84 g (6.9 mmol) of 4-dimethylaminopyridine, and 0.61 g (6.0 mmol) of triethylamine in 10 mL of methylene chloride was added 1.32 g (6.9 mmol) of toluenesulfonyl chloride and the mixture was stirred overnight. The mixture was diluted with chloroform and washed twice each with 10% HCl, saturated aqueous bicarbonate and brine, dried over MgSO$_4$ and concentrated. The product was purified by silica gel chromatography using a gradient elution of 35% ethyl acetate in hexane to 100% ethyl acetate to give 30C as a white solid (700 mg).

D. 4-Methyl-N-pyrrolidin-3-yl-benzenesulfonamide

To 0.70 g (1.9 mmol) of 30C in 20 mL of ethanol was added 0.40 g of 10% palladium on carbon and the mixture was hydrogenated on a Parr shaker for 17 h at 45 psi. The mixture was diluted with 110 mL of a (9:1:1) mixture of ethanol:water:ammonium hydroxide and was stirred for 20 min. The solution was filtered through celite and concentrated to give 300 mg of 30D as a yellow solid.

E. (1-{1-(R)-Benzyloxymethyl-2-oxo-2-[3-(toluene-4-sulfonylamino)-pyrrolidin-1-yl]-ethylcarbamoyl}-1-methyl-ethyl)-carbamic acid tert-butyl ester According to General Procedure A, 94 mg (0.39 mmol) of 30D and 100 mg (0.26 mmol) of 3 were coupled and the residue was purified by silica gel chromatography using a gradient elution of 50% ethyl acetate in hexane, to 100% ethyl acetate to give 100 mg of 30E.

F. 2-Amino-N-{1-(R)-benzyloxymethyl-2-oxo-2-[3-(toluene-4-sulfonylamino)-pyrrolidin-1-yl]-ethyl}-isobutyramide trifluoroacetate To 100 mg (0.16 mmol) of 30E was added 2 mL of trifluoroacetic acid at 0°C. and the mixture was stirred for 1.5 h at 24° C. The mixture was concentrated, and coevaporated once each with ethyl acetate and hexane. The product was precipitated from methylene chloride/hexane and was collected by filtration and dried under vacuum to give 95 mg of the title compound.

$^1$H NMR (CD$_3$OD 250 MHz) δ (rotamers) 7.75–7.84 (m, 2H), 7.29–7.50 (m, 7H), 4.76–4.93 (m, 1H), 4.57 (d, 2H), 3.69–3.80 (m, 5H), 3.39–3.65 (m, 2.5H), 3.22–3.31 (m, 0.5H), 2.45 (m, 3H), 1.62 (m, 6H).

MS (Cl, NH$_3$) 503 (MH$^+$)

EXAMPLE 31

(R)-2-Amino-N-[1-(3,4-dihydro-1H-isoquinoline-2-carbonyl)-2-(1H-indol-3-yl)-ethyl]-isobutyramide Hydrochloride A. (R)-{1-[1-(3,4-Dihydro-1H-isoquinoline-2-carbonyl)-2-(1H-indol-3-yl)-ethylcarbamoyl]-1-methyl-ethyl}-carbamic acid tert-butyl ester According to General Procedure A, 60 mg (0.154 mmol) of 4C and 26 mg (0.154 mmol) of 1,2,3,4-tetrahydroisoquinoline were coupled and the product was purified by silica gel chromatography (40:60 v/v ethyl acetate:hexanes) to give 71 mg of 31A.

B. (R)-2-Amino-N-[1-(3,4-dihydro-1H-isoquinoline-2-carbonyl)-2-(1H-indol-3-yl)-ethyl]-isobutyramide hydrochloride According to the method outlined in General Procedure C, 57 mg (0.106 mmol) of 31B was deprotected to give 49 mg of the title compound.

$^1$H NMR (CD$_3$OD 250 MHz) (mixture of rotamers) δ 8.32 (d, 1H), 7.56 (d,1H), 7.32 (d, 0.5H), 6.96–7.22 (m, 7H), 6.61 (d, 0.5H), 5.17–5.32 (m, 1H), 4.61–4.73 (d, 0.5H), 4.45–4.58 (d, 0.5H), 4.29–4.41 (d, 0.5H), 3.96–4.05 (d, 0.5H), 3.37–3.72 (m, 2H), 3.13–3.26 (m, 2H), 2.54–2.74 (m, 1H), 2.39–2.55 (m, 0.5H), 2.11–2.25 (m, 0.5H), 1.49–1.62 (m, 6H).
MS (Cl, $NH_3$) 405 ($MH^+$)

EXAMPLE 32

(R)-N-{1-[2-(2-Amino-2-methyl-propionylamino)-3-benzyloxy-propionyl]-pyrrolidin-3-yl}-benzamide Trifluoroacetate A. 3-Benzoylamino-pyrrolidine-1-carboxylic acid benzyl ester To a mixture of 2.00 g (6.0 mmol) of 30B, 0.84 g (6.9 mmol) of 4-dimethylaminopyridine and 0.610 g (6.9 mmol) of triethylamine in 10 mL of methylene chloride was added 0.97 g (6.9 mmol) of benzoyl chloride and the mixture stirred for 72 h. The reaction mixture was diluted with chloroform and washed twice with 10% HCl, twice with saturated sodium bicarbonate solution and once with brine. The mixture was dried over $MgSO_4$ and concentrated. The product was purified by silica gel chromatography (75:25 v/v ethyl acetate/hexanes) to give 690 mg of 32A.

B. N-Pyrrolidin-3-yl-benzamide

To 0.69 g (2.1 mmol) of 32A in 20 mL of ethanol was added 0.30 g of 10% palladium on carbon and the mixture was hydrogenated on the Parr shaker for 17 h at 45 psi. The mixture was diluted with 110 mL of a (9:1:1) mixture of ethanol:water:ammonium hydroxide and stirred for 15 min. The solution was filtered through celite and concentrated to give 265 mg of 32B.

C. {1-[2-(3-Benzoylamino-pyrrolidin-1-yl)-1-(R)-benzyloxymethyl-2-oxo-ethylcarbamoyl-]-1-methyl-ethyl}-carbamic acid tert-butyl ester According to General Procedure A, 100 mg (0.52 mmol) of 32B and 75 mg (0.20 mmol) of 3 were coupled and the residue was purified by silica gel chromatography using a gradient elution of 75% ethyl acetate in hexane, to 100% ethyl acetate to give 50 mg of 32C.

D. (R)-N-{1-[2-(2-Amino-2-methyl-propionylamino)-3-benzyloxy-propionyl]-pyrrolidin-3-yl}-benzamide trifluoroacetate To 50 mg (0.10 mmol) of 32C at 0° C. was added 2 mL of trifluoroacetic acid. The reaction mixture was stirred for 4 h at 24° C., and the residue was diluted with ethyl acetate and coevaporated with heptane and ethyl acetate/hexane. The residue was diluted with chloroform by addition of hexane to give 22 mg of the title compound as a solid.

$^1$H NMR ($CD_3OD$ 250 MHz) δ 7.86–7.99 (m, 2H), 7.46–7.65 (m, 3H), 7.23–7.45 (m, 5H), 4.52–4.74 (m, 3H), 3.39–4.26 (m, 7H), 1.59 (bs, 6H).
LSIMS-MS 453 ($MH^+$)

EXAMPLE 33

2-Amino-N-{1-(5-fluoro-1H-indol-3-ylmethyl)-2-oxo-2-[4-(2-oxo-2.3-dihydro-benzoimidazol-1-yl)-piperidin-1-yl]-ethyl}-isobutyramide Hydrochloride A. 2-tert-Butoxycarbonylamino-2-methyl-propionic acid 2.5-dioxo-pyrrolidin-1-yl ester To a slurry of 5.0 g (24.6 mmol) of N-t-BOC-α-methylalanine in 13.5 mL of methylene chloride was added 3.40 g (29.6 mmol) of N-hydroxysuccinimide and 5.65 g (29.6 mmol) of EDC. The slurry was stirred for 17 h at room temperature. The mixture was diluted with ethyl acetate and washed twice each with water, saturated aqueous sodium bicarbonate and brine. Dried over $MgSO_4$ and concentrated. The residue was purified by silica gel chromatography (1:1 v/v ethyl acetate:hexanes) to give 5.2 g of 33A as a white solid.

B. -2-(2-tert-Butoxycarbonylamino-2-methyl-propionylamino)-3-(5-fluoro-1H-indol-3-yl)-propionic acid A mixture of 100 mg (0.33 mmol) of 33A, 62 mg (0.278 mmol) of 5-fluoro-DL-tryptophan and 79 mg (0.611 mmol) of diisopropylethylamine in 1.0 mL of DMF was stirred for 17 h at room temperature. The reaction mixture was poured into water and extracted twice with ethyl acetate. An equal volume of hexane was added to the ethyl acetate and the mixture was washed three times with water and once with brine. The organic phase was dried over $Na_2SO_4$ and concentrated. The product was purified by silica gel chromatography (9:1 v/v $CHCl_3$:MeOH) to give 52 mg of 33B.

C. -(1-{1-(5-Fluoro-1H-indol-3-ylmethyl)-2-oxo-2-[4-(2-oxo-2,3-dihydro-benzoimidazol-1-yl)-piperidin-1-yl]-ethylcarbamoyl}-1-methyl-ethyl)-carbamic acid tert-butyl ester According to General Procedure A, 44 mg (0.11 mmol) of 33B and 23.5 mg (0.11 mmol) of 4-(2-keto-1-benzimidazolinyl)piperidine were coupled and the product was purified by silica gel chromatography (100% ethyl acetate) to give 39 mg of 33C as an amorphous solid.

D. -2-Amino-N-{1-(5-fluoro-1H-indol-3-ylmethyl)-2-oxo-2-[4-(2-oxo-2,3-dihydro-benzoimidazol-1-yl)-piperidin-1-yl]-ethyl}-isobutyramide hydrochloride According to General Procedure C, 39 mg (0.064 mmol) of 33C was deprotected to give 32 mg of the title compound as a white solid.

$^1$H NMR ($CD_3OD$ 250 MHz) (partial) (1:1 mixture of diastereomers ) δ 8.36 (d, 1H), 7.03–7.39 (m, 7.5H), 6.89 (t, 1H), 6.76 (d, 0.5H), 5.14–5.35 (m, 1H), 4.59–4.71 (m,1H), 4.23–4.46 (m, 1H), 3.94–4.11 (m, 1H), 2.45–2.72 (m, 2H), 1.50–1.64 (m, 6H).
MS (Cl, $NH_3$) 507 ($MH^+$)

EXAMPLE 34

(R)-N-[1-[4-(Acetyl-phenyl-amino)-piperidine-1-carbonyl]-2-(1H-indol-3-yl)-ethyl]-2-amino-isobutyramide A. (R)-{1-[1-l[4-(Acetyl-phenyl-amino)-piperidine-1-carbonyl]-2-(1H-indol-3-yl)-ethylcarbamoyl-1l-methyl-ethyl}-carbamic acid tert-butyl ester According to General Procedure A, 45 mg (0.116 mmol) of 4C and 27 mg (0.124 mmol) of N-phenyl-N-piperidin-4-yl-acetamide were coupled and the product was purified by silica gel chromatography using a gradient of 1% to 5% methanol in methylene chloride to give 63 mg of 34A.

B. (R)-N-[1-[4-(Acetyl-phenyl-amino)-piperidine-1-carbonyl]-2-(1H-indol-3-yl)-ethyl]-2-amino-isobutyramide According to General Procedure B, 63 mg (0.107 mmol) of 34A was deprotected to give 33 mg of the title compound as a white solid.

$^1$H NMR ($CD_3OD$ 300 MHz) (1:1 mixture of rotamers) δ 7.31–7.62 (m, 4H), 6.89–7.23 (m, 5H), 5.11–5.20 (t, 1H), 4.99–5.19 (t, 1H), 4.40–4.63 (m, 2H), 3.68–3.83 (m, 2H), 3.02–3.17 (t, 2H), 2.90–3.01 (t, 0.5H), 2.50–2.60 (t, 0.5H), 2.32–2.41 (m, 1H), 1.64–1.82 (m, 1H), 1.69 (s, 3H), 1.32 (s, 6H).
MS (Cl, $NH_3$) 490 ($MH^+$)

EXAMPLE 35

(R)-2-Amino-N-{1-naphthalen-2-ylmethyl-2-oxo-2-[4-(2-oxo-2,3-dihydro-benzoimidazol-1-yl)-piperidin-1-yl]-ethyl}-isobutyramide Hydrochloride A. {1-Naphthalen-2-ylmethyl-2-oxo-2-[4-(2-oxo-2,3-dihydro-benzoimidazol-1-yl)-piperidin-1-yl]-ethyl}-carbamic acid tert-butyl ester According to General Procedure A, 605 mg (1.92 mmol) of BOC-D-3-2-(Napthyl)alanine and 417 mg (1.92 mmol) of 4-(2-keto-1-benzimidazolinyl) piperidine were coupled to give 890 mg of 35A as a solid which was used without further purification.

B. 1-[1-(2-Amino-3-naphthalen-2-yl-propionyl)-piperidin-4-yl]-1,3-dihydro-benzoimidazol-2-one According to General Procedure B, 830 mg (1.61 mmol) of 35A was deprotected to give 582 mg of 35B as a tan solid.

C. (R)-(1-Methyl-1-{1-naphthalen-2-ylmethyl-2-oxo-2-[4-(2-oxo-2,3-dihydro-benzoimidazol-1-yl)-piperidin-1-yl]-ethylcarbamoyl}-ethyl)-carbamic acid tert-butyl ester According to General Procedure A, 570 mg (1.38 mmol) of 35B and 266 mg (1.31 mmol) of N-t-BOC-α-methylalanine were coupled to give 63 mg of 35C after silica gel chromatography using a gradient of 1% to 3% methanol in methylene chloride.

D. (R)-2-Amino-N-{1-naphthalen-2-ylmethyl-2-oxo-2-[4-(2-oxo-2,3-dihydro-benzoimidazol-1-yl)-piperidin-1-yl]-ethyl}-isobutyramide hydrochloride According to General Procedure C, 620 mg (1.03 mmol) of 35C was deprotected to give 404 mg of the title compound as a light yellow solid.

$^1$H NMR (CD$_3$OD 300 MHz) (mixture of rotamers) (partial) δ 7.73–7.87 (m, 4H), 7.40–7.50 (m, 3H), 7.19–7.28 (m, 0.5H), 6.91–7.05 (m, 3H), 6.74–6.79 (d, 0.5H), 5.26–5.48 (m, 1H), 4.67–4.71 (m, 1H), 4.33–4.50 (m, 1H), 4.10–4.32 (m, 1H), 3.12–3.39 (m, 2H), 1.55–1.61 (d, 3H), 1.38 (s, 3H).

MS (Cl, NH$_3$) 500 (MH$^+$)

EXAMPLE 36

(R)-2-Amino-N-{2-(1H-indol-3-yl)-1-[7-(toluene-4-sulfonylamino)-3,4-dihydro-1H-isoquinoline-2-carbonyl]-ethyl}-isobutyramide A. (R)-{1-[2-(1H-Indol-3-yl)-1-(7-nitro-3,4-dihydro-1H-isoquinoline-2-carbonyl)-ethylcarbamoyl]-1-methyl-ethyl}-carbamic acid tert-butyl ester According to General Procedure A, 750 mg (4.21 mmol) of 6A and 1.64 g (4.21 mmol) of 4C were coupled and the product was purified by silica gel chromatography (30:70 v/v EtOAc:hexanes) to give 1.50 g of 36A as a foam.

B. (R)-{1-[1-(7-Amino-3,4-dihydro-1H-isoquinoline-2-carbonyl)-2-(1H-indol-3-yl)-ethylcarbamoyl]-1-methyl-ethyl}-carbamic acid tert-butyl ester To 800 mg (1.46 mmol) of 36A in 10 mL of methanol was added 300 mg of 10% palladium hydroxide on carbon and the mixture hydrogenated at 50 psi for 17 h. The mixture was filtered through celite and concentrated to give 700 mg of 36B as a brown powder.

C. (R)-(1-{2-(1H-Indol-3-yl)-1-[7-(toluene-4-sulfonylamino)-3,4-dihydro-1H-isoquinoline-2-carbonyl]-ethylcarbamoyl}-1-methyl-ethyl)-carbamic acid tert-butyl ester To 71 mg (0.14 mmol) of 36B in 10 mL of methylene chloride at 0° C. was added 17 mg (0.165 mmol) of triethylamine, followed by 29 mg (0.15 mmol) of toluene-sulfonyl chloride. The mixture was allowed to warm to room temperature over 3 h. The reaction mixture was diluted with ethyl acetate and washed twice with 1 N NaOH and once with brine. The solution was dried over Na$_2$SO$_4$ and concentrated, and the residue was purified by silica gel chromatography (1:2 v/v EtOAc:hexanes) to give 90 mg of 36C as a foam.

D. (R)-2-Amino-N-{2-(1H-indol-3-yl)-1-[7-(toluene-4-sulfonylamino)-3,4-dihydro-1H-isoquinoline-2-carbonyl]-ethyl}-isobutyramide According to General Procedure B, 50 mg (0.74 mmol) of 36C was deprotected to give 20 mg of the title compound as a white powder.

MS (Cl, NH$_3$) 574 (MH$^+$)

EXAMPLE 37

(R)-N-{2-[2-(2-Amino-2-methyl-propionylamino)-3-(1H-indol-3-yl)-propionyl]-1,2,3,4-tetrahydro-isoquinolin-7-yl}-benzamide A. (R)-{1-[1-(7-Benzoylamino-3,4-dihydro-1H-isoquinoline-2-carbonyl)-2-(1H-indol-3-yl)-ethylcarbamoyl]-1-methyl-ethyl}-carbamic acid tert-butyl ester To 86 mg (0.17 mmol) of 36B in 10 mL of methylene chloride at 0° C. was added 20 mg (0.20 mmol) of triethylamine and 26 mg (0.18 mmol) of benzoyl chloride. The mixture was warmed to room temperature over 2 h and diluted with ethyl acetate and washed twice with 1 N NaOH and once with brine. The solution was dried over Na$_2$SO$_4$ and concentrated, and the residue was purified by silica gel chromatography (1:1 v/v EtOAc/hexanes) to give 95 mg of 37A as a foam.

B. (R)-N-{2-[2-(2-Amino-2-methyl-propionylamino)-3-(1H-indol-3-yl)-propionyl]-1,2,3,4-tetrahydro-isoquinolin-7-yl}-benzamide According to General Procedure B, 95 mg (0.15 mmol) of 37A was deprotected to give 65 mg of the title compound.

MS (Cl, NH$_3$) 524 (MH$^+$)

EXAMPLE 38

2-Amino-N-{1-(R)-benzyloxymethyl-2-[4-(2-cyclopropyl-5,7-dimethyl-imidazo[4,5-b]pyridin-3-yl)-piperidin-1-yl]-2-oxo-ethyl}-isobutyramide A. 4-(2-Cyclopropyl-5.7-dimethyl-imidazo[4,5-b]pyridin-3-yl)-piperidine-1-carboxylic acid tert-butyl ester 2-Cyclopropyl-5,7-dimethyl-3H-imidazo[4,5-b]pyridine was prepared according to literature methods (for preparation see Carpino et al., Bioorg. & Med. Chem. Lett. 4, pp. 93–98 1994 (ref.13)). To 625 mg (2.4 mmol) of triphenylphosphine in 10 mL of toluene was added 460 mg (2.0 mmol) of di-tert-butylazodicarboxylate, and the mixture was stirred for 15 min. A mixture of 430 mg (2.3 mmol) of 2-cyclopropyl-5,7-dimethyl-3H-imidazo[4,5-b]pyridine and 325 mg (1.62 mmol) of 4-hydroxy-piperidine-1-carboxylic acid tert-butyl ester was added to the stirring solution and the mixture was stirred for 17 h at room temperature. The mixture was concentrated and the product was purified by silica gel chromatography (50:50 v/v hexanes:ethyl acetate) to give 150 mg of 38A.

B. 2-Cyclopropyl-5,7-dimethyl-3-piperidin-4-yl-3H-imidazo[4,5-b]pyridine

According to General Procedure B, 150 mg (0.39 mmol) of 38A was deprotected to give 60 mg of 38B.

C. (1-{1-(R) Benzyloxymethyl-2-[4-(2-cyclopropyl-5,7-dimethyl-imidazo[4,5-b]pyridin-3-yl)-piperidin-1-yl]-2-oxo-ethylcarbamoyl}-1-methyl-ethyl)-carbamic acid tert-butyl ester According to General Procedure A, 60 mg (0.22 mmol) of 38B was coupled to 84 mg (0.22 mmol) of 3 and the product was purified by silica gel chromatography (9:1 v/v ethyl acetate:hexanes) to give 37 mg of 38C.

D. 2-Amino-N-{1-(R)-benzyloxymethyl-2-[4-(2-cyclopropyl-5,7-dimethyl-imidazo[4.5-b]pyridin-3-yl)-piperidin-1-yl]-2-oxo-ethyl}-isobutyramide According to General Procedure B, 37 mg of 38C was deprotected to give 25 mg of the title compound.

$^1$H NMR (CDCl$_3$, 300 MHz) δ 7.29–7.37 (m, 3H); 7.16–7.24 (m, 2H), 6.87–6.89 (s, 1H), 5.13–5.21 (m, 1H), 4.92–5.03 (m, 1H), 4.68–4.82 (m, 1H) 4.50–4.67 (m, 3H), 4.71–4.89 (m, 1H), 3.66–3.77 (m, 2H), 2.73–2.92 (m, 3H), 2.51 (s, 5H), 2.43 (s, 1H), 2.10–2.30 (m, 1H),1.86–2.94 (m, 2H), 1.32 (d, 6H), 1.02–1.26 (m, 4H).
MS (Cl, NH$_3$) 533 (MH$^+$)

EXAMPLE 39

(R)-2-Amino-N-[2-(4-cyano-4-phenyl-piperidin-1-yl)-1-(1H-indol-3-ylmethyl)-2-oxo-ethyl]-isobutyramide A. (R)-{1-[2-(4-Cyano-4-phenyl-piperidin-1-yl)-1-(1H-indol-3-ylmethyl)-2-oxo-ethylcarbamoyl]-1-methyl-ethyl}-carbamic acid tert-butyl ester According to General Procedure A, 53 mg (0.24 mmol) of 4-phenyl-piperidine-4-cyano hydrochloride and 92 mg (0.24 mmol) of 4C were coupled and the product was purified by silica gel chromatography (1:1 v/v ethyl acetate:hexanes) to give 124 mg of 39A.

B. (R)-2-Amino-N-[2-(4-cyano-4-phenyl-piperidin-1-yl)-1-(1H-indol-3-ylmethyl)-2-oxo-ethyl]-isobutyramide According to General Procedure B, 105 mg (0.19 mmol) of 39C was deprotected to give 82 mg of the title compound as a foam.

$^1$H NMR (CDCl$_3$, 250 MHz) (60:40 mixture of rotamers) δ 8.13–8.34 (m, 2H), 7.75 (d, 0.6H), 7.68 (d, 0.4H), 7.28–7.41 (m, 4H), 7.08–7.27 (m, 3H), 6.94–7.01 (m, 1H), 5.13–5.33 (m, 1H), 4.62–4.78 (m, 1H), 3.73–3.90 (m, 1H), 3.20–3.31 (m, 2H), 2.64–2.93 (m, 2H), 1.66–2.43 (bm, 6H), 1.43 (s, 6H).
MS (Cl, NH$_3$) 458 (MH$^+$)

EXAMPLE 40

(R)-2-Amino-N-{1-(1H-indol-3-ylmethyl)-2-[4-(morpholine-4-carbonyl)-4-phenyl-piperidin-1-yl]-2-oxo-ethyl}-isobutyramide Hydrochloride A. (R)-(1-{1-(1H-Indol-3-ylmethyl)-2-[4-(morpholine-4-carbonyl)-4-phenyl-piperidin-1-yl]-2-oxo-ethylcarbamoyl}-1-methyl-ethyl)-carbamic acid tert-butyl ester According to General Procedure A, 27 mg (0.087 mmol) of morpholin-4-yl-(4-phenyl-piperidin-4-yl)-methanone hydrochloride and 32 mg (0.081 mmol) of 4C were coupled and the product was purified by silica gel chromatography using a gradient of 50% ethyl acetate in hexane to 100% ethyl acetate to give 24 mg of 40A as a foam.

B. (R)-2-Amino-N-{1-(1H-indol-3-ylmethyl)-2-[4-(morpholine-4-carbonyl)-4-phenyl-piperidin-1-yl]-2-oxo-ethyl}-isobutyramide hydrochloride According to the method outlined in General Procedure C, 36 mg of 40A was deprotected to give 17 mg of the title compound as a yellow solid.

$^1$H NMR (CD$_3$OD, 300 MHz) (rotamers) δ 7.52–7.67 (m,1H), 6.99–7.40 (m, 8H), 6.87 (d,1H), 5.07–5.21 (m, 1H), 4.03–4.30 (m,1H), 3.52–3.68 (m, 1H), 2.74–3.39 (m, 13H), 1.94–2.18 (m, 1H), 1.74–1.90 (m, 1H), 1.58–1.66 (m, 1H), 1.30–1.47 (d, 6H), 1.25–1.30 (m, 2H).
MS (Cl, NH$_3$) 546 (MH$^+$)

EXAMPLE 41

1-Amino-cyclopentanecarboxylic Acid {1-(R)-benzyloxymethyl-2-oxo-2-[4-(2-oxo-2,3-dihydro-benzoimidazol-1-yl)-piperidin-1-yl]-ethyl}-amide Trifluoroacetate A. 1-tert-Butoxycarbonylamino-cyclopentanecarboxylic acid To 1.66 g (12.88 mmol) of 1-amino-1-cyclopentane-carboxylic acid in 12.5 mL of 2N NaOH was added 283 mg (13.0 mmol) of di-tert-butyl-dicarbonate and the mixture was stirred for 17 h at room temperature. The mixture was acidified with 10% HCl and extracted three times with ethyl acetate. The combined organic extracts were washed with brine, dried over MgSO$_4$ and concentrated to give 1.71 g of 41 A.

B. (1-{1-(R)-Benzyloxymethyl-2-oxo-2-[4-(2-oxo-2,3-dihydro-benzoimidazol-1-yl)-piperidin-1-yl]-ethylcarbamoyl}-cyclopentyl)-carbamic acid tert-butyl ester According to General Procedure A, 20 mg (0.05 mmol) of 1 B and 11.6 mg (0.05 mmol) of 41A were coupled, and 23 mg of 41B was recovered. The crude material was used without further purification in the following step.

C. 1-Amino-cyclopentanecarboxylic acid {1-(R)-benzyloxymethyl-2-oxo-2-[4-(2-oxo-2,3-dihydro-benzoimidazol-1-yl)-piperidin-1-yl]-ethyl}-amide trifluoroacetate To 23 mg (0.04 mmol) of 41 B was added 2 mL of trifluoroacetic acid at 0° C. The ice bath was removed and the mixture was stirred for 2.5 h, and then was diluted with ethyl acetate and concentrated. The residue was coevaporated once from heptane, dissolved in methylene chloride and the product precipitated with hexane to give 10 mg of the title compound as a solid.

$^1$H NMR (CD$_3$OD, 250 MHz) δ 7.29–7.45 (m, 7H), 7.06–7.28 (m, 4H), 5.17–5.36 (m, 1H), 4.04–4.31 (m, 4H), 4.19–4.38 (m, 1H), 3.72–3.87 (m, 2H), 2.25–2.44 (m, 3H), 1.80–2.12 (m, 9H).
MS (Cl, NH$_3$) 506 (MH$^+$)

EXAMPLE 42

2-Amino-N-[1-(R)-benzyloxymethyl-2-(3-diphenylacetylamino-pyrrolidin-1-yl)-2-oxo-ethyl]-isobutyramide Trifluoroacetate A. 3-Diphenylacetylamino-pyrrolidine-1-carboxylic acid benzyl ester To a mixture of 2.40 g (7.19 mmol) of 30B, 1.10 g (9.02 mmol) of 4-dimethylaminopyridine, and 0.73 g (7.19 mmol) of triethylamine in 10 mL of methylene chloride was added 1.91 g (8.26 mmol) of diphenylacetylchloride and the mixture stirred overnight at room temperature. The mixture was diluted with chloroform and washed twice each with 10% HCl, saturated aqueous sodium bicarbonate, and brine. The mixture was dried over MgSO$_4$ and concentrated to give 2.43 9 of 42A as a white solid.

B. 2.2-Diphenyl-N-pyrrolidin-3-yl-acetamide

To 2.40 g (5.8 mmol) of 42A in 40 mL of ethanol was added 1.20 g of 10% palladium on carbon and the mixture was hydrogenated at 45 psi for 17 h. The reaction mixture was filtered through celite and was concentrated to give 1.67 g of 42B as a yellow oil.

C. {1-[1-(R)-Benzyloxymethyl-2-(3-diphenylacetylamino-pyrrolidin-1-yl)-2-oxo-ethylcarbamoyl]-1-methyl-ethyl}-carbamic acid tert-butyl ester According to General Procedure A, 150 mg (0.53 mmol) of 42B and 200 mg (0.53 mmol) of 3 were coupled and the product was purified by silica gel chromatography using a gradient of 50% ethyl acetate in hexane to 100% ethyl acetate to give 100 mg of 42C as a white solid.

D. 2-Amino-N-1-(R)-benzyloxymethyl-2-(3-diphenylacetylamino-pyrrolidin-1-yl)-2-oxo-ethyl]-isobutyramide trifluoroacetate To 100 mg (0.16 mmol) of 42C was added 3 mL of trifluoroacetic acid at 0° C. The ice bath was removed and the mixture stirred for 3 h, diluted with ethyl acetate and concentrated. The residue was coevaporated once with heptane. Hexane and chloroform were added to the residue and the precipitated product was collected by filtration. Recovered 55 mg of the title compound as a solid.

$^1$H NMR (CD$_3$OD, 250 MHz) (partial) δ 7.22–7.40 (m, 15H), 4.95–5.00 (m, 1H), 4.38–4.57 (m, 3H), 1.60 (s, 6H). LSIMS-MS 543 (MH$^+$)

EXAMPLE 43

(R)-N-{2-[2-(2-Amino-2-methyl-propionylamino)-3-benzyloxy-propionyl]-2,3-dihydro-1H-isoindol-5-yl}-benzamide Trifluoroacetate A. 1,2-Bis-bromomethyl-4-nitro-benzene To 8.00 g (53.0 mmol) of 4-Nitro-o-xylene in 80 mL of carbon tetrachloride was added 18.8 g (106 mmol) of N-Bromosuccinimide followed by 100 mg (0.60 mmol) of 2,2'-azobis (isobutyronitrile) and the mixture was refluxed overnight. The precipitated solid was removed by filtration and washed with carbon tetrachloride and the filtrate concentrated to give 15.4 g of 43A as a yellow oil. The crude product was used without further purification in the following step.

B. 2-Benzyl-5-nitro-2,3-dihydro-1H-isoindole

To a mixture of 15.4 g (50.5 mmol) of 43A and 35.4 g (430 mmol) of sodium carbonate in 160 mL of acetone and 35 mL of water was added 5.68 g (53 mmol) of benzylamine in 10 mL of acetone over 3 h. The mixture was then stirred for 17 h at room temperature. The precipitated solids were removed by filtration and the filtrate concentrated. The residue was dissolved in ethyl acetate and washed three times with 1 N HCl. The combined HCl washes were neutralized with sodium carbonate solution and extracted three times with ethyl acetate. The combined organics were washed with brine, dried over MgSO$_4$ and concentrated. The product was purified by silica gel chromatography (15:85 v/v ethyl acetate:hexanes) to give 2.55 g of 43B as a yellow solid.

C. 5-Amino-2,3-dihydro-1H-isoindole

To 1.50 g (5.9 mmol) of 43B in 50 mL of ethanol was added 1.25 g of 10% palladium on carbon and the mixture hydrogenated at 40° C. and 5 psi for 17 h. The mixture was filtered through celite and concentrated to give 600 mg of 43C as a pale purple solid.

D. {1-[2-(5-Amino-1,3-dihydro-isoindol-2-yl)-1-(R)-benzyloxymethyl-2-oxo-ethylcarbamoyl]-1-methyl-ethyl}-carbamic acid tert-butyl ester According to General Procedure A, 300 mg (2.2 mmol) of 43C and 850 mg (2.2 mmol) of 3 were coupled to give 950 mg of 43D as a yellow solid. The crude product was used without further purification.

E. {1-[2-(5-Benzoylamino-1,3-dihydro-isoindol-2-yl)-1-(R)-benzyloxymethyl-2-oxo-ethylcarbamoyl]-1-methyl-ethyl}-carbamic acid tert-butyl ester To a mixture of 300 mg (0.60 mmol) of 43D and 85 mg (0.69 mmol) of 4-dimethylaminopyridine in 5 mL of methylene chloride was added 98 mg (0.69 mmol) of benzoyl chloride, and the mixture stirred for 17 h at room temperature. The reaction mixture was diluted with chloroform and washed twice each with 10% HCl, saturated aqueous sodium bicarbonate and brine, dried over MgSO$_4$ and concentrated. The product was purified by silica gel chromatography (87:13 v/v ethyl acetate:hexanes) to give 120 mg of the title compound as a white solid.

F. (R)-N-{2-[2-(2-Amino-2-methyl-propionylamino)-3-benzyloxy-propionyl]-2,3-dihydro-1H-isoindol-5-yl}-benzamide trifluoroacetate To 120 mg (0.20 mmol) of 43D was added 3 mL of trifluoroacetic acid at 0° C. The ice bath was removed and the mixture stirred for 3 h. The reaction mixture was diluted with ethyl acetate and concentrated. The product crystallized upon addition of hexane and chloroform. Filtration of the precipitate provided 50 mg of the title compound as a white solid.

$^1$H NMR (CD$_3$OD, 250 MHz) δ 7.82–8.00 (d, 2H), 7.78–7.85 (m,1H), 7.00–7.17 (m, 4H), 7.37–7.42 (m, 6H), 5.08–5.32 (m, 1H), 4.99–5.10 (m, 2H), 4.75–4.80 (d, 2H), 4.61 (s, 2H), 3.82–3.90 (m, 2H), 1.62 (s, 6H)
MS (Cl, NH$_3$) 501 (MH$^+$)

EXAMPLE 44

(R)-2-Amino-N-{1-(4-benzyloxy-benzyl)-2-oxo-2-[4-(2-benzoimidazol-1-yl)-piperidin-1-yl]-ethyl}-isobutyramide A. (R)-3-(4-Benzyloxy-phenyl)-2-tert-butoxycarbonylamino-propionic acid methyl ester To a mixture of 2.00 g (5.38 mmol) of N-t-BOC-O-benzyl-D-Tyrosine and 0.819 g (5.92 mmol) of potassium carbonate in 30 mL of DMF was added 0.802 g (5.65 mmol) of iodomethane, and the mixture stirred for 17 h at room temperature. The mixture was diluted with 150 mL water and extracted three times with ethyl acetate. The organics were washed four times with water and once with brine. Drying over MgSO$_4$ and concentration provided 2.27 g of 44A as a yellow oil.

B. (R)-2-Amino-3-(4-benzyloxy-phenyl)-propionic acid methyl ester

Following the method outlined in General Procedure B, 2.27 g (5.4 mmol) of 44A was deprotected to give 1.00 g of 44B as a yellow oil.

C. (R)-3-(4-Benzyloxy-phenyl)-2-(2-tert-butoxycarbonylamino-2-methyl-propionylamino)-propionic acid methyl ester According to General Procedure A, 1.00 g (3.5 mmol) of 44B and 0.72 g (3.9 mmol) of N-t-BOC-α-methylalanine were coupled and the product was purified by silica gel chromatography (25:75 v/v ethyl acetate:hexanes) to give 1.00 g of 44C as a white solid.

D. (R)-3-(4-Benzyloxy-phenyl)-2-(2-tert-butoxycarbonylamino-2-methyl-propionylamino)-propionic acid Following the method outlined in General Procedure D, 1.00 g (2.2 mmol) of 44C was hydrolyzed to give 1.00 g of 44D.

E. (R)-(1-{1-(4-Benzyloxy-benzyl)-2-oxo-2-[4-(2-oxo-2,3-dihydro-benzoimidazol-1-yl)-piperidin-1-yl]-ethylcarbamoyl}-1-methyl-ethyl)-carbamic acid tert-butyl ester According to General Procedure A, 150 mg (0.34 mmol) of 44D and 75 mg (0.34 mmol) of 4-(2-keto-1-benzimidazolinyl)piperidine were coupled and the product was purified by silica gel chromatography using a gradient of (75:25 v/v ethyl acetate:hexanes) to (5:95 v/v methanol:ethyl acetate) to give 100 mg of 44E as a white solid.

F. (R)-2-Amino-N-{1-(4-benzyloxy-benzyl)-2-oxo-2-[4-(2-benzoimidazol-1-yl)-piperidin-1-yl]-ethyl}-isobutyramide According to General Procedure B, 100 mg (0.15 mmol) of 44E was deprotected to give 60 mg of the title compound as a white solid.

$^1$H NMR (CD$_3$OD, 250 MHz) (rotamers) δ 7.26–7.52 (m, 6H), 6.91–7.22 (m, 7H), 5.04–5.18 (m, 2H), 4.96–5.01 (m, 1H), 4.60–4.81 (m, 1H), 4.36–4.60 (m, 1H), 3.95–4.14 (m, 1H), 2.94–3.10 (m, 2H), 2.45–2.80 (m, 2H), 2.08–2.40 (m, 1H), 1.69–1.92 (m, 2H), 1.55–1.68 (m,1H), 1.28–1.40 (m, 8H).
MS (Cl, NH$_3$) 556 (MH$^+$)

EXAMPLE 45

(R)-2-Amino-N-{3-(3,4-dihydro-1H-isoquinolin-2-yl)-3-oxo-1-[4-(2-oxo-2,3-dihydro-benzoimidazol-1-yl)-piperidine-1-carbonyl]-propyl}-isobutyramide A. (R)-3-tert-Butoxycarbonylamino-4-oxo-4-[4-(2-oxo-2,3-dihydro-benzoimidazol-1-yl)-piperidin-1-yl]-butyric acid benzyl ester According to General Procedure A, 2.33 g (7.21 mmol) of N-a-t-BOC-D-aspartic-b-benzyl ester and 1.49 g (6.86 mmol) of 4-(2-keto-1-benzimidazolinyl) piperidine were coupled and the product was purified by silica gel chromatography using an elution gradient of 2% to 4% methanol in methylene chloride to provide 2.56 g of 45A.

B. (R)-3-Amino-4-oxo-4-[4-(2-oxo-2,3-dihydro-benzoimidazol-1-yl)-piperidin-1-yl]-butyric acid benzyl ester Following the method outlined in General Procedure B, 2.49 g (4.78 mmol) of 45A was deprotected to give 1.77 g of 45B.

C. (R)-3(2-tert-Butoxycarbonylamino-2-methyl-propionylamino)-4-oxo-4-[4-(2-oxo-2,3-dihydro-benzoimidazol-1-yl)-piperidin-1-yl]-butyric acid benzyl ester According to General Procedure A, 1.60 g (3.8 mmol) of 45B and 0.77 g (3.8 mmol) of N-t-BOC-α-methylalanine were coupled and the product was purified by silica gel chromatography using an elution gradient of 2% to 4% methanol in methylene chloride to provide 2.46 g of 45C.

D. (R)-3-(2-tert-Butoxycarbonylamino-2-methyl-propionylamino)-4-oxo-4-[4-(2-oxo-2,3-dihydro-benzoimidazol-1-yl)-piperidin-1-yl]-butyric acid To 2.44 g (4.0 mmol) of 45C in 40 mL of ethanol was added 250 mg of 10% palladium on carbon and the mixture hydrogenated at 50 psi for 2 h. The mixture was filtered through celite and concentrated to give 2.00 g of 45D.

E. (R)-(1-{3-(3,4-Dihydro-1H-isoquinolin-2-yl)-3-oxo 1-[4-(2-oxo-2,3-dihydro-benzoimidazol-1-yl)-piperidine-1-carbonyl]-propylcarbamoyl}-1-methyl-ethyl)-carbamic acid tert-butyl ester According to General Procedure A, 80 mg (0.19 mmol) of 45D and 22 mg (0.20 mmol) of 1,2,3,4-tetrahydroisoquinoline were coupled and the product was purified by silica gel chromatography using an elution gradient of 2% to 4% methanol in methylene chloride to provide 52 mg of 45E.

F. (R)-2-Amino-N-{3-(3,4-dihydro-1H-isoquinolin-2-yl)-3-oxo-1-[4-(2-oxo-2,3-dihydro-benzoimidazol-1-yl)-piperidine-1-carbonyl]-propyl}-isobutyramide Following the method outlined in General Procedure B, 45 mg (0.07 mmol) of 45E was deprotected to give 22 mg of the title compound.

$^1$H NMR (CD$_3$OD, 300 MHz) (1:1 mixture of rotamers) (partial) δ 7.54–7.62 (m, 0.5H), 7.20–7.32 (m, 0.5H), 7.10–7.21 (m, 4H), 7.01–7.19 (m, 3H), 5.33–5.49 (m, 1H), 3.67–3.92 (m, 2H), 2.58–3.01 (m, 5H), 1.74–1.89 (m, 2H), 1.39–1.42 (m, 8H).
MS (Cl, NH$_3$) 533 (MH$^+$)

EXAMPLE 46

(R)-2-Amino-N-{1-(1H-indol-3-ylmethyl)-2-oxo-2-[4-phenyl-4-(pyrrolidine-1-carbonyl)-piperidin-1-yl]-ethyl}-isobutyramide Hydrochloride A. (1-{1-(1H-Indol-3-ylmethyl)-2-oxo-2-[4-phenyl-4-(pyrrolidine-1-carbonyl)-piperidin-1-yl]-ethylcarbamoyl}-1-methyl-ethyl)-carbamic acid tert-butyl ester According to General Procedure A, 71 mg (0.24 mmol) of (4-Phenyl-piperidin-4-yl)-pyrrolidin-1-yl-methanone hydrochloride and 94 mg (0.24 mmol) of 4C were coupled and the product was purified by silica gel chromatography using 100% ethyl acetate to elute to give 142 mg of 46A.

B. (R)-2-Amino-N-{1-(1H-indol-3-ylmethyl)-2-oxo-2-[4-phenyl-4-(pyrrolidine-1-carbonyl)-piperidin-1-yl]-ethyl}-isobutyramide hydrochloride According to General Procedure C, 133 mg (0.21 mmol) of 46A was deprotected to give 119 mg of the title compound as a solid.

$^1$H NMR (CD$_3$OD, 250 MHz) δ 7.52–7.63 (m, 1H), 7.00–7.37 (m, 8H), 6.80–6.91 (m, 1H), 5.02–5.26 (m, 1H), 3.99–4.27 (m, 1H), 3.04–3.72 (m, 6H), 2.61–3.02 (m, 3H), 1.44–2.28 (m, 13H).
MS (Cl, NH$_3$) 530 (MH$^+$)

EXAMPLE 47

(R)-2-Amino-N-{1-(1H-indol-3-ylmethyl)-2-oxo-2-[4-(1-phenyl-1H-indol-3-yl)-piperidin-1-yl]-ethyl}-isobutyramide Hydrochloride A. [4-(1H-Indol-3-yl)-4H-pyridin-1-yl]-phenyl-methanone To a solution of 23.4 g (0.20 mol) of indole in 250 mL of pyridine was added 23.2 mL (0.20 mol) of benzoyl chloride with mechanical stirring and the mixture was stirred for 48 h. After dilution with 100 mL of water and acidification with 6 N HCl, the mixture was extracted twice with ether and the ether was washed once with 6 N HCl. Drying over MgSO$_4$ and filtration through celite provided an oil which was triturated with methanol to give 18.4 g of 47A as a pale yellow solid.

B. 3-Pyridin-4-yl-1H-indole

A mixture of 12.0 g (0.04mol) of 47A, 0.6 g of 10% palladium on carbon, 8 mL of dibenzylamine and 70 mL of diphenyl ether were heated at 210° C. for 7.5 h. Off-white needles precipitated from solution on cooling and these needles were filtered and washed with ether. The solids were suspended in 50 mL of 1 N HCl and washed once with ether. The aqueous solution was filtered through celite and concentrated. To the residue was added 10 mL of 5 N NaOH, and the resulting solid was filtered and washed with water to provide 4.02 g of 47B.

C. 1-Phenyl-3-pyridin-4-yl-1H-indole

To a mixture of 4.0 g (20.6 mmol) of 47B, 5.91 g (20.6 mmol) of cuprous bromide, 2.84 g (20.6 mmol) of potassium carbonate in 40 mL of N-methylpyrrolidine was added 9.1 mL (86.5 mmol) of bromobenzene and the mixture heated at 190° C. for 20 h. After cooling to room temperature the mixture was filtered through celite and the filter pad washed with ethyl acetate. The solution was refiltered and washed with 5 N ammonium hydroxide solution until a blue color no longer appeared in the aqueous layer. The organic portion was washed twice with water, once with brine, dried over $MgSO_4$ and concentrated to give 3.3 g of 47C as a light brown solid.

D. 3-(1-Benzyl-pyridin-4-yl)-1-phenyl-1H-indole bromide

A mixture of 2.7 g (10.0 mmol) of 47C and 1.18 mL (10.0 mmol) of benzyl bromide in 50 mL of benzene was heated on a steam bath for 3 h. After cooling to room temperature, the precipitated yellow solid was removed by filtration and washed with benzene to give 3.03 g of 47D.

E. 3-(1-Benzyl-1,2,3,6-tetrahydro-pyridin-4-yl)-1-phenyl-1H-indole

To 3.0 g (6.8 mmol) of 47D in 100 mL of methanol was added 18.5 g (490 mmol) of sodium borohydride over 40 min. The mixture was stirred at room temperature for 1 h and then heated on a steam bath for 1.5 h. After cooling to room temperature, the mixture was diluted with water and ether, and potassium carbonate was added until the lower layer clouded. The mixture was filtered and the ether phase dried over $MgSO_4$ and potassium carbonate. Filtration and concentration provided 2.13 g of 47E as a yellow oil.

F. 1-Phenyl-3-piperidin-4-yl-1H-indole hydrochloride

A mixture of 1.7 g (6.21 mmol) 47E and 1.0 g of 10% palladium on carbon in 200 mL of ethanol was hydrogenated at 50° C. for 5 h. 0.78 mL of concentrated HCl was added and hydrogenation continued at 50° C. for another 17 h. The mixture was filtered through celite and concentrated to give 1.26 g of 47F as a tan solid.

G. (R)-(1-{1-(1H-Indol-3-ylmethyl)-2-oxo-2-[4-(1-phenyl-1H-indol-3-yl)-piperidin-1-yl]-ethylcarbamoyl}-1-methyl-ethyl)-carbamic acid tert-butyl ester According to General Procedure A, 70 mg (0.21 mmol) of 47F and 83 mg of 4C were coupled and the product was purified by silica gel chromatography (65:35 v/v ethyl acetate:hexane) to give 90 mg of 47G as a white solid.

H. (R)-2-Amino-N-{1-(1H-indol-3-ylmethyl)-2-oxo-2-[4-(1-phenyl-1H-indol-3-yl)-piperidin-1-yl]-ethyl}-isobutyramide hydrochloride To a solution of 90 mg (0.14 mmol) of 47G in 4 mL of ethanol was added 2 mL of concentrated HCl and the mixture was stirred at room temperature for 1 h. The mixture was concentrated and the residue crystallized from chloroform/hexane to give 72 mg of the title compound as a solid.

$^1$H NMR ($CD_3OD$, 250 MHz) (mixture of rotamers) δ (partial)7.34–7.74 (m, 8H), 7.01–7.29 (m, 6H), 6.78 (s, 1H), 5.22–5.39 (m,1H), 4.45–4.69 (m,1H), 3.93–4.06 (m, 1H), 1.68 (s, 6H).
MS (Cl, $NH_3$) 548 (MH$^+$)

EXAMPLE 48

(R)-2-Amino-N-{1-(1H-indol-3-ylmethyl)-2-[4-(1H-indol-3-yl)-piperidin-1-yl-2-oxo-ethyl}-isobutyramide Hydrochloride

A. 3-(1,2,3,6-Tetrahydro-pyridin-4-yl)-1H-indole 50 mL of methanol was treated with 3.45 g (150 mmol) of sodium metal with stirring until the sodium had completely dissolved. To the methoxide solution was added 3.00 g (25.6 mmol) of indole and 10.23 g (66.6 mmol) of 4-piperidone monohydrate hydrochloride. The mixture was refluxed for 16 h and then concentrated. The residue was dissolved in ethyl acetate and washed once with water. The aqueous phase was extracted three times with ethyl acetate and the combined organics were washed once with brine, dried over $Na_2SO_4$, and concentrated to give 2.85 g of 48A as a yellow solid.

B. 3-Piperidin-4-yl-1H-indole

A mixture of 400 mg (2.0 mmol) of 48A in 100 mL of ethanol was hydrogenated at 45 psi for 17 h. The mixture was filtered through celite and concentrated to give 400 mg of 48B as a white solid.

C. (R)-(1-{1-(1H-Indol-3-ylmethyl)-2-[4-(1H-indol-3-yl)-piperidin-1-yl]-2-oxo-ethylcarbamoyl}-1-methyl-ethyl)-carbamic acid tert-butyl ester According to General Procedure A, 100 mg (0.50 mmol) of 48B and 195 mg (0.50 mmol) of 4C were coupled and the product was purified by silica gel chromatography using a gradient elution of 75% ethyl acetate in hexane to 87.5% ethyl acetate in hexane to give 220 mg of 48C as a white solid.

D. 2-Amino-N-{1-(1H-indol-3-ylmethyl)-2-[4-(1H-indol-3-yl)-piperidin-1-yl]-2-oxo-ethyl}-isobutyramide hydrochloride To 220 mg (0.39 mmol) of 48C in 3 mL of ethanol was added 2 mL of concentrated HCl. The mixture was stirred at room temperature for 1 h and then concentrated. Methanol and a small amount of methylene chloride were added and the mixture was concentrated to give 200 mg of the title compound as a white solid.

$^1$H NMR ($CD_3OD$, 250 MHz) (1:1 mixture of rotamers) (partial) δ 8.32–8.45 (m, 1H), 7.53–7.69 (m,1H), 7.30–7.43 (m, 3H), 6.94–7.29 (m, 6H), 5.23–5.37 (m,1H), 4.46–4.63 (m,1H), 3.90–4.04 (m, 1H), 1.62–1.68 (m, 6H).
MS (Cl, $NH_3$) 471 (MH$^+$)

EXAMPLE 49

(R)-2-Amino-N-{1-(1H-indol-3-ylmethyl)-2-[4-(2-methyl-benzoimidazol-1-yl)-piperidin-1-yl]-2-oxo-ethyl}-isobutyramide Hydrochloride

A. 4-(2-Methyl-benzoimidazol-1-yl)-piperidine-1-carboxylic acid tert-butyl ester To 325 mg (3.00 mmol) of 2-methylbenzimidazole in 12 mL of DMSO was added 100 mg (3.00 mmol) of sodium hydride (60% oil dispersion) and the mixture was stirred at room temperature for 30 min. The mixture was heated at 70° C. for 15 min and then cooled to room temperature. A solution of 520 mg (3.00 mmol) of 4-methanesulfonyloxy-piperidine-1-carboxylic acid tert-butyl ester (Yoon et al., WO9204342) in 3 mL of DMSO was added to the imidazole solution, and the mixture was stirred at room temperature for 12 h. The mixture was diluted with ethyl acetate and washed twice with a solution of saturated sodium bicarbonate and brine. The solution was dried over $MgSO_4$ and concentrated. The product was purified by silica gel chromatography (95:5 v/v chloroform:methanol) to give 89 mg of 49A as a white solid.

B. 2-Methyl-1-piperidin-4-yl-1H-benzoimidazole trifluoroacetate

To 89 mg (0.28 mmol) of 49A at 0° C. was added 3 mL of trifluoroacetic acid and the mixture was stirred for 30 min.

Dilution with ethyl acetate and concentration provided 92 mg of 49B as a yellow syrup.

C. (R)-(1-{1-(1H-Indol-3-ylmethyl)-2-[4-(2-methyl-benzoimidazol-1-yl)-piperidin-1-yl]-2-oxo-ethylcarbamoyl}-1-methyl-ethyl)-carbamic acid tert-butyl ester According to General Procedure A, 90 mg (0.42 mmol) of 49B and 163 mg (0.42 mmol) of 4C were coupled and the product was purified by silica gel chromatography using (75:25 v/v ethyl acetate:hexanes) followed by (95:5 v/v $CH_2Cl_2$:MeOH) to give 126 mg of 49C as a white solid.

D. (R)-2-Amino-N-{1-(1H-indol-3-ylmethyl)-2-[4-(2-methyl-benzoimidazol-1-yl)-piperidin-1-yl]-2-oxo-ethyl}-isobutyramide hydrochloride To 126 mg (0.21 mmol) of 49C in 6 mL of ethanol was added 6 mL of concentrated HCl, and the mixture was stirred at room temperature for 80 min. The mixture was concentrated and the residue redissolved in a small amount of methanol. Ethyl acetate was added until the product precipitated from solution, and the precipitated material was collected by filtration to give 85 mg of the title compound.

$^1$H NMR ($CD_3OD$, 250 MHz) (1:1 mixture of rotamers) (partial) δ 7.53–7.81 (m, 4H), 7.19–7.40 (m, 2H), 7.00–7.19 (m, 3H), 2.91 (s, 1.5H), 2.81 (s, 1.5H), 1.59–1.68 (m, 6H).
MS (Cl, $NH_3$) 487 ($MH^+$)

EXAMPLE 50

(R)-2-Amino-N-{1-(1H-indol-3-ylmethyl)-2-oxo-2-[4-(2-phenyl-benzoimidazol-1-yl)-piperidin-1-yl]-ethyl}-isobutyramide Hydrochloride A. (1-Benzyl-piperidin-4-yl)-(2-nitro-phenyl)-amine A mixture of 22.0 g (116 mmol) of 4-amino-1-benzylpiperidine, 16.31 g (116 mmol) of 1-fluoro-2-nitrobenzene, 19.17 g (116 mmol) of potassium iodide and 16.00 g (116 mmol) of potassium carbonate in 200 mL of DMSO was heated at 150° C. for 16 h. The mixture was diluted with ethyl acetate and washed four times with water and once with brine. Drying over $MgSO_4$ and concentration provided the crude product, which was purified by silica gel chromatography (30:70 v/v ethyl acetate:hexanes) and crystallized from 10% ethyl acetate in hexane to give 27.0 g of 50A as yellow crystals.

B. N-(1-Benzyl-piperidin-4-yl)-benzene-1,2-diamine

A mixture of 10.0 g (32.2 mmol) of 50A and 1.00 g of 10% palladium on carbon in 50 mL of ethanol was hydrogenated at 50 psi for 3 h. The mixture was filtered through celite and concentrated to give 9.00 g of 50B as a dark solid.

C. 1-(1-Benzyl-piperidin-4-yl)-2-phenyl-1H-benzoimidazole

A mixture of 1.00 g (3.56 mmol) of 50B and 1.89 g (17.8 mmol) of benzaldehyde in 4 mL of nitrobenzene was heated at 110° C. for 16 h. The mixture was purified by silica gel chromatography (30:70 v/v ethyl acetate:hexanes) to give 550 mg of 50C as a yellow foam.

D. 2-Phenyl-1-piperidin-4-yl-1H-benzoimidazole

To 540 mg (1.47 mmol) of 50C in 2 mL of methylene chloride at –10° C. was added 294 mg (2.06 mmol) of a-chloroethyl chloroformate and the mixture was stirred for 20 min and then concentrated. The residue was dissolved in 4 mL methanol and refluxed for 1 h. The mixture was concentrated to give 400 mg of 50D.

E. (R)-(1-{1-(1H-Indol-3-ylmethyl)-2-oxo-2-[4-(2-phenyl-benzoimidazol-1-yl)-piperidin-1-yl]-ethylcarbamoyl}-1-methyl-ethyl)-carbamic acid tert-butyl ester According to General Procedure A, 70 mg (0.25 mmol) of 50D and 98 mg (0.25 mmol) of 4C were coupled and the product was purified by silica gel chromatography using a gradient elution of 50% ethyl acetate in hexane to 100% ethyl acetate 30 mg of 50E was obtained as a white solid.

F. (R)-2-Amino-N-{1-(1H-indol-3-ylmethyl)-2-oxo-2-[4-(2-phenyl-benzoimidazol-1-yl)-piperidin-1-yl]-ethyl}-isobutyramide hydrochloride To 30 mg (0.046 mmol) of 50E in 2 mL of ethanol was slowly added 2 mL of concentrated HCl with stirring. The mixture was stirred at room temperature for 75 min and then concentrated. Crystallization from ethyl acetate/hexane provided 22 mg of the title compound as a white solid.

$^1$H NMR ($CD_3OD$, 250 MHz) (1:1 mixture of rotamers) (partial) δ 8.29 (d, 0.5H), 7.63–7.80 (m, 8.5H), 7.26–7.54 (m, 2.5H), 6.98–7.18 (m, 2.5H), 5.29–5.40 (m, 0.5H), 5.00–5.10 (m, 0.5H), 4.48–4.78 (m, 2H), 2.36–2.61 (m, 2H), 1.56–1.72 (m, 6H).
MS (Cl, $NH_3$) 549 ($MH^+$)

EXAMPLE 51

(R)-2-Amino-N-[2-[4-(6-fluoro-benzo[d]isoxazol-3-yl)-piperidin-1-yl]-1-(1H-indol-3-ylmethyl)-2-oxo-ethyl]-isobutyramide Hydrochloride A. 1-Acetyl-piperidine-4-carboxylic acid A mixture of 129.2 g (1.00 mmol) of isonipecotic acid and 400 mL of acetic anhydride was refluxed for 2.5 h. The mixture was allowed to cool to room temperature and stirred for 17 h. The precipitated solids were filtered, washed with diethyl ether and dried under vacuum to give 150.1 g of 51A as a white solid.

B. 1-Acetyl-piperidine-4-carbonyl chloride

To 250 mL of thionyl chloride was added 50.0 g (292 mmol) of 51A with mechanical stirring. The mixture was stirred for 1 h and then 200 mL of petroleum ether was added. The precipitated solids were collected by filtration and washed with cold petroleum ether. The solids were dried under vacuum to give 53.97 g of 51 B.

C. 1-[4-(2.4-Difluoro-benzoyl)-piperidin-1-yl]-ethanone

To a suspension of 75.0 g (562 mmol) of aluminum chloride in 95 mL of m-difluorobenzene was added 51 B over 10 min. The mixture was refluxed for 3 h under nitrogen, and after cooling to room temperature the mixture was poured slowly onto ice. The product was extracted with methylene chloride and the combined organics were washed twice with water and once with brine. Drying over $MgSO_4$ provided 63.21 g of 51C as a yellow solid.

D. (2,4-Difluoro-phenyl)-piperidin-4-yl-methanone hydrochloride

A mixture of 10.0 g (37.4 mmol) of 51C in 40 mL each of concentrated HCl and glacial acetic acid was refluxed for 7 h. An additional 20 mL of concentrated HCl was added to the reaction mixture and refluxing was continued for an additional 6 h. The mixture was concentrated and the residue triturated with 2-propanol to give 8.0 g of 51 D as a white solid.

E. (2,4-Difluoro-phenyl)-piperidin-4-yl-methanone oxime

A mixture of 10.0 g (38.21 mmol) of 51 D, 2.66 g (38.2 mmol) of hydroxylamine hydrochloride, and 4.6 mL (33.0 mmol) of triethylamine in 150 mL of ethanol was stirred at room temperature for 30 min., and then refluxed for 2.5 h. During reflux, the product began precipitating from solution. After cooling to room temperature, filtration provided 6.7 g of 51 E.

F. 6-Fluoro-3-piperidin-4-yl-benzo[d]isoxazole

A mixture of 10.0 g (41.62 mmol) of 51 E and 250 mL of 50% NaOH was refluxed for 5 h. After cooling to room temperature, the mixture was diluted with toluene and washed once each with water and brine. The mixture was dried over MgSO$_4$ and concentrated to provide a residue, which was triturated with ethyl acetate and petroleum ether to give 0.56 g of 51 F as a solid.

G. (R)-{1-[2-[4-(6-Fluoro-benzo[d]isoxazol-3-yl)-piperidin-1-yl]-1-(1H-indol-3-ylmethyl)-2-oxo-ethylcarbamoyl]-1-methyl-ethyl}-carbamic acid tert-butyl ester According to General Procedure A, 11 mg (0.045 mmol) of 51F and 18 mg (0.045 mmol) of 4C were coupled and the product was purified by silica gel chromatography (95:5 v/v CH$_2$Cl$_2$:MeOH) to give 16 mg of 51G as a white solid.

H. (R)-2-Amino-N-[2-]4-(6-fluoro-benzo[d]isoxazol-3-yl)-piperidin-1-yl]-1-(1H-indol-3-ylmethyl)-2-oxo-ethyl]-isobutyramide hydrochloride To 16 mg (0.027 mmol) of 51G in 2 mL of ethanol at room temperature was added 2 mL of concentrated HCl and the mixture stirred for 1 h. The mixture was concentrated and the residue crystallized from ethyl acetate/hexanes to give 11 mg of the title compound as a white solid.

$^1$H NMR (CD$_3$OD, 250 MHz) (1:1 mixture of rotamers) (partial) δ 8.21–8.29 (m, 1H), 7.51–7.63 (m, 2H), 7.26–7.34 (m, 2H), 6.90–7.21 (m, 5H), 5.07–5.24 (m, 1H), 4.43–4.49 (m, 1H), 3.79–3.92 (m, 1H), 2.58–2.74 (m, 2H), 1.44–1.53 (d, 6H).
MS (Cl, NH$_3$) 492 (MH$^+$)

EXAMPLE 52

(R)-1-[2-(2-Amino-2-methyl-propionylamino)-3-(1H-indol-3-yl)-propionyl]-4-phenyl-piperidine-4-carboxylic acid (4-hydroxy-butyl)-amide Hydrochloride A. 4-Phenyl-piperidine-1,4-dicarboxylic acid mono-tert-butyl ester To a suspension of 42.84 g (114 mmol) of 4-phenyl-4-piperidine carboxylic acid 4-methylbenzenesulfonate in 250 mL of dioxane and 50 mL of water was added 200 mL of 1 N NaOH, and the mixture was stirred until homogeneous. To the stirring mixture was added 27.3 g (125 mmol) of di-tert-butyldicarbonate over 15 min. Another 200 mL of 1 N NaOH was added and the mixture was stirred until a pH of 10–11 was maintained. Stirring was continued for an additional 17 h at room temperature, then the solution was diluted with 350 mL of water and extracted three times with diethyl ether. The aqueous layer was acidified to pH 4–5 with glacial acetic acid, then extracted three times with ethyl acetate. The combined organics were washed three times with water and once with brine. Drying over MgSO$_4$ and concentration provided a clear oil, which was triturated with diethyl ether to give 32.3 g of 52A as a white solid.

B. 4-Phenyl-piperidine-1,4-dicarboxylic acid benzyl ester tert-butyl ester

To 14.39 g (47 mmol) of 52A in 200 mL of DMF was added 7.2 g (52 mmol) of potassium carbonate followed by 8.22 g (48 mmol) of benzyl bromide. The mixture was stirred at room temperature for 17 h under nitrogen. The reaction mixture was diluted with 600 mL of ethyl acetate and washed five times with water and once with brine. Drying over MgSO$_4$ and concentration provided 15.95 g of 52B as a clear oil that crystallized on standing.

C. 4-Phenyl-piperidine-4-carboxylic acid benzyl ester trifluoroacetate

To 4.5 g (11.4 mmol) of 52B at 0° C. was added 50 mL of cold trifluoroacetic acid and the mixture stirred for 1.5 h. The mixture was concentrated to give 5.10 g of 52C.

D. (R)-1-[2-(2-tert-Butoxycarbonylamino-2-methyl-propionylamino)-3-(1H-indol-3-yl)-propionyl]-4-phenyl-piperidine-4-carboxylic acid benzyl ester According to General Procedure A, 1.09 g (2.8 mmol) of 4C and 885 mg (3.0 mmol) of 52C were coupled and the product was purified by silica gel chromatography using a gradient elution of 0% to 3% methanol in methylene chloride. 1.04 g of 52D was isolated as a light pink solid.

E. (R)-1-[2-(2-tert-Butoxycarbonylamino-2-methyl-propionylamino)-3-(1H-indol-3-yl)-propionyl]-4-phenyl-piperidine-4-carboxylic acid A mixture of 1.0 g (1.5 mmol) of 52D, and 200 mg of 20% palladium hydroxide on carbon in 30 mL of methanol was hydrogenated for 17 h at 50 psi. The mixture was filtered through celite and concentrated to give 772 mg of 52E as an orange solid.

F. (R)-{1[2-[4-(4-Hydroxy-butylcarbamoyl)-4-phenyl-piperidin-1-yl]-1-(1H-indol-3-ylmethyl)-2-oxo-ethylcarbamoyl]-1-methyl-ethyl}-carbamic acid tert-butyl ester To a mixture of 66 mg (0.114 mmol) of 52E, 9.4 mg (0.105 mmol) of 4-amino-1-butanol, and 27 mg (0.210 mmol) of diisopropylethylamine in 1.5 mL of methylene chloride was added 56 mg (0.126 mmol) of benzotriazol-1-yloxy-tris(dimethylamino)phosphonium hexafluorophosphate (BOP) and the mixture was stirred overnight at room temperature. Concentration provided a residue which was dissolved in ethyl acetate and washed twice with 1 N NaOH and once with brine. Drying over MgSO$_4$ and concentration provided the crude product, which was purified by silica gel chromatography using a gradient elution of 0% to 5% methanol in methylene chloride. 50 mg of 52F was isolated as a white solid.

G. (R)-1-[2-(2-Amino-2-methyl-propionylamino)-3-(1H-indol-3-yl)-propionyl[-4-phenyl-piperidine-4-carboxylic acid (4-hydroxy-butyl)-amide hydrochloride According to General Procedure C, 44 mg (0.068 mmol) of 52F was deprotected to give 30 mg of the title compound as a light pink solid.

$^1$H NMR (CD$_3$OD, 300 MHz) (mixture of rotamers) (partial) δ 7.52–7.61 (m, 1H), 7.08–7.49 (m, 4H), 7.09–7.20 (m, 2H), 6.97–7.08 (m, 3H), 5.19–5.24 (m, 1H), 3.39–3.51 (m, 3H), 2.90–3.27 (m, 5H), 1.50–1.61 (m, 6H).
MS (Cl, NH$_3$) 548 (MH$^+$)

EXAMPLE 53

(R)-1-[2-(2-Amino-2-methyl-propionylamino)-3-(1H-indol-3-yl)-propionyl]-4-phenyl-piperidine-4-carboxylic Acid Amide Hydrochloride A. (R)-{1-[2-(4-Carbamoyl-4-phenyl-piperidin-1-yl)-1-(1H-indol-3-ylmethyl)-2-oxo-ethylcarbamoyl]-1-methyl-ethyl}-carbamic acid tert-butyl ester To a mixture of 255 mg (0.44 mmol) of 52E, 118 mg (2.21 mmol) of ammonium chloride and 400 mg (3.09 mmol) of diisopropylethylamine in 4 mL of methylene chloride was added 235 mg (0.53 mmol) of BOP and the mixture stirred at room temperature for 24 h. The mixture was concentrated and the residue dissolved in ethyl acetate. The organic portion was washed twice with 1 N NaOH and once with brine. Drying over MgSO₄ and concentration provided a crude product which was purified by silica gel chromatography using a gradient elution of 50% ethyl acetate in hexane to 100% ethyl acetate. 128 mg of 53A was isolated as a white solid.

B. (R)-1-[2-(2-Amino-2-methyl-propionylamino)-3-(1H-indol-3-yl)-propionyl]-4-phenyl-piperidine-4-carboxylic acid amide hydrochloride According to General Procedure C, 118 mg (0.20 mmol) of 53A was deprotected to give 90 mg of the title compound as a pink solid.

$^1$H NMR (CD$_3$OD, 300 MHz) (mixture of rotamers) (partial) δ 7.52–7.63 (m, 1H), 7.19–7.47 (m, 4H), 6.98–7.17 (m, 5H), 5.13–5.25 (m, 1H), 3.82–4.21 (m, 1H), 3.98–3.27 (m, 3H), 1.50–1.65 (m, 6H).
MS (Cl, NH$_3$) 476 (MH$^+$)

EXAMPLE 54

(R)-1-[2-(2-Amino-2-methyl-propionylamino)-3-(1H-indol-3-yl)-propionyl]-4-phenyl-piperidine-4-carboxylic Acid Ethylamide Hydrochloride A. (R)-{1-[2-(4-Ethylcarbamoyl-4-phenyl-piperidin-1-yl)-1-(1H-indol-3-ylmethyl)-2-oxo-ethylcarbamoyl]-1-methyl-ethyl}-carbamic acid tert-butyl ester To a mixture of 255 mg (0.44 mmol) of 52E, 180 mg (2.21 mmol) of ethylamine hydrochloride and 400 mg (3.09 mmol) of diisopropylethylamine in 4 mL of methylene chloride was added 235 mg (0.53 mmol) of BOP and the mixture was stirred at room temperature for 24 h. The mixture was concentrated and the residue was dissolved in ethyl acetate and washed twice with 1 N NaOH and once with brine. Drying over MgSO₄ and concentration provided a crude product, which was purified by silica gel chromatography (1:1 v/v ethyl acetate:hexanes) to give 167 mg of 54A as a white foam.

B. (R)-1-[2-(2-Amino-2-methyl-propionylamino)-3-(1H-indol-3-yl)-propionyl]-4-phenyl-piperidine-4-carboxylic acid ethylamide hydrochloride According to General Procedure C, 167 mg (0.28 mmol) of 54A was deprotected to give 132 mg of the title compound as a pink solid.

$^1$H NMR (CD$_3$OD, 300 MHz) (mixture of rotamers) (partial) δ 7.50–7.65 (m, 1H), 6.95–7.32 (m, 9H), 5.07–5.22 (m, 1H), 4.11–4.22 (m, 1H), 3.56–3.67 (m, 1H), 2.88–3.30 (m, 5H), 2.61–2.79 (m, 1H), 1.52–1.61 (m, 6H).
MS (Cl, NH$_3$) 504 (MH$^+$)

EXAMPLE 55

(R)-1-Amino-cyclopropanecarboxylic Acid {1-benzyloxymethyl-2-oxo-2-[4-(2-oxo-2,3-dihydro-benzoimidazol-1-yl)-piperidin-1-yl]-ethyl}-amide Trifluoroacetate A. (R)-(1-{1-Benzyloxymethyl-2-oxo-2-[4-(2-oxo-2,3-dihydro-benzoimidazol-1-yl)-piperidin-1-yl]-ethylcarbamoyl}-cyclopropyl)-carbamic acid tert-butyl ester According to General Procedure A, 20 mg (0.05 mmol) of 1B and 20 mg (0.10 mmol) of 1-tert-butoxycarbonylamino-cyclopropanecarboxylic acid (Kienzler et al., Helv. Chim. Acta (1992), 75 (4) pp 1078–84) were coupled and the product was purified by silica gel chromatography using a gradient elution of 45% ethyl acetate in hexane to 100% ethyl acetate to 2% methanol in ethyl acetate to give 10 mg of 55A.

B. (R)-1-Amino-cyclopropanecarboxylic acid {1-benzyloxymethyl-2-oxo-2-[4-(2-oxo-2,3-dihydro-benzoimidazol-1-yl)-piperidin-1-yl]-ethyl}-amide trifluoroacetate To 10 mg (0.017 mmol) of 55A at 0° C. was added 2 mL of cold trifluoroacetic acid and the mixture stirred for 1 h. The mixture was concentrated and then diluted with heptane and concentrated again. The product was crystallized from methylene chloride/hexane to give 7 mg of 55B as a solid.

$^1$H NMR (CD$_3$OD, 300 MHz) (mixture of rotamers) δ 7.19–7.40 (m, 5H), 6.89–7.12 (m, 4H), 5.16–5.24 (m, 1H), 4.45–4.78 (m, 4H), 4.17–4.30 (d, 1H), 3.64–3.81 (m, 2H), 3.15–3.30 (m, 1H), 2.72–2.99 (m, 1H), 2.50–2.67 (m, 0.5H), 2.37–2.45 (m, 1.5H), 1.74–1.89 (m, 2H), 1.50–1.74 (m, 2H), 1.26–1.45 (m, 2H).
MS (Cl, NH$_3$) 478 (MH$^+$)

EXAMPLE 56

(R)-2-Amino-N-{1-(1H-indol-3-ylmethyl)-2-oxo-2-[4-(2-oxo-1,2-dihydro-imidazo[4,5-b]pyridin-3-yl)-piperidin-1-yl]-ethyl}-isobutyramide Hydrochloride A. (1-Benzyl-piperidin-4-yl)-(3-nitro-pyridin-2-yl)-amine A mixture of 1.66 g (10.5 mmol) of 2-chloro-3-nitropyridine, 2.00 g (10.5 mmol) of 4-amino-1-benzylpiperidine, 1.74 g (10.5 mmol) of potassium iodide and 1.44 g (10.5 mmol) of potassium carbonate in 10 ml of DMSO was heated at 100° C. for 17 h. After cooling to room temperature, the mixture was diluted with ethyl acetate and washed with saturated sodium bicarbonate solution and brine. Drying over MgSO₄ and concentration provided 1.25 g of 56A.

B. N2-(1-Benzyl-piperidin-4-yl)-pyridine-2,3-diamine

A mixture of 1.25 g (4.16 mmol) of 56A and 200 mg of 10% palladium on carbon in 150 mL of ethanol and 50 mL of ethyl acetate was hydrogenated at 50 psi for 3 h. The mixture was filtered through celite and concentrated to give 1.07 g of 56B.

C. 3-(1-Benzyl-piperidin-4-yl)-1,3-dihydro-imidazo[4,5-b]pyridin-2-one

A mixture of 1.07 g (3.74 mmol) of 56B, 2.43 g (15.0 mmol) of N,N'-carbonyldiimidazole, and 760 mg (7.52 mmol) of triethylamine in 10 mL of ethylene glycol dimethyl ether was heated at 80° C. for 17 h. The mixture was diluted with ethyl acetate and washed with saturated sodium bicarbonate solution and brine. Drying over MgSO₄ and concentration provided a crude product which was purified by silica gel chromatography using a gradient elution of 75% ethyl acetate in hexane to 100% ethyl acetate to give 270 mg of 56C.

D. 3-Piperidin-4-yl-1,3-dihydro-imidazo[4,5-b]pyridin-2-one

To a solution of 270 mg (6.88 mmol) of 56C in 1 mL of 1,2-dichloroethane at 0° C. was added 286 mg (2.0 mmol) of a-chloroethyl chloroformate. The ice bath was removed and the mixture stirred for 1 h. The mixture was concentrated and the residue dissolved in 10 mL of methanol and heated at 60° C. for 3 h. The mixture was diluted with 2 N NaOH and brine and extracted five times with chloroform. The organic extracts were dried over MgSO₄ and concentrated to give 70 mg of 56D.

E. (R)-(1-{1-(1H-Indol-3-ylmethyl)-2-oxo-2-[4-(2-oxo-1,2-dihydro-imidazo[4,5-b]pyridin-3-yl)-piperidin-1-yl]-ethylcarbamoyl}-1-methyl-ethyl)-carbamic acid tert-butyl ester According to General Procedure A, 70 mg (0.32 mmol) of 56D and 125 mg (0.32 mmol) of 4C were coupled and the product was purified by silica gel chromatography using a gradient elution of 70% ethyl acetate in hexane to 100% ethyl acetate to give 100 mg of 56E.

F. (R)-2-Amino-N-{1-(1H-indol-3-ylmethyl)-2-oxo-2-[4-(2-oxo-1,2-dihydro-imidazo[4,5-b]pyridin-3-yl)-piperidin-1-yl]-ethyl}-isobutyramide hydrochloride To 100 mg (0.28 mmol) of 56E in 3 mL of ethanol at 0° C. was added 1.5 mL of concentrated HCl, the ice bath was removed and the mixture stirred for 2 h. The mixture was concentrated several times from ethanol. The residue was diluted with ethyl acetate/hexanes and the precipitated solid collected by filtration to give 52 mg of the title compound.

$^1$H NMR (CD$_3$OD, 300 MHz) (mixture of rotamers) (partial) δ 7.97–8.06 (m, 1H), 7.53–7.69 (m, 2H), 7.25–7.38 (m, 2H), 7.09–7.21 (m, 3H), 5.22–5.33 (m, 1H), 4.49–4.74 (m, 2H), 1.48–1.64 (m, 6H).
MS (Cl, NH$_3$) 490 (MH$^+$)

EXAMPLE 57

(R)-2-Amino-N-[2-[4-(5-chloro-2-oxo-2,3-dihydro-benzoimidazol-1-yl)-piperidin-1-yl]-1-(1H-indol-3-ylmethyl)-2-oxo-ethyl]-isobutyramide A. (1-Benzyl-piperidin-4-yl)-(4-chloro-2-nitro-phenyl)-amine A mixture of 10.0 g (53.0 mmol) of 4-amino-1-benzylpiperidine, 10.0 g (53.0 mmol) of 2,5-dichloronitrobenzene, 8.80 g (53.0 mmol) of potassium iodide, and 7.30 g (53 mmol) of potassium carbonate in 60 mL of DMSO was heated at 140° C. for 48 h. The mixture was diluted with ethyl acetate and washed five times with water and once with brine. The mixture was dried over MgSO$_4$ and concentrated. The residue was triturated with 30% ethyl acetate in hexane to give 8.3 g of 57A as a red solid.

B. N1-(1-Benzyl-piperidin-4-yl)-4-chloro-benzene-1,2-diamine

A mixture of 8.30 g (26.28 mmol) of 57A was hydrogenated for 3 h at 45 psi The mixture was filtered through celite and concentrated. The product was purified by silica gel chromatography using a gradient elution of 100% ethyl acetate to 10% diethylamine in ethyl acetate to give 6.41 g of the title compound.

C. 1-(1-Benzyl-piperidin-4-yl)-5-chloro-1,3-dihydro-benzoimidazol-2-one

A mixture of 1.00 g (3.50 mmol) of 57B, 2.84 g (17.5 mmol) of N,N'-carbonyldiimidazole, and 764 mg (7.0 mmol) of triethylamine in 3 mL of ethylene glycol dimethyl ether was heated at 92° C. for 5 h. The mixture was concentrated and the product was purified by silica gel chromatography (75:25 v/v ethyl acetate:hexanes) to give 680 mg of 57C as a pink solid.

D. 5-Chloro-1-piperidin-4-yl-1,3-dihydro-benzoimidazol-2-one

To a solution of 680 mg (2.18 mmol) of 57C in 3 mL of methylene chloride at –10° C. was added 468 mg (3.27 mmol) of a-chloroethyl chloroformate and the mixture stirred for 40 min. Concentration provided a dissolved residue which was in 10 mL of methanol and warmed to reflux for 1 h. The mixture was concentrated and 50 mL of chloroform was added to the residue followed by a solution of 90 mg of sodium hydroxide in 10 mL of water.

The mixture was stirred for 15 min. The layers were separated and the organic portion was washed once with brine. Drying over MgSO$_4$ and concentrations provided 510 mg of 57D as a pink solid.

E. (R)-{1-[2-[4-(5-Chloro-2-oxo-2,3-dihydro-benzoimidazol-1-yl)-piperidin-1-yl]-1-(1H-indol-3-ylmethyl)-2-oxo-ethylcarbamoyl]-1-methyl-ethyl}-carbamic acid tert-butyl ester According to General Procedure A, 40 mg (0.16 mmol) of 57D and 62 mg (0.16 mmol) of 4C were coupled and the product was purified by silica gel chromatography eluting with 50% ethyl acetate in hexane followed by 5% methanol in methylene chloride to give 31 mg of 57E as a white solid.

F. (R)-2-Amino-N-[2-[4-(5-chloro-2-oxo-2,3-dihydro-benzoimidazol-1-yl)-piperidin-1-yl]-1-(1H-indol-3-ylmethyl)-2-oxo-ethyl]-isobutyramide To a mixture of 31 mg (0.05 mmol) of 57E in 3 mL of ethanol was added 3 mL of concentrated HCl and the mixture was stirred at room temperature for 80 min. The mixture was concentrated, and the residue crystallized from ethyl acetate/hexane to give 26 mg of the title compound as a white solid.

$^1$H NMR (CD$_3$OD, 300 MHz) (mixture of rotarhers) (partia;) δ 8.19–8.30 (m, 1H), 7.42–7.64 (m, 1H), 6.94–7.37 (m, 8H), 5.05–5.30 (m, 1H), 4.12–4.54 (m, 3H), 2.37–2.61 (m, 2H), 1.48–1.64 (m, 6H).
MS (Cl, NH$_3$) 523, 525 (MH$^+$)

EXAMPLE 58

(R)-2-Amino-N-{1-benzyloxymethyl-2-oxo-2-[7-(toluene-4-sulfonylamino)-3,4-dihydro-1H-isoquinolin-2-yl]-ethyl}-isobutyramide A. (R)-(1-{1-Benzyloxymethyl-2-oxo-2-[7-(toluene-4-sulfonylamino)-3,4-dihydro-1H-isoquinolin-2-yl]-ethylcarbamoyl}-1-methyl-ethyl)-carbamic acid tert-butyl ester To a mixture of 42 mg (0.846 mmol) of 6C and 10.3 mg (0.102 mmol) of triethylamine in 5 mL of methylene chloride at 0° C. was added 18 mg (0.93 mmol) of toluenesulfonyl chloride and the mixture was allowed to warm to room temperature and stirred overnight. The residue was dissolved in ethyl acetate and washed once each with 1 N NaOH and brine, dried over Na$_2$SO$_4$ and concentrated. The product was purified by silica gel chromatography (60:40 v/v ethyl acetate:hexanes) to give 19 mg of 58A as a foam.

B. (R)-2-Amino-N-{1-benzyloxymethyl-2-oxo-2-[7-(toluene-4-sulfonylamino)-3,4-dihydro-1H-isoquinolin-2-yl]-ethyl}-isobutyramide According to General Procedure C, 19 mg (0.029 mmol) of 58A was deprotected to give 12 mg of the title compound.

$^1$H NMR (CD$_3$OD, 250 MHz) (1:1 mixture of rotamers) (partial) δ 7.46–7.67 (m, 2H), 6.79–7.29 (m, 11H), 5.06–5.21 (m, 1H), 2.29–2.32 (d, 3H), 1.48–1.60 (bs, 6H).
MS (Cl, NH$_3$) 565 (MH$^+$)

EXAMPLE 59

(R)-2-Amino-N-{1-benzo[b]thiophen-3-ylmethyl-2-oxo-2-[4-(2-oxo-2,3-dihydro-benzoimidazol-1-yl)-piperidin-1-yl]-ethyl}-isobutyramide Hydrochloride A. (R)-3-Benzo[b]thiophen-3-yl-2-(2-tert-butoxycarbonylamino-2-methyl-propionylamino)-propionic acid A mixture of 193 mg (0.64 mmol) of D-3-(3-benzothienyl)alanine trifluoroacetate, 180 mg (0.53 mmol) of 33A, and 219 mg (1.70 mmol) of diisopropylethylamine in 10 mL of DMF was stirred overnight at room temperature. The mixture was acidified with 1 N HCl and diluted with ethyl acetate. The aqueous phase was extracted three times with ethyl acetate and the combined organics were washed five times with water, dried over $MgSO_4$ and concentrated. The product was purified by silica gel chromatography, eluting with 100% chloroform, followed by 5% methanol in chloroform, followed by (9:1:0.1 v/v/v chloroform:methanol:acetic acid) to give 110 mg of 59A.

B. (R)-(1-{1-Benzo[b]thiophen-3-ylmethyl-2-oxo-2-[4-(2-oxo-2,3-dihydro-benzoimidazol-1-yl)-piperidin-1-yl]-ethylcarbamoyl}-1-methyl-ethyl)-carbamic acid tert-butyl ester According to General Procedure A, 58 mg (0.27 mmol) of 4-(2-keto-1-benzimidazolinyl) piperidine and 105 mg (0.27 mmol) of 59A were coupled and the product was purified by silica gel chromatography using a gradient elution of 20% hexane in ethyl acetate to 100% ethyl acetate. 95 mg of 59B was isolated as a foam.

C. (R)-2-Amino-N-{1-benzo[b]thiophen-3-ylmethyl-2-oxo-2-[4-(2-oxo-2,3-dihydro-benzoimidazol-1-yl)-piperidin-1-yl]-ethyl}-isobutyramide hydrochloride According to General Procedure C, 85 mg (0.14 mmol) of 59B was deprotected to give 55 mg of the title compound as an off-white solid.

$^1$H NMR ($CD_3OD$, 300 MHz) (1:1 mixture of rotamers) (partial) δ 7.83–7.99 (m, 2H), 7.30–7.48 (m, 3H), 7.20–7.28 (m, 0.5H), 7.51–7.26 (m, 3H), 6.86–6.92 (m, 0.5H), 5.29–5.45 (m, 1H), 4.57–4.71 (m, 1H), 4.29–4.44 (m, 1H), 3.96–4.09 (m, 1H), 2.20–2.83 (m, 3H), 1.55–1.64 (d, 3H), 1.44–1.51 (d, 3H).
MS (Cl, $NH_3$) 506 (MH$^+$)

EXAMPLE 60

(R)-2-Amino-N-{1-(4-benzyloxy-benzyl)-2-oxo-2-[7-(toluene-4-sulfonylamino)-3,4-dihydro-1H-isoquinolin-2-yl]-ethyl}-isobutyramide Hydrochloride A. 1,2,3,4-Tetrahydro-isoquinolin-7-ylamine A mixture of 500 mg (2.8 mmol) of 6A and 500 mg of 10% palladium on carbon was hydrogenated at 45 psi overnight. The mixture was filtered through celite and concentrated to give 350 mg of 60A as a white solid.

B. (R)-{1-[2-(7-Amino-3,4-dihydro-1H-isoquinolin-2-yl)-1-(4-benzyloxy-benzyl)-2-oxo-ethylcarbamoyl]-1-methyl-ethyl}-carbamic acid tert-butyl ester According to General Procedure A, 300 mg (0.68 mmol) of 44D and 100 mg (0.68 mmol) of 60A were coupled and the product was purified by silica gel chromatography (75:25 v/v ethyl acetate:hexanes) to give 230 mg of 60B as a white solid.

C. (R)-(1-{1-(4-Benzyloxy-benzyl)-2-oxo-2-[7-(toluene-4-sulfonylamino)-3,4-dihydro-1H-isoquinolin-2-yl]-ethylcarbamoyl}-1-methyl-ethyl)-carbamic acid tert-butyl ester A mixture of 220 mg (0.39 mmol) of 60B, 85 mg (0.44 mmol) of p-toluenesulfonyl chloride and 55 mg (0.44 mmol) of 4-dimethylaminopyridine in 5 mL of methylene chloride was stirred overnight at room temperature. The mixture was diluted with chloroform and washed twice each with 10% HCl solution, saturated sodium bicarbonate solution and brine. Drying over $MgSO_4$ and concentration provided a crude product, which was purified by silica gel chromatography (75:25 v/v ethyl acetate:hexanes) to give 200 mg of 60C.

D. (R)-2-Amino-N-{1-(4-benzyloxy-benzyl)-2-oxo-2-[7-(toluene-4-sulfonylamino)-3,4-dihydro-1H-isoquinolin-2-yl]-ethyl}-isobutyramide hydrochloride To a solution of 150 mg (0.21 mmol) of 60C in 3 mL of ethanol was added 2 mL of concentrated HCl and the mixture was stirred at room temperature for 1 h. The mixture was concentrated, and the residue crystallized from methylene chloride/hexane to give 112 mg of the title compound.

$^1$H NMR ($CD_3OD$, 300 MHz) (1:1 mixture of rotamers) (partial) δ 7.64 (d, 2H), 7.17–7.39 (m, 7H), 7.04–7.10 (m, 1H), 6.79–6.92 (m, 5H), 4.90–5.12 (m, 2H), 4.29–4.57 (m, 1.5H), 4.11–4.20 (m, 0.5H), 2.82–2.97 (m, 2H), 2.34 (d, 3H), 1.46–1.52 (m, 6H).
MS (Cl, $NH_3$) 641 (MH$^+$)

EXAMPLE 61

(R)-2-Amino-N-[1-(7-amino-3,4-dihydro-1H-isoquinoline-2-carbonyl)-2-(1H-indol-3-yl)-ethyl]-isobutyramide Dihydrochloride A. (R)-2-Amino-N-[1-(7-amino-3,4-dihydro-1H-isoquinoline-2-carbonyl)-2-(1H-indol-3-yl)-ethyl]-isobutyramide dihydrochloride According to General Procedure C, 29 mg (0.056 mmol) of 36B was deprotected to give 14 mg of the title compound.

$^1$H NMR ($CD_3OD$, 300 MHz) (1:1 mixture of rotamers) (partial) δ 7.51–7.60 (m, 1H), 7.24–7.31 (d, 0.5H), 6.91–7.18 (m, 6.5H), 5.14–5.33 (m, 1H), 4.42–4.68 (m, 1.5H), 4.12–4.23 (m, 0.5H), 2.53–2.75 (m, 1H), 2.35–2.51 (m, 0.5H), 2.08–2.22 (m, 0.5H), 1.52–1.63 (m, 6H).
MS (Cl, $NH_3$) 420 (MH$^+$)

EXAMPLE 62

(R)-2-Amino-N-{1-[4-(2-oxo-2,3-dihydro-benzoimidazol-1-yl)-piperidine-1-carbonyl]-4-phenyl-butyl}-isobutyramide Hydrochloride A. 2-Oxo-5,6-diphenyl-3-(3-phenyl-allyl)-morpholine-4-carboxylic acid To a −78° C. solution of 13.8 g (70.0 mmol) of cinnamyl bromide and 4.94 g (14.0 mmol) of t-butyl-(2S, 3R)-(+)-6-oxo-2,3-diphenyl-4-morpholine carboxylate in 350 mL of anhydrous THF was added 28 mL (28 mmol) of 1 M sodium bistrimethylsilylamide in THF. The mixture was stirred at −78° C. for 1.5 h and then poured into 750 mL of ethyl acetate. The mixture was washed twice with brine, dried over $MgSO_4$ and concentrated to give a yellow oil. The oil was stirred in 150 mL of hexane overnight and the precipitated solid was then collected by filtration to give 3.2 g of 62A as a white solid.

B. 5.6-Diphenyl-3-(3-phenyl-allyl)-morpholin-2-one

According to General Procedure B, 2.97 g (6.33 mmol) of 62A was deprotected to give an orange oil which was purified by silica gel chromatography (10:90 v/v ethyl acetate:hexane) to give 880 mg of 62B as a white solid.

C. 2-(2-Amino-2-methyl-propionylamino)-5-phenyl-pentanoic acid

A mixture of 440 mg (1.19 mmol) of 62B and 120 mg of palladium chloride in 20 mL of ethanol and 10 mL of THF was hydrogenated at 45 psi for 16 h. The mixture was filtered through celite and concentrated, and the residue was triturated with ether to give 240 mg of 62C as a white solid.

D. (R)-2-(2-tert-Butoxycarbonylamino-2-methyl-propionylamino)-5-phenyl-pentanoic acid A mixture of 203 mg (1.05 mmol) of 33A, 378 mg (1.26 mmol) of 62C and 434 mg (3.36 mmol) of diisopropylethylamine in 2 mL of DMF was stirred overnight. The mixture was diluted with ethyl acetate and extracted twice with 1 N HCl. The aqueous phase was extracted once with ethyl acetate. The pooled organic extracts were washed three times with water and once with brine. The mixture was dried over MgSO$_4$ and concentrated. The residue was purified by silica gel chromatography using 80% chloroform in hexane followed by 100% chloroform followed by 10% methanol in chloroform to give 127 mg of 62D.

E. (R)-(1-Methyl-1-{1-[4-(2-oxo-2,3-dihydro-benzoimidazol-1-yl)-piperidine-1-carbonyl]-4-phenyl-butylcarbamoyl}-ethyl)-carbamic acid tert butyl ester According to General Procedure A, 45 mg (0.12 mmol) of 62D and 26 mg (0.12 mmol) of 4-(2-keto-1-benzimidazolinyl) piperidine were coupled and the product purified by silica gel chromatography using a gradient of 100% methylene chloride to 3% methanol in methylene chloride to give 39 mg of 62E as a yellow foam.

F. (R)-2-Amino-N-{1-[4-(2-oxo-2,3-dihydro-benzoimidazol-1-yl)-piperidine-1-carbonyl]-4-phenyl-butyl}-isobutyramide hydrochloride According to General Procedure C, 36 mg (0.062 mmol) of 62E was deprotected to give 28 mg of the title compound as a white solid.

$^1$H NMR (CD$_3$OD, 250 MHz) (mixture of rotamers) (partial) δ 7.03–7.36 (m, 9H), 4.62–4.73 (m, 1H), 4.43–4.59 (m, 1H), 3.97–4.19 (m, 1H), 2.52–2.87 (m, 3H), 1.60 (s, 6H).

MS (Cl, NH$_3$) 578 (MH$^+$)

EXAMPLE 63

2-Amino-N-{1-(1-methyl-1H-indol-3-ylmethyl)-2-oxo-2-[4-(2-oxo-2,3-dihydro-benzoimidazol-1-yl)-piperidin-1-yl]-ethyl}-isobutyramide Hydrochloride A. 2-(2-tert-Butoxycarbonylamino-2-methyl-propionylamino)-3-(1-methyl-1H-indol-3-yl)-propionic acid A mixture of 1.00 g (4.58 mmol) of 1-methyl-dl-tryptophan, 1.65 g (5.5 mmol) of 33A, and 1.30 g (10.0 mmol) of diisopropylethylamine in 2 mL of DMF was heated overnight at 50° C. The mixture was diluted with ethyl acetate and washed once each with 10% HCl and brine. The solution was dried over MgSO$_4$ and concentrated, and the product was purified using a gradient of 2% to 5% methanol in methylene chloride to give 173 mg of 63A.

B. (1-Methyl-1-{1-(1-methyl-1H-indol-3-ylmethyl)-2-oxo-2-[4-(2-oxo-2,3-dihydro-benzoimidazol-1-yl)-piperidin-1-yl]-ethylcarbamoyl}-ethyl)-carbamic acid tert-butyl ester According to General Procedure A, 173 mg (0.42 mmol) of 63A and 131 mg (0.42 mmol) of 4-(2-keto-1-benzimidazolinyl) piperidine were coupled and the product was purified by silica gel chromatography in 100% ethyl acetate to give 210 mg of 63B.

C. 2-Amino-N-{1-(1-methyl-1H-indol-3-ylmethyl)-2-oxo-2-[4-(2-oxo-2,3-dihydro-benzoimidazol-1-yl)-piperidin-1-yl]-ethyl}-isobutyramide hydrochloride According to General Procedure C, 209 mg (0.35 mmol) of 63B was deprotected to give 166 mg of the title compound.

$^1$H NMR (CD$_3$OD, 250 MHz) (mixture of rotamers) (partial) (1:1 mixture of diastereomers) δ 7.67 (d, 0.5H), 7.55 (d, 0.5H), 7.31–7.39 (m, 1H), 6.99–7.26 (m, 6.5H), 6.74 (d, 0.5H), 5.12–5.33 (m, 1H), 3.78 (s, 3H), 1.49–1.63 (m, 6H).

MS (Cl, NH$_3$) 503 (MH$^+$)

EXAMPLE 64

(R)-2-Amino-N-{1-naphthalen-1-ylmethyl-2-oxo-2-[4-(2-oxo-2,3-dihydro-benzoimidazol-1-yl)-piperidin-1-yl]-ethyl}-isobutyramide Trifluoroacetate A. (R)-2-(2-tert-Butoxycarbonylamino-2-methyl-propionylamino)-3-naphthalen-1-yl-propionic acid A mixture of 500 mg (1.52 mmol) of D-3-(1'-napthyl) alanine, 547 mg (1.82 mmol) of 33A and 0.80 mL (4.56 mmol) of diisopropylamine in 5 mL of DMF was heated at 50° C. overnight. The mixture was concentrated and the residue diluted with methylene chloride. The organic portion was washed once with water, twice with 1 N HCl and once with brine. The solution was dried over MgSO$_4$ and concentrated, and the product was purified by silica gel chromatography (0.1:5:95 v/v/v acetic acid:methanol:methylene chloride) to give 484 mg of 64A.

B. (R)-(1-Methyl-1-{1-naphthalen-1-ylmethyl-2-oxo-2-[4-(2-oxo-2,3-dihydro-benzoimidazol-1-yl)-piperidin-1-yl]-ethylcarbamoyl}-ethyl)-carbamic acid tert-butyl ester According to General Procedure A, 100 mg (0.25 mmol) of 64A and 50 mg (0.23 mmol) of 4-(2-keto-1-benzimidazolinyl)-piperidine were coupled and the product was purified by silica gel chromatography using a gradient of 100% methylene chloride to 4% methanol in methylene chloride to give 97 mg of 64B.

C. (R)-2-Amino-N-{1-naphthalen-1-ylmethyl-2-oxo-2-[4-(2-oxo-2,3-dihydro-benzoimidazol-1-yl)-piperidin-1-yl]-ethyl}-isobutyramide trifluoroacetate To 91 mg (0.15 mmol) of 64B at 0° C. was added 2 mL of cold TFA and the mixture was stirred at 0° C. for 2 h. The mixture was concentrated, then coevaporated twice each from methylene chloride and toluene to give 99 mg of the title compound as a white powder.

$^1$H NMR (CD$_3$OD, 250 MHz) (mixture of rotamers) (partial) δ 8.22 (d, 0.5H), 8.17 (d, 0.5H), 7.79–7.94 (m, 2H), 7.39–7.67 (m, 4H), 7.01–7.26 (m, 3.5H), 6.75 (d, 0.5H), 5.42–5.51 (m, 1H), 5.29–5.40 (m, 1H), 4.54–4.67 (m, 1H), 4.19–4.37 (m, 2H), 3.51–3.82 (m, 3H), 2.29–2.72 (m, 3H), 1.49–1.68 (m, 6H).

MS (Cl, NH$_3$) 500 (MH$^+$)

EXAMPLE 65

(R)-2-Amino-N-{2-(1H-indol-3-yl)-1-[6-(morpholine-4-carbonyl)-3,4-dihydro-1H-isoquinoline-2-carbonyl]-ethyl}-isobutyramide Hydrochloride A. (R)-(1-{2-(1H-Indol-3-yl)-1-[6-(morpholine-4-carbonyl)-3,4-dihydro-1H-isoquinoline-2-carbonyl]-ethylcarbamoyl}-1-methyl-ethyl)-carbamic acid tert-butyl ester According to the method outlined in General Procedure A, 121 mg (0.22 20 mmol) of 26A and 19 mg (0.33 mmol) of morpholine were coupled to give 140 mg of 65A as a yellow oil.

B. (R)-2-Amino-N-{2-(1H-indol-3-yl)-1-[6-(morpholine-4-carbonyl)-3,4-dihydro-1H-isoquinoline-2-carbonyl]-ethyl}-isobutyramide hydrochloride To 86 mg (0.14 mmol) of 65A in 6 mL of ethanol was added 2.0 mL of concentrated HCl and the mixture was stirred for 1.5 h at room temperature. The mixture was concentrated to give 68 mg of the title compound as a tan solid.

$^1$H NMR (CD$_3$OD, 300 MHz) (mixture of rotamers) (partial) δ 7.51–7.61 (m, 1H), 6.92–7.30 (m, 6.5H), 6.58 (d, 0.5H), 5.14–5.39 (m, 1H), 4.56–4.66 (d, 0.5H), 4.41–4.50 (d, 1H), 4.09–4.18 (d, 0.5H).

EXAMPLE 66

(R)-2-Amino-N-{1-(1H-indol-3-ylmethyl)-2-oxo-2-[4-(2-oxo-2,3-dihydro-imidazo[4,5-c]pyridin-1-yl)-piperidin-1-yl]-ethyl}-isobutyramide Dihydrochloride A. 1-Piperidin-4-yl-1,3-dihydro-imidazo[4,5-c]pyridin-2-one 66A was prepared by the same route illustrated in Example 56 using 4-chloro-3-nitro-pyridine and 4-amino-1-benzylpiperidine as starting materials. The 4-chloro-3-nitro-pyridine was prepared by adding 3.00 g (23.8 mmol) of 4-hydroxy-3-nitropyridine to 10 mL of phosphorous oxychloride and heating the mixture at 130° C. for 3 h. The mixture was poured into ice water, neutralized with 2 N NaOH and allowed to stand for 1 h. The mixture was extracted with ethyl acetate and the combined organics were washed with brine. The solution was dried and concentrated to give 2.92 g of 4-chloro-3-nitro-pyridine.

B. (R)-(1-{1-(1H-Indol-3-ylmethyl)-2-oxo-2-[4-(2-oxo-2,3-dihydro-imidazo[4,5-c]pyridin-1-yl)-piperidin-1-yl]-ethylcarbamoyl}-1-methyl-ethyl)-carbamic acid tert-butyl ester According to General Procedure A, 90 mg (0.29 mmol) of 66A and 113 mg (0.29 mmol) of 4C were coupled and the product was purified by silica gel chromatography using an elution gradient of 1% methanol in methylene chloride to 5% methanol in methylene chloride followed by 5% methanol plus 1% acetic acid in methylene chloride to give 80 mg of 66B.

C. (R)-(1-{1-(1H-Indol-3-ylmethyl)-2-oxo-2-[4-(2-oxo-2,3-dihydro-imidazo[4,5-c]pyridin-1-yl)-piperidin-1-yl]-ethylcarbamoyl}-1-methyl-ethyl)-carbamic acid tert-butyl ester dihydrochloride To 80 mg (0.14 mmol) of 66B in 3 mL of ethanol was added 3 mL of concentrated HCl and the mixture was stirred at room temperature for 3 h. The mixture was concentrated and then coevaporated three times with ethanol. The residue was crystallized from ethyl acetate/hexane to give 60 mg of the title compound.

$^1$H NMR (CD$_3$OD, 300 MHz) (mixture of rotamers) (partial) δ 8.41–8.57 (m, 2H), 7.87 (d, 0.5H), 7.58 (d, 0.5H), 7.21–7.39 (m, 2H), 7.07–7.13 (m, 3H), 5.24–5.34 (m, 0.5H), 5.12–5.20 (m, 1H), 4.60–4.71 (m, 1H), 1.52–1.67 (m, 6H). MS (Cl, NH$_3$) 491 (MH$^+$)

EXAMPLE 67

2-Amino-N-{1-biphenyl-4-ylmethyl-2-oxo-2-[4-(2-oxo-2,3-dihydro-benzoimidazol-1-yl)-piperidin-1-yl]-ethyl}-isobutyramide Hydrochloride A. (R)-2-Amino-3-biphenyl-4-yl-propionic acid trifluoroacetate To 1.50 g (4.4 mmol) of BOC-D-4–4'-phenylalanine at 0° C. was added 25 mL of cold TFA and the mixture was stirred for 2 h. The mixture was concentrated and then heptane was added to the residue and the mixture concentrated again and dried under vacuum to give 1.59 g of 67A as a pale red solid.

B. (R)-3-Biphenyl-4-yl-2-(2-tert-butoxycarbonylamino-2-methyl-propionylamino)-propionic acid A mixture of 1.59 g (4.4 mmol) of 67A, 1.59 g (5.3 mmol) of 33A and 1.82 g (14.1 mmol) of diisopropylethylamine in 50 mL of DMF was stirred at 0° C. for 6 days. The mixture was diluted with ethyl acetate, washed twice with 10% HCl and once with water, and twice with brine. The solution was dried over MgSO$_4$ filtered and concentrated and the product was purified by silica gel chromatography using a gradient of 100% ethyl acetate to 10% methanol in ethyl acetate to give 900 mg of 67B.

C. (R)-(1-{1-Biphenyl-4-ylmethyl-2-oxo-2-[4-(2-oxo-2,3-dihydro-benzoimidazol-1-yl)-piperidin-1-yl]-ethylcarbamoyl}-1-methyl-ethyl)-carbamic acid tert-butyl ester According to General Procedure A, 250 mg (0.59 mmol) of 67B and 127 mg (0.059 mmol) of 4-(2-keto-1-benzimidazolinyl)-piperidine were coupled to give 270 mg of 67C as a white solid which was used in the next step without further purification.

D. (R)-2-Amino-N-{1-biphenyl-4-ylmethyl-2-oxo-2-[4-(2-oxo-2,3-dihydro-benzoimidazol-1-yl)-piperidin-1-yl]-ethyl}-isobutyramide hydrochloride To 270 mg (0.43 mmol) of 67C in 3 mL of ethanol was added 3 mL of concentrated HCl and the mixture was stirred at room temperature for 1.5 h. The mixture was concentrated to dryness and the residue was triturated with hexane/ethanol to give 200 mg of the title compound as a white solid.

$^1$H NMR (CD$_3$OD, 250 MHz) (mixture of rotamers) (partial) δ 7.52–7.70 (m, 4H), 7.28–7.51 (m, 6H), 6.91–7.11 (m, 3H), 5.25–5.33 (m, 1H), 4.67–4.80 (m, 1H), 4.43–4.58 (m, 1H), 4.16–4.27 (m, 1H), 1.53–1.66 (m, 6H). MS (Cl, NH$_3$) 527 (MH$^+$)

EXAMPLE 68

(R)-2-Amino-N-[2-(1H-indol-3-yl)-1-(7-sulfamoyl-3,4-dihydro-1H-isoquinoline-2-carbonyl)-ethyl]-isobutyramide Hydrochloride A. (R)-{1-[2-(1H-Indol-3-yl)-1-(7-sulfamoyl-3,4-dihydro-1H-isoquinoline-2-carbonyl)-ethylcarbamoyl]-1-methyl-ethyl}-carbamic acid tert-butyl ester The preparation of 1,2,3,4-tetrahydro-isoquinoline-7-sulfonic acid amide is described by Pendleton et al., J. Pharmacol. Exp. Ther., 208 (1979) p24. According to General Procedure A, 83 mg (0.39 mmol) of 1,2,3,4-Tetrahydro-isoquinoline-7-sulfonic acid amide and 150 mg (0.39 mmol) of 4C were coupled and the product was purified by silica gel chromatography (19:1 v/v chloroform:methanol) to give 206 mg of 68A.

B. (R)-2-Amino-N-[2-(1H-indol-3-yl)-1-(7-sulfamoyl-3,4-dihydro-1H-isoquinoline-2-carbonyl)-ethyl]-isobutyramide hydrochloride To 144 mg (0.25 mmol) of 68A in 12 mL of ethanol was added 4 mL of concentrated HCl and the mixture was stirred at room temperature for 5 h. The reaction mixture was concentrated to give 118 mg of the title compound as a white solid.

$^1$H NMR (CD$_3$OD, 300 MHz) (mixture of rotamers) (partial) δ 7.48–7.53 (m, 2H), 7.21–7.30 (m, 1H), 6.92–7.13 (m, 4H), 5.11–5.25 (m, 1H), 4.41–4.62 (m, 2H), 4.11–4.22 (d, 0.5H), 3.75–3.86 (m, 1H), 3.50–3.63 (m, 1H), 2.53–2.72 (m, 1H), 2.26–2.42 (m, 0.5H), 2.06–2.19 (m, 0.5H), 1.57 (m, 6H). MS (Cl, NH$_3$) 519 (MH$^+$)

EXAMPLE 69

2-Amino-N-{1-(6-fluoro-1H-indol-3-ylmethyl)-2-oxo-2-[4-(2-oxo-2,3-dihydro-benzoimidazol-1-yl)-piperidin-1-yl]-ethyl}-isobutyramide Hydrochloride A. 2-(2-tert-Butoxycarbonylamino-2-methyl-propionylamino)-3-(6-fluoro-1H-indol-3-yl)-propionic acid A mixture of 150 mg (0.50 mmol) of 33A, 100 mg (0.45 mmol) of 6-fluorotryptophan and 128 mg (1.0 mmol) of diisopropylethylamine was stirred overnight at room temperature. The mixture was acidified to pH 1 with 1 N HCl, diluted with water and extracted three times with ethyl acetate. The combined organic extracts were washed four times with water, once with brine, dried over MgSO$_4$ and concentrated to give 154 mg of 69A.

B. (1-{1-(6-Fluoro-1H-indol-3-ylmethyl)-2-oxo-2-[4-(2-oxo-2,3-dihydro-benzoimidazol-1-yl)-piperidin-1-yl]-ethylcarbamoyl}-1-methyl-ethyl)-carbamic acid tert-butyl ester According to General Procedure A, 79 mg (0.194 mmol) of 69A and 42 mg (0.194 mmol) of 4-(2-keto-1-benzimidazolinyl)-piperidine were coupled and the product was purified by silica gel chromatography using a gradient of 1% methanol in methylene chloride to 3% methanol in methylene chloride to give 84 mg of 69B as a white foam.

C. 2-Amino-N-{1-(6-fluoro-1H-indol-3-ylmethyl)-2-oxo-2-[4-(2-oxo-2,3-dihydro-benzoimidazol-1-yl)-piperidin-1-yl]-ethyl}-isobutyramide hydrochloride According to General Procedure C, 78 mg (0.129 mmol) of 69B was deprotected to give 54 mg of the title compound.

$^1$H NMR (CD$_3$OD, 300 MHz) (mixture of rotamers) (partial) (1:1 mixture of diastereomers) δ 7.56–7.62 (m, 0.5H), 7.46–7.53 (m, 0.5H), 7.01–7.26 (m, 6H), 6.70–6.88 (m, 1H), 5.17–5.37 (m, 1H), 4.60–4.69 (m, 1H), 4.25–4.41 (m, 1H), 3.94–4.12 (m, 1H), 3.04–3.24 (m, 2H), 2.45–2.62 (m, 2H), 1.48–1.65 (m, 6H).
MS (Cl, NH$_3$) 519 (MH$^+$)

EXAMPLE 70

(R)-2-Amino-N-[1-(1H-indol-3-ylmethyl)-2-(4-indol-1-yl-piperidin-1-yl)-2-oxo-ethyl]-isobutyramide Hydrochloride A. (1-Benzyl-piperidin-4-yl)-phenyl-amine To a mixture of 10.9 g (57.6 mmol) of 1-benzyl-4-piperidone, 100.0 g (576 mmol) of sodium sulfate and 175 mL of acetic acid under nitrogen was added 7.00 g (74.9 mmol) of aniline by syringe and the mixture was stirred at room temperature for 15 min. To the stirring solution was added 61.0 g (288 mmol) of sodium triacetoxyborohydride and the mixture was stirred overnight. The mixture was concentrated and the residue was poured onto ice and neutralized with 2 N NaOH to pH 7.5. The mixture was extracted four times with chloroforn, and the organics washed once with brine. The solution was dried over Na$_2$SO$_4$ and concentrated. The residue was triturated with ether to give 4.2 g of 70A as a white solid.

B. 1-[2-(1-Benzyl-piperidin-4-ylamino)-phenyl]-2-chloro-ethanone hydrochloride

To a flame-dried flask containing 2.50 g (9.4 mmol) of 70A, and 40 mL of dichloroethane at 0° C. was added 11.3 mL (11.3 mmol) of 1 M boron trichloride in methylene chloride over 5 min., followed by 1.2 mL (18.8 mmol) of chloroacetonitrile over 3 min. The mixture was warmed to room temperature and stirred for 10 min. The mixture was refluxed overnight and then allowed to cool to room temperature. Ice was added to the stirring solution followed by 10 mL of 10% HCl and the mixture was heated to 100° C. for 0.5 h. The layers were separated and the aqueous phase was extracted with methylene chloride. The organic portion was dried over MgSO$_4$ and concentrated to give 1.50 g of 70B.

C. 1-(1-Benzyl-piperidin-4-yl)-1H-indole

To 1.50 g (4.0 mmol) of 70B dissolved in 11 mL of ethanol at 0° C. was added 2.0 mL (4.0 mmol) of 2N NaOH and the mixture stirred for 10 min. Sodium borohydride, 80 mg (2.1 mmol), was added to the stirring solution and the mixture was stirred at 0° C. for 1 h. Ice was added to the solution and the mixture was extracted three times with methylene chloride. The combined organics were washed with water and dried over MgSO$_4$ and the residue dissolved in 1,4-dioxane and refluxed for 2 h. After cooling to room temperature, ice and a saturated aqueous sodium carbonate solution was added to the reaction mixture and the solution was extracted three times with methylene chloride and the combined organics were washed twice with water. The solution was dried over Na$_2$SO$_4$ and concentrated. The product was purified by silica gel chromatography (80:20 v/v hexanes:ethyl acetate) to give 350 mg of 70C as a white foam.

D. 4-Indol-1-yl-piperidine-1-carboxylic acid ethyl ester

To a refluxing solution of 350 mg (1.2 mmol) of 70C in 40 mL of dichloroethane was added 0.28 mL (3.6 mmol) of ethyl chloroformate and the mixture was refluxed for 2.5 h. The mixture was concentrated to give 330 mg of 70D as a yellow solid.

E. 1-Piperidin-4-yl-1H-indole

A mixture of 325 mg (1.2 mmol) of 70D, 440 mg (15.7 mmol) of sodium hydroxide, 1 mL of water and 2 mL of ethylene glycol was heated at 150° C. for 17 h. After cooling to room temperature, ice and concentrated HCl were added to the mixture and the solution was stirred for 30 min. Ice and saturated aqueous sodium carbonate solution were added to the mixture until the solution was basic. The mixture was extracted twice with ether and the combined organic extracts were washed twice with water. The solution was dried over MgSO$_4$ and concentrated to give 150 mg of 70E as a colorless oil.

F. (R)-{1-[1-(1H-Indol-3-ylmethyl)-2-(4-indol-1-yl-piperidin-1-yl)-2-oxo-ethylcarbamoyl]-1-methyl-ethyl}-carbamic acid tert-butyl ester According to General Procedure A, 150 mg (0.75 mmol) of 70E, and 291 mg (0.75 mmol) of 4C were coupled to give 260 mg of 70F as a white solid.

G. (R)-2-Amino-N-[1-(1H-indol-3-ylmethyl)-2-(4-indol-1-yl-piperidin-1-yl)-2-oxo-ethyl]-isobutyramide hydrochloride To 250 mg (0.44 mmol) of 70F in 5 mL of ethanol was added 3 mL of concentrated HCl and the mixture was stirred at room temperature for 2 h. The mixture was concentrated and ethanol and hexane were added to the residue. The precipitated off-white solid was filtered and dried to give 10 mg of the title compound.
MS (Cl, NH$_3$) 473 (MH$^+$)

EXAMPLE 71

(R)-2-Amino-N-{1-(1H-indol-3-ylmethyl)-2-oxo-2-[4-(2-phenyl-imidazo[4,5-b]pyridin-3-yl)-piperidin-1-yl]-ethyl}-isobutyramide Dihydrochloride A. 2-Phenyl-3-piperidin-4-yl-3H-imidazo[4,5-b]pyridine 71 A was prepared according to the method outlined in Example 50 using 4-amino-1-benzylpiperidine and 2-chloro-3-nitro-pyridine as starting materials.

B. (R)-(1-{1-(1H-Indol-3-ylmethyl)-2-oxo-2-[4-(2-phenyl-imidazo[4,5-b]pyridin-3-yl)-piperidin-1-yl]-ethylcarbamoyl}-1-methyl-ethyl)-carbamic acid tert-butyl ester According to General Procedure A, 90 mg (0.32 mmol) of 71A and 161 mg (0.41 mmol) of 4C were coupled and the product was purified by silica gel chromatography (100% ethyl acetate) to give 45 mg of 71B.

C. (R)-2-Amino-N-{1-(1H-indol-3-ylmethyl)-2-oxo-2-[4-(2-phenyl-imidazo[4,5-b]pyridin-3-yl)-piperidin-1-yl]-ethyl}-isobutyramide dihydrochloride To 45 mg (0.069 mmol) of 71 B in 2 mL of ethanol was added 2 mL of concentrated HCl and the mixture was stirred at room temperature for 2 h. The mixture was concentrated and coevaporated twice with ethanol. Ethyl acetate and hexane were added to the residue until the product crystallized. The solid was collected by filtration to give 20 mg of the title compound.

$^1$H NMR (CD$_3$OD, 250 MHz) (mixture of rotamers) (partial) δ 8.74 (d, 0.5H), 8.56 (d, 0.5H), 8.06–8.23 (m, 1H), 7.43–7.79 (m, 8H), 7.18–7.28 (m, 2H), 6.87–7.02 (m, 3H), 5.14–5.28 (m, 1H), 4.52–4.63 (m, 1H), 3.93–4.08 (m, 1H), 1.37–1.49 (d, 6H).
MS (Cl, NH$_3$) 551 (MH$^+$)

EXAMPLE 72

2-Amino-N-{1-(6-fluoro-1H-indol-3ylmethyl)-2-oxo-2-[4-(2-phenyl-benzimidazol-1-yl)-piperidin-1-yl]-ethyl}-isobutyramide Hydrochloride A. (1-{6-Fluoro-1H-indol-3ylmethyl)-2-oxo-2-{4-(2-phenyl-benzoimidazol-1-yl)-piperidin-1-yl]-ethylcarbamoyl}-1-methyl-ethyl)-carbamic acid tert-butyl ester According to General Procedure A, 101 mg (0.25 mmol) of 69A and 70 mg (0.25 mmol) of 50D were coupled and the product was purified by silica gel chromatography (90:10 v/v chloroform:methanol) to give 84 mg of 72A.

B. 2-Amino-N-f 1-(6-fluoro-1H-indol-3ylmethyl)-2-oxo-2-[4-(2-phenyl-benzimidazol-1-yl)-piperidin-1-yl]-ethyl}-isobutyramide hydrochloride According to General Procedure C, 76 mg (0.114 mmol) of 72A was deprotected to give 58 mg of the title compound.

$^1$H NMR (CD$_3$OD, 300 MHz) δ (mixture of rotamers) (partial) (1:1 mixture of diastereomers) 8.21–8.30 (m, 0.5H), 7.65–7.88 (m, 8.5H), 7.44–7.51 (m, 0.5H), 7.27–7.33 (m, 1H), 6.99–7.14 (m, 1.5H), 6.72–6.95 (m, 1H), 5.27–5.35 (m, 0.5H), 5.02–5.10 (m, 0.5H), 4.52–4.79 (m, 2H), 2.34–2.69 (m, 2H), 1.94–2.16 (m, 2H), 1.51–1.71 (m, 6H).
MS (Cl, NH$_3$) 568 (MH$^+$)

EXAMPLE 73

(R)-2-Amino-N-{4-phenyl-1-[4-(2-phenyl-benzoimidazol-1-yl)-piperidine-1-carbonyl]-butyl}-isobutyramide Hydrochloride A. (R)-(1-Methyl-1-{4-phenyl-1-[4-(2-phenyl-benzoimidazol-1-yl)-piperidine-1-carbonyl]-butylcarbamoyl}-ethyl)-carbamic acid tert-butyl ester According to General Procedure A, 112 mg (0.30 mmol) of 62D and 84 mg (0.30 mmol) of 50D were coupled and the product was purified by silica gel chromatography using a gradient elution of 1% to 10% methanol in methylene chloride to provide 55 mg of 73A as a white foam.

B. (R)-2-Amino-N-{4-phenyl-1-[4-(2-phenyl-benzoimidazol-1-yl)-piperidine-1-carbonyl]-butyl}-isobutyramide hydrochloride To 50 mg (0.08 mmol) of 73A in 1 mL of ethanol was added 0.5 mL of concentrated HCL and the mixture was stirred at room temperature for 1 h. The reaction mixture was concentrated and coevaporated twice from ethanol. The residue was triturated twice with ether to give 38 mg of the title compound as a yellow solid.

$^1$H NMR (CD$_3$OD, 300 MHz) (mixture of rotamers) (partial) δ 7.78–7.98 (m, 0.5H), 7.54–7.74 (m, 6.5H), 7.29–7.42 (m, 2H), 7.02–7.29 (m, 5H), 4.58–4.80 (m, 2H), 3.80–4.17 (m, 1H), 1.56–1.71 (m, 6H).
MS (Cl, NH$_3$) 538 (MH$^+$)

EXAMPLE 74

(R)-2-Amino-N-{2-(1H-indol-3-yl)-1-[6-(7-sulfamoyl-3,4-dihydro-1H-isoquinoline-2-carbonyl)-3,4-dihydro-1H-isoquinoline-2-carbonyl]-ethyl}-isobutyramide Hydrochloride A. (R)-(1-{2-(1H-Indol-3-yl)-1-[6-(7-sulfamoyl-3,4-dihydro-1H-isoquinoline-2-carbonyl)-3,4-dihydro-1H-isoquinoline-2-carbonyl]-ethylcarbamoyl}-1-methyl-ethyl)-carbamic acid tert-butyl ester According to General Procedure A, 121 mg (0.22 mmol) of 26A and 47 mg (0.22 mmol) of 1,2,3,4-tetrahydro-isoquinoline-7-sulfonic acid amide were coupled to give 165 mg of 74A.

B. (R)-2-Amino-N-{2-(1H-indol-3-yl)-1-[6-(7-sulfamoyl-3,4-dihydro-1H-isoquinoline-2-carbonyl)-3,4-dihydro-1H-isoquinoline-2-carbonyl]-ethyl}-isobutyramide hydrochloride To 107 mg (0.14 mmol) of 74A in 8 mL of ethanol was added 2 mL of concentrated HCl and the mixture was stirred at room temperature for 1.5 h. An additional 1 mL of concentrated HCl was added and the reaction mixture was stirred for 3 h. The mixture was concentrated and then coevaporated several times with ethanol to give 61 mg of the title compound.

$^1$H NMR (CD$_3$OD, 300 MHz) (mixture of rotamers) (partial) δ 7.57–7.80 (m, 2H), 7.43–7.62 (m, 1.5H), 6.96–7.41 (m, 7.5H), 1.51–1.67 (d, 6H).
MS (Cl, NH$_3$) 643 (MH$^+$)

EXAMPLE 75

(R)-Piperidine-4-carboxylic acid {1-(1H-indol-3-ylmethyl)-2-oxo-2-[4-(2-oxo-2,3-dihydro-benzoimidazol-1-yl)-piperidin-1-yl]-ethyl}-amide Hydrochloride A. {2-(1H-Indol-3-yl)-1-[4-(2-oxo-2,3-dihydro-benzoimidazol-piperidine-1-carbonyl]-ethyl}-carbamic acid tert-butyl ester According to General Procedure A, 2.82 g (13.0 mmol) of 4-(2-keto-1-benzimidazolinyl)-piperidine and 3.95 g (13.0 mmol) of N-t-BOC-D-tryptophan were coupled and the product triturated with ether to give 2.5 g of 75A.

B. 1-{1-[2-Amino-3-(1H-indol-3-yl)-propionyl]-piperidin-4-yl}-1,3-dihydro-benzoimidazol-2-one According to General Procedure B, 2.50 g (4.97 mmol) of 75A was deprotected to give 1.70 g of 75B.

C. (R)-4-{1-(1H-Indol-3-ylmethyl)-2-oxo-2-[4-(2-oxo-2,3-dihydro-benzoimidazol-1-yl)-piperidin-1-yl]-ethylcarbamoyl}-piperidine-1-carboxylic acid tert-butyl ester To a solution of 150 mg (0.372 mmol) of piperidine-1,4-dicarboxylic acid mono-tert-butyl ester, 87 mg (0.216 mmol) of 75B and 96 mg (0.744 mmol) of diisopropylethylamine in 4 mL of methylene chloride was added 197 mg (0.446 mmol) of BOP reagent and the mixture was stirred overnight at room temperature. The reaction mixture was diluted with 20 mL of ethyl acetate and washed twice each with 10% citric acid and saturated aqueous sodium bicarbonate and once with brine. The solution was dried over MgSO$_4$ and concentrated to give a white foam which was purified by silica gel chromatography using a gradient of 100% methylene chloride followed by 1% methanol in methylene chloride to give 52 mg of 75C as a clear oil.

D. (R)-Piperidine-4-carboxylic acid {1-(1H-indol-3-ylmethyl)-2-oxo-2-[4-(2-oxo-2,3-dihydro-benzoimidazol-1-yl)-piperidin-1-yl]-ethyl}-amide hydrochloride To 20 mg (0.032 mmol) of 75C in 2 mL of ethanol was added 1 mL of concentrated HCl and the mixture was stirred at room temperature for 1 h. The solution was concentrated and coevaporated twice from ethanol, once from methylene chloride and twice from ether to give the title compound as a white solid.

$^1$H NMR (CD$_3$OD, 300 MHz) (mixture of rotamers) (partial) δ 8.19 (d, 0.5H), 7.63–7.69 (m, 0.5H), 7.55–7.61 (m, 0.5H), 7.30–7.39 (m, 1.5H), 7.00–7.31 (m, 5.5H), 5.26–5.37 (m, 0.5H), 5.01–5.24 (m, 0.5H).
MS (Cl, NH$_3$) 516 (MH$^+$)

EXAMPLE 76

(R)-2-Amino-N-{1-(2-methyl-1H-indol-3-ylmethyl)-2-oxo-2-[4-(2-oxo-2,3-dihydro-benzoimidazol-1-yl)-piperidin-1-yl]-ethyl}-isobutyramide Trifluoroacetate A. (R)-2-(2-Amino-2-methyl-propionylamino)-3-(2-methyl-1H-indol-3-yl)-propionic acid To 1.00 g (4.58 mmol) of 2-D-methyltryptophan in 37 mL of dioxane and 9.2 mL of water was added 1.4 mL (10.0 mmol) of triethylamine and 1.51 g (5.08 mmol) of 33A and the mixture was stirred overnight at room temperature. The mixture was concentrated to remove excess dioxane and acidified to pH 5 with acetic acid. The aqueous phase was extracted three times with methylene chloride and the combined organics were washed twice with water and once with brine. The organic phase was dried over MgSO$_4$ and concentrated and the product was purified by silica gel chromatography (98:2:0.1 v/v/v CH$_2$Cl$_2$:MeOH:acetic acid) to give 1.98 g of 76A.

B. (R)-(1-Methyl-1-{1-(2-methyl-1H-indol-3-ylmethyl)-2-oxo-2-[4-(2-oxo-2,3-dihydro-benzoimidazol-1-yl)-piperidin-1-yl]-ethylcarbamoyl}-ethyl)-carbamic acid tert-butyl ester According to General Procedure A, 107 mg (0.49 mmol) of 4-(2-keto-1-benzimidazolinyl)-piperidine and 200 mg (0.49 mmol) of 76A were coupled and the product was purified by silica gel chromatography (94:6 v/v CH$_2$Cl$_2$:MeOH) to give 1.87 g of 76B.

C. (R)-2-Amino-N-{1-(2-methyl-1 H-indol-3-ylmethyl)-2-oxo-2-[4-(2-oxo-2,3-dihydro-benzoimidazol-1-yl)-piperidin-1-yl]-ethyl}-isobutyramide trifluoroacetate To 187 mg (0.31 mmol) of 76B at 0° C. was added 2 mL of cold TFA and the mixture was stirred for 1 h at 0° C. The mixture was concentrated and coevaporated once from methylene chloride and twice from toluene to give 180 mg of the title compound as a solid.

$^1$H NMR (CD$_3$OD, 250 MHz) (mixture of rotamers) (partial) δ 8.32 (d, 0.5H), 7.50–7.57 (m, 0.5H), 7.44 (d, 0.5H), 5.23–5.35 (m, 0.5H), 5.18–5.20 (m, 0.5H), 2.42 (s, 1.5H), 2.32 (s, 1.5H), 1.58–1.66 (m, 6H).

MS (Cl, NH$_3$) 503 (MH$^+$)

EXAMPLE 77

(R)-Piperidine-4-carboxylic Acid {1-(1H-indol-3-ylmethyl)-2-oxo-2-[4-(2-phenyl-benzoimidazol-1-yl)-piperidin-1-yl]-ethyl}-amide Hydrochloride A. Piperidine-1,4-dicarboxylic acid tert-butyl ester 2,5-dioxo-pyrrolidin-1yl To 15.0 g (65.4 mmol) of piperidine-1,4-dicarboxylic acid mono-tert-butyl ester was added 150 mL of methylene chloride and 20 mL of DMF. To the stirring solution was added 9.30 g (78.5 mmol) of N-hydroxysuccinimide followed by 15.0 g (78.5 mmol) of DEC, and the mixture was stirred overnight at room temperature. The reaction mixture was diluted with ethyl acetate and washed twice with 10% citric acid, four times with a saturated aqueous sodium bicarbonate and once each with water and brine. The solution was dried over MgSO$_4$ and concentrated to give 20.4 g of 77A as a white solid.

B. (R)-4-{1-Carboxy-2-(1H-indol-3-yl)-ethylcarbamoyl]-piperidine-1-carboxylic acid tert-butyl ester A mixture of 2.04 g (6.28 mmol) of 77A, 2.00 g (6.28 mmol) of D-tryptophan trifluoroacetate and 1.16 g (11.5 mmol) of triethylamine in 120 mL of dioxane and 30 mL of water was stirred at room temperature for 17 h. The reaction mixture was concentrated to remove excess dioxane and then was diluted with water. The aqueous portion was extracted four times with chloroform and concentrated. The crude product was purified by silica gel chromatography (9:1 v/v CHCl$_3$:MeOH) followed by (36:4:1 v/v/v CHCl$_3$:MeOH:acetic acid) to give 0.87 g of 77B.

C. (R)-4-{1-(1H-Indol-3-ylmethyl)-2-oxo-2-[4-(2-phenyl-benzoimidazol-1-yl)-piperidin-1-yl]-ethylcarbamoyl}-piperidine-1-carboxylic acid According to General Procedure A, 100 mg (0.36 mmol) of 50D and 150 mg (0.36 mmol) of 77B were coupled and the product was purified by silica gel chromatography using a gradient elution of 75% ethyl acetate in hexane to 100% ethyl acetate and 144 mg of 77C was isolated as a white solid.

D. (R)-Piperidine-4-carboxylic acid {1-(1H-indol-3-ylmethyl)-2-oxo-2-[4-(2-phenyl-benzoimidazol-1-yl)-piperidin-1-yl]-ethyl}-amide hydrochloride To 144 mg (0.21 mmol) of 77C in 2 mL of ethanol was added 4 mL of concentrated HCl and the mixture was stirred at room temperature for 30 min. The solution was concentrated and then coevaporated several times from ethanol. The residue was crystallized from methanol/ethyl acetate and the precipitated product was collected by filtration to give 140 mg of the title compound as a white solid.
MS (Cl, NH$_3$) 576 (MH$^+$)

EXAMPLE 78

(R)-Piperidine-4-carboxylic Acid {1-naphthalen-1-ylmethyl-2-oxo-2-[4-(2-oxo-2,3-dihydro-benzoimidazol-1-yl)-piperidin-1-yl]-ethyl)-amide Hydrochloride A. 4-(1-Carboxy-2-naphthalen-1-yl-ethylamino)-piperidine-1-carboxylic acid tert-butyl ester To 200 mg (0.607 mmol) of piperidine-1,4-dicarboxylic acid mono-tert-butyl ester in 5 mL of dioxane and 1.2 mL of water was added 0.186 mL (1.33 mmol) of triethylamine and 198 mg (0.607 mmol) of D-3-(1'-Napthyl)alanine and the mixture was stirred overnight at room temperature. Excess solvent was removed by concentration and the residue was diluted with water and acidified to pH 5 with acetic acid. The solution was extracted three times with methylene chloride, and the combined organics were washed twice with water and once with brine. The organic portion was dried over MgSO$_4$ and the product was purified by silica gel chromatography (96:4:0.1 v/v/v methylene chloride:methanol:acetic acid) to give 132 mg of 78A.

B. (R)-4-{1-Naphthalen-1-ylmethyl-2-oxo-2-[4-(2-oxo-2,3-dihydro-benzoimidazol-1-yl)-piperidin-1-yl]-ethylcarbamoyl}-piperidine-1-carboxylic acid tert-butyl ester According to General Procedure A, 132 mg (0.32 mmol) of 78A and 70 mg (0.32 mmol) of 4-(2-keto-1-benzimidazolinyl)-piperidine were coupled and the product was purified by silica gel chromatography (96:4 v/v methylene chloride:methanol) to give 132 mg of 78B.

C. (R)-Piperidine-4-carboxylic acid {1-naphthalen-1-ylmethyl-2-oxo-2-[4-(2-oxo-2,3-dihydro-benzoimidazol-1-yl)-piperidin-1-yl]-ethyl}-amide hydrochloride To 132 mg (0.21 mmol) of 78B dissolved in 2.5 mL of ethanol was added 0.25 mL of concentrated HCl at 0° C. The ice bath was removed and the solution stirred for 1 h. The mixture was coevaporated from methanol and then methylene chloride to give 102 mg of the title compound.

$^1$H NMR (CD$_3$OD, 250 MHz) (mixture of rotamers) (partial) δ 8.23 (d, 0.5H), 8.18 (d, 0.5H), 7.79–7.92 (m, 2H), 7.46–7.68 (m, 3H), 7.37–7.44 (m, 1H), 7.14–7.27 (m, 1H), 7.02–7.13 (m, 2.5H), 6.73 (d, 0.5H), 5.38–5.48 (m, 0.5H), 5.26–5.36 (m, 0.5H).
MS (Cl, NH$_3$) 527 (MH$^+$)

EXAMPLE 79

(R)-2-Amino-N-{1-(1H-indol-3-ylmethyl)-2-[7-(morpholine-4-sulfonyl)-3,4-dihydro-1H-isoquinolin-2-yl]-2-oxo-ethyl}-isobutyramide Hydrochloride A. 2,2,2-Trifluoro-1-[7-(morpholine-4-sulfonyl)-3,4-dihydro-1H-isoquinolin-2-yl]-ethanone 2-Trifluoroacetyl-1,2,3,4-tetrahydroisoquinoline-7-sulfonyl chloride can be prepared according to the method outlined by Pendleton et al., J. Pharmacol. Exp. Ther., 208 (1979) p24. A mixture of 250 mg (0.76 mmol) of 2-Trifluoroacetyl-1,2,3,4-tetrahydro-isoquinoline-7-sulfonyl chloride, 86 mg (0.99 mmol) of morpholine and 0.3 mL of anhydrous pyridine in 10 mL of acetone was refluxed for 1 h. The mixture was concentrated and the residue dissolved in chloroform and washed once with water. The organic portion was dried over MgSO$_4$ and concentrated. The residue was purified by silica gel chromatography (6:4 v/v hexane:ethyl acetate) to give 289 mg of 79A.

B. 7-(Morpholine-4-sulfonyl)-1,2,3,4-tetrahydro-isoquinoline

A mixture of 218 mg (0.58 mmol) of 79A and 90 mg (0.65 mmol) of potassium carbonate in 10 mL of methanol was stirred at room temperature for 3 h. The mixture was concentrated and the residue was purified by silica gel chromatography (18:2:1 v/v/v ethyl acetate:methanol:triethylamine) to give 163 mg of 79B.

C. (R)-(1-{1-(1H-Indol-3-ylmethyl)-2-[7-(morpholine-4-sulfonyl)-3,4-dihydro-1H-isoquinolin-2-yl]-2-oxo-ethylcarbamoyl}1-methyl-ethyl)-carbamic acid tert-butyl ester According to General Procedure A, 136 mg (0.35 mmol) of 4C and 100 mg (0.35 mmol) of 79B were coupled and the product was purified by silica gel chromatography (39:1 v/v chloroform:methanol) to give 194 mg of 79C.

D. (R)-2-Amino-N-{1-(1H-indol-3-ylmethyl)-2-[7-(morpholine-4-sulfonyl)-3,4-dihydro-1H-isoquinolin-2-yl]-2-oxo-ethyl}-isobutyramide hydrochloride To 141 mg (0.22 mmol) of 79C in 12 mL of ethanol was added 5 mL of concentrated HCl and the mixture was stirred at room temperature for 3 h. The reaction mixture was concentrated to give 123 mg of the title compound as an off-white solid.

$^1$H NMR (CD$_3$OD, 300 MHz) (mixture of rotamers) (partial) δ 7.98–8.07 (bs, 1H), 7.43–7.61 (m, 2.5H), 6.91–7.37 (m, 5H), 5.14–5.29 (m, 1H), 4.48–4.70 (m, 1H), 3.66–3.78 (m, 4H), 3.29–3.46 (m, 4H), 2.84–3.07 (m, 7H), 1.56–1.67 (m, 6H).
MS (Cl, NH$_3$) 554 (MH$^+$)

EXAMPLE 80

(R)-Piperidine-4-carboxylic acid [2-(3,4-dihydro-1H-isoquinolin-2-yl)-1-naphthalen-2-ylmethyl-2-oxo-ethyl]-amide Hydrochloride A. (R)-4-(1-Carboxy-2-naphthalen-2-yl-ethylcarbamoyl)-piperidine-1-carboxylic acid tert-butyl ester A mixture of 3.08 g (9.4 mmol) of 77A, 2.03 g (9.4 mmol) of D-3-(2-Naphthyl)-alanine and 2.9 g (28.7 mmol) of triethylamine in 40 mL of dioxane and 10 mL of water was stirred for 72 h at room temperature. Excess dioxane was removed by concentration and the remaining aqueous solution was diluted with 200 mL of water and acidified to pH 5 with 10% citric acid. The aqueous portion was extracted twice with ethyl acetate. The combined organics were washed twice with saturated aqueous sodium bicarbonate. The orange oil was separated from the aqueous extracts and acidified with 10% acetic acid. The aqueous portion was extracted three times with ethyl acetate and the combined organics were washed three times with water, once with brine, dried over MgSO$_4$ and concentrated to give 3.7 g of a yellow oil which was taken up in 200 mL of ether. A white crystalline solid precipitated from solution and was collected by filtration to give 3.31 g of 80A.

B. (R)-4-[2-(3,4-Dihydro-1H-isoquinolin-2-yl)-1-naphthalen-2-ylmethyl-2-oxo-ethylcarbamoyl]-piperidine-1-carboxylic acid tert-butyl ester According to General Procedure A, 95 mg (0.22 mmol) of 80A and 29.6 mg (0.22 mmol) of 1,2,3,4,-tetrahydroisoquinoline were coupled and the resulting oil triturated with ethyl acetate/hexane to give 70 mg of 80B as a white solid.

C. (R)-Piperidine-4-carboxylic acid [2-(3,4-dihydro-1H-isoquinolin-2-yl)-1-naphthalen-2-ylmethyl-2-oxo-ethyl]-amide hydrochloride To 70 mg (0.13 mmol) of 80B in 6 mL of ethanol was added 2 mL of concentrated HCl at room temperature and the mixture was stirred for 1.5 h. The mixture was concentrated and coevaporated twice from methylene chloride to give 50 mg of the title compound as a white foam.

$^1$H NMR (CD$_3$OD, 300 MHz) (mixture of rotamers) (partial) δ 7.62–7.80 (m, 4H), 7.34–7.48 (m, 3H), 7.05–7.19 (m, 1.5H), 6.82–7.00 (m, 2.5H), 5.18–5.21 (m, 1H), 4.51–4.73 (m, 1.5H), 4.29–4.39 (m,1H).
MS (Cl, NH$_3$) 442 (MH$^+$)

EXAMPLE 81

(R)-Piperidine-4-carboxylic acid {2-[4-(2-cyclopropyl-benzoimidazol-1-yl)-piperidin-1-yl]-1-naphthalen-2-ylmethyl-2-oxo-ethyl}-amide Hydrochloride A. 1-(1-Benzyl-piperidin-4-yl)-2-cyclopropyl-1H-benzoimidazole A mixture of 530 mg (1.90 mmol) of 50B and 651 mg (7.56 mmol) of cyclopropanecarboxylic acid were heated at 160° C. for 16 h. After cooling to room temperature, 10 mL of ethanol was added to the reaction mixture, followed by the slow addition of 20 mL of 2N NaOH in 90 mL of ethanol. The mixture was stirred for 30 min at room temperature and then concentrated. The residue was dissolved in ethyl acetate and washed once each with saturated aqueous sodium bicarbonate and brine. The solution was dried over $MgSO_4$ and concentrated, and the product was purified by silica gel chromatography using an elution gradient of 75% ethyl acetate in hexane to 100% ethyl acetate to give 340 mg of 81A.

B. 2-Cyclopropyl-1-piperidin-4-yl-1H-benzoimidazole hydrochloride

To 340 mg (1.03 mmol) of 81A in 3 mL of methylene chloride at −100° C was added 220 mg (1.54 mmol) of a-chloroethylchloroformate and the mixture was stirred at −10° C. for 50 min. The mixture was concentrated and the residue dissolved in methanol and heated at 70° C. for 1 h. The mixture was concentrated and dried in vacuo to give 230 mg of 81B as a light purple solid.

C. (R)-4-{2-[4-(2-Cyclopropyl-benzoimidazol-1-yl)-piperidin-1-yl]-1-naphthalen-2-ylmethyl-2-oxo-ethylcarbamoyl}-piperidine-1-carboxylic acid tert-butyl ester According to General Procedure A, 80 mg (0.29 mmol) of 81B and 123 mg (0.29 mmol) of 80A were coupled and the product was purified by silica gel chromatography (75:25 v/v ethyl acetate:hexane) to give 50 mg of 81C as a red solid.

D. (R)-Piperidine-4-carboxylic acid {2-[4-(2-cyclopropyl-benzoimidazol-1-yl)-piperidin-1-yl]-1-naphthalen-2-ylmethyl-2-oxo-ethyl}-amide hydrochloride To 42 mg (0.065 mmol) of 81C in 2 mL of ethanol was added 2 mL of concentrated HCl at room temperature and the mixture was stirred for 30 min. The mixture was concentrated to give 40 mg of the title compound as a white solid.

MS (CI, $NH_3$) 550 ($MH^+$)

EXAMPLE 82

(R)-Piperidine-4-carboxylic acid {1-naphthalen-2-ylmethyl-2-oxo-2-[4-(2-phenyl-benzoimidazol-1-yl)-piperidin-1-yl]-ethyl}-amide Hydrochloride A. (R)-4-{1-Naphthalen-2-ylmethyl-2-oxo-2-[4-(2-phenyl-benzoimidazol-1-yl)-piperidin-1-yl]-ethylcarbamoyl}-piperidine-1-carboxylic acid According to General Procedure A, 95 mg (0.34 mmol) of 50D and 100 mg (0.23 mmol) of 80A were coupled and the product was purified by silica gel chromatography using a gradient elution of 55% ethyl acetate in hexane to 100% ethyl acetate to give 97 mg of 82A as a white solid.

B. (R)-Piperidine-4-carboxylic acid {1-naphthalen-2-ylmethyl-2-oxo-2-[4-(2-phenyl-benzoimidazol-1-yl)-piperidin-1-yl]-ethyl}-amide hydrochloride To 97 mg (0.14 mmol) of 82A in 4 mL of ethanol was added 2 mL of concentrated HCl and the mixture was stirred at room temperature for 2 h. The mixture was concentrated to give 70 mg of the title compound.

$^1$H NMR ($CD_3OD$, 250 MHz) (mixture of rotamers) (partial) δ 7.77–8.00 (m, 12H), 7.32–7.77 (m, 4H), 5.18–5.38 (m, 1H), 4.68–4.89 (m, 2H), 4.10–4.36 (m, 1H). MS (CI, $NH_3$) 587 ($MH^+$)

EXAMPLE 83

(R)-Piperidine-4-carboxylic acid (1-naphthalen-2-ylmethyl-2-oxo-2-[5-(toluene-4-sulfonylamino)-1,3-dihydro-isoindol-2-yl]-ethyl}-amide Hydrochloride A. (R)-4-[2-(5-Amino-1,3-dihydro-isoindol-2-yl)-1-naphthalen-2-ylmethyl-2-oxo-ethylcarbamoyl]-piperidine-1-carboxylic acid tert-butyl ester According to General Procedure A, 47 mg (0.35 mmol) of 43C and 150 mg (0.35 mmol) of 80A were coupled to give 150 mg of 83A.

B. (R)-4-{1-Naphthalen-2-ylmethyl-2-oxo-2-[5-(toluene-4-sulfonylamino)-1,3-dihydro-isoindol-2-yl]-ethylcarbamoyl}-piperidine-1-carboxylic acid tert-butyl ester A mixture of 150 mg (0.28 mmol) of 83A, 61 mg (0.32 mmol) of p-toluenesulfonyl chloride and 39 mg (0.32 mmol) of 4-dimethylaminopyridine was stirred at room temperature overnight. The mixture was diluted with methylene chloride and washed twice each with 10% HCl, saturated aqueous sodium bicarbonate, and brine, dried over $MgSO_4$ and concentrated. The product was purified by silica gel chromatography using a gradient elution of 75% ethyl acetate in hexane to 2% methanol in ethyl acetate to give 50 mg of 83B.

C. (R)-Piperidine-4-carboxylic acid {1-naphthalen-2-ylmethyl-2-oxo-2-[5-(toluene-4-sulfonylamino)-1,3-dihydro-isoindol-2-yl]-ethyl}-amide hydrochloride To 50 mg (0.07 mmol) of 83B in 4 mL of ethanol was added 2 mL of concentrated HCl and the mixture was stirred at room temperature for 3 h. The mixture was concentrated and the residue was crystallized from ethanol/hexane to give 25 mg of the title compound.

$^1$H NMR ($CD_3OD$, 250 MHz) (mixture of rotamers) (partial) δ 8.56 (d, 1H), 7.72–7.89 (m, 5H), 7.57–7.68 (m, 2H), 7.39–7.52 (m, 5H), 7.24–7.31 (m, 2H), 6.91–7.16 (m, 3H), 4.49–4.73 (m, 2H), 4.36–4.47 (m, 1H), 2.47–2.68 (m, 2H), 2.39 (s, 3H).

MS (CI, $NH_3$) 598 ($MH^+$)

EXAMPLE 84

(R)-Piperidine-4-carboxylic acid [1-(5-benzoylamino-1,3-dihydro-isoindole-2-carbonyl)-2-(1H-indol-3-yl)-ethyl]-amide Hydrochloride A. (R)-4-[1-(5-Amino-1,3-dihydro-isoindole-2-carbonyl)-2-(1H-indol-3-yl)-ethylcarbamoyl]-piperidine-1-carboxylic acid tert-butyl ester According to General Procedure A, 40 mg (0.30 mmol) of 43C and 125 mg (0.30 mmol) of 77B were coupled to give 170 mg of 84A.

B. (R)-4-[1-(5-Benzoylamino-1,3-dihydro-isoindole-2-carbonyl)-2-(1H-indol-3-yl)-ethylcarbamoyl]-piperidine-1-carboxylic acid tert-butyl ester A mixture of 170 mg (0.32 mmol) of 84A, 52 mg (0.37 mmol) of benzoyl chloride and 45 mg (0.37 mmol) of 4-dimethylaminopyridine in 15 mL of methylene chloride was stirred overnight at room temperature. The reaction mixture was diluted with methylene chloride and washed twice each with 10% HCl, saturated aqueous sodium bicarbonate and brine. The organic portion was dried over $MgSO_4$ and concentrated. The product was purified by silica gel chromatography using an elution gradient of 90% ethyl acetate in hexane to 2% methanol in ethyl acetate to give 100 mg of 84B.

C. (R)-Piperidine-4-carboxylic acid [1-(5-benzoylamino-1,3-dihydro-isoindole-2-carbonyl)-2-(1H-indol-3-yl)-ethyl]-amide hydrochloride To 100 mg (0.16 mmol) of 84B in 4 mL of ethanol was added 2 mL of concentrated HCl and the mixture was stirred at room temperature for 1 h. The mixture was diluted with ethanol and concentrated. The residue was crystallized from ethanol/hexane to give 50 mg of the title compound.

$^1$H NMR ($CD_3OD$, 250 MHz) (mixture of rotamers) (partial) δ 7.91–7.99 (m, 2H), 7.48–7.70 (m, 6H), 7.03–7.38

(m, 5H), 4.68–4.80 (m, 1H), 4.45–4.59 (m, 1H), 4.03–4.16 (dd, 1H), 2.98–3.13 (m, 2H), 2.59–2.76 (m, 1H), 1.76–2.10 (m, 4H).
MS (Cl, NH$_3$) 537 (MH$^+$)

EXAMPLE 85

(R)-Piperidine-4-carboxylic acid {1-naphthalen-2-ylmethyl-2-oxo-2-[4-(2-oxo-2,3-dihydro-benzoimidazol-1-yl)-piperidin-1-yl]-ethyl}-amide Hydrochloride A. (R)-4–1-Naphthalen-2-ylmethyl-2-oxo-2-[4-(2-oxo-2,3-dihydro-benzoimidazol-1-yl)-piperidin-1-yl]-ethylcarbamoyl}-piperidine-1-carboxylic acid tert-butyl ester According to General Procedure A, 225 mg (0.53 mmol) of 80A and 117 mg (0.54 mmol) of 4-(2-keto-1-benzimidazolinyl)piperidine were coupled and the product was purified by silica gel chromatography using an elution gradient of 1% to 3% methanol in methylene chloride to give 178 mg of 85A.

B. (R)-Piperidine-4-carboxylic acid {1-naphthalen-2-ylmethyl-2-oxo-2-[4-(2-oxo-2.3-dihydro-benzoimidazol-1-yl)-piperidin-1-yl]-ethyl}-amide hydrochloride To 165 mg (0.26 mmol) of 85A in 3 mL of ethanol was added 1.5 mL of concentrated HCl and the mixture was stirred at room temperature for 3 h. The mixture was concentrated to give 117 mg of the title compound as a solid.

$^1$H NMR (CD$_3$OD, 300 MHz) (mixture of rotamers) (partial) δ 7.70–7.89 (m, 4H), 7.37–7.50 (m, 3H), 7.22–7.29 (m, 0.5H0, 6.90–7.04 (m, 3H), 6.68 (d, 0.5H), 5.25–5.36 (m,1H), 4.67–4.74 (m, 1H), 4.38–4.50 (m,1H), 4.11–4.32 (m, 1H).
MS (Cl, NH$_3$) 527 (MH$^+$)

EXAMPLE 86

(R)-Piperidine-4-carboxylic acid [1-(7-ethylsulfamoyl-3,4-dihydro-1H-isoquinoline-2-carbonyl)-2-(1H-indol-3-yl)-ethyl]-amide Hydrochloride A. 2-Trifluoroacetyl-1,2,3,4-tetrahydro-isoquinoline-7-sulfonic acid 2-Trifluoroacetyl-1,2,3,4-tetrahydro-isoquinoline-7-sulfonyl chloride can be prepared according to the method outlined by Pendleton et al., J. Pharmacol. Exp. Ther., 208 (1979) p24. A mixture of 295 mg (0.90 mmol) of 2-Trifluoroacetyl-1,2,3,4-tetrahydro-isoquinoline-7-sulfonyl chloride, 95 mg (1.17 mmol) of ethylamine hydrochloride and 0.3 mL (2.15 mmol) of triethylamine in 10 mL of acetone was refluxed for 1.5 h. The reaction mixture was filtered and concentrated and the product was purified by silica gel chromatography (6:4 v/v hexane:ethyl acetate) to give 283 mg of 86A.

B. 1,2,3,4-Tetrahydro-isoquinoline-7-sulfonic acid ethylamide

To 225 mg (0.67 mmol) of 86A and 104 mg (0.75 mmol) of potassium carbonate in 10 mL of methanol and 0.5 mL of water was stirred at room temperature for 3 h. The mixture was concentrated to give 335 mg of 86B.

C. (R)4-[1-(7-Ethylsulfamoyl-3,4-dihydro-1H-isoquinoline-2-carbonyl)-2-(1H-indol-3-yl)-ethylcarbamoyl]-piperidine-1-carboxylic acid tert-butyl ester According to General Procedure A, 145 mg (0.35 mmol) of 86B and 85 mg (0.35 mmol) of 77B were coupled and the product was purified by silica gel chromatography (39:1 v/v chloroform:methanol) to give 68 mg of 86C.

D. (R)-Piperidine-4-carboxylic acid [1-(7-ethylsulfamoyl-3,4-dihydro-1H-isoquinoline-2-carbonyl)-2-(1H-indol-3-yl)-ethyl]-amide hydrochloride To 68 mg (0.11 mmol) of 86C in 6 mL of ethanol was added 2.5 mL of concentrated HCl and the mixture was stirred at room temperature for 5 h. The reaction mixture was concentrated to give 62 mg of the title compounds as a tan solid.

$^1$H NMR (CD$_3$OD, 300 MHz) (mixture of rotamers) (partial) δ 7.96–8.02 (bs, 0.5H), 7.62–7.53 (m, 0.5H), 7.52–7.61 (m, 2H), 6.91–7.37 (m, 5H), 5.09–5.20 (m, 1H), 4.42–4.70 (m, 1H), 1.00–1.11 (m, 3H).
MS (Cl, NH$_3$) 538 (MH$^+$)

EXAMPLE 87

(R)-2-Amino-N-[1-(7-ethylsulfamoyl-3,4-dihydro-1H-isoquinoline-2-carbonyl)-2-(1H-indol-3-yl)-ethyl]-isobutyramide Hydrochloride A. (R)-{1-[1-(7-Ethylsulfamoyl-3,4-dihydro-1H-isoquinoline-2-carbonyl)-2-(1H-indol-3-yl)-ethylcarbamoyl]-1-methyl-ethyl}-carbamic acid tert-butyl ester According to General Procedure A, 136 mg (0.35 mmol) of 4C and 85 mg (0.35 mmol) of 86B were coupled and the product was purified by silica gel chromatography (39:1 v/v chloroform:methanol) followed by (9:1 v/v chloroform:methanol) to give 73 mg of 87A.

B. (R)-2-Amino-N-[1-(7-ethylsulfamoyl-3,4-dihydro-1H-isoquinoline-2-carbonyl)-2-(1H-indol-3-yl)-ethyl]-isobutyramide hydrochloride To 62 mg (0.10 mmol) of 87A in 6 mL of ethanol was added 2.5 mL of concentrated HCl and the mixture was stirred at room temperature for 5 h and then concentrated to give 56 mg of the title compound as an off-white solid.

$^1$H NMR (CD$_3$OD, 300 MHz) (mixture of rotamers) (partial) δ 8.28–8.41 (bs, 0.5H), 7.42–7.59 (m, 2H), 6.85–7.07 (m, 5H), 5.19–5.25 (m, 1H), 4.39–4.68 (m, 2H), 2.71–2.87 (m, 2H), 1.40–1.63 (m, 6H), 0.92–1.06 (m, 3H).
MS (Cl, NH$_3$) 513 (MH$^+$)

EXAMPLE 88

(R)-2-{3-(1H-Indol-3-yl)-2-[(piperidine-4-carbonyl)-amino]-propionyl}-1,2,3,4-tetrahydro-isoquinoline-6-carboxylic Acid Ethylamide Hydrochloride A. 3,4-Dihydro-1H-isoquinoline-2,6-dicarboxylic acid 2-tert-butyl ester To 1.20 g (4.1 mmol) of 5C in 36 mL of methanol was added 0.62 g (4.5 mmol) of potassium carbonate and the mixture was heated at reflux for 7 h. The product was purified by silica gel chromatography (9:1 v/v chloroform:methanol) to give 1.49 g of 88A.

B. 6-Ethylcarbamoyl-3,4-dihydro-1H-isoquinoline-2-carboxylic acid tert-butyl ester According to General Procedure A. 650 mg (2.34 mmol) of 88A and 191 mg (2.34 mmol) of ethylamine hydrochloride were coupled and the product was purified by silica gel chromatography (39:1 v/v chloroform:methanol) followed by (1:1 v/v ethyl acetate:methanol) to give 566 mg of 88B.

C. 1,2,3,4-Tetrahydro-isoquinoline-6-carboxylic acid ethylamide hydrochloride

To 493 mg (1.62 mmol) of 88B in 30 mL of ethanol was added 12.5 mL of concentrated HCl and the mixture was stirred at room temperature for 5 h. The mixture was concentrated to give 384 mg of 88C as a white solid.

D. (R)-4-[1-(6-Ethylcarbamoyl-3,4-dihydro-1H-isoquinoline-2-carbonyl)-2-(1H-indol-3-yl)-ethylcarbamoyl]-piperidine-1-carboxylic acid tert-butyl ester According to General Procedure A, 99 mg (0.41 mmol) of 88C and 170 mg (0.41 mmol) of 77B were coupled and the product was purified by silica gel chromatography (39:1 v/v chloroform:methanol) followed by (9:1 v/v chloroform:methanol) to give 107 mg of 88D.

E. (R)-2-{3-(1H-Indol-3-yl)-2-[(piperidine-4-carbonyl)-amino]-propionyl}-1,2,3,4-tetrahydro-isoquinoline-6-carboxylic acid ethylamide hydrochloride To 66 mg (0.11 mmol) of 88D in 6 mL of ethanol was added 2.5 mL of concentrated HCl and the mixture was stirred at room temperature for 5 h. The mixture was concentrated to give 56 mg of the title compound as an off-white solid.

$^1$H NMR (CD$_3$OD, 300 MHz) (mixture of rotamers) (partial) δ 7.52–7.60 (m, 1.5H), 7.38–7.45 (m,1H), 7.24 (d, 0.5H), 5.11–5.24 (m,1H), 4.40–4.69 (m, 1.5H), 4.04–4.13 (m, 0.5H), 1.13–1.24 (m, 3H).
MS (Cl, NH$_3$) 502 (MH$^+$)

EXAMPLE 89

(R)-2-{3-Naphthalen-2-yl-2-[(piperidine-4-carbonyl)-amino]-propionyl}1,2,3,4-tetrahydro-isoquinoline-6-carboxylic Acid Ethylamide Hydrochloride A. 4-[2-(6-Ethylcarbamoyl-3,4-dihydro-1H-isoquinolin-2-yl)-1-naphthalen-2-ylmethyl-2-oxo-ethylcarbamoyl]-piperidine-1-carboxylic acid According to General Procedure A, 96 mg (0.40 mmol) of 88C and 170 mg (0.40 mmol) of 80A were coupled and the product was purified by silica gel chromatography (39:1 v/v chloroform:methanol) to give 88 mg of 89A.

B. (R)-2-{3-Naphthalen-2-yl-2-[(piperidine-4-carbonyl)-amino]-propionyl}-1,2,3,4-tetrahydro-isoquinoline-6-carboxylic acid ethylamide hydrochloride To 61 mg (0.10 mmol) of 89B in 6 mL of ethanol was added 2.5 mL of concentrated HCl and the mixture was stirred at room temperature for 5 h. The reaction mixture was concentrated to give 58 mg of the title compound as an off-white solid.

$^1$H NMR (CD$_3$OD, 300 MHz) (mixture of rotamers) (partial) δ 7.46–7.76 (m, 4.5H), 7.09–7.43 (m, 5.5H), 5.08–5.32 (m, 1H), 1.09–1.24 (m, 3H).
MS (Cl, NH$_3$) 513 (MH$^+$)

EXAMPLE 90

(R)-2-Dimethylamino-N-{1-naphthalen-2-ylmethyl-2-oxo-2-[4-(2-oxo-2,3-dihydro-benzoimidazol-1-yl)-piperidin-1-yl]-ethyl}-isobutyramide Hydrochloride A. (R)-2-Dimethylamino-N-{1-naphthalen-2-ylmethyl-2-oxo-2-[4-(2-oxo-2,3-dihydro-benzoimidazol-1-yl)-piperidin-1-yl]-ethyl}-isobutyramide hydrochloride To a solution of 92 mg (0.17 mmol) of 35D in 2 mL of methanol was added 127 mg of powdered 3A sieves, 12 mg (0.40 mmol) of 37% w/w formaldehyde, 27 mg (0.43 mmol) of sodium cyanoborohydride and 103 mg (1.72 mmol) of acetic acid. The mixture was stirred for 60 h at room temperature and then filtered through celite and concentrated. The residue was dissolved in ethyl acetate and washed three times with 1 N NaOH, once with water and once with brine, dried over MgSO$_4$ and concentrated. The resulting oil was triturated to give 39 mg of the title compound as a white solid.

$^1$H NMR (CD$_3$OD, 300 MHz) (mixture of rotamers) (partial) δ 7.68–7.89 (m, 4H), 7.42–7.54 (m, 4H), 6.90–7.08 (m, 3H), 5.32–5.47 (m, 1H), 4.68–4.77 (m, 1H), 4.33–4.51 (m, 1H), 4.16–4.28 (m, 1H), 2.64 (d, 3H), 2.34 (d, 3H).
MS (Cl, NH$_3$) 529 (MH$^+$)

EXAMPLE 91

(R)-3-Amino-N-{1-(1H-indol-3-ylmethyl)-2-oxo-2-[4-(2-phenyl-benzoimidazol-1-yl)-piperidin-1-yl]-ethyl}-3-methyl-butyramide Hydrochloride A. (R)-2-Amino-3-(1H-indol-3-yl)-propionic acid methyl ester To 9.65 g (30.3 mmol) of 4A in 40 mL of ethanol was added 20 mL of concentrated HCl and the mixture was stirred at room temperature for 2.5 h. The mixture was concentrated and the residue was diluted with ethyl acetate. The mixture was washed twice with saturated aqueous sodium bicarbonate and once with brine, dried over MgSO$_4$ and concentrated to give 5.12 g of 91 A as a yellow oil.

B. (R)-2-(3-tert-Butoxycarbonylamino-3-methyl-butyrylamino)-3-(1H-indol-3-yl)-propionic acid According to General Procedure A, 2.01 g (9.2 mmol) of 91A and 2.00 g (9.2 mmol) of 3-tert-Butoxycarbonylamino-3-methyl-butyric acid were coupled to give (R)-2-(3-tert-Butoxycarbonylamino-3-methyl-butyrylamino)-3-(1H-indol-3-yl)-propionic acid methyl ester. The crude ester was hydrolyzed according to General Procedure D to give 3.53 g of 91 B as a white solid.

C. (R)-(2-{2-(1H-Indol-3-yl)-1-[4-(2-phenyl-benzoimidazol-1-yl)-piperidine-1-carbonyl]-ethylcarbamoyl}-1,1-dimethyl-ethyl)-carbamic acid tert-butyl ester According to General Procedure A, 350 mg (1.3 mmol) of 91B and 510 mg (1.3 mmol) of 50D were coupled and the product was purified by silica gel chromatography using a gradient of 60% ethyl acetate in hexane to 100% ethyl acetate to give 180 mg of 91C.

D. (R)-3-Amino-N-{1-(1H-indol-3-ylmethyl)-2-oxo-2-[4-(2-phenyl-benzoimidazol-1-yl)-piperidin-1-yl]-ethyl}-3-methyl-butyramide hydrochloride To 100 mg (0.27 mmol) of 91C in 3 mL of ethanol was added 2 mL of concentrated HCl and the mixture was stirred at room temperature for 2 h. The mixture was concentrated and precipitated from ethanol/hexane to give 125 mg of the title compound as a white solid.
MS (Cl, NH$_3$) 564 (MH$^+$)

EXAMPLE 92

(R)-Piperidine-4-carboxylic acid {2-[4-(3-methyl-2-oxo-2,3-dihydro-benzoimidazol-1-yl)-piperidin-1-yl]-1-naphthalen-2-ylmethyl-2-oxo-ethyl}-amide Hydrochloride A. 4-(2-Oxo-2,3-dihydro-benzoimidazol-1-yl)-piperidine-l-carboxylic acid tert-butyl ester To a mixture of 1.00 g (4.6 mmol) of 4-(2-keto-1-benzimidazolinyl)-piperidine and 1.00 g (4.6 mmol) of 4-dimethylaminopyridine in 20 mL of methylene chloride at 0° C. was added 80 mL of di-tert-butyl dicarbonate in 80 mL of methylene chloride dropwise over 30 min. The mixture was allowed to warm to room temperature and stirred overnight. The mixture was washed three times each with 10% HCl, saturated aqueous sodium bicarbonate and brine, dried over MgSO$_4$ and concentrated. The residue was purified by silica gel chromatography using an elution gradient of 50% ethyl acetate in hexane to 100% ethyl acetate to give 1.16 g of 92A.

B. 4-(3-Methyl-2-oxo-2,3-dihydro-benzoimidazol-1-yl)-piperidine-1-carboxylic acid tert-butyl ester To 390 mg (1.2 mmol) of 92A in 3 mL of DMF was added 47 mg (1.2 mmol) of sodium hydride (60% dispersion in mineral oil), followed by 520 mg (3.7 mmol) of iodomethane and the mixture was stirred for 72 h at room temperature. The mixture was diluted with ethyl acetate and filtered. The filtrate was washed twice with brine and concentrated to give 400 mg of 92B.

C. 1-Methyl-3-piperidin-4-yl-1,3-dihydro-benzoimidazol-2-one hydrochloride

To 400 mg (1.2 mmol) of 92B in 6 mL of ethanol was added 3 mL of concentrated HCl and the mixture was stirred at room temperature for 1.5 h. The mixture was concentrated to give 330 mg of 92C as a white solid.

D. (R)-4-{2-[4-(3-Methyl-2-oxo-2,3-dihydro-benzoimidazol 1-yl)-piperidin-1-yl]-1-naphthalen-2-ylmethyl-2-oxo-ethylcarbamoyl}-piperidine-1-carboxylic acid tert-butyl ester According to General Procedure A, 100 mg (0.37 mmol) of 92C and 159 mg (0.37 mmol) of 80A were coupled and the product was purified by silica gel chromatography using an elution gradient of 100% ethyl acetate to 4% methanol in ethyl acetate to give 120 mg of 92D.

E. (R)-Piperidine-4-carboxylic acid {2-[4-(3-methyl-2-oxo-2,3-dihydro-benzoimidazol-1-yl)-piperidin-1-yl]-1-naphthalen-2-ylmethyl-2-oxo-ethyl}-amide hydrochloride To 120 mg (0.19 mmol) of 92D in 5 mL of ethanol was added 2 mL of concentrated HCl and the mixture was stirred at room temperature for 1.5 h. The mixture was diluted with ethanol and concentrated, and the residue was crystallized from ethanol/hexane to give 45 mg of the title compound.

$^1$H NMR (CD$_3$OD, 250 MHz) (mixture of rotamers) (partial) δ 7.79–7.99 (m, 4H), 7.43–7.78 (m, 3.5H), 7.30–7.39 (m, 0.5H), 7.01–7.19 (m, 3H), 5.26–5.39 (m, 1H), 4.68–4.79 (m, 1H), 4.41–4.60 (m, 1H), 4.13–4.32 (m, 1H). MS (CI, NH$_3$) 540 (MH$^+$)

EXAMPLE 93

(R)-2-{3-Naphthalen-2-yl-2-[(piperidine-4-carbonyl)-amino]-propionyl}-2,3-dihydro-1H-isoindole-5-carboxylic Acid Ethylamide Hydrochloride A. 3,4-Dimethyl-benzoic acid ethyl ester A mixture of 10.00 g (66.6 mmol) of 3,4-dimethylbenzoic acid and 3 mL of concentrated sulfuric acid in 200 mL of ethanol was heated at 50° C. for 2 h, and 65° C. for 6 h. The mixture was concentrated and the residue was diluted with ethyl acetate and washed twice each with brine, saturated aqueous sodium bicarbonate, and brine. The solution was dried over MgSO$_4$ and concentrated to give 12.0 g of 93A.

B. 3,4-Bis-bromomethyl-benzoic acid ethyl ester

A mixture of 12.0 g (67.3 mmol) of 93A, 26.10 g (146.6 mmol) of N-bromosuccinimide and 130 mg (0.79 mmol) of 2,2'-azobis(isobutyronitrile) in 130 mL of carbon tetrachloride was heated at reflux for 17 h. After cooling to room temperature, the mixture was filtered and concentrated to give 22.0 g of 93B as a yellow oil.

C 2,3-Dihydro-1H-isoindole-5-carboxylic acid ethyl ester

To 22.0 g (65.4 mmol) of 93B in 150 mL of benzene was added a solution of 7.87 g (73.4 mmol) of benzylamine and 15.27 g (151 mmol) of triethylamine in 50 mL of benzene dropwise over 30 min, and the mixture was then refluxed for 18 h. After standing at room temperature for 24 h, the mixture was filtered and the filtrate washed once each saturated aqueous sodium bicarbonate and water. The solution was dried over MgSO$_4$ and concentrated. The crude 2-Benzyl-2,3-dihydro-1H-isoindole-5-carboxylic acid ethyl ester was dissolved in 100 mL of ethanol and 20 mL of water and 2.00 g of 10% palladium on carbon was added. The mixture was hydrogenated for 18 h at 45 psi, filtered and concentrated and the residue was purified by silica gel chromatography using an elution gradient of 100% ethyl acetate to 10% diethylamine in ethyl acetate to give 220 mg of 93C.

D. 2-{2-[(1-tert-Butoxycarbonyl-piperidine-4-carbonyl)-amino]-3-naphthalen-2-yl-propionyl}-2,3-dihydro-1H-isoindole-5-carboxylic acid ethyl ester According to General Procedure A, 200 mg (1.05 mmol) of 93C and 446 mg (1.05 mmol) of 80A were coupled to give 460 mg of 93D as a brown solid.

E. (R)-2-{2-[(1-tert-Butoxycarbonyl-piperidine-4-carbonyl)-amino]-3-naphthalen-2-yl-propionyl}-2,3-dihydro-1H-isoindole-5-carboxylic acid To 410 mg (0.68 mmol) of 93D in 50 mL of ethanol containing 1.05 mL of 2 N NaOH was stirred overnight at room temperature. The mixture was concentrated and the residue partitioned between chloroform and 10% HCl. The layers were separated and the aqueous portion was extracted twice with chloroform. The combined organics were concentrated to give 350 mg of 93E.

F. 4-[2-(5-Ethylcarbamoyl-1,3-dihydro-isoindol-2-yl)-1-naphthalen-2-ylmethyl-2-oxo-ethylcarbamoyl]-piperidine-1-carboxylic acid tert-butyl ester According to General Procedure A, 350 mg (0.61 mmol) of 93E and 50 mg (0.61 mmol) of ethylamine hydrochloride were coupled and the product was purified by silica gel chromatography using a gradient of 100% ethyl acetate to 4% methanol in ethyl acetate to give 40 mg of 93F.

G. (R)-2-{3-Naphthalen-2-yl-2-[(piperidine-4-carbonyl)-amino]-propionyl}-2,3-dihydro-1H-isoindole-5-carboxylic acid ethylamide hydrochloride To 40 mg (0.07 mmol) of 93F in 5 mL of ethanol was added 2 mL of concentrated HCl, and the mixture was stirred at room temperature for 2 h. The mixture was concentrated and the residue crystallized from ethanol/hexane to give 16 mg of the title compound as a white solid.

$^1$H NMR (CD$_3$OD, 250 MHz) (mixture of rotamers) (partial) δ 8.63 (d, 1H), 7.71–7.90 (m, 6H), 7.39–7.65 (m, 4H), 5.01–5.20 (m, 2H), 4.67–4.93 (q, 2H), 4.48–4.59 (m, 1H).
MS (CI, NH$_3$) 499 (MH$^+$)

EXAMPLE 94

(R)-1-Methyl-piperidine-4-carboxylic acid {1-naphthalen-2-yl methyl-2-oxo-2-[4-(2-phenyl-benzoimidazol-1-yl)-piperidin-1-yl]-ethyl}-amide Hydrochloride A. (R)-1-Methyl-piperidine-4-carboxylic acid {1-naphthalen-2-ylmethyl-2-oxo-2-[4-(2-phenyl-benzoimidazol-1-yl)-piperidin-1-yl]-ethyl}-amide hydrochloride To 40 mg (0.06 mmol) of 82B in 4 mL of methanol was added 40 mL (0.64 mmol) of acetic acid, 0.16 mL (0.16 mmol) of 1 M sodium cyanoborohydride in THF, 12 mL (0.15 mmol) of formaldehyde and 40 mg of 3A molecular sieves and the mixture was stirred for 72 h at room temperature. The mixture was concentrated and the residue dissolved in ethyl acetate, washed twice with 2 N NaOH and once with brine, dried over $MgSO_4$ and concentrated. The solid was recrystallized from ethanol/hexane to give 24 mg of the title compound.

$^1$H NMR ($CD_3OD$, 250 MHz) (mixture of rotamers) (partial) δ 7.81–7.98 (m, 4H), 7.40–7.76 (m, 10H), 7.27–7.39 (m, 2H), 5.24–5.38 (m,1H) 2.37 (s, 3H).
MS (Cl, $NH_3$) 600 (MH$^+$)

EXAMPLE 95

(R)-2-Amino-N-{1-benzyl-2-oxo-2-[4-(2-phenyl-benzoimidazol-1-yl)-piperidin-1-yl]-ethyl}-isobutyramide Hydrochloride A. (R)-2-(2-tert-Butoxycarbonylamino-2-methyl-propionylamino)-3-phenyl-propionic acid To a mixture of 500 mg (3.03 mmol) of D-phenylalanine and 910 mg (3.03 mmol) of 33A in 10 mL of water and 40 mL of dioxane was added 1.26 mL (9.08 mmol) of triethylamine and the mixture was stirred at room temperature for 30 min., and then heated at 30° C. for 16 h. The mixture was diluted with chloroform and the aqueous portion acidified to pH 4 with acetic acid. The layers were separated and the organic phase was washed three times with brine, dried over $MgSO_4$ and concentrated to give 488 mg of 95A.

B. (R)-(1-{1-Benzyl-2-oxo-2-[4-(2-phenyl-benzoimidazol-1-yl)-piperidin-1-yl]-ethylcarbamoyl}-1-methyl-ethyl)-carbamic acid tert-butyl ester According to General Procedure A, 76 mg (0.22 mmol) of 95A and 60 mg (0.22 mmol) of 50D were coupled and the product was purified by silica gel chromatography (75:25 v/v ethyl acetate:hexanes) to give 120 mg of 95B.

C. (R)-2-Amino-N-{1-benzyl-2-oxo-2-[4-(2-phenyl-benzoimidazol-1-yl)-piperidin-1-yl]-ethyl}-isobutyramide hydrochloride To 120 mg (0.20 mmol) of 95B in 5 mL of ethanol was added 5 mL of concentrated HCl and the mixture was stirred at room temperature for 40 min. The mixture was diluted with ethanol and concentrated and the residue was crystallized from methanol/hexanes to give 65 mg of the title compound as a white solid.

$^1$H NMR ($CD_3OD$, 300 MHz) (mixture of rotamers) (partial) δ 8.24 (d, 0.5H), 7.64–7.90 (m, 8.5H), 7.21–7.43 (m, 5H), 5.17–5.27 (m, 0.33H), 5.02–5.09 (m, 0.67H), 4.18–4.26 (m, 0.33H), 3.94–4.06 (m, 0.67H), 1.71 (s, 2H), 1.56 (s, 3H), 1.48 (s,1H).
MS (Cl, $NH_3$) 510 (MH$^+$)

EXAMPLE 96

(R)-2-Amino-N-[2-(2-methyl-1H-indol-3-yl)-1-(4-phenyl-piperidine-1-carbonyl)-ethyl]-isobutyramide Hydrochloride A. (R)-2-(2-tert-Butoxycarbonylamino-2-methyl-propionylamino)-3-(2-methyl-1H-indol-3-yl)-propionic acid To a mixture of 1 g of D-2-Methyl tryptophan (4.6 mmol) and 1.51 g (5 mmol) of 33A in 9.2 mL of water and 57 mL of dioxane was added 1.4 mL (10 mmol) of triethylamine and the mixture was stirred at room temperature for 16 h. The mixture was diluted with chloroform and the aqueous portion acidified to pH 4 with acetic acid. The layers were separated and the organic phase was washed three times with brine, dried over $MgSO_4$ and concentrated to give 1.9 g of 96A. $^1$H NMR ($CDCl_3$, 250 MHz) (partial): δ 2.4 (s, 3H), 3.2 (dd, 2H), 4.6 (m,1H), 6.9 (m, 2H), 7.18 (m,1H), 7.35 (bd,1H), 7.45 (m,1H)
MS (Cl, $NH_3$) 404 (MH$^+$)

B. (R)-{1-Methyl-1-[2-(2-methyl-1H-indol-3-yl)-1-(4-phenyl-piperidine-1-carbonyl)-ethylcarbamoyl]-ethyl}-carbamic acid tert-butyl ester.

According to General Procedure A, 250 mg (0.62 mmol) of 96A was coupled to 109 mg (0.68 mmol) of 4-phenylpiperidine and the product was purified by silica gel chromatography (2% MeOH-$CH_2Cl_2$) to give 140 mg of 96B as a brown oil.

C. (R)-2-Amino-N-[2-(2-methyl-1H-indol-3-yl)-1-(4-phenyl-piperidine-1-carbonyl)-ethyl]-isobutyramide hydrochloride.

To 140 mg of 96B in 4 mL of ethanol was added 2 mL of concentrated HCl and the mixture was stirred at room temperature for 4 h. The mixture was concentrated to give 85 mg of the title compound after activated charcoal treatment and trituration of the pink solid with ether.

$^1$H NMR ($CD_3OD$, 250 MHz) (partial) (mixture of rotamers): δ 1.65 (6H), 2.35(s,3H)3.8 (bd,1H), 4.45 (bd,1H), 5.7 (m,1H), 6.8 (d, 2H).
MS (Cl, $NH_3$) 447 (MH$^+$)

EXAMPLE 97

(R)-2-Amino-N-[1-(4-benzyl-piperidine-1-carbonyl)-2-(1H-indol-3-yl)-ethyl]-isobutyramide Hydrochloride A. (R)-{1-[1-(4-Benzyl-piperidine-1-carbonyl)-2-(1H-indol-3-yl)-ethylcarbamoyl]-1-methyl-ethyl}-carbamic acid tert-butyl ester.

According to General Procedure A, 122 mg (0.03 mmol) of 4C was coupled to 50 mg (0.028 mmol) of 4-benzylpiperidine and the product was purified by silica gel chromatography (2% MeOH-$CH_2Cl_2$) to give 145 mg of 96A as a brown oil.

$^1$H NMR ($CD_3OD$, 250 MHz) (partial): δ 1.4H (15H), 3.1 (t, 2H), 3.55 (bd, 1H), 4.3 (bd, 1H), 7.45 (d, 1H), 7.6 (d,1H).
MS (Cl, $NH_3$) 547 (MH$^+$).

B. (R)-2-Amino-N-[1-(4-benzyl-piperidine-1-carbonyl)-2-(1H-indol-3-yl)-ethyl]-isobutyramide hydrochloride To 135 mg of 96A in 3 mL of ethanol was added 1 mL of concentrated HCl and the mixture was stirred at room temperature for 4 h. The mixture was concentrated to give 95 mg of the title compound.

$^1$H NMR ($CD_3OD$, 250 MHz) (partial): δ 1.6H (6H), 3.7 (bd, 1H), 4.3 (bd, 1H), 5.1 (m, 1H), 7.4 (d, 1H), 7.55 (d,1H).
MS (Cl, $NH_3$) 447 (MH$^+$).

EXAMPLE 98

(R)-2-Amino-N-[2-(1H-indol-3-yl)-(4-phenylpiperidine-1-carbonyl)-ethyl]-isobutyramide Hydrochoride A. 1-{1-(R)-(1H-Indol-3-ylmethyl)-2-oxo-2-[4-phenyl-piperidin-1-yl]-ethylcarbamoyl}-1-methyl-ethyl)-carbamic acid tert-butyl ester Using General Procedure A, 4-phenylpiperidine (150 mg, 0.93 mmol) was coupled with 4C (362 mg, 0.93 mmol) and the product was purified on silica gel using a gradient of 50% EtOAc/hexanes to 75% EtOAc/hexanes to give 530 mg of a white solid.

$^1$H NMR (CDCl$_3$, 250 MHz) (mixture of rotamers): δ 8.15 (s, 1H), 8.05 (s, 1H), 7.78 (d, 1H), 7.64 (d, 1H), 7.25 (m, 1H), 7.25 (m, 14H), 6.80 (d, 2H), 5.26 (m, 2H), 5.0 (bs, 2H), 4.52 (m, 2H), 4.35 (m, 2H), 3.18 (m, 4H), 2.4 (m, 4H), 1.68 (s, 6H), 1.58 (s, 3H), 1.55 (s, 3H), 1.50 (s, 18H); MS (Cl, NH$_3$): 534 (MH$^+$).

B. (R)-2-Amino-N-[2-(1H-indol-3-yl)-(4-phenylpiperidine-1-carbonyl)-ethyl]-isobutyramide hydrochoride The product from step A (514 mg) was deprotected according to General Procedure C to give 430 mg of the title compound as a white solid.

$^1$H NMR (CD$_3$OD, 250 MHz): δ 7.55 (m, 1H), 7.32 (m, 1H), 7.05 (m, 7H), 6.75 (d, H), 5.18 (m, 1H), 5.18 (m, 1H), 4.45 (m, 1H), 3.85 (m, 1H), 3.12 (m, 2H), 2.4 (m, 2H), 1.55 (s, 12H), 1.4 (s, 3 H); MS (Cl, NH$_3$): 434 (MH$^+$).

EXAMPLE 99

(R)-2-Amino-N-[2-(5-fluoro-1H-indol-3-yl)-1-(4-phenylpiperidine-1-carbonyl)-ethyl]-isobutyramide Hydrochoride A. (1-{1-(R)-(5-fluoro-1H-Indol-3-ylmethyl)-2-oxo-2-[4-phenyl-piperidin-1-yl]-ethylcarbamoyl}-1-methyl-ethyl)-carbamic acid tert-butyl ester Using General Procedure A, 4-phenylpiperidine (20 mg, 0.123 mmol) was coupled with 33B (50 mg, 0.123 mmol) and the product was purified on silica gel using a gradient of 75% EtOAc/hexanes to 100% EtOAc to give 60 mg of 99A as a white solid.

$^1$H NMR (CDCl$_3$, 250 MHz): δ 8.55 (m, 1H), 7.45 (m, 6H), 7.0 (m, 1H), 6.9 (d, 1H), 5.3 (m, 1H), 5.1 (m, 1H), 4.7 (m, 1H), 3.78 (d, 1H), 3.2 (m, 2H), 2.5 (m, 2 H), 1.55 (s, 3H), 1.50 (s, 9H), 1.35 (s, 3H); MS (Cl, NH$_3$): 552 (MH$^+$).

B. (R)-2-Amino-N-[2-(5-fluoro-1H-indol-3-yl)-(4-phenylpiperidine-1-carbonyl)-ethyl]-isobutyramide hydrochoride The product from 99A, (60 mg), was deprotected according to General Procedure C to give 50 mg of the hydrochloride salt of the title compound as a white solid.

$^1$H NMR (d$_4$-MeOH, 300 MHz): δ 7.25 (m, 7H), 6.85 (m, 2H), 5.2 (m, 1H), 4.5 (m, 1H), 3.9 (d, 1H), 3.1 (m, 1H), 2.94 (t, 1H), 2.5 (m, 2H), 1.59 (s, 12H), 1.45 (s, 3 H); MS (Cl, NH$_3$): 452 (MH$^+$).

EXAMPLE 100

(R)-2-Amino-N-[2-benzylsulfanyl-1-(4-phenyl-piperidine-1-carbonyl)-ethyl]-isobutyramide Hydrochloride A. [1-(R)-Benzylsulfanylmethyl-2-oxo-2-(4-phenyl-piperidin-1-yl)-ethyl]-carbamic acid tert-butyl ester.

According to General Procedure A, 400 mg (1.28 mmol) of N-t-BOC-S-benzyl-D-cysteine and 206 mg (1.28 mmol) of 4-phenylpiperidine were coupled and the product purified by silica gel chromatography (9:1 v/v CHCl$_3$MeOH) to afford 572 mg of 100A.

$^1$H NMR (CDCl$_3$ 250 MHz) δ 7.37–7.13 (m, 10H), 5.49 (dd, 1H), 4.81 (dd, 1H), 4.73 (d, 1H), 3.91–3.71 (m, 3H), 3.14–2.92 (m, 1H), 2.80–2.55 (m, 4H), 1.91–1.53 (m, 4H), 1.46 (s, 9H). MS (Cl, NH$_3$) 456 (MH$^+$)

B. (R)-2-Amino-3-benzylsulfanyl-1-(4-phenyl-piperidin-1-yl)-propan-1-one.

According to General Procedure B, 514 mg (1.13 mmole) of the product from 100A was deprotected to afford 445 mg of 100B.

$^1$HNMR (CD$_3$OD 250 MHz) δ 7.44–7.14 (m, 10H), 4.60 (d, 1H), 4.48 (dd, 1H), 3.89 (d, 1H), 3.87 (s, 1H), 3.68–3.63 (m, 1H), 3.21–3.01 (m, 1H), 2.96–2.73 (m, 4H), 1.88–1.73 (m, 2H), 1.67–1.34 (m, 2H). MS (Cl, NH$_3$) 355 (MH$^+$)

C. {1-[1-(R)-Benzylsulfanylmethyl-2-oxo-2-(4-phenyl-piperidin-1-yl)-ethylcarbamoyl]-1-methyl-ethyl}-carbamic acid tert-butyl ester.

According to General Procedure A, 78 mg (0.38 mmol) of N-t-Boc-a-methylalanine and 150 mg (0.38 mmol) of 100B were coupled and the product purified by silica gel chromatography (19:1 v/v CHCl$_3$/MeOH) to afford 212 mg of 100C.

$^1$H NMR (CDCl$_3$ 250 MHz) δ 7.37–7.04 (m, 10H), 5.06 (dd, 1H), 4.96 (s, 1H), 4.70 (d,1H), 3.85–3.69 (m, 3H), 3.11–2.88 (m,1H), 2.85–2.77 (m,1H), 2.74–2.58 (m, 3H), 1.89–1.74 (m, 3H), 1.63–1.54 (m, 2H), 1.50 (s, 3H), 1.49 (s, 3H), 1.42 (s, 9H). MS (Cl, NH$_3$) 540 (MH$^+$)

D. (R)-2-Amino-N-[1l-benzylsulfanylmethyl-2-oxo-2-(4-phenyl-piperidin-1-yl)-ethyl]-isobutyramide hydrochloride.

The product from 100C (153 mg, 0.28 mmol) was dissolved in 4 mL of ethanol and 2 mL of concentrated HCl were added and the mixture stirred at room temperature for 4 h. The mixture was concentrated, azeotroped 3× with MeOH and 2× with methylene chloride to give 124 mg of the title compound as a white solid.

$^1$H NMR (CD$_3$OD 250 MHz) δ 7.37–7.19 (m, 10H), 4.97–4.95 (m, 2H), 4.58 (d, 1H), 3.81–3.78 (m, 3H), 3.12–3.01 (m, 1H), 2.86–2.66 (m, 4H), 1.82–1.74 (m, 2H), 1.63 (s, 3H), 1.60 (d, 3H). MS (Cl, NH$_3$) 440 (MH$^+$)

EXAMPLE 101

(R)-2-Amino-N-[4-phenyl-1-(4-phenyl-piperidine-1-carbonyl)-butyl]-isobutyramide Hydrochloride A. {1-Methyl-1-[4-phenyl-1-(4-phenyl-piperidine-1-carbonyl)-butylcarbamoyl]-ethyl}-carbamic acid tert-butyl ester.

The product from 62D (116 mg, 0.307 mmol) was coupled to 4-phenylpiperidine (49 mg, 0.307 mmol ) using General Procedure A to give 135mg of 101A as an oil. MS (Cl, NH$_3$): 522 (MH$^+$).

B. (R)-2-Amino-N-[4-phenyl-1-(4-phenyl-piperidine-1-carbonyl)-butyl]-isobutyramide hydrochloride.

The product from 101A (109 mg, 0.209 mmol) was deprotected according to General Procedure C and the product was purified on silica gel (chromatatron) using a gradient of 0% MeOH/CH$_2$Cl$_2$ to 100% MeOH. The product was concentrated in vacuo, dissolved in 5 mL of MeOH, and 0.2mL of 0.98 N HCl were added. The solution was stirred at room temperature for 30 min., concentrated, azeotroped 3× with methanol, 2× with methylene chloride and dried to give 63 mg of the title compound as a white foam.

$^1$H NMR (d$_4$-MeOH, 300 MHz) (partial ) δ 7.2(m, 10H), 4.6(m, 1H), 4.05(m,1H), 3.19(m, 1H), 2.78(m, 4H); MS (Cl, NH$_3$): 422 (MH$^+$).

EXAMPLE 102

(R)-2-Amino-N-[2-benzyloxy-1-(4-phenyl-piperidine-1-carbonyl)-ethyl]-isobutyramide Hydrochloride A. (R)-{1-[1-Benzyloxymethyl-2-oxo-2-(4-phenyl-piperidin-1-yl)-ethylcarbamoyl]-1-methyl-ethyl}-carbamic acid tert-butyl ester.

According to General Procedure A, 4-phenylpiperidine (237 mg, 1.47 mmol) was coupled with 559 mg (1.47 mmol) of the product from Example 3. Purification on silica gel using a gradient of 0% MeOH/CH$_2$Cl$_2$ to 1% MeOH/CH$_2$Cl$_2$ gave 500 mg of an oil. MS (Cl, NH$_3$): 524 (MH$^+$).

B. (R)-2-Amino-N-[2-benzyloxy-1-(4-phenyl-piperidine-1-carbonyl)-ethyl]-isobutyramide hydrochloride.

The product from 102A (480 mg, 0.917 mmol) was dissolved in 12 mL of ethanol and 6 mL of concentrated HCl were added and the mixture stirred at room temperature for 4 h. The mixture was concentrated, azeotroped 3× with MeOH and 2× with methylene chloride to give 369 mg of the title compound as a white foam.

$^1$H NMR (d$_4$-MeOH, 300 MHz):δ 7.25(m, 9H), 7.05(d, 1H), 5.15(t, 1H), 4.6(bd, 1H), 3.75(m, 2H), 3.18(m, 1H), 2.8(m, 2H), 1.6(m, 11H); MS (Cl, NH$_3$): 424 (MH$^+$).

EXAMPLE 103

(R)-2-Amino-N-[2-benzo[b]thiophen-3-yl-1-(4-phenyl-piperidine-1-carbonyl)-ethyl]-isobutyramide Hydrochloride A. (R)-[2-Benzo[b]thiophen-3-yl-1-(4-phenyl-piperidine-1-carbonyl)-ethyl]-carbamic acid tert-butyl ester.

According to General Procedure A, 534 mg of (R)-3-Benzo[b]thiophen-3-yl-2-tert-butoxycarbonylamino-propionic acid was coupled with 4-phenylpiperidine (268 mg) to give 700 mg of 103A as a colorless foam. MS (Cl, NH$_3$): 465 (MH$^+$).

B. (R)-2-Amino-3-benzo[b]thiophen-3-yl-1-(4-phenyl-piperidin-1-yl)-propan-1-one.

The poduct from Example 103A, (740 mg,1.59 mmol) was dissolved in 12 mL of ethanol and 6 mL of concentrated HCl were added and the mixture stirred at room temperature for 4 h. The mixture was concentrated, azeotroped 3× with MeOH and 2× with methylene chloride to give 528 mg of 103B as a white solid. MS (Cl, NH$_3$): 365 (MH$^+$).

C. {1-[2-Benzo[b]thiophen-3-yl-1-(4-phenyl-piperidine-1-carbonyl)-ethylcarbamoyl]-1-methyl-ethyl}-carbamic acid tert-butyl ester.

Using General Procedure A, N-t-BOC-α-methylalanine (118 mg, 0.581 mmol) was coupled with the product from 103B (233 mg, 0.581 mmol) to give 100 mg of 103C as an oil.

MS (Cl, NH$_3$): 550 (MH$^+$).

D. (R)-2-Amino-N-[2-benzo[b]thiophen-3-yl-1-(4-phenyl-piperidine-1-carbonyl)-ethyl]-isobutyramide hydrochloride.

The product from 103C (95 mg, 0.173 mmol) was dissolved in 4 mL of ethanol and 2 mL of concentrated HCl were added and the mixture stirred at room temperature for 4 h. The mixture was concentrated, azeotroped 3× with MeOH and 2× with methylene chloride to give the title compound as a light-yellow solid (67 mg).

$^1$H NMR (CD$_3$OD, 300 MHz) (partial) δ 7.9(m, 2H), 7.41(m, 3H), 7.19(m, 4H), 6.9(d, 1H), 5.35(m, 1H), 4.55(m, 1H), 3.9(bt, 1H), 3.45(m, 1H), 2.95(m, 1H), 2.65(bt, 1H), 2.49(m, 2H); MS (Cl, NH$_3$): 450 (MH$^+$).

EXAMPLE 104

(R)-Piperidine-4-carboxylic acid {2-naphthalen-1-yl-1-[4-(phenyl-propionyl-amino)-piperidine-1-carbonyl]-ethyl}-amide Hydrochloride A. (R)-4-{2-Naphthalen-1-yl-1-[4-(phenyl-propionyl-amino)-piperidine-1-carbonyl]-ethylcarbamoyl}-piperidine-1-carboxylic acid tert-butyl ester.

According to the method outlined in General Procedure A (substituting DMF for solvent in place of CH$_2$Cl$_2$), 54 mg (0.23 mmol) of 4-(N-propionylanilino)-piperidine and 99 mg (0.23 mmol) of 78A were coupled to give 165 mg of 104A as a pale yellow oil.

$^1$H NMR (CDCl$_3$, 250 MHz, partial) δ 8.25–8.21 (m, 1H), 7.74–7.71 (m, 1H), 7.50–7.08 (m, 7H), 6.92–6.69 (m, 3H), 5.20–5.12 (m, 1H), 4.50–4.32 (m, 2H), 4.18–4.02 (m, 2H), 3.09–2.85 (m, 2H), 2.72–2.60 (m, 2H), 2.30–2.08 (m, 2H), 1.82–1.73 (m, 2H), 1.41 (s, 9H), 0.92–0.84 (m, 3H).

MS (Cl, NH$_3$) 641 (MH$^+$)

B. (R)-Piperidine-4-carboxylic acid {2-naphthalen-1-yl-1-[4-(phenyl-propionyl-amino)-piperidine-1-carbonyl]-ethyl}-amide hydrochloride 165 mg (0.23 mmol) of 104A was treated with 2 mL of HCl-saturated dioxane for 17 hours. Concentration in vacuo, followed by three concentrations from 1:5 MeOH-toluene provided 108 mg of the title compound as a white solid.

$^1$H NMR (CD$_3$OD, 250MHz, partial) δ 8.13–8.08 (m, 1H), 7.88–6.85 (m, 11H), 5.27–5.19 (m, 1H), 1.88–1.80 (m, 2H), 0.93–0.88 (m, 3H).

MS (Cl, NH$_3$) 541 (MH$^+$)

EXAMPLE 105

(R)-2-Amino-N-[2-naphthalen-1-yl-1-(4-phenyl-piperidine-1-carbonyl)-ethyl]-isobutyramide Hydrochloride A. (R)-{1-Methyl-1-[2-naphthalen-1-yl-1-(4-phenyl-piperidine-1-carbonyl)-ethylcarbamoyl]-ethyl}-carbamic acid tert-butyl ester.

According to the method outlined in General Procedure A (substituting DMF for solvent in place of CH$_2$Cl$_2$), 88 mg (0.55 mmol) of 4-phenylpiperidine and 219 mg (0.55 mmol) of 64A were coupled and the resulting product was purified by silica gel chromatography (2:1 to 1:1 to 1:2 hexane-EtOAc) to give 183 mg of 105A as a white solid.

$^1$H NMR (CDCl$_3$, 250 MHz) δ 8.46–8.40 (m,1H), 7.84–7.75 (m, 2H), 7.65–7.59 (m, 1H), 7.51–7.14 (m, 7H), 6.83–6.82 (m, 1H), 5.52–5.47 (m, 1H), 5.05 (br s,1H), 4.65–4.53 (m,1H), 3.86–3.75 (m,1H), 3.34–3.06 (m, 2H), 2.71–2.63 (m, 1H), 2.46–2.18 (m, 2H), 1.91–1.63 (m, 2H), 1.58 (s, 3H), 1.53 (s, 3H), 1.48 (s, 9H), 1.29–1.26 (m, 2H), 0.83–0.75 (m,1H).

MS (Cl, NH$_3$) 544 (MH$^+$)

B. (R)-2-Amino-N-[2-naphthalen-1-yl-1-(4-phenyl-piperidine-1-carbonyl)-ethyl]-isobutyramide hydrochloride.

120 mg (0.22 mmol) of 105A was treated with 2 mL of HCl-saturated dioxane for 17 hours. Concentration in vacuo, followed by three concentrations from 1:5 MeOH-toluene provided 60 mg of the title compound as a white solid.

$^1$H NMR (CD$_3$OD, 250MHz, partial) δ 8.24–8.12 (m, 1H), 7.91–7.83 (m, 2H), 7.57–7.40 (m, 3H), 7.26–7.10 (m, 5H), 6.81 (d, J=7.3, 1H), 5.42–5.38 (m, 1H), 4.48–4.40 (m,1H), 3.68–3.48 (m, 2H), 2.89–2.78 (m,1H), 2.48–2.39 (m, 2H), 1.63 (s, 6H), 0.98–0.91 (m, 1H), 0.71–0.54 (m, 1H).

MS (Cl, NH$_3$) 444 (MH$^+$)

EXAMPLE 106

(R)-2-Amino-N-[1-naphthalen-1-ylmethyl-2-oxo-2-(4-phenoxy-piperidin-1-yl)-ethyl]-isobutyramide Hydrochloride A. 4-Phenoxy-piperidine-1-carboxylic acid tert-butyl ester To a solution of 403 mg (2.0 mmol) of N-tert-butoxycarbonyl-4-hydroxypiperidine, 188 mg (2.0 mmol) of phenol, and 525 mg (2.0 mmol) of triphenylphosphine in 50 mL of THF was added 0.315 mL of diethylazodicarboxylate. The resulting solution was stirred at room temperature for 2 days. Concentration in vacuo and purification via silica gel chromatography (10:1 hexane-EtOAc) provided 366 mg of the title compound as a colorless oil.

$^1$H NMR (CDCl$_3$ 250 MHz) δ 7.31–7.21 (m, 2H), 6.97–6.83 (m, 3H), 4.49–4.44 (m, 1H), 3.75–3.66 (m, 2H), 3.38–3.30 (m, 2H), 2.05–1.91 (m, 2H), 1.81–1.72 (m, 2H), 1.47 (s, 9H). MS (Cl, NH$_3$) 278 (MH$^+$)

B. 4-phenoxypiperidine 355 mg (1.28 mmol) of 106A was treated with 5 mL of HCl-saturated dioxane for 16 hours. Concentration in vacuo, followed by trituration with ether provided 196 mg of 106B compound as a white solid. $^1$H NMR (CD$_3$OD 250 MHz) δ 7.31–7.26 (m, 2H), 7.00–6.93 (m, 3H), 4.72–4.68 (m, 1H), 3.43–3.35 (m, 2H), 3.25–3.17 (m, 2H), 2.19–2.10 (m, 2H), 2.07–1.99 (m, 2H). MS (Cl, NH$_3$) 178 (MH$^+$)

C. (R)-{1-Methyl-1-[1-naphthalen-1-ylmethyl-2-oxo-2-(4-phenoxy-piperidin-1-yl)-ethylcarbamoyl]-ethyl}-carbamic acid tert-butyl ester According to the method outlined in General Procedure A (substituting DMF for solvent in place of CH$_2$Cl$_2$), 57 mg (0.32 mmol) of 106B and 117 mg (0.29 mmol) of 64A were coupled and the resulting product was purified by silica gel chromatography (1:1 hexane-EtOAc) to give 126 mg of the title compound as a white solid. $^1$H NMR (CDCl$_3$ 250 MHz) δ 8.46–8.37 (m, 1H), 7.87–7.76 (m, 2H), 7.63–7.59 (m, 1H), 7.53–7.48 (m, 1H), 7.41–7.17 (m, 4H), 6.93–6.89 (m, 1H), 6.76–6.69 (m, 2H), 5.38–5.35 (m, 1H), 4.99 (br s, 1H), 3.78–3.72 (m, 2H), 1.64 (s, 3H), 1.52 (s, 3H), 1.47 (s, 9H). MS (Cl, NH$_3$) 560 (MH$^+$)

D. 2-Amino-N-[1-naphthalen-1-ylmethyl-2-oxo-2-(4-phenoxy-piperidin-1-yl)-ethyl]-isobutyramide To 135 mg of 106C in 2 mL of ethanol was added 2 mL of concentrated HCl and the mixture was stirred at room temperature for 2 h. The mixture was concentrated, azeotroped with acetonitrile, triturated with ether, filtered, and dried to give 57 mg of the title compound as a white solid. MS (Cl, NH$_3$) 460 (MH$^+$)

EXAMPLE 107

(R)-2-Amino-N-[1-(1H-indol-3-ylmethyl)-2-oxo-2-(4-phenylamino-piperidin-1-yl)-ethyl]-isobutyramide Hydrochloride A. 4-Phenylamino-piperidine-1-carboxylic acid tert-butyl ester 1.53 g (7.68 mmol) of BOC-piperidone and 13.4 g (77 mmol) of sodium sulfate in 28 mL acetic acid were treated with 0.78 mL (8.6 mmol) of aniline. After 10 min, 8.2 g (39 mmol) of sodium triacetoxyborohydride was added. After 45 min, the solution was poured onto ice, and neutralized by portionwise addition of solid sodium bicarbonate (ca. 45 g). The resulting solution was extracted with five portions of CHCl$_3$; the organics were washed with brine, dried over MgSO$_4$, filtered, concentrated, and purified via flash chromatography (10:1 to 5:1 to 2:1 hexane-EtOAc) to provide 1.703 g of the title compound as a white solid.

$^1$H NMR (CDCl$_3$, 250 MHz) δ 7.19–7.13 (m, 2H), 6.73–6.58 (m, 3H), 4.11–4.02 (m, 2H), 3.52–3.40 (m, 2H), 2.98–2.90 (m, 2H), 2.10–2.02 (m, 2H), 1.48 (s, 9H), 1.42–1.28 (m, 2H).

B. Phenyl-piperidin-4-yl-amine 124 mg (0.45 mmol) of 107A was treated with 3 mL of HCl-saturated dioxane for 15 hours. Concentration in vacuo, followed by three concentrations from 1:5 MeOH-toluene provided 105 mg of the title compound as a white solid.

$^1$H NMR (CD$_3$OD, 250 MHz) δ 7.66–7.52 (m, 5H), 3.97–3.86 (m, 1H), 3.62–3.50 (m, 2H), 3.16–3.05 (m, 2H), 2.30–2.22 (m, 2H), 2.15–1.98 (m, 2H).
MS (Cl, NH$_3$) 177 (MH$^+$)

C. {1-[1-(1H-Indol-3-ylmethyl)-2-oxo-2-(4-phenylamino-piperidin-1-yl)-ethylcarbamoyl]-1-methyl-ethyl}-carbamic acid tert-butyl ester According to the method outlined in General Procedure A (substituting DMF for solvent in place of CH$_2$Cl$_2$), 100 mg (0.40 mmol) of 107B and 134 mg (0.36 mmol) of 64A were coupled and the resulting product was purified by silica gel chromatography (0–2% MeOH in CHCl$_3$) to give 205 mg of 107C as a white solid.

$^1$H NMR (CDCl$_3$, 250 MHz, partial) δ 8.22–8.14 (m, 1H), 7.71–7.60 (m, 1H), 7.39–7.06 (m, 7H), 6.60–6.52 (m, 1H), 6.52–6.44 (m, 2H), 5.27–5.19 (m, 1H), 4.93 (br s, 1H), 4.38–4.24 (m, 1H), 3.52–3.47 (m, 1H), 3.30–3.08 (m, 3H), 2.68–2.50 (m, 1H), 1.52 (s, 3H), 1.50 (s, 3H), 1.46 (2, 9H).
MS (Cl, NH$_3$) 548 (MH$^+$)

D. 2-Amino-N-[1-(1-H-indol-3-ylmethyl)-2-oxo-2-(4-phenylamino-piperidin-1-yl)-ethyl]-isobutyramide 197 mg (0.36 mmol) of 107C was treated with 2 mL of HCl-saturated dioxane for 15 hours. Concentration in vacuo, followed by three concentrations from 1:5 MeOH-toluene provided 141 mg of the title compound as a white solid.

$^1$H NMR (CD$_3$OD, 250MHz, partial) δ 7.52–7.30 (m, 8H), 7.15–6.97 (m, 4H), 5.23–5.12 (m, 1H), 4.60–4.52 (m, 1H), 4.00–3.82 (m, 1H), 3.24–3.12 (m, 2H), 1.59 (s, 3H), 1.48 (s, 3H).

MS (Cl, NH$_3$) 448 (MH$^+$)

We claim:

1. A compound of the formula:

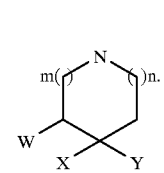

(I)

wherein

Z is —COCR$^1$R$^{2c}$LCOANR$^4$R$^5$, where L is NR$^6$;

W in combination with X is a benzo fusion in which W and X are linked to form a phenyl ring substituted with T-R$^{3b}$;

X in combination with W is a benzo fusion in which W and X are linked to form a phenyl ring substituted with T-R$^{3b}$;

Y is hydrogen;

R$^1$ is indolyl (C$_1$–C$_6$) alkyl; or phenyl (C$_0$–C$_5$) alkyl-K$^1$-(C$_1$–C$_5$) alkyl where K$^1$ is O;

R$^{2c}$ is hydrogen or (C$_1$–C$_6$) alkyl;

T is a bond;

R$^{3D}$ is CONR$^8$OR$^9$; SO$_2$NR$^8$R$^9$; NR$^2$SO$_2$R$^9$; or NR$^2$C(O)R$^D$;

R$^2$ is hydrogen, C$_1$–C$_6$ alkyl, C$_3$–C$_7$ cycloalkyl or C$_1$–C$_6$ halogenated alkyl;

R$^4$ and R$^5$ are independently hydrogen of (C$_1$–C$_6$) alkyl;

R$^6$ is hydrogen or (C$_1$–C$_6$) alkyl;

A is

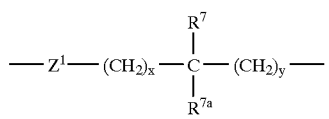

where x and y art independently 0–3;

$Z^1$ is a bond; and $R^7$ and $R^{7a}$ are independently hydrogen, $(C_1-C_6)$ alkyl; or trifluoromethyl;

$R^8$ is hydrogen or $(C_1-C_6)$ alkyl;

$R^9$ is hydrogen, $(C_1-C_6)$ alkyl; or phenyl optionally substituted with $CH_3$ or $CF_3$; provided that $R^9$ may not be hydrogen where $R^{3b}$ is $NR^2SO_2R^9$; and m and n are both 1.

2. A compound of claim 1 wherein

Z is $—COCR^1R^{2c}NHCOANR^4R^5$

A is $—CR^7R^{7a}(CH_2)_y—$; y is 0 to 3;

and $R^{2c}$ is H or $CH_3$;

$R^7$ is $C_1-C_3$ alkyl;

$R^{7a}$ is H or $C_1-C_3$ alkyl;

$R^4$ is hydrogen or $C_1-C_3$ alkyl;

$R^5$ is hydrogen or $C_1-C_3$ alkyl.

3. A compound of claim 2 wherein $R^1$ is selected from the group consisting of 1-indolyl-$CH_2$-, 2-indolyl-$CH_2$-; 3-indolyl-$CH_2$-.

4. A compound of claim 3 wherein $R^{2c}$ is hydrogen; y=0; $R^7$ and $R^{7a}$ are methyl and $R^4$ and $R^5$ are hydrogen and $R^1$ is $C_6H_5CH_2—O-CH_2—$, or,

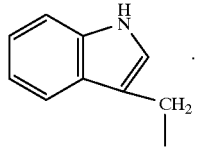

5. A compound of claim 3 which is of the formula

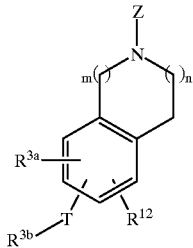

wherein n is one; m is one;

$R^{3a}$ is H, F;

$R^{12}$ is H, F;

T is a bond;

$R^{3b}$ is $CONR^8R^9$, $SO_2NR^8R^9$, $NHSO_2R^9$, or $NHC(O)R^9$;

$R^9$ is hydrogen, $C_1-C_6$ alkyl or phenyl, each optionally substituted with one $CH_3$ or $CF_3$;

$R^8$ is hydrogen or $C_1-C_6$ alkyl.

6. A compound of claim 5 wherein:

m is one; and

T is a bond.

7. A compound of claim 6 wherein n is one;

$R^{3a}$ and $R^{12}$ are hydrogen;

$R^{3b}$ is $CONR^8R^9$, $SO_2NR^8R^9$, $NHSO_2R^9$, $NHC(O)R^9$ or $OR^8$;

$R^9$ is hydrogen or phenyl optionally substituted with $CH_3$, or $CF_3$; or $R^9$ is $C_1-C_6$ alkyl; and $R^8$ is hydrogen or $C_1-C_6$ alkyl.

8. A compound of claim 3 wherein Z is

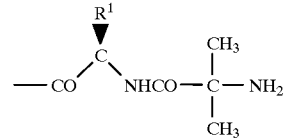

9. A compound of claim 8 wherein $R^1$ is $—CH_2OCH_2C_6H_5$ or $—CH_2CH_2CH_2C_6H_5$.

10. A compound of claim 5 selected from the group consisting of:

(R)-2-Amino-N-{2-(1H-indol-3-yl)-1-[6-(toluene-4-sulfonylamino)-3,4-dihydro-1H-isoquinoline-2-carbonyl]-ethyl}-isobutyramide hydrochloride;

(R)-2-Amino-N-{2-(1H-indol-3-yl)-1-[7-(toluene-4-sulfonylamino)-3,4-dihydro-1H-isoquinoline-2-carbonyl]-ethyl}-isobutyramide;

(R)-N-{2-[2-(2-Amino-2-methyl-propionylamino)-3-(1H-indol-3-yl)-propionyl]-1,2,3,4-tetrahydro-isoquinolin-7-yl}-benzamide;

(R)-2-Amino-N-{1-benzyloxymethyl-2-oxo-2-[7-(toluene-4-sulfonylamino)-3,4-dihydro-1H-isoquinolin-2-yl]-ethyl}-isobutyramide hydrochloride.

11. A method for increasing levels of endogenous growth hormone in a human or an animal which comprises administering to such human or animal an effective amount of a compound of claim 1.

12. A composition useful for increasing the endogenous production or release of growth hormone in a human or an animal which comprises an inert carrier and an effective amount of a compound of claim 1.

13. A method for the treatment of osteoporosis which comprises administering to a patient with osteoporosis a combination of a bisphosphonate compound, and a compound of claim 1.

14. A method according to claim 13 wherein said bisphosphonate compound is alendronate.

* * * * *